United States Patent
Harkin et al.

(10) Patent No.: US 11,091,809 B2
(45) Date of Patent: Aug. 17, 2021

(54) MOLECULAR DIAGNOSTIC TEST FOR CANCER

(71) Applicant: ALMAC DIAGNOSTICS LIMITED, Craigavon (GB)

(72) Inventors: Denis Paul Harkin, Dromore (GB); Fionnuala Patterson, Greenisland (GB); Claire Trinder, Stratford-upon-Avon (GB); Eamonn J. O'Brien, Hillsborough (GB); Caroline Michie, Nr Kirkcaldy (GB); Charlie Gourley, Dumfermline (GB); Laura A. Hill, Lisburn (GB); Katherine E. Keating, Magherafelt (GB); Jude O'Donnell, Galbally (GB); Max Bylesjo, Glasglow (GB); Steve Deharo, Hillsborough (GB); Vitali Proutski, Oxford (GB); Richard Kennedy, Belfast (GB); Timothy Davison, Hillsborough (GB); Andreas Winter, Gersthofen (DE); Andrena McCavigan, Lurgan (GB)

(73) Assignee: Almac Diagnostic Services Limited, Craigavon (GB)

( * ) Notice: Subject to any disclaimer, the term of this patent is extended or adjusted under 35 U.S.C. 154(b) by 1119 days.

(21) Appl. No.: 14/649,421

(22) PCT Filed: Dec. 3, 2013

(86) PCT No.: PCT/GB2013/053202
§ 371 (c)(1),
(2) Date: Jun. 3, 2015

(87) PCT Pub. No.: WO2014/087156
PCT Pub. Date: Jun. 12, 2014

(65) Prior Publication Data
US 2016/0002732 A1 Jan. 7, 2016

Related U.S. Application Data

(60) Provisional application No. 61/732,761, filed on Dec. 3, 2012.

(51) Int. Cl.
*G16B 25/00* (2019.01)
*C12Q 1/6886* (2018.01)
(Continued)

(52) U.S. Cl.
CPC .......... *C12Q 1/6886* (2013.01); *G16B 25/00* (2019.02); *G16B 25/10* (2019.02); *G16B 40/00* (2019.02);
(Continued)

(58) Field of Classification Search
None
See application file for complete search history.

(56) References Cited

U.S. PATENT DOCUMENTS

| 5,143,854 A | 9/1992 | Pirrung et al. |
| 5,288,644 A | 2/1994 | Beavis et al. |

(Continued)

FOREIGN PATENT DOCUMENTS

| CA | 2726811 A1 | 12/2009 |
| CA | 2 730 614 A1 | 1/2010 |

(Continued)

OTHER PUBLICATIONS

Bauerschlag et al., "Evaluation of Potentially Predictive Markers for Anti-Angiogenic Therapy with Sunitinib in Recurrent Ovarian Cancer Patients", Translational Oncology, 6:305-310, (2013).

(Continued)

*Primary Examiner* — Karlheinz R. Skowronek
(74) *Attorney, Agent, or Firm* — Finnegan, Henderson, Farabow, Garrett & Dunner, LLP

(57) ABSTRACT

Methods and compositions are provided for the identification of a molecular diagnostic test for cancer. The test identifies cancer subtypes that have an up-regulation or a down-regulation in biomarker expression related to angiogenesis and vascular development. The present invention
(Continued)

can be used to determine whether patients with cancer are clinically responsive or non-responsive to a therapeutic regimen prior to administration of any anti-angiogenic agent. This test may be used in different cancer types and with different drugs that directly or indirectly affect angiogenesis or angiogenesis signalling. In addition, the present invention may be used as a prognostic indicator for certain cancer types. In particular, the present invention is directed to the use of certain combinations of predictive markers, wherein the expression of the predictive markers correlates with responsiveness or non-responsiveness to a therapeutic regimen.

22 Claims, 22 Drawing Sheets

Specification includes a Sequence Listing.

(51) Int. Cl.
G16B 40/00 (2019.01)
G16B 40/20 (2019.01)
G16B 25/10 (2019.01)
G16B 40/30 (2019.01)

(52) U.S. Cl.
CPC .............. G16B 40/20 (2019.02); G16B 40/30 (2019.02); C12Q 2600/106 (2013.01); C12Q 2600/158 (2013.01)

(56) References Cited

U.S. PATENT DOCUMENTS

| | | | |
|---|---|---|---|
| 5,324,633 | A | 6/1994 | Fodor et al. |
| 5,432,049 | A | 7/1995 | Fischer et al. |
| 5,470,710 | A | 11/1995 | Weiss et al. |
| 5,492,806 | A | 2/1996 | Drmanac et al. |
| 5,503,980 | A | 4/1996 | Cantor |
| 5,510,270 | A | 4/1996 | Fodor et al. |
| 5,525,464 | A | 6/1996 | Drmanac et al. |
| 5,547,839 | A | 8/1996 | Dower et al. |
| 5,580,732 | A | 12/1996 | Grossman et al. |
| 5,661,028 | A | 8/1997 | Foote |
| 5,800,992 | A | 9/1998 | Fodor et al. |
| 2002/0123044 | A1 | 9/2002 | Blashuk et al. |
| 2002/0137680 | A1 | 9/2002 | Ahmed |
| 2003/0215424 | A1 | 11/2003 | Seul et al. |
| 2005/0186208 | A1 | 8/2005 | Fyfe et al. |
| 2006/0127928 | A1 | 6/2006 | Bacus et al. |
| 2006/0134663 | A1 | 6/2006 | Harkin et al. |
| 2006/0211060 | A1 | 9/2006 | Haley et al. |
| 2007/0065858 | A1 | 3/2007 | Haley |
| 2008/0199855 | A1 | 8/2008 | Nister et al. |
| 2008/0286771 | A1 | 11/2008 | Hudson et al. |
| 2008/0305962 | A1 | 12/2008 | Wirtz |
| 2009/0023149 | A1 | 1/2009 | Knudsen |
| 2009/0082218 | A1 | 3/2009 | Harkin et al. |
| 2009/0232814 | A1 | 9/2009 | Goldberg et al. |
| 2009/0304594 | A1 | 12/2009 | Fantin et al. |
| 2010/0196366 | A1 | 8/2010 | Bunn et al. |
| 2010/0304989 | A1 | 12/2010 | Von Hoff et al. |
| 2016/0002732 | A1 | 1/2016 | Harkin et al. |

FOREIGN PATENT DOCUMENTS

| | | |
|---|---|---|
| CA | 2747937 A1 | 7/2010 |
| EP | 0373203 B2 | 6/1990 |
| EP | 0785280 B1 | 7/1997 |
| JP | A-2010-504530 | 2/2010 |
| JP | A-2012-513422 | 6/2012 |
| JP | A-2012-525159 | 10/2012 |
| WO | WO 95/21265 | 8/1995 |
| WO | WO 96/31622 | 10/1996 |
| WO | WO 97/10365 | 3/1997 |
| WO | WO 97/27317 | 7/1997 |
| WO | WO 2003/095977 A2 | 11/2003 |
| WO | WO 2004/005883 A2 | 1/2004 |
| WO | WO 2004/108896 A2 | 12/2004 |
| WO | WO 2005/066371 A2 | 7/2005 |
| WO | WO 2005/100606 A2 | 10/2005 |
| WO | WO 2007/067500 A2 | 6/2007 |
| WO | WO 2007/090076 A2 | 8/2007 |
| WO | WO 2007/122369 A2 | 11/2007 |
| WO | WO 2008/082730 A2 | 7/2008 |
| WO | WO 2009/022129 A1 | 2/2009 |
| WO | WO 2009/042814 A1 | 4/2009 |
| WO | WO 2009/045115 A1 | 4/2009 |
| WO | WO 2009/061800 A2 | 5/2009 |
| WO | WO 2009/076229 A2 | 6/2009 |
| WO | WO 2009/149297 A1 | 12/2009 |
| WO | WO 2010/009337 A2 | 1/2010 |
| WO | WO 2010/010153 A1 | 1/2010 |
| WO | WO 2010/072348 A1 | 7/2010 |
| WO | WO 2010/088688 A2 | 8/2010 |
| WO | WO 2010/127322 A1 | 11/2010 |
| WO | WO 2011/005273 A1 | 1/2011 |
| WO | WO 2011/033006 A1 | 3/2011 |
| WO | WO 2012/037378 A2 | 3/2012 |
| WO | WO 2012/052757 A1 | 4/2012 |
| WO | WO 2012/092336 A2 | 7/2012 |
| WO | WO 2012/167278 A1 | 12/2012 |
| WO | WO 2013/106765 A1 | 7/2013 |
| WO | WO 2013/175429 A1 | 11/2013 |
| WO | WO 2014/087156 A1 | 6/2014 |

OTHER PUBLICATIONS

Collinson et al., "Predicting response to bevacizumab in ovarian cancer: a panel of potential biomarkers informing treatment selection", Clin Cancer Res, 19(18):5227-5239, (2013).
Li et al., "Possible angiogenic roles for claudin-4 in ovarian cancer", Cancer Biology & Therapy, 8(19):1806-1814, (2009).
Reinmuth et al., "Current data on predictive markers for anti-angiogenic therapy in thoracic tumours", Eur Respir J, 36:915-924, (2010).
Quackenbush, "Microarray Analysis and Tumor Classification", N Engl J Med, 354:2463-2472, (2006).
Yang et al., "Gene Expression Profile and Angiogenic Markers Correlate with Response to Neoadjuvant Bevacizumab Followed by Bevacizumab plus Chemotherapy in Breast Cancer", Clin Cancer Res, 14(18):5893-5899, (2008).
Communication Pursuant to Article 94(3) EPC for Application No. 13 808 178.1-1404, dated Aug. 22, 2016.
International Search Report for International Application No. PCT/GB2015/050352, dated Jul. 5, 2015. (U.S. Appl. No. 15/116,641).
International Search Report for International Application No. PCT/GB2015/051557, dated Sep. 9, 2015. (U.S. Appl. No. 15/311,618).
Chinese Notification of the First Office Action for corresponding Chinese Patent Application No. 201380071098.3, dated Jun. 3, 2016. 23 pages. English excerpt included.
Written Opinion from the Intellectual Property Office of Singapore for Application No. 11201504023S, dated Jun. 3, 2016. 8 pages.
Written Opinion of the International Searching Authority for International Application No. PCT/GB2015/050352, dated Jul. 5, 2015. (U.S. Appl. No. 15/116,641).
Written Opinion of the International Searching Authority for International Application No. PCT/GB2015/051557, dated Sep. 9, 2015. (U.S. Appl. No. 15/311,618).
Co-pending U.S. Appl. No. 14/123,406.
Co-pending U.S. Appl. No. 14/649,421.
Co-pending U.S. Appl. No. 15/116,641.
International Search Report and Written Opinion dated Apr. 24, 2014, for PCT International Application No. PCT/GB2013/053202 (23 pages).
Database Geneseq [Online], "Human Expression Signature Biomarker DNA, Seq ID: 853.", retrieved from EBI Accession No. GSN: BAH85778, Database Accession No. BAH85778 Sequence.

(56) References Cited

OTHER PUBLICATIONS

International Search Report and Written Opinion dated Oct. 5, 2012 for PCT/US2012/040805 (12 pages).
Aghajanian et al., "OCEANS: A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer," Journal of Clinical Oncology, Jun. 10, 2012; vol. 30, No. 17: pp. 2039-2045.
Ahdesmäki and Strimmer, "Feature Selection In Omics Prediction Problems Using Cat Scores And False Nondiscovery Rate Control," The Annals of Applied Statistics, 2010; vol. 4, No. 1: pp. 503-519.
Aresu et al, "Matrix metalloproteinases and their inhibitors in canine mammary tumors," BMC Veterinary Research, Jul. 4, 2011, vol. 7: 33.
Bredel et al, "A Network Model of a Cooperative Genetic Landscape in Brain Tumors," JAMA, Jul. 15, 2009, vol. 302, No. 3: 261-275.
Benjamini et al., "Controlling the False Discovery Rate: A Practical and Powerful Approach to Multiple Testing," Journal of the Royal Statistical Society. Series B (Methodological), 1995; vol. 57, No. 1: 289-300.
Breiman, "Random Forests," Machine Learning, 2001; vol. 45: pp. 5-32.
Brieger et al, "Recurrence of pleomorphic adenoma of the parotid gland-predictive value of cadherin-11 and fascin," APMIS, Dec. 1, 2008 vol. 116, No. 12: pp. 1050-1057.
Burger, "Phase II Trial of Bevacizumab in Persistent or Recurrent Epithelial Ovarian Cancer or Primary Peritoneal Cancer: A Gynecologic Oncology Group Study," Journal of Clinical Oncology, Nov. 20, 2007; vol. 25, No. 33: pp. 5165-5171.
Burlingame et al., "Mass Spectrometry," Anal. Chem., Jun. 15, 1988; vol. 60, No. 12: pp. 294R-342R.
Costa et al., "Reversing HOXA9 Oncogene Activation by PI3K Inhibition: Epigenetic Mechanism and Prognostic Significance in Human Glioblastoma," Cancer Research, 2010; vol. 70, No. 2: pp. 453-4786 (Published OnlineFirst Jan. 12, 2010).
Davies et al, "Effects of bevacizumab in mouse model of endometrial cancer: Defining the molecular basis for resistance," Oncology Reports, Jan. 14, 2011, vol. 25, No. 3: pp. 855-862.
Dudoit et al., "Comparison of Discrimination Methods for the Classification of Tumors Using Gene Expression Data," Journal of the American Statistical Association, Mar. 2002, vol. 97, No. 457: pp. 77-87.
Elgaaen et al, "POLD2 and KSP37 (FGFBP2) Correlate Strongly with Histology, Stage and Outcome in Ovarian Carcinomas," PLoS One, Nov. 4, 2010; vol. 5, No. 11: p. e13837.
Escudier et al., Phase III Trial of Bevacizumab Plus Interferon Alfa-2a in Patients With Metastatic Renal Cell Carcinoma (AVOREN): Final Analysis of Overall Survival, Journal of Clinical Oncology, May 1, 2010; vol. 28, No. 13: pp. 2144-2150.
Faber et al, "Alteration of MMP-2 and -14 expression by imatinib in HPV-positive and -negative squamous cell carcinoma," Oncology Reports, Apr. 20, 2012; vol. 28, No. 1: pp. 172-178.
Friedman et al., Bevacizumab Alone and in Combination With Irinotecan in Recurrent Glioblastoma, Journal of Clinical Oncology, Oct. 1, 2009; vol. 27, No. 28: pp. 4733-4740.
Hassan et al, "Prognostic molecular biomarkers in GISTs," Gastroenterology, Apr. 1, 2004; vol. 126, No. 4, Suppl. 2: pp. A392-A393, Abstract No. M2077.
Hu et al, "Expression of matrix metalloproteinases-9,2,7 and tissue inhibitor of metalloproteinases—1,2,3 mRNA in ovarian tumors and their clinical significance," Ai Zheng (Chinese Journal of Cancer), Oct. 1, 2004, vol. 23, No. 10, pp. 1194-1198.
Hurwitz et al., "Bevacizumab plus Irinotecan, Fluorouracil, and Leucovorin for Metastatic Colorectal Cancer," The New England Journal of Medicine, Jun. 3, 2004, vol. 350 No. 23, pp. 2335-2342.
Italiano et al., "Patterns of Deregulation of Insulin Growth Factor Signaling Pathway in Pediatric and Adult Gastrointestinal Stromal Tumors," Eur J Cancer. Nov. 2012; vol. 48 No. 17: pp. 3215-3222.

Jang et al, "Suppression of hepatic tumor growth and metastasis by metronomic therapy in a rat model of hepatocellular carcinoma," Experimental and Molecular Medicine, May 31, 2011; vol. 43, No. 5: pp. 305-312.
Kikuchi et al, "Frequent Inactivation of a Putative Tumor Suppressor, Angiopoietin-Like Protein 2, in Ovarian Cancer," Cancer Research, Jul. 1, 2008, vol. 68, No. 13; pp. 5067-5075.
Liu et al. "Vascular gene expression patterns are conserved in primary and metastatic brain tumors," Journal of Neuro-Oncology, 2010; vol. 99, No. 1: pp. 13-24.
Llovet and Bruix, "Molecular targeted therapies in hepatocellular carcinoma," Hepatology, Oct. 1, 2008; vol. 48, No. 4 pp. 1312-1327.
Lopez et al., "The disparate nature of "intergenic" polyadenylation sites," RNA, 2006; vol. 12: pp. 1794-1801.
Lu et al., "Insulin-Like Growth Factor-I Receptor Signaling and Resistance to Trastuzumab (Herceptin)," Journal of the National Cancer Institute, Dec. 19, 2001; vol. 93, No. 24: pp. 1852-1857.
Mannelqvist et al, "Gene Expression Patterns Related to Vascular Invasion and Aggressive Features in Endometrial Cancer," The American Journal of Pathology, Feb. 1, 2011; vol. 178, No. 2: pp. 861-871.
McCluggage, "Morphological subtypes of ovarian carcinoma: a review with emphasis on new developments and pathogenesis," Pathology, Aug. 2011; vol. 43, No. 5: pp. 420-432.
Review of "Molecular Biology and Biotechnology A Comprehensive Desk Reference," VCH, Weinheim Germany, 1995, Meyers (Ed.), in Biochemical Education, 1996; vol. 24, No. 1; p. 66.
Miller et al., "Randomized Phase III Trial of Capecitabine Compared With Bevacizumab Plus Capecitabine in Patients With Previously Treated Metastatic Breast Cancer," Journal of Clinical Oncology, Feb. 1, 2005; vol. 23, No. 4: pp. 792-799.
Miller et al., "Paclitaxel plus Bevacizumab versus Paclitaxel Alone for Metastatic Breast Cancer," The New England Journal of Medicine, Dec. 27, 2007; vol. 357: pp. 2666-2676.
Morimoto et al "Gene expression profiling of human colon xenograft tumors following treatment with SU11248, a multitargeted tyrosine kinase inhibitor," Oncogene, Feb. 26, 2004, vol. 23, No. 8: pp. 1618-1626.
Nakajima et al, "CDH11 expression is associated with survival in patients with osteosarcoma," Cancer Genomics & Proteomics, Jan. 1, 2008; vol. 5, No. 1: pp. 37-42.
Nakamura et al., "KRN951, a Highly Potent Inhibitor of Vascular Endothelial Growth Factor Receptor Tyrosine Kinases, Has Antitumor Activities and Affects Functional Vascular Properties," Cancer Res, Sep. 15, 2006; vol. 66, No. 18, pp. 9134-9142.
Nguyen and Rocke., "Tumor classification by partial least squares using microarray gene expression data," Bioinformatics, 2002; vol. 18, No. 1: pp. 39-50.
Pal et al, "Breaking through a Plateau in Renal Cell Carcinoma Therapeutics: Development and Incorporation of Biomarkers," Molecular Cancer Therapeutics, Dec. 1, 2010; vol. 9, No. 12; pp. 3115-3125.
O'Shaughnessy, "A meta-analysis of overall survival data from three randomized trials of bevacizumab (BV) and first-line chemotherapy as treatment for patients with metastatic breast cancer (MBC)," Journal of Clinical Oncology, 2010 ASCO Annual Meeting Abstracts, 2010; vol. 28, No. 15_suppl (May 20 Supplement): Abstract 1005.
Perren et al., "A Phase 3 Trial of Bevacizumab in Ovarian Cancer," The New England Journal of Medicine, Dec. 29, 2011; vol. 365, No. 26:2484-96.
Phillips et al., "Molecular subclasses of high-grade glioma predict prognosis, delineate a pattern of disease progression, and resemble stages in neurogenesis," Cancer Cell, Mar. 2006; vol. 9: 157-173.
Reck et al., "Phase III Trial of Cisplatin Plus Gemcitabine With Either Placebo or Bevacizumab As First-Line Therapy for Nonsquamous Non-Small-Cell Lung Cancer: AVAiL," Journal of Clinical Oncology, Mar. 10, 2009; vol. 27, No. 8: pp. 1227-1234.
Rini et al., "Bevacizumab Plus Interferon Alfa Compared With Interferon Alfa Monotherapy in Patients With Metastatic Renal Cell Carcinoma: CALGB 90206," Journal of Clinical Oncology, Nov. 20, 2008; vol. 26, No. 33: pp. 5422-5428.

(56) References Cited

OTHER PUBLICATIONS

Ripley et al, "Expression of matrix metalloproteinase-26 and tissue inhibitors of metalloproteinase-3 and-4 in normal ovary and ovarian carcinoma," International Journal of Gynecological Cancer, Sep. 1, 2006; vol. 16, No. 5: pp. 1794-1800.

Sandler et al., "Paclitaxel-Carboplatin Alone or with Bevacizumab for Non-Small-Cell Lung Cancer," The New England Journal of Medicine, Dec. 14, 2006; vol. 355, No. 24: pp. 2542-2550.

Schena et al., "Parallel human genome analysis: Microarray-based expression monitoring of 1000 genes," Proc. Natl. Acad. Sci. USA, Oct. 1996; vol. 93: pp. 10614-10619.

Singleton and Sainsbury, "Dictionary of Microbiology and Molecular Biology, Third Edition," 2006 John Wiley & Sons.

Stadlmann et al, "Cytokine-regulated expression of collagenase-2 (MMP-8) is involved in the progression of ovarian cancer," European Journal of Cancer, Nov. 1, 2003; vol. 39, No. 17: pp. 2499-2505.

Ståhle et al., "Partial Least Squares Analysis With Cross-Validation For The Two-Class Problem: A Monte Carlo Study," Journal of Chemometrics,1987; vol. 1: pp. 185-196.

Tanney et al., "Generation of a non-small cell lung cancer transcriptome microarray," BMC Medical Genomics, May 30, 2008, 1:20.

Tibshirani et al., "Estimating the number of clusters in a data set via the gap statistic," J. R. Statist. Soc. B, 2001; vol. 63, Part 2: pp. 411-423.

Tibshirani et al., "Diagnosis of multiple cancer types by shrunken centroids of gene expression," PNAS, May 14, 2002; vol. 99, No. 10: pp. 6567-6572.

Tothill et al., "Novel Molecular Subtypes of Serous and Endometrioid Ovarian Cancer Linked to Clinical Outcome," Clin Cancer Res Aug. 15, 2008; vol. 14, No!. 16; pp. 5198-5208.

Wang et al., "Identification of candidate predictive and surrogate molecular markers for dasatinib in prostate cancer: rationale for patient selection and efficacy monitoring," Nov. 29, 2007; Genome Biology vol. 8, No. 11: R255.

Watanabe et al, "Gene expression of vascular endothelial growth factor A, thymidylate synthase, and tissue inhibitor of metalloproteinase 3 in prediction of response to bevacizumab treatment in colorectal cancer patients", Diseases of the Colon & Rectum, Aug. 1, 2011; vol. 54, No. 8: pp. 1026-1035.

Willett et al., "Direct evidence that the VEGF-specific antibody bevacizumab has antivascular effects in human rectal cancer," Nat Med, Feb. 2004; vol. 10, No. 2: pp. 145-147.

Wold, "Pattern Recognition By Means of Disjoint Principal Components Models," Pattern Recognition, Pergamon Press 1976, vol. 8, pp. 127-139.

Wolmark, A phase III trial comparing mFOLFOX6 to mFOLFOX6 plus bevacizumab in stage II or III carcinoma of the colon: Results of NSABP Protocol C-08, Journal of Clinical Oncology, 2009 ASCO Annual Meeting Proceedings (Post-Meeting Edition). 2009; vol. 27, No. 18S, 2009: Abstract LBA4.

Wray et al., "The Genetic Interpretation of Area under the ROC Curve in Genomic Profiling," PLoS Genetics, Feb. 2010, vol. 6, No. 2: e1000864.

Yang et al., "A Randomized Trial of Bevacizumab, an Anti-Vascular Endothelial Growth Factor Antibody, for Metastatic Renal Cancer," The New England Journal of Medicine, Jul. 31, 2003; vol. 349, No. 5: pp. 427-434.

Azad et al., "Correlative studies of a phase I trial of combination anti-vascular endothelial growth factor (VEGF) therapy with sorafenib and bevacizumab," Developmental Therapeutics: Molecular Therapeutics, Abstract 3545, (2008).

Garcia et al., "Phase II clinical trial of bevacizumab and low-dose metronomic oral cyclophosphamide in recurrent ovarian cancer: a trial of the California, Chicago, and Princess Margaret Hospital phase II consortia," J Clin Oncol, 26(1):76-82, (2008).

Gerger et al., "Molecular predictors of response to antiangiogenesis therapies," Cancer J, 17(2):134-141, (2011).

Jubb et al., "Impact of vascular endothelial growth factor-A expression, thrombospondin-2 expression, and microvessel density on the treatment effect of bevacizumab in metastatic colorectal cancer," J Clin Oncol, 24(2):217-227, (2006).

Jubb et al., "Biomarkers to predict the clinical efficacy of bevacizumab in cancer," Lancet Oncol, 11(12):1172-1183, (2010).

Japanese Office Action for co-pending Japanese Patent Application No. 2015-544542, dated Sep. 26, 2017, 15 pages, English translation included.

Burgess et al., "Possible disassociation of the heparin-binding and mitogenic activities of heparin-binding (acidic fibroblast) growth factor-1 from its receptor-binding activities by site-directed mutagenesis of a single lysine residue," J Cell Biol 111(5 Pt 1):2129-2138, (1990).

Dean et al., "Identification of candidate angiogenic inhibitors processed by matrix metalloproteinase 2 (MMP-2) in cell-based proteomic screens: disruption of vascular endothelial growth factor (VEGF)/ heparin affin regulatory peptide (pleiotrophin) and VEGF/ Connective tissue growth factor angiogenic inhibitory complexes by MMP-2 proteolysis," Mol Cell Biol 27(24):8454-8465, (2007).

Huang et al., "Stat1 negatively regulates angiogenesis, tumorigenicity and metastasis of tumor cells," Oncogene 21(16) :2504-2512, (2002).

Lazar et al., "Transforming growth factor alpha: mutation of aspartic acid 47 and leucine 48 results in different biological activities," Mol Cell Biol 8(3):1247-1252, (1988).

Notification of the Fourth Office Action for co-pending Chinese Patent Application No. 201380071098.3, dated Apr. 11, 2018, 17 pages, English translation included.

A

B

A

B

SEQUENCE LISTING

<160> NUMBER OF SEQ ID NOS: 975

<210> SEQ ID NO 1
<211> LENGTH: 589
<212> TYPE: DNA
<213> ORGANISM: Homo sapiens

<400> SEQUENCE: 1

```
ctggatatat caagactgag ttgatttctg tgtctgaagt tcacccttct agacttcaga    60
ccacagacaa cctgctcccc atgtctcctg aggagtttga cgaggtgtct cggatagtgg   120
gctctgtaga attcgacagt atgatgaaca cagtatagag catgaatttt tttcatcttc   180
tctggcgaca gttttccttc tcatctgtga ttccctcctg ctactctgtt ccttcacatc   240
ctgtgtttct agggaaatga agaaaggcc agcaaattcg ctgcaacctg ttgatagcaa    300 gtgaatttt ctctaactca gaaacatcag ttactctgaa gggcatcatg catcttactg    360
aaggtaaaat tgaaaggcat tctctgaaga gtgggtttca caagtgaaaa acatccagat   420
acacccaaag tatcaggacg agaatgaggg tcctttggga aaggagaagt taagcaacat   480
ctagcaaatg ttatgcataa agtcagtgcc caactgttat aggttgttgg ataaatcagt   540
ggttatttag ggaactgctt gacgtaggaa cggtaaattt ctgtgggag              589
```

<210> SEQ ID NO 2
<211> LENGTH: 235
<212> TYPE: DNA
<213> ORGANISM: Homo sapiens

<400> SEQUENCE: 2

```
gcagcttcct gataaagcgt gctgtgctgt gcagtaggaa cacatcctat ttattgtgat    60
gttgtggttt tattatttta aactttgttc catacacttg tataaataca tggatatttt   120
tatgtacaga agtatgtttt ttaaccagtt cacttattgt actttggcaa tttaaaagaa   180
aatcagtaaa atattttgct tgtaaaatgc ttaatatcgt gcctaggtta tgtgg         235
```

<210> SEQ ID NO 3
<211> LENGTH: 139
<212> TYPE: DNA
<213> ORGANISM: Homo sapiens

<400> SEQUENCE: 3

| ccctccaag acctgtgtt catttggtgt tcctggaagc aggtgctaca acatgtgagg | 60 |
| cattcgggga agctgcacat gtgccacaca gtgacttggc cccagacgca tagactgagg | 120 |
| tataaagaca agtatgaat | 139 |

<210> SEQ ID NO 4
<211> LENGTH: 172
<212> TYPE: DNA
<213> ORGANISM: Homo sapiens

<400> SEQUENCE: 4

| agccaatgga aaatctgggt tcaaccagcc cctgccattt cttaagactt tttgctgcac | 60 |
| tcacaggatc ctgagctgca cttacctgtg agagtcttca aacttttaaa ccttgccagt | 120 |
| caggactttt gctattgcaa atagaaaacc caactcaacc tgcttaagca ga | 172 |

<210> SEQ ID NO 5
<211> LENGTH: 217
<212> TYPE: DNA
<213> ORGANISM: Homo sapiens

<400> SEQUENCE: 5

| ttctttgtca atctatggac atgcccatat atgaaggaga tgggtgggtc aaaaagggat | 60 |
| atcaaatgaa gtgatagggg tcacaatggg gaaattgaag tggtgcataa cattgccaaa | 120 |
| atagtgtgcc actagaaatg gtgtaaaggc tgttttttttt ttttttttta aagaaaagtt | 180 |
| attaccatgt attttgtgag gcaggtttac aacacta | 217 |

<210> SEQ ID NO 6
<211> LENGTH: 156
<212> TYPE: DNA
<213> ORGANISM: Homo sapiens

<400> SEQUENCE: 6

| gcagcaacag caaatcacga ccactgatag atgtttattt ttgttggaga catgggatga | 60 |
| ttatttctg ttctatttgt gcttagtcca attccttgca catagtaggt acccaattca | 120 |
| attactattg aatgaattaa gaattggttg ccataa | 156 |

<210> SEQ ID NO 7
<211> LENGTH: 221
<212> TYPE: DNA
<213> ORGANISM: Homo sapiens

<400> SEQUENCE: 7

| taatgtcatc ctgtactcgg cacaaatcaa aggccaatac aagtctgaaa agcagaaata | 60 |
| aatattttc caggtttttg ctcgggcaca tactaactgc tttgggcatt ttaatctggt | 120 |
| ctccaaacac caaagaccca tttcgagcct gctattagcc tgctgctgac tctatcactt | 180 |
| ggagcaataa tgtggggtta tggtggtgga atcttgtata t | 221 |

<210> SEQ ID NO 8
<211> LENGTH: 145
<212> TYPE: DNA
<213> ORGANISM: Homo sapiens

<400> SEQUENCE: 8

| tttagcttgt tcacactttg ccctatgaca tttctacatc actggctgct cttcatcaaa | 60 |
| cctactataa aaaacattca agttcaactg tttctttggg cctttatttc cttatggagg | 120 |

```
ccctcgtgtc gtgtaaaact tatat                                        145
```

<210> SEQ ID NO 9
<211> LENGTH: 213
<212> TYPE: DNA
<213> ORGANISM: Homo sapiens

<400> SEQUENCE: 9

```
gaccaacttc tgtattcgtg gaccaaactg aagctatatt tttcacagaa gaagaagcag    60
tgacggggac acaaattctg ttgcctggtg aaagaaggc aaaggccttc agcaatctat    120
attaccagcg ctggatcctt tgacagagag tggtccctaa acttaaattt caagacggta   180
taggcttgat ctgtcttgct tattgttgcc ccc                                213
```

<210> SEQ ID NO 10
<211> LENGTH: 287
<212> TYPE: DNA
<213> ORGANISM: Homo sapiens

<400> SEQUENCE: 10

```
gattggatta aagacctggc acttcagtaa ctcagcacgc ttccacttca ctcaacttaa    60
gagagttcat tgacagtgtt aggatgtgaa ggctgggaaa cacttatttt gcttcaagag   120
ttccacttgg ctctcccaaa taggtacctc aaaaactgtt agcaagcggc atttggatgt   180
cttgacaggg gctttgcagg gattttttagg gttttttcca cattgtccac attaatggtt   240
ggcatgattg tgcttgcagg ccaagaaatg atcataccc ttgccaa                  287
```

<210> SEQ ID NO 11
<211> LENGTH: 231
<212> TYPE: DNA
<213> ORGANISM: Homo sapiens

<400> SEQUENCE: 11

```
agctttgtgc tcagatccca ggtcccaagg agtgacaggg gcttcctccc accttctgtc    60
cttgtccagt catgtaaata atgtgctttt tctctccccg agtctttttt ttttaaacct   120
accgtggttc ctcagctaac tgcattccct acccaggcag agactgtcct atgcctcgag   180
cttccaaacg agactcagac cgcgacacag ccaccgtatt tatggaatga c             231
```

<210> SEQ ID NO 12
<211> LENGTH: 245
<212> TYPE: DNA
<213> ORGANISM: Homo sapiens

<400> SEQUENCE: 12

```
gaaatacgaa tgtagagatc cctaatcatc aaattgttga ttgaaagact gatcataaac    60
caatgctggt attgcacctt ctggaactat gggcttgaga aaaccccag gatcacttct    120 ccttggcttc cttcttttct gtgcttgcat cagtgtggac tcctagaacg tgcgacctgc   180
ctcaagaaaa tgcagttttc aaaaacagac tcagcattca gcctccaatg aataagacat   240
cttcc                                                                245
```

<210> SEQ ID NO 13
<211> LENGTH: 190
<212> TYPE: DNA
<213> ORGANISM: Homo sapiens

<400> SEQUENCE: 13

```
aattcgccaa tcatcccacc atataacctt cgattgtgct tctcaactcc accccataat    60
ttctcccaga gaccatctat cacctttttcc ccaaagaaga aacaaaacca gttgcacctt   120
aaaccatgga tattttttcc tcaggggctt taaatagttt cctatgcaac gtgtcttgta   180
gcacaaataa                                                          190
```

<210> SEQ ID NO 14
<211> LENGTH: 115
<212> TYPE: DNA
<213> ORGANISM: Homo sapiens

<400> SEQUENCE: 14

```
tgaacaaatg gcctttatta aaaactgagt gactctatat agctgatcag ttttttcacc    60
tggaagcatt tgttttttact ttgatatgac tgttttttcgg acagtttatt tgttg       115
```

<210> SEQ ID NO 15
<211> LENGTH: 179
<212> TYPE: DNA
<213> ORGANISM: Homo sapiens

<400> SEQUENCE: 15

```
tgtggtagcc tcacttttaa tgaacaaatg gcctttatta aaaactgagt gactctatat    60
agctgatcag ttttttcacc tggaagcatt tgttttttact ttgatatgac tgttttttcgg   120 acagtttatt tgttgagagt gtgaccaaaa gttacatgtt tgcacctttt tagttgaaa    179
```

<210> SEQ ID NO 16
<211> LENGTH: 113
<212> TYPE: DNA
<213> ORGANISM: Homo sapiens

<400> SEQUENCE: 16

```
caaagtgcta ataattaact caaccaggtc tactttttaa tggctttcat aacactaact    60
cataaggtta ccgatcaatg catttcatac ggatatagac ctagggctct gga          113
```

<210> SEQ ID NO 17
<211> LENGTH: 59
<212> TYPE: DNA
<213> ORGANISM: Homo sapiens

<400> SEQUENCE: 17

```
aaagcagact acgagaaaca caaactctac gcctgcgaag tcacccatca gggcctgag      59
```

<210> SEQ ID NO 18
<211> LENGTH: 92
<212> TYPE: DNA
<213> ORGANISM: Homo sapiens

<400> SEQUENCE: 18

```
gctgagcaaa gcagactacg agaaacacaa agtttacgcc tgcgaagtca cccatcaggg    60
cctgagctcg cccgtcacaa agagcttcaa ca                                  92
```

<210> SEQ ID NO 19
<211> LENGTH: 298
<212> TYPE: DNA
<213> ORGANISM: Homo sapiens

<400> SEQUENCE: 19

```
agcagactac gagaaacaca agtttacgc ctgcgaagtc acccatcagg gcctgagctc     60
gcccgtcaca aagagcttca acaggggaga gtgttagagg gagaagtgcc cccacctgct   120
```

```
cctcagttcc agcctgaccc cctcccatcc tttggcctct gacccttttt ccacagggga    180 cctacccta ttgcggtcct ccagctcatc tttcacctca cccccctcct cctccttggc     240
tttaattatg ctaatgttgg aggagaatga ataaataaag tgaatctttg cacctgtg     298

<210> SEQ ID NO 20
<211> LENGTH: 228
<212> TYPE: DNA
<213> ORGANISM: Homo sapiens

<400> SEQUENCE: 20
gtcagagccg ttggtgtttt tcattgttta aaatgtcacc tgtaaaatgg gcattattta    60 tgttttttt tttgcattcc tgataattgt atgtattgta taaagaacgt ctgtacattg    120
ggttataaca ctagtatatt taaacttaca ggcttatttg taatgtaaac caccatttta   180
atgtactgta attaacatgg ttataatacg tacaatcctt ccctcatc               228

<210> SEQ ID NO 21
<211> LENGTH: 86
<212> TYPE: DNA
<213> ORGANISM: Homo sapiens

<400> SEQUENCE: 21 actgagggg tcctggtgtg catttgcacc ctaaagctgc ttacggtgaa aaggcaaata    60
ggtatagcta ttttgcaggc accttt                                        86

<210> SEQ ID NO 22
<211> LENGTH: 158
<212> TYPE: DNA
<213> ORGANISM: Homo sapiens

<400> SEQUENCE: 22
tttggtgcag tttccagggt gcagtacagc agggcctgaa tactggccct ggactccctt    60
ttccagaaca ccaggtgtgg ccacctgggg ctcaggtaca cagtggggtc tctcggaagc   120
caccgtgtgg ttctttcaca ggcacgttta ttttgctg                          158

<210> SEQ ID NO 23
<211> LENGTH: 223
<212> TYPE: DNA
<213> ORGANISM: Homo sapiens

<400> SEQUENCE: 23
tggtcatgag aagaaggtaa tttccagcct tcaagaagac agacatttag aagaagagct    60
gaaatgtcag gaacaaaaag aagaacagct gcaggaaggg gtgcaccgga aggagcccca   120
gggggccacg tagcagcggc tcagtgggtg gccatcgatt tggaccgtcc cctgcccact   180
tgctccccgt gagcactgcg tacaaacatc caaaagttca aca                    223

<210> SEQ ID NO 24
<211> LENGTH: 262
<212> TYPE: DNA
<213> ORGANISM: Homo sapiens

<400> SEQUENCE: 24
ccaggttagg aaaggattca gcactacagc ataccctct acaacataca gccctgtcac    60
attgagatca taatccctcc tgtcccactc ctctctacca accccaccct actagctagg   120
tcttcagtgt tttacattga atattggtac attttaatta ttttttctca taaatgggtt   180
```

```
atttatagaa attttgttaa ctcttgagcc atatgcatgt gtagatactg gcagggctat    240
gtttgtttat gatgctctgc aa                                             262

<210> SEQ ID NO 25
<211> LENGTH: 245
<212> TYPE: DNA
<213> ORGANISM: Homo sapiens

<400> SEQUENCE: 25
attgtgctat aatccctatt tagttcaaaa ttaaccagaa ttttttccatg tgaaatggac    60 caaactcata ttattgttat gtaaatacag agtttttaatg cagtatgaca tcccacaggg   120
gaaaagaatg tctgtagtgg gtgactgtta tcaaatattt tatagaatac aatgaacggt   180
gaacagactg gtaacttgtt tgagttccca tgacagattt gagacttgtc aatagcaaat   240
cattt                                                                245

<210> SEQ ID NO 26
<211> LENGTH: 202
<212> TYPE: DNA
<213> ORGANISM: Homo sapiens

<400> SEQUENCE: 26
taatggttaa cgaaccgggt cgacatcaca aaggagggtg gagactcttt ttactaactt    60
gaatgagaca aaagcagtgg tgtcagttta taatcctgat gcatttcagt aataatgtag   120
aaaaacatta ttttaaaaaa gttccaacac acagccatga ggagcctcag ttttgaaaga   180
ggtgcataat aaaactacta ac                                            202

<210> SEQ ID NO 27
<211> LENGTH: 132
<212> TYPE: DNA
<213> ORGANISM: Homo sapiens

<400> SEQUENCE: 27
acagcccacc cttgtgtcca ctgtgacccc tgttcccatg ctgacctgtg tttcctcccc    60
agtcatcttt cttgttccag agaggtgggg ctggatgtct ccatctctgt ctcaacttta   120
tgtgcactga gc                                                       132

<210> SEQ ID NO 28
<211> LENGTH: 53
<212> TYPE: DNA
<213> ORGANISM: Homo sapiens

<400> SEQUENCE: 28
aagcaagata tcaatgtagc agaattgcac ttgtgcctca cgaacataca taa             53

<210> SEQ ID NO 29
<211> LENGTH: 102
<212> TYPE: DNA
<213> ORGANISM: Homo sapiens

<400> SEQUENCE: 29
ttcctgttcc agagaagtgg gctggatgtc tccatctctg tttcaacttc atggtgcgct    60
gagctgcaac ttcttacttc cctaatgaag ttaagaacct ga                      102

<210> SEQ ID NO 30
<211> LENGTH: 162
<212> TYPE: DNA
<213> ORGANISM: Homo sapiens
```

```
<400> SEQUENCE: 30
tttcctacca cttaactgca ctgtggctga gttttctgat ctgtaaggtg ggaataataa    60
tgatacctat ctcatagggg aatgaaagga tcaaatgagt tcatatttgt aaagcaattt   120
gaaagagtgc ctagcccaca gtaagtgcta cataagagtt tg                      162

<210> SEQ ID NO 31
<211> LENGTH: 159
<212> TYPE: DNA
<213> ORGANISM: Homo sapiens

<400> SEQUENCE: 31
taacagcaga atctacctcc caactgccat gtgattaaga aatgggtctt gagtcctgtg    60
ctgttggcaa agttccaggc acagttgggg agggggggt ccttaacaag cgtgactttg    120
ctcattctgt catcactaag gcaataaacc tttgccagg                          159

<210> SEQ ID NO 32
<211> LENGTH: 153
<212> TYPE: DNA
<213> ORGANISM: Homo sapiens

<400> SEQUENCE: 32
atgggatggt cggatctcac aggctgagaa ctcgttcacc tccaagcatt tcatgaaaaa    60
gctgcttctt attaatcata caaactctca ccatgatgtg aagagtttca caaatctttc   120
aaaataaaaa gtaatgactt agaaactgcc caa                                153

<210> SEQ ID NO 33
<211> LENGTH: 114
<212> TYPE: DNA
<213> ORGANISM: Homo sapiens

<400> SEQUENCE: 33
tcatccccat ggagcattgc accacccgct ttttcgagac ctgtgacctg acaatgaca     60 agtacatcgc cctggatgag tgggccggct gcttcggcat caagcagaag gata         114

<210> SEQ ID NO 34
<211> LENGTH: 112
<212> TYPE: DNA
<213> ORGANISM: Homo sapiens

<400> SEQUENCE: 34
atttgggtgg gatgggtagg atgaagtata ttgcccaact ctatgtttct ttgatttaa    60 cacaattaat taagtgacat gatttttact aatgtattac tgagactagt aa          112

<210> SEQ ID NO 35
<211> LENGTH: 274
<212> TYPE: DNA
<213> ORGANISM: Homo sapiens

<400> SEQUENCE: 35
tgtttcacaa tacctcatgc ttcacttagc catggtggac ccagcgggca ggttctgcct    60
gctttggcgg gcagacacgc gggcgcgatc ccacacaggt ggcggggc cggccccgag     120 gccgcgtgcg tgagaaccgc gccggtgtcc ccagagacca ggctgtgtcc ctcttctctt   180
ccctgcgcct gtgatgctgg gcacttcatc tgatcggggg cgtagcatca tagtagtttt   240
tacagctgtg ttattctttg cgtgtagcta tgga                              274
```

<210> SEQ ID NO 36
<211> LENGTH: 189
<212> TYPE: DNA
<213> ORGANISM: Homo sapiens

<400> SEQUENCE: 36

```
cctctggctt ctcaggcctc tgctctccga cctctctcct ctgaaaccct cctccacagc    60
tgcagcccat cctcccggct ccctcctagt ctgtcctgcg tcctctgtcc ccgggtttca   120
gagacaactt cccaaagcac aaagcagttt ttcccctag gggtgggagg aagcaaaaga   180
ctctgtacc                                                           189
```

<210> SEQ ID NO 37
<211> LENGTH: 151
<212> TYPE: DNA
<213> ORGANISM: Homo sapiens

<400> SEQUENCE: 37

```
ttggaatgtt gtagttacct actgagtagg cggcgatttt tgtatgttat gaacatgcag    60
ttcattattt tgtggttcta ttttactttg tacttgtgtt tgcttaaaca aagtgactgt   120
ttggcttata aacacattga atgcgcttta t                                  151
```

<210> SEQ ID NO 38
<211> LENGTH: 201
<212> TYPE: DNA
<213> ORGANISM: Homo sapiens

<400> SEQUENCE: 38

```
atctccatca tatgcctgac cccttgctcc cttcaatgct agaaaatcga gttggcaaaa    60
tggggtttgg gcccctcaga gccctgccct gcacccttgt acagtgtctg tgccatggat   120
ttcgtttttc ttggggtact cttgatgtga agataaatttg catattctat tgtattattt   180
ggagttaggt cctcacttgg g                                             201
```

<210> SEQ ID NO 39
<211> LENGTH: 138
<212> TYPE: DNA
<213> ORGANISM: Homo sapiens

<400> SEQUENCE: 39

```
tcatgtttgc tgtagtgctc atatttattg ttgttttttgt tttagtactc acttgtttca    60
taatatcaag attactaaaa atgggggaaa ggacttttaa tcttttttttc ataatatctt   120
tgacacatat tacagaag                                                 138
```

<210> SEQ ID NO 40
<211> LENGTH: 205
<212> TYPE: DNA
<213> ORGANISM: Homo sapiens

<400> SEQUENCE: 40

```
aatcccaatt ttcaggagtg gtggtgtcaa taaacgctct gtggccagtg taaaagaaaa    60
tccctcgcag ttgtggacat ttctgttcct gtccagatac cattttttcct agtatttctt   120
tgttatgtcc cagaactgat gttttttttt taaggtactg aaaagaaatg aagttgatgt   180
atgtcccaag ttttgatgaa actgt                                         205
```

<210> SEQ ID NO 41
<211> LENGTH: 269

<212> TYPE: DNA
<213> ORGANISM: Homo sapiens

<400> SEQUENCE: 41

| | | | | | |
|---|---|---|---|---|---|
| gcctggcctg | attcagggcc | ttgtggcccc | cagcttctgt | ttcaagctgg | gcagacccca | 60 |
| ggatcccttc | cctccctaag | gactcagctg | aggggcccct | ctgccccctt | ctacctccac | 120 |
| ctcagcaccc | tcccccagct | tgatgtttgg | gtctccccag | caccctcctc | cctggccggt | 180 |
| gcaaagtaca | gggaggtaaa | gcaggaccct | tgcagacatg | ttgcccagca | cacagtaggc | 240 |
| cctcaataaa | agccatttgc | actttaaat | | | | 269 |

<210> SEQ ID NO 42
<211> LENGTH: 169
<212> TYPE: DNA
<213> ORGANISM: Homo sapiens

<400> SEQUENCE: 42

| | | | | | |
|---|---|---|---|---|---|
| gagaagtcac | tcacactggc | cacaaggacg | ctggctactg | tctattaaaa | ttttgatgtt | 60 |
| tctgtgaaat | tctcagagtg | tttaattgta | ctcaatggta | tcattacaat | tttctgtaag | 120 |
| agaaaatatt | acttatttat | cctagtattc | ctaacctgtc | agaataata | | 169 |

<210> SEQ ID NO 43
<211> LENGTH: 234
<212> TYPE: DNA
<213> ORGANISM: Homo sapiens

<400> SEQUENCE: 43

| | | | | | |
|---|---|---|---|---|---|
| ctgtggcatg | ctcagaggtt | cctgctggat | tccagctgga | gcggtgtgat | accttctttt | 60 |
| ttcagctgtt | cgtgccttcc | tttcttgtat | ccaccaaagt | ggagacaaat | acatgatttc | 120 |
| aaagatacac | agtacctact | taattccagc | tgatgggaga | ccaaagaatt | tgcaagtgga | 180 |
| tggtttggta | tcactgtaaa | taaaagagg | gcctgggaat | tcttgcgatt | ccat | 234 |

<210> SEQ ID NO 44
<211> LENGTH: 168
<212> TYPE: DNA
<213> ORGANISM: Homo sapiens

<400> SEQUENCE: 44

| | | | | | |
|---|---|---|---|---|---|
| cagcttttcag | acagagccca | cttagcttgt | ccacatggat | ttcaatgcca | atcctccatt | 60 |
| tttcctctcc | agatattttt | gggagtgaca | aacattcttt | catcctactt | agcctaccta | 120 |
| gatttttcat | gacgagttaa | tgcatgtccg | tggttgggtg | cacctgta | | 168 |

<210> SEQ ID NO 45
<211> LENGTH: 232
<212> TYPE: DNA
<213> ORGANISM: Homo sapiens

<400> SEQUENCE: 45

| | | | | | |
|---|---|---|---|---|---|
| tgaaccaaaa | tagagtcagc | tgacccagca | tcagccacac | tttgggttgg | aaaatgtttg | 60 |
| cctgttggaa | ttaatttaag | cttaagtata | tatcaacatt | attttattgt | gcaattaaaa | 120 |
| caatacaaat | tcatggtttt | ttaaagttaa | aaattttaac | cactgtaaca | acagtttttg | 180 |
| tgttattttc | tgtattaaac | atcttgttgc | acgcatttga | ggtcatcagg | gt | 232 |

<210> SEQ ID NO 46
<211> LENGTH: 234
<212> TYPE: DNA

<213> ORGANISM: Homo sapiens

<400> SEQUENCE: 46

| | |
|---|---|
| caatgccgtc attttcagtt agatgatttt gcactttgag attaaaatgc catgtttatt | 60 |
| tgattagttt tattttttta ttttacagg cttatcagtc tcactgttgg ctgtcattgt | 120 |
| gacaaagtca ataaacccc caaggacgac acacagtatg gatcacatat tgtttgacat | 180 |
| taagcttttg ccagaaaatg ttgcatgtgt tttacctcga cttgctaaaa tcga | 234 |

<210> SEQ ID NO 47
<211> LENGTH: 147
<212> TYPE: DNA
<213> ORGANISM: Homo sapiens

<400> SEQUENCE: 47

| | |
|---|---|
| atgttcatag gttctcaacc ctcaccccc accacgggag actagagctg caggatccca | 60 |
| ggggaggggt ctctcctccc accccaaggc atcaagccct tctccctgca ctcaataaac | 120 |
| cctcaatata tattctcatt gtcaatc | 147 |

<210> SEQ ID NO 48
<211> LENGTH: 149
<212> TYPE: DNA
<213> ORGANISM: Homo sapiens

<400> SEQUENCE: 48

| | |
|---|---|
| aatgttcata ggttctaaac cctcaccccc cccacgggag actagagctg caggatccca | 60 |
| ggggaggggt ctctcctccc accccaaggc atcaagccct tctccctgca ctcaataaac | 120 |
| cctcaataaa tattctcatt gtcaatcag | 149 |

<210> SEQ ID NO 49
<211> LENGTH: 152
<212> TYPE: DNA
<213> ORGANISM: Homo sapiens

<400> SEQUENCE: 49

| | |
|---|---|
| aatgttcata ggttctaaac cctcaccccc cccacgggag actagagctg caggatccca | 60 |
| ggggaggggt ctctcctccc accccaaggc atcaagccct tctccctgca ctcaataaac | 120 |
| cctcaataaa tattctcatt gtcaatcagc aa | 152 |

<210> SEQ ID NO 50
<211> LENGTH: 150
<212> TYPE: DNA
<213> ORGANISM: Homo sapiens

<400> SEQUENCE: 50

| | |
|---|---|
| aatgttcata ggttctcaac cctcaccccc caccacggga gactagagct gcaggatccc | 60 |
| aggggagggg tctctcctcc caccccaagg catcaagccc ttctccctgc actcaataaa | 120 |
| ccctcaataa atattctcat tgtcaatcag | 150 |

<210> SEQ ID NO 51
<211> LENGTH: 151
<212> TYPE: DNA
<213> ORGANISM: Homo sapiens

<400> SEQUENCE: 51

| | |
|---|---|
| atgttcatag gttctcaacc ctcaccccc ccacgggaga ctagagctgc aggatcccag | 60 |
| gggaggggtc tctcctccca ccccaaggca tcaagccctt ctccctgcac tcaataaacc | 120 | ctcaataaat attctcattg tcaatcagca a         151

<210> SEQ ID NO 52
<211> LENGTH: 147
<212> TYPE: DNA
<213> ORGANISM: Homo sapiens

<400> SEQUENCE: 52
atgttcatag gttcccaact ctaaccccac ccacgggagc ctggagctgc aggatcccag     60
gggaggggtc tctctcccca tcccaagtca tccagcccTT ctccctgcac tcatgaaacc    120
ccaataaata tcctcattga caaccag                                         147

<210> SEQ ID NO 53
<211> LENGTH: 150
<212> TYPE: DNA
<213> ORGANISM: Homo sapiens

<400> SEQUENCE: 53
atgttcatag gttcccaact ctaaccccac ccacgggagc ctggagctgc aggatcccag     60
gggaggggtc tctctcccca tcccaagtca tccagcccTT ctccctgcac tcatgaaacc    120
ccaataaata tcctcattga caaccagcaa                                      150

<210> SEQ ID NO 54
<211> LENGTH: 254
<212> TYPE: DNA
<213> ORGANISM: Homo sapiens

<400> SEQUENCE: 54
gcagctattt gagcctgacg cctgagcagt ggaagtccca cagaagctac agctgccagg     60
tcacgcatga agggagcacc gtggagaaga cagtggcccc tacagaatgt tcataggttc    120
taaaccctca ccccccccac gggagactag agctgcagga tcccagggga ggggtctctc    180
ctcccacccc aaggcatcaa gcccttctcc ctgcactcaa taaaccctca ataaatattc    240
tcattgtcaa tcag                                                       254

<210> SEQ ID NO 55
<211> LENGTH: 239
<212> TYPE: DNA
<213> ORGANISM: Homo sapiens

<400> SEQUENCE: 55
aagaacaact cctcaccagt tcatcctgag gctgggagga ccgggatgct ggattctgtt     60
ttccgaagtc actgcagcgg atgatggaac tgaatcgata cggtgttttc tgtccctcct    120
actttccttc acaccagaca gcccctcatg tctccaggac aggacaggac tacagacaac    180
tctttcttta ataaattaa gtctttacaa taaaaacaca actgcaaagt accttcata     239

<210> SEQ ID NO 56
<211> LENGTH: 270
<212> TYPE: DNA
<213> ORGANISM: Homo sapiens

<400> SEQUENCE: 56
gaaagagcat cgttccaatg cttgttcact gttcctctgt catactgtat ctggaatgct     60
ttgtaatact tgcatgcttc ttagaccaga acatgtaggt cccccttgtgt ctcaatactt    120 ttttttctt aattgcattt gttggctcta ttttaatttt tttcttttaa aataaacagc     180

| | |
|---|---|
| tgggaccatc ccaaaagaca agccatgcat acaactttgg tcatgtatct ctgcaaagca | 240 |
| tcaaattaaa tgcacgcttt tgtcatgtca | 270 |

<210> SEQ ID NO 57
<211> LENGTH: 147
<212> TYPE: DNA
<213> ORGANISM: Homo sapiens

<400> SEQUENCE: 57

| | |
|---|---|
| acttggaagc agatgataca gacttctttt tttcataatc aggttagtgt aagaaattgc | 60 |
| catttgaaac aatccatttt gtaactgaac cttatgaaat atatgtattt catggtacgt | 120 |
| attctctagc acagtctgag caattaa | 147 |

<210> SEQ ID NO 58
<211> LENGTH: 97
<212> TYPE: DNA
<213> ORGANISM: Homo sapiens

<400> SEQUENCE: 58

| | |
|---|---|
| ttctccccaa ccacttagta gcaacgctac cccaggggggt aatgactgca cactgggctt | 60 |
| cttttcagaa tgaccctaac gagacacatt tgcccaa | 97 |

<210> SEQ ID NO 59
<211> LENGTH: 213
<212> TYPE: DNA
<213> ORGANISM: Homo sapiens

<400> SEQUENCE: 59

| | |
|---|---|
| tgtgttgggg tagactgctc ctgcagagtt tggaagaagt caccagcaaa gccggcctaa | 60 |
| ccaagaaaag tcaaggccct tcatgacctt gctgggcaca gaaaacaccc tcgtggagta | 120 |
| cactaatttg aactggactg gtctcagtgt gagcacttgg cacactttac taaacacata | 180 |
| tacaaccccca ccgtgagtca actttaaagt aaa | 213 |

<210> SEQ ID NO 60
<211> LENGTH: 151
<212> TYPE: DNA
<213> ORGANISM: Homo sapiens

<400> SEQUENCE: 60

| | |
|---|---|
| tgtaatgcta aaactgaaat ggtccgtgtt tgcattgtta aaaatgatgt gtgaaataga | 60 |
| atgagtgcta tggtgttgaa aactgcagtg tccgttatga gtgccaaaaa tttgtcttga | 120 |
| aggcagctac actttgaagt ggtctttgaa t | 151 |

<210> SEQ ID NO 61
<211> LENGTH: 116
<212> TYPE: DNA
<213> ORGANISM: Homo sapiens

<400> SEQUENCE: 61

| | |
|---|---|
| ctgggccttg gtccccagaa gatggcggct agggcctcgc cgccaggaca gagaagggac | 60 |
| ggggtggctg ggcagtcagg gaaggagggt cgcccggatc cgacattttg gagaga | 116 |

<210> SEQ ID NO 62
<211> LENGTH: 220
<212> TYPE: DNA
<213> ORGANISM: Homo sapiens

<400> SEQUENCE: 62

```
gaacaggaac gccttctcaa ggagggattc gagaatgaga gcaagagact tcaaaaagac    60
atatgggata tccagatgag aagcaaatca ttggagccaa tatgtaacat actttaaaag   120
tccaaggagc aaaatttgcc tgtccagctc cctctcccca agaaacaaca tgaatgagca   180
acttcagagt gtcaaacaac tgccattaaa cttaactcaa                        220
```

<210> SEQ ID NO 63
<211> LENGTH: 262
<212> TYPE: DNA
<213> ORGANISM: Homo sapiens

<400> SEQUENCE: 63

```
taagaatctc acaggacctc ttagttttg ccctatacgc cgccttcact ccacagcctc    60
acccctccca cccccatact ggtactgctg taatgagcca agtggcagct aaaagttggg   120
ggtgttctgc ccagtcccgt cattctgggc tagaaggcag gggaccttgg catgtggctg   180
gccacaccaa gcaggaagca caaactcccc caagctgact catcctaact aacagtcacg   240
ccgtgggatg tctctgtcca ca                                           262
```

<210> SEQ ID NO 64
<211> LENGTH: 72
<212> TYPE: DNA
<213> ORGANISM: Homo sapiens

<400> SEQUENCE: 64

```
gttatcaatc tctagttgtc actttcctct tccactttga taccattggg tcattgaata    60 taacttttc ca                                                        72
```

<210> SEQ ID NO 65
<211> LENGTH: 232
<212> TYPE: DNA
<213> ORGANISM: Homo sapiens

<400> SEQUENCE: 65

```
tttgttagta catttcagtg tagtcattca tttctagctg tacataggat gaaggagaga    60
tcagatacat gaacatgttt tacatgggtt gctgtattta gaattataaa cattttcat   120 tattggaaag tgtaacgggg acctttgca tacctgttta gaaccaaaac caccatgaca   180 cagttttat agtgtctgta tatttgtgat gcaatggtct gtaaaggtt tt             232
```

<210> SEQ ID NO 66
<211> LENGTH: 53
<212> TYPE: DNA
<213> ORGANISM: Homo sapiens

<400> SEQUENCE: 66

```
gaccaggaat tcggcttcga cgttggccct gtctgcttcc tgtaaactcc ctc           53
```

<210> SEQ ID NO 67
<211> LENGTH: 76
<212> TYPE: DNA
<213> ORGANISM: Homo sapiens

<400> SEQUENCE: 67

```
ggaggatgcg ctgtgggggtt gttttttgcca taagcgaact ttgtgcctgt cctagaagtg   60
aaaattgttc agtcca                                                   76
```

<210> SEQ ID NO 68

```
<211> LENGTH: 132
<212> TYPE: DNA
<213> ORGANISM: Homo sapiens

<400> SEQUENCE: 68
aaaagttcac agtcaaatgg ggaggggtat ttttcatgca ggagacccca ggccctggag    60
gctgcaacat acctcaatcc tgtcccaggc cggatcctcc tgaagccctt ttcgcagcac   120
tgctatcctc ca                                                      132

<210> SEQ ID NO 69
<211> LENGTH: 287
<212> TYPE: DNA
<213> ORGANISM: Homo sapiens

<400> SEQUENCE: 69
agtgagactg actgcaagcc ccaccctcct tgagactgga gctggcgtct gcatacgaga    60
gacttggttg aacttggttg gtccttgtct gcaccctcga caagaccaca ctttgggact   120
tgggagctgg ggctgaagtt gctctgtacc catgaactcc cagtttgcga attatagaga   180
caatctattt tgttacttgc acttgttatt cgaaccactg agagcgagat gggaagcata   240
gatatctata ttttattttt tactatgagg gccttgtaat aaatttc                287

<210> SEQ ID NO 70
<211> LENGTH: 36
<212> TYPE: DNA
<213> ORGANISM: Homo sapiens

<400> SEQUENCE: 70
tgggggggca gaggcgtctg accccaggaa cctgca                             36

<210> SEQ ID NO 71
<211> LENGTH: 157
<212> TYPE: DNA
<213> ORGANISM: Homo sapiens

<400> SEQUENCE: 71
tatgaattcc attcaaatcg ttcctttttg ttaacaaggg gcatggggag gggtgggggt    60
gggggggcag aggcgtctga ccccaggaac ctgcagggcg gggctgggtc ggtgcccttt   120
aaggacaatt ttgaccttgt tcaacctttc cacaaag                           157

<210> SEQ ID NO 72
<211> LENGTH: 212
<212> TYPE: DNA
<213> ORGANISM: Homo sapiens

<400> SEQUENCE: 72
gatgcatgag gctctgcaca accactacac gcagaagagc ctctccctgt ctccgggtaa    60
atgagtgcga cggccggcaa gccccgctc cccaggctct cggggtcgcg cgaggatgct   120
tggcacgtac cccgtgtaca tacttcccgg gcgcccagca tggaaataaa gcacccagcg   180
ctgccctggg cccctgcgca actttcttgt ac                                212

<210> SEQ ID NO 73
<211> LENGTH: 225
<212> TYPE: DNA
<213> ORGANISM: Homo sapiens

<400> SEQUENCE: 73
tttgctgtga taaatgaata cggtactttg aaggagaaaa aagttttttca aatgagctta    60
```

```
aactgcaagt gatttaaaaa ttagagaata taattttaa agctattgaa agtttcaacc      120
agaaaacctc aagtgaattt tgtatgtaaa tgaaattttg aatgtaagtt ctgtgattct      180
ttaagcaaac aattagctga aaacttggta ttgttgtagt ttatg                     225
```

<210> SEQ ID NO 74
<211> LENGTH: 287
<212> TYPE: DNA
<213> ORGANISM: Homo sapiens

<400> SEQUENCE: 74

```
gaaatgcaaa ctatccctgt attttaatat ttgttattct ttcatgaata gaaatttatg      60
tagaagcaaa caaatatactt ttacccactt aaaagagaa tataacattt tatgtcacta     120
taatcttttg ttttttaagt tagtgtatat tttgttgtga ttatctttt gtggtgtgaa      180 taaatctttt atcttgaatg taataagaat ttggtggtgt caattgctta tttgttttcc    240
cacggttgtc cagcaattaa taaaacataa ccttttttac tgcctat                   287
```

<210> SEQ ID NO 75
<211> LENGTH: 276
<212> TYPE: DNA
<213> ORGANISM: Homo sapiens

<400> SEQUENCE: 75

```
agaatcatgt acagagctta aatgtaattt atatgttttt aatatgccat ttcattgaa       60 gtattttggt cttaagatga ctttagtaat ttaactgttt atgttaccca cgttgggatc    120
cagttggtct tggtttgctt ctctctgtac cacgtgcaca tgaggtccat tcattttaca    180
gcccctgtta cacacagacc cacaggcagc cgtctgtgcc ccgcacacat tgttggtcct    240
atttgtaaat cccacacccg gtgtatccaa taaagt                              276
```

<210> SEQ ID NO 76
<211> LENGTH: 222
<212> TYPE: DNA
<213> ORGANISM: Homo sapiens

<400> SEQUENCE: 76

```
tttcacatag gttagattct cattcacggg actagttagc tttaagcacc ctagaggact      60
agggtaatct gacttctcac ttcctaagtt cccttctata tcctcaaggt agaaatgtct    120 atgttttta ctccaattca taaatctatt cataagtctt tggtacaagt ttacatgata    180
aaaagaaatg tgatttgtct tcccttcttt gcacttttga aa                       222
```

<210> SEQ ID NO 77
<211> LENGTH: 182
<212> TYPE: DNA
<213> ORGANISM: Homo sapiens

<400> SEQUENCE: 77

```
atcaaggctc ttccgttcca catccacaca gccaatccaa ttaatcaaac cactgttatt      60
aacagataat agcaacttgg gaaatgctta tgttacaggt tacgtgagaa caatcatgta    120
aatctatatg atttcagaaa tgttaaaata gactaacctc taccagcaca ttaaaagtga    180
tt                                                                    182
```

<210> SEQ ID NO 78
<211> LENGTH: 212
<212> TYPE: DNA

<213> ORGANISM: Homo sapiens

<400> SEQUENCE: 78

| | |
|---|---|
| ttcctttagg ccctgtgagc gtcccttgtc aggatacatt ctctcatttt gctgaagctg | 60 |
| atttgattgg gtgtctgttt ctcgcagcca aaagagcttt gaatgaggaa agtgcttctg | 120 |
| tgctaactcc ccgcgtctcc tgaatttcag tcattcatgt acccgcctcg aaattttgc | 180 |
| aatatctgtg taccaactgt ccatttactt aa | 212 |

<210> SEQ ID NO 79
<211> LENGTH: 238
<212> TYPE: DNA
<213> ORGANISM: Homo sapiens

<400> SEQUENCE: 79

| | |
|---|---|
| gtgtgtatgt gtagacaagc tctcgttctg tcacccaggc tggagtgcag tggtgcaatc | 60 |
| atggttcact gcagtcttga ccttttgggc tcaagtgatc ctcccacctc agcctcctga | 120 |
| gtagctggga ccataggctc acaacaccac acctggcaaa tttgattttt tttttttttc | 180 |
| cagagacggg gtctcgcaac attgcccaga cttcctttgt gttagttaat aaagctttt | 238 |

<210> SEQ ID NO 80
<211> LENGTH: 262
<212> TYPE: DNA
<213> ORGANISM: Homo sapiens

<400> SEQUENCE: 80

| | |
|---|---|
| gtcctctcta tcctggatga gctcatgaac atttctcttg tgttcctgac tccttcccaa | 60 |
| tgaacacctt tctgccaccc caagctttgc tctcctcctc tgtgagctct gggcttccca | 120 |
| gtttgtttac ccgggaaagt acgtctagat tgtgtggttt gcctcattgt gctatttgcc | 180 |
| cactttcctt ccctgaagaa atatctgtga accttctttc tgttcagtcc taaaattcga | 240 |
| aataaagtga gactatggtt ca | 262 |

<210> SEQ ID NO 81
<211> LENGTH: 129
<212> TYPE: DNA
<213> ORGANISM: Homo sapiens

<400> SEQUENCE: 81

| | |
|---|---|
| agtgggggg cattataaat ctataaaatg tacttctatt ggcatgccta atacgtcttt | 60 |
| atatgtatgt atgtgttgtg tacacgatgt tttagtgcta aaaatatgta aaagagctct | 120 |
| acttggctt | 129 |

<210> SEQ ID NO 82
<211> LENGTH: 178
<212> TYPE: DNA
<213> ORGANISM: Homo sapiens

<400> SEQUENCE: 82

| | |
|---|---|
| aagtctaatt tcgactggtt gtatctctttt atgatttatt gccccccctaa caacatttga | 60 |
| aacaatataa tattttaaaa tgtataaata attatgaatt tttgtttaga acaaagagga | 120 |
| ttactgatat ttgtttccct atgaatggca aaaggtttag cttactactg catttctg | 178 |

<210> SEQ ID NO 83
<211> LENGTH: 135
<212> TYPE: DNA
<213> ORGANISM: Homo sapiens

<400> SEQUENCE: 83
gggcccagct cagaaccggg cagacacccc cttcaaatgt cttcgcacgt aggttttgca      60
cagtgtttat ttgctggtgt ctcagggatt tgacagtttc cttaatattc ccacacatgg     120
ccgagaaaaa taaat                                                      135

<210> SEQ ID NO 84
<211> LENGTH: 235
<212> TYPE: DNA
<213> ORGANISM: Homo sapiens

<400> SEQUENCE: 84
ttctacacta gtgccatggg aaccaggtct gaaaaagtag agagaagtga agtagagtc       60 tgggaagtag ctgcctataa ctgagactag acggaaaagg aatactcgtg tattttaaga    120
tatgaatgtg actcaagact cgaggccgat acgaggctgt gattctgcct ttggatggat    180
gttgctgtac acagatgcta cagacttgta ctaacacacc gtaatttggc atttg         235

<210> SEQ ID NO 85
<211> LENGTH: 177
<212> TYPE: DNA
<213> ORGANISM: Homo sapiens

<400> SEQUENCE: 85
gataacagtc ttgcatgttt atcatgttac aatttaatat tccatcctgc ccaacccttc     60
cttccccatc ctcaaaaaag ggccatttta tgatgcattg cacccctct ggggaaattg    120 atctttaaat tttgagacag tataaggaaa atctggttgg tgtcttacaa gtgagct       177

<210> SEQ ID NO 86
<211> LENGTH: 236
<212> TYPE: DNA
<213> ORGANISM: Homo sapiens

<400> SEQUENCE: 86
attggagtgg atgggttctg ccttaaattg ggaggactcc aagccgggaa ggaaaattcc      60
cttttccaac ctgtatcaat ttttacaact ttttcctga aagcagttta gtccatactt     120
tgcactgaca tactttttcc ttctgtgcta aggtaaggta tccaccctcg atgcaatcca    180
ccttgtgttt tcttagggtg gaatgtgatg ttcagcagca aacttgcaac agactg        236

<210> SEQ ID NO 87
<211> LENGTH: 243
<212> TYPE: DNA
<213> ORGANISM: Homo sapiens

<400> SEQUENCE: 87
gggatctcct tttgtgaaaa ccagtttgat gtgctaaaag taaaagtct attttccagt      60 gtggtcttgt tcagaagcag ccagatttcc aatgttgttt ttcccctcca ctcagaaacc    120
cctgcccttt cccttcagaa aacgatggca ggcattcctt tgagtttaca agcagagact    180
cactccaacc caaactagct gggagttcag aaccatggtg gaataaagaa atgtgcatct    240
ggt                                                                   243

<210> SEQ ID NO 88
<211> LENGTH: 221
<212> TYPE: DNA
<213> ORGANISM: Homo sapiens -continued

```
<400> SEQUENCE: 88
cctgtaagac aataggccat gttaattaaa ctgaagaagg atatatttgg ctgggtgttt    60
tcaaatgtca gcttaaaatt ggtaattgaa tggaagcaaa attataagaa gaggaaatta   120
aagtcttcca ttgcatgtat tgtaaacaga aggagatggg tgattccttc aattcaaaag   180
ctctctttgg aatgaacaat gtgggcgttt gtaaattctg g                       221

<210> SEQ ID NO 89
<211> LENGTH: 273
<212> TYPE: DNA
<213> ORGANISM: Homo sapiens

<400> SEQUENCE: 89
aatgaccacc gccattcaca agaactttga ctgtttgaag ttgatcctga gactcttgaa    60
gtaatggctg atcctgcatc agcattgtat atatggtctt aagtgcctgg cctccttatc   120
cttcagaata tttattttac ttacaatcct caagttttaa ttgattttaa atatttttca   180
atacaacagt ttaggtttaa gatgaccaat gacaatgacc acctttgcag aaagtaaact   240
gattgaataa ataaatctcc gttttcttca att                                273

<210> SEQ ID NO 90
<211> LENGTH: 225
<212> TYPE: DNA
<213> ORGANISM: Homo sapiens

<400> SEQUENCE: 90
gagtaccgcg cagacattaa aagtcatgta aagaacatt tgactgaaag aaaaatgctc     60
cttgaatatt aaaaggttgt aaaaatagtg catgttatgt gatttcaatt ttgtttttta   120
aaatatgggt gtatgcttgt atacgtagag cagataaaaa agacggaagg catactaaaa   180
aatgttgagt ggttatcttt gtatggtgga acaaagtcac tgtaa                   225

<210> SEQ ID NO 91
<211> LENGTH: 182
<212> TYPE: DNA
<213> ORGANISM: Homo sapiens

<400> SEQUENCE: 91
atgctgagtg acactcttgt gtatatttcc aaattttgt acagtcgctg cacatatttg     60
aaatcatata ttaagacttt ccaaagatga ggtccctggt ttttcatggc aacttgatca   120
gtaaggattt cacctctgtt tgtaactaaa accatttact atatgttaga catgacattc   180
tt                                                                  182

<210> SEQ ID NO 92
<211> LENGTH: 157
<212> TYPE: DNA
<213> ORGANISM: Homo sapiens

<400> SEQUENCE: 92
tgtgttttca gagctaggta cagaggaatg tttgctacct ttagcggtga aaaagaaag     60 agagtcaaga attttgttgg attgtgtttg tgtgtgcata tatttgatat catcattata   120
tttgtaatct ttggacttgt aatcatagcc tgtttat                            157

<210> SEQ ID NO 93
<211> LENGTH: 201
<212> TYPE: DNA
<213> ORGANISM: Homo sapiens
```

<400> SEQUENCE: 93

```
ctccctccct ttatagaatg tcaaccaaag agtgccctcc tccctctca gcctcctctt        60 tagctagcct ccccatctca tcacaacgca tgtctgtgac ctttggtaat catttacagt      120
gccacacgga accctgtatt ttgcacacag caaaacaaac aatgtttagc tttatttatg      180
gtatttgatg ctgtaaatgg a                                                201
```

<210> SEQ ID NO 94
<211> LENGTH: 35
<212> TYPE: DNA
<213> ORGANISM: Homo sapiens

<400> SEQUENCE: 94

```
atattattgg attatggttc ctgaaggtca ttaaa                                  35
```

<210> SEQ ID NO 95
<211> LENGTH: 249
<212> TYPE: DNA
<213> ORGANISM: Homo sapiens

<400> SEQUENCE: 95

```
tctccagagg gcacttcggc tgcctttgct tcctttcatt cgaggcccgg ctcttgctga       60
cagaataggt tccgttttgg gcggtggttc tcgagcctgc cattcaaaac caaagcaaat     120
tggagcattt ctcacaacat ggtattgaag ttcctttttg ttctcaaaag ttgtgaccgt     180
gttaaattgt actcccttag tcctgtaagg tatgttaagt gaatcgcagt tacgctgtac     240
tttattaa                                                              249
```

<210> SEQ ID NO 96
<211> LENGTH: 203
<212> TYPE: DNA
<213> ORGANISM: Homo sapiens

<400> SEQUENCE: 96

```
ctgccgagcc tctttggacc cagatctgtt catgcttttg tcttcgtcac tgcggcgggg       60 cccttgatg tcttcatctg tatggggtgg aaaaatcacc gggaatcccc cttcagttct      120
ttgaaaaagt tccatgactc gaatatctga atgaagaaa acaaaccgac tcacaaacct      180
ccaagtagct ccaaatgcaa ttt                                             203
```

<210> SEQ ID NO 97
<211> LENGTH: 73
<212> TYPE: DNA
<213> ORGANISM: Homo sapiens

<400> SEQUENCE: 97

```
tctgtaattc attgagcagt tagctcattt gagataaagt caaatgccaa acactagctc       60
tgtattaatc ccc                                                         73
```

<210> SEQ ID NO 98
<211> LENGTH: 123
<212> TYPE: DNA
<213> ORGANISM: Homo sapiens

<400> SEQUENCE: 98

```
atggtataat ggttgactgg gtttctctgt atagtactgg catggtacgg agatgtttca       60
cgaagtttgt tcatcagact cctgtgcaac tttcccaatg tggcctaaaa atgcaacttc     120
``` ttt                                                               123

<210> SEQ ID NO 99
<211> LENGTH: 132
<212> TYPE: DNA
<213> ORGANISM: Homo sapiens

<400> SEQUENCE: 99
atattttgtg ttgatcatta tttccattct taatgtgaaa aaaagtaatt atttatactt    60
attataaaaa gtatttgaaa tttgcacatt taattgtccc aatagaaag ccacctattc   120 tttgttggat tt                                                      132

<210> SEQ ID NO 100
<211> LENGTH: 189
<212> TYPE: DNA
<213> ORGANISM: Homo sapiens

<400> SEQUENCE: 100
tgaggccgac agcgtcttca gcggcttcct catcttccca tctgcctgag ccagggaagg    60
accccctccc ccacccacct ctctggcttc catgctccgc ctgtaaaatg ggggcgctat   120
tgcttcagct gctgaaggga gggggctggc tttgagagcc ccaggactgg ctgccccgtg   180
acacatgct                                                          189

<210> SEQ ID NO 101
<211> LENGTH: 265
<212> TYPE: DNA
<213> ORGANISM: Homo sapiens

<400> SEQUENCE: 101
aaaagggtca catttaccag ggctttgagg ccgacagcgt cttcagcggc ttcctcatct    60
tcccatctgc ctgagccagg gaaggacccc ctcccccacc cacctctctg gcttccatgc   120
tccgcctgta aaatgggggc gctattgctt cagctgctga agggaggggg ctggctttga   180
gagccccagg actggctgcc ccgtgacaca tgctttaaga agctcgtttt ttagacctct   240
tcctggaata aacatctgtg tctgt                                        265

<210> SEQ ID NO 102
<211> LENGTH: 174
<212> TYPE: DNA
<213> ORGANISM: Homo sapiens

<400> SEQUENCE: 102
caccccagga ctttatcaac ttgttcaagt tctgaatccc agcacatgac aacacttcag    60
aagggtcccc ctgctgactg gagagctggg aatatggcat tggacacttc catttgtaaa   120
tagtgtacat tttaaacatt ggctcgaaac ttcagagata agtcatggag agga         174

<210> SEQ ID NO 103
<211> LENGTH: 239
<212> TYPE: DNA
<213> ORGANISM: Homo sapiens

<400> SEQUENCE: 103
gggatacagt tccatattgc cttaaacctc cttgttttag acacactaac atttatacca    60
aattgcagat tattttgcag agagggaatt gcatgtttgt gttgtatatt tagtatgaac   120
ttttttcaga atataatatt ttttagttat caaaagtagt tggaaaacat ttgcaagact   180
atgaacatag aattgctgct tttatatttt aactgcagat tgtgaatttc actgcctta   239

<210> SEQ ID NO 104
<211> LENGTH: 110
<212> TYPE: DNA
<213> ORGANISM: Homo sapiens

<400> SEQUENCE: 104
gacttcttgc ttgtacatat aggagcaata ctattatatt atgtagtccg ttaacactac    60
ttaaaagttt agggttttct cttggttgta gagtggccca gaattgcatt              110

<210> SEQ ID NO 105
<211> LENGTH: 292
<212> TYPE: DNA
<213> ORGANISM: Homo sapiens

<400> SEQUENCE: 105
acagtgttgt atgaggtttg aggattttga tccaagctgg tcccactcag tccatagcag    60
agaatgaaag gcccagaga gggtggtgac ctctgcctga agtcacacag tgagtcgagg    120
acagggaggt gaccccaggt ttctatgtgt agggcgggag gatgttttgg gacacagttc    180
aattctcatt tgtcacacac tttggctatt agagatcaac ccttcgctc ctgtgtcttg    240 caatggcagc cttggcaaac gctaaatgaa atcgtgaca acacttgtgt ta            292

<210> SEQ ID NO 106
<211> LENGTH: 223
<212> TYPE: DNA
<213> ORGANISM: Homo sapiens

<400> SEQUENCE: 106
tcatgttaaa gagccgtgtc tcccgccagc actcctcacc ccggtatgaa tgtgtttcct    60
ccacattgta tatccttcca ccctctggct gcctagatca gtaaataaaa ttgatgtaat    120
ataatttata agtaacactg ttgaaaccct gatcccagtg gaggctgtaa cccacctgcc    180
cccgcaccac ccccctgacc cctgttaccg catttgtgtg tat                     223

<210> SEQ ID NO 107
<211> LENGTH: 275
<212> TYPE: DNA
<213> ORGANISM: Homo sapiens

<400> SEQUENCE: 107
gttatggtgc taatgtactt tcacttttaa actctagatc agaattgttg acttgcattc    60
agaacataaa tgcacaaaat ctgtacatgt ctcccatcag aaagattcat ggcatgcca    120 caggggattt tcctccttca tcctgtaaag gtcaacaata aaaccaaat tatggggctg    180 cttttgtcac actagcatag agaatgtgtt gaaatttaac tttgtaagct tgtatgtggt    240
tgttgatctt ttttttcctt acagacaccc ataat                              275

<210> SEQ ID NO 108
<211> LENGTH: 196
<212> TYPE: DNA
<213> ORGANISM: Homo sapiens

<400> SEQUENCE: 108
tctggcccgc aatactgtag gaacaagcat gatcttgtta ctgtgatatt ttaaatatcc    60
acagtactca cttttccaa atgatcctag taattgccta gaaatatctt tttcttacct    120
gttatttatc aattttctccc agtattttta tacggaaaaa attgtattga aaacacttag   180

```
tatgcagttg ataaga                                                     196

<210> SEQ ID NO 109
<211> LENGTH: 129
<212> TYPE: DNA
<213> ORGANISM: Homo sapiens

<400> SEQUENCE: 109
gctgcggaga gctcatggaa ggcgagtggg aacccggctg cctgcctttt tttttgatcc     60
agaccctcgg cacctgctac ttaccaactg gaaaatttta tgcatcccat gaagcccaga    120
tacacaaaa                                                            129

<210> SEQ ID NO 110
<211> LENGTH: 296
<212> TYPE: DNA
<213> ORGANISM: Homo sapiens

<400> SEQUENCE: 110
tgaggatgtc accaattaac cagaaatcca gttatttttcc gccctcaaaa tgacagccat    60
ggccggccgg gtgcttttgg gggctcgtcg gggggacagc tccactttga ctggcacagt    120 cttttgcatgg agacttgagg agggagggct tgaggttggt gaggttaggt gcgtgtttcc    180
tgtgcaagtc aggacatcag tttgattaaa ggtggtgcca atttatttac atttaaactt    240
gtcagggtat aaaatgacat cccattaatt atattgttaa tcaatcacgt gtatag         296

<210> SEQ ID NO 111
<211> LENGTH: 108
<212> TYPE: DNA
<213> ORGANISM: Homo sapiens

<400> SEQUENCE: 111
acatgcagta ctgtataccc cccatccctc cctcggtcca ctgaacttca gagcagttcc     60
cattcctgcc ccgcccatct ttttgtgtct cgctgtgata gatcaata                 108

<210> SEQ ID NO 112
<211> LENGTH: 243
<212> TYPE: DNA
<213> ORGANISM: Homo sapiens

<400> SEQUENCE: 112
acaaaagagc cagagttctg gacccatgtt tggagcattt gtagccttat ttttttgcgt     60
gtgaatcttt taccctgaaa aaagccata atgaattaag ccagactgac cacttgcttg     120
gagtgtgtgc ttgaaaaaac cagagcaata ctgttgggta ttgtatcagg cttcagtaca    180
aactggtaac accaatgtgg atcctgacag cttttcagttt tagcaaaaat acacgtgaaa   240
tct                                                                  243

<210> SEQ ID NO 113
<211> LENGTH: 52
<212> TYPE: DNA
<213> ORGANISM: Homo sapiens

<400> SEQUENCE: 113
agtgcaacgt attcaagtcc tcaatatcct gatcataata ccatgctata gg              52

<210> SEQ ID NO 114
<211> LENGTH: 294
<212> TYPE: DNA
<213> ORGANISM: Homo sapiens
```

<400> SEQUENCE: 114

```
tccatcaggg ccagattttc cacgtctcca tctcagtaca caatcattta atatttccct      60
gttttacccc tattcaagca actagaggcc agaaaatggg caaattatca ctaacaggtc     120
tttgactcag gttccagtag ttcattttaa tgcctagatt cttttgtggt tgttgctggc     180
ccaatgagtc cctagtcaca tcccctgcca gagggagttt ttttttttgtg agagacactg    240 taaacgacac aagagaacaa gaataaaaca ataactgtgt gtgttttggc tgag           294
```

<210> SEQ ID NO 115
<211> LENGTH: 277
<212> TYPE: DNA
<213> ORGANISM: Homo sapiens

<400> SEQUENCE: 115

```
acaggttagt tcagtcaaag caggcaaccc ccttgtgggc actgaccctg ccactggggt      60
catggcggtt gtggcagctg ggaggtttg gccccaacag ccctcctgtg cctgcttccc      120
tgtgtgtcgg ggtcctccag ggagctgacc cagaggtgga ggccacggag gcagggtctc    180
tggggactgt cgggggtac agaggagaa ggctctgcaa gagctccctg gcaatacccc     240
cttgtgtaat tgctttgtgt gcgacaggga ggaagtt                              277
```

<210> SEQ ID NO 116
<211> LENGTH: 173
<212> TYPE: DNA
<213> ORGANISM: Homo sapiens

<400> SEQUENCE: 116

```
ggcttcctac cttgcaacaa aataattgca ccaactcctt agtgccgatt ccgcccccag      60
agagtcctgg agccacagtt ttttttgctt tgcattgtag gagagggaat aagtgctaga    120
gactatgtcg ctttcctgag ctaccgagag cgctcgtgaa ctggaatcaa ctg           173
```

<210> SEQ ID NO 117
<211> LENGTH: 217
<212> TYPE: DNA
<213> ORGANISM: Homo sapiens

<400> SEQUENCE: 117

```
agaagtggta aaagtggata atcttgtctt gtactttatt ttagaggaaa agctgtcagt      60
ttttcactgc tgaatatgat gttaactatg aacttttat acatgtattt actatgttga     120
ggtaatttcc ttttactcct ggtttaagtg ttttttgttt ttttttgttt ttttttttttt   180 ttaaatcatg gaaggacttg ggttttatca aatgtct                              217
```

<210> SEQ ID NO 118
<211> LENGTH: 286
<212> TYPE: DNA
<213> ORGANISM: Homo sapiens

<400> SEQUENCE: 118

```
actttgccgg cgagcacacc gcctacccgc acggctgggt ggagacggcg gtcaagttgg      60
cgctgcgcgc cgccatcaag atcaacagcc ggaaggggcc tgcatcggac acggccagcc    120
ccgaggggca cgcatttgac atggaggggc aggggcatgt gcatgggggtg ccagcagcc     180 cctcgcatga cctggcaaag gaagaaggca gccacccctcc agtccaaggc cagttatctt    240
tccaaaacac gacccacacg aggacctcgc attaaagtat tttcgg                   286
```

```
<210> SEQ ID NO 119
<211> LENGTH: 168
<212> TYPE: DNA
<213> ORGANISM: Homo sapiens

<400> SEQUENCE: 119
catttcatgt ttggcgggca tgtgagtgca caagatggaa agagcgattg gagcatcctg      60
gtataattac ccccattgtg cttttaatgg aaatttcaaa ggacgggagt attttgttgg     120
ttggtgtcca ggtttgtggc actgttccaa gaggccttac acacacac                  168

<210> SEQ ID NO 120
<211> LENGTH: 150
<212> TYPE: DNA
<213> ORGANISM: Homo sapiens

<400> SEQUENCE: 120
aatgttcata ggttctcaac cctcaccccc caccacggga gactagagct gcaggatccc      60
aggggagggg tctctcctcc caccccaagg catcaagccc ttctccctgc actcaataaa     120
ccctcaataa atattctcat tgtcaatcaa                                      150

<210> SEQ ID NO 121
<211> LENGTH: 177
<212> TYPE: DNA
<213> ORGANISM: Homo sapiens

<400> SEQUENCE: 121
ctactgccag ggaaatgcta cattatttt ctaattggaa gtataattag agtgatgttg      60
gtagggtaga aaagaggga gtcacttgat gctttcaggt taatcagagc tatgggtgct     120
acaggcttgt ctttctaagt gacatattct tatctaattc tcagatcagg ttttgaa       177

<210> SEQ ID NO 122
<211> LENGTH: 124
<212> TYPE: DNA
<213> ORGANISM: Homo sapiens

<400> SEQUENCE: 122
ggcagcatac tgagaccctg cctttaaaaa caaacagaac aaaaacaaaa caccagggac      60
acatttctct gtcttttttg atcagtgtcc tatacatcga aggtgtgcat atatgttgaa     120
tgac                                                                  124

<210> SEQ ID NO 123
<211> LENGTH: 64
<212> TYPE: DNA
<213> ORGANISM: Homo sapiens

<400> SEQUENCE: 123
atgttcatag gttctcaacc ctcaccccc accacgggag actagagctc aggatcccag      60
ggga                                                                   64

<210> SEQ ID NO 124
<211> LENGTH: 167
<212> TYPE: DNA
<213> ORGANISM: Homo sapiens

<400> SEQUENCE: 124
tctgagcggg tcatggggca acacggttag cggggagagc acggggtagc cggagaaggg      60
cctctggagc aggtctggag gggccatggg gcagtcctgg gtgtggggac acagtcgggt     120
```
tgacccaggg ctgtctccct ccagagcctc cctccggaca atgagtc     167

<210> SEQ ID NO 125
<211> LENGTH: 36
<212> TYPE: DNA
<213> ORGANISM: Homo sapiens

<400> SEQUENCE: 125
caccactaaa agatcgcagt ttgcctggtg cagtgg     36

<210> SEQ ID NO 126
<211> LENGTH: 129
<212> TYPE: DNA
<213> ORGANISM: Homo sapiens

<400> SEQUENCE: 126
aatgcatatg gaggtaggct gaaaagaatg taatttttat tttctgaaat acagatttga     60
gctatcagac caacaaacct tccccctgaa aagtgagcag caacgtaaaa acgtatgtga     120
agcctctct     129

<210> SEQ ID NO 127
<211> LENGTH: 150
<212> TYPE: DNA
<213> ORGANISM: Homo sapiens

<400> SEQUENCE: 127
aatgttcata ggttctcatc cctcaccccc caccacggga gactagagct gcaggatccc     60
aggggagggg tctctcctcc caccccaagg catcaagccc ttctccctgc actcaataaa     120
ccctcaataa atattctcat tgtcaatcaa     150

<210> SEQ ID NO 128
<211> LENGTH: 83
<212> TYPE: DNA
<213> ORGANISM: Homo sapiens

<400> SEQUENCE: 128
ttccaccatc aaatgctgta gaatgcttgg cactccctaa ccaaatgctg tctccataat     60
gccactggtg ttaagatata ttt     83

<210> SEQ ID NO 129
<211> LENGTH: 121
<212> TYPE: DNA
<213> ORGANISM: Homo sapiens

<400> SEQUENCE: 129
atataccata ggctaaaact aaggctttca ctctagaatg caaagctgtt ttgcagctgt     60
tttcccttaa agatgtcctg ttgctttagt gatatttaga ccctctcag ttaagaaatg     120 c     121

<210> SEQ ID NO 130
<211> LENGTH: 257
<212> TYPE: DNA
<213> ORGANISM: Homo sapiens

<400> SEQUENCE: 130
ttatctgaag gttaaagggc aagtgtttgg tatagaagag cagtatgtgt taagaaaaga     60
aaaatattgg ttcacgtaga gtgcaaatta gaactagaaa gttttatacg attatcattt     120

```
tgagatgtgt taaagtaggt tttcactgta aaatgtatta gtgtttctgc attgccatag    180
ggcctggtta aaactttctc ttaggtttca ggaagactgt cacatacagt aagcttttt    240 ccttctgact tataata                                                   257

<210> SEQ ID NO 131
<211> LENGTH: 285
<212> TYPE: DNA
<213> ORGANISM: Homo sapiens

<400> SEQUENCE: 131
caagacctag gctcatggac gagatgggaa ggcacaggga gaagggataa ccctacaccc    60
agaccccagg ctggacatgc tgactgtcct ctcccctcca gcctttggcc ttggcttttc   120
tagcctattt acctgcaggc tgagccactc tcttcccttt ccccagcatc actcccaag    180 gaagagccaa tgttttccac ccataatcct ttctgccgac ccctagttcc ctctgctcag   240
ccaagcttgt tatcagcttt cagggccatg gttcacatta gaata                   285

<210> SEQ ID NO 132
<211> LENGTH: 105
<212> TYPE: DNA
<213> ORGANISM: Homo sapiens

<400> SEQUENCE: 132
gtatttattg agtcacggat tattgtgcat caagcaattg ttaatatgac ctggtcctat    60
ggggtagaac ttaggaaaaa taaagttggt tcttattcaa tattt                   105

<210> SEQ ID NO 133
<211> LENGTH: 205
<212> TYPE: DNA
<213> ORGANISM: Homo sapiens

<400> SEQUENCE: 133
atggacccac cttactggcc agtctgcatc cttgcctaga ccattctccc caccagatgg    60
acttctcctc cagggagccc accctgaccc accccactg caccccctcc ccatgggttc   120
tctccttcct ctgaacttct ttaggagtca ctgcttgtgt ggttcctggg acacttaacc   180
aatgccttct ggtactgcca ttctt                                          205

<210> SEQ ID NO 134
<211> LENGTH: 189
<212> TYPE: DNA
<213> ORGANISM: Homo sapiens

<400> SEQUENCE: 134
ctggttttag cattattaga ataagacttt atacattaac taaagtggag ctttaatcac    60 tataaaagc aaaagtatct atagacacag acacttgcct atacagagac ataaccacac    120
acactcagag gatagtgaac aaatctgtct ttgacttacg acccattttg caagacttaa   180
agccggaag                                                            189

<210> SEQ ID NO 135
<211> LENGTH: 248
<212> TYPE: DNA
<213> ORGANISM: Homo sapiens

<400> SEQUENCE: 135
atgccctgag gccagttggc gagggtggc tcctgagggt ttttataccc tttgtttgct    60
aatgtttaat tttgcatcat aatttctaca ttgtccctga gtgtcagaac tataatttat   120
```

```
tccatttctc tctgtgtctg tgccaagaaa cgcaggctct gggcctgccc cttgcccagg    180
aggccttgcc agcctgtgtg cttgtgggaa caccttgtac ctgagcttac aggtaccaat    240
aaagaggc                                                              248
```

<210> SEQ ID NO 136
<211> LENGTH: 99
<212> TYPE: DNA
<213> ORGANISM: Homo sapiens

<400> SEQUENCE: 136

```
gcccgaatca tgacagtcag caacatgata cctggatcca gccattcctg aagcccaccc    60
tgcacctcat tccaactcct accgcgatac agacccaca                            99
```

<210> SEQ ID NO 137
<211> LENGTH: 250
<212> TYPE: DNA
<213> ORGANISM: Homo sapiens

<400> SEQUENCE: 137

```
gctataaagt gcttgaccag taatgtggtt gtaattttgt gtatgttccc ccacatcgcc    60
cccaacttcg gatgtggggt caggaggttg aggttcacta ttaacaaatg tcataaatat    120
ctcatagagg tacagtgcca atagatattc aaatgttgca tgttgaccag agggatttta    180
tatctgaaga acatacacta ttaataaata ccttagagaa agattttgac ctggctttag    240
ataaaactgt                                                            250
```

<210> SEQ ID NO 138
<211> LENGTH: 55
<212> TYPE: DNA
<213> ORGANISM: Homo sapiens

<400> SEQUENCE: 138

```
atactggaaa cctaactgca atgtggatgt tttacccaca tgacttatta tgcat          55
```

<210> SEQ ID NO 139
<211> LENGTH: 237
<212> TYPE: DNA
<213> ORGANISM: Homo sapiens

<400> SEQUENCE: 139

```
agaagaccca cgtgctaggg gatgaggggc ttcctgggtc ctgttcccta ccccatttgt    60
ggtcacagcc atgaagtcac cgggatgaac ctatccttcc agtggctcgc tccctgtagc    120
tctgcctccc tctccatatc tccttcccct acacctccct ccccacacct ccctactccc    180
ctgggcatct tctggcttga ctggatggaa ggagacttag gaacctacca gttggcc       237
```

<210> SEQ ID NO 140
<211> LENGTH: 216
<212> TYPE: DNA
<213> ORGANISM: Homo sapiens

<400> SEQUENCE: 140

```
gaggcagagg cttgggtaaa ctcattccac aaaccctatg ggggctgcca cgtcacaggc    60
ccaaaggact cttcttcagc agcatctttg caaaatgtct ttctctcaat gaagagcata    120
tctggacgac tgtgcaatgc tgtgtgctcc cgggatcagt aacccttccg ctgttcctga    180
aataaccttt cataaagtgc tttgggtgcc attcca                                216
```

<210> SEQ ID NO 141
<211> LENGTH: 156
<212> TYPE: DNA
<213> ORGANISM: Homo sapiens

<400> SEQUENCE: 141

```
gatgtatagc tttagctttta gcctggcaac ctggagaatc cacatacctt gtgtattgaa    60
ccccaggaaa aggaagaggt cgaaccaacc ctgcggaagg agcatggttt caggagttta   120
ttttaagact gctgggaagg aaacaggccc catttt                              156
```

<210> SEQ ID NO 142
<211> LENGTH: 151
<212> TYPE: DNA
<213> ORGANISM: Homo sapiens

<400> SEQUENCE: 142

```
ctgactctgg gttcgttggg gacatgagat tttatttttt gtgagtgaga ctgagggatc    60
gtagattttt acaatctgta tctttgacaa ttctgggtgc gagtgtgaga gtgtgagcag   120
ggcttgctcc tgccaaccac aattcaatga a                                  151
```

<210> SEQ ID NO 143
<211> LENGTH: 151
<212> TYPE: DNA
<213> ORGANISM: Homo sapiens

<400> SEQUENCE: 143

```
gcagaaatat gtaaccttag actcagccag tttcctctgc agctgctaaa actacatgtg    60
gccagctcca ttcttccaca ctgcgtacta catttcctgc cttttctttt cagtgttttt   120
ctaagactaa ataaatagca aactttcacc t                                  151
```

<210> SEQ ID NO 144
<211> LENGTH: 132
<212> TYPE: DNA
<213> ORGANISM: Homo sapiens

<400> SEQUENCE: 144

```
caactctaac cccacccacg ggagcctgga gctgcaggat cccaggggag gggtctctct    60
ccccatccca agtcatccag cccttctccc tgcactcatg aaaccccaat aaatatcctc   120
attgacaacc aa                                                       132
```

<210> SEQ ID NO 145
<211> LENGTH: 80
<212> TYPE: DNA
<213> ORGANISM: Homo sapiens

<400> SEQUENCE: 145

```
cctttgactt ctgaccctct catcctggat ggtgtgtggt ggcacaggaa cccccgcccc    60
aacttttgga ttgtaataaa                                                80
```

<210> SEQ ID NO 146
<211> LENGTH: 94
<212> TYPE: DNA
<213> ORGANISM: Homo sapiens

<400> SEQUENCE: 146

```
ctgggcttgg gtgcccatat aggaggtctg tatgttcacc aacagtgcgg aggggtcaca    60
cattgcaaaa cactgcccag aacagtaaaa agag                                94
```

<210> SEQ ID NO 147
<211> LENGTH: 264
<212> TYPE: DNA
<213> ORGANISM: Homo sapiens

<400> SEQUENCE: 147

```
atgagaatga tggttgaagg ttacatttta ggaaatgaag aaacttagaa aattaatata      60
aagacagtga tgaatacaaa gaagattttt ataacaatgt gtaaaatttt tggccaggga     120
aaggaatatt gaagttagat acaattactt acctttgagg gaaataattg ttggtaatga     180
gatgtgatgt ttctcctgcc acctggaaac aaagcattga agtctgcagt tgaaaagccc     240
aacgtctgtg agatccagga aacc                                            264
```

<210> SEQ ID NO 148
<211> LENGTH: 286
<212> TYPE: DNA
<213> ORGANISM: Homo sapiens

<400> SEQUENCE: 148

```
taaagacgca tgttatggtg ctaatgtact ttcactttta aactctagat cagaattgtt      60
gacttgcatt cagaacataa atgcacaaaa tctgtacatg tctcccatca gaaagattca     120
ttggcatgcc acaggggatt ctcctccttc atcctgtaaa ggtcaacaat aaaaaccaaa     180
ttatggggct gcttttgtca cactagcata gagaatgtgt tgaaatttaa ctttgtaagc     240
ttgtatgtgg ttgttgatct ttttttttcct tacagacacc cataat                   286
```

<210> SEQ ID NO 149
<211> LENGTH: 42
<212> TYPE: DNA
<213> ORGANISM: Homo sapiens

<400> SEQUENCE: 149

```
ccattcctcg ccctgtcccc acagccgagt cctgcatcag cc                         42
```

<210> SEQ ID NO 150
<211> LENGTH: 189
<212> TYPE: DNA
<213> ORGANISM: Homo sapiens

<400> SEQUENCE: 150

```
ttaccctcca aaagcaagta gccaaagccg ttgccaaacc ccacccataa atcaatgggc      60
cctttattta tgacgacttt atttattcta atatgatttt atagtattta tatatattgg     120
gtcgtctgct tcccttgtat ttttcttcct tttttgtaa tattgaaaac gacgatataa      180
ttattataa                                                             189
```

<210> SEQ ID NO 151
<211> LENGTH: 211
<212> TYPE: DNA
<213> ORGANISM: Homo sapiens

<400> SEQUENCE: 151

```
gtcaggtctt ggtaggtgcc tgcatctgtc tgccttctgg ctgacaatcc tggaaatctg      60
ttctccagaa tccaggccaa aaagttcaca gtcaaatggg gaggggtatt cttcatgcag     120
gagaccccag gccctggagg ctgcaacata cctcaatcct gtcccaggcc ggatcctcct     180
gaagcccttt tcgcagcact gctatcctcc a                                    211
```

<210> SEQ ID NO 152
<211> LENGTH: 211
<212> TYPE: DNA
<213> ORGANISM: Homo sapiens

<400> SEQUENCE: 152
gaaaaaactt tctctttgcc atttcttctt cttcttttt aactgaaagc tgaatccttc      60
catttcttct gcacatctac ttgcttaaat tgtgggcaaa agagaaaaag aaggattgat    120
cagagcattg tgcaatacag tttcattaac tccttccccc gctccccaa aaatttgaat    180 tttttttca acactcttac acctgttatg g                                    211

<210> SEQ ID NO 153
<211> LENGTH: 89
<212> TYPE: DNA
<213> ORGANISM: Homo sapiens

<400> SEQUENCE: 153
tgactgaatt gctgacccctt caagctctgt ccttatccat tacctcaaag cagtcattcc    60
ttagtaaagt ttccaacaaa tagaaatta                                       89

<210> SEQ ID NO 154
<211> LENGTH: 162
<212> TYPE: DNA
<213> ORGANISM: Homo sapiens

<400> SEQUENCE: 154
gcattctcaa gaggtcgtgc caatcagcca ctgaaaggaa aggcatcact atggactttc     60
tctattttaa aatggtaaca atcagaggaa ctataagaac accttttagaa ataaaaatac   120 tgggatcaaa ctggcctgca aaaccatagt cagttaattc tt                       162

<210> SEQ ID NO 155
<211> LENGTH: 86
<212> TYPE: DNA
<213> ORGANISM: Homo sapiens

<400> SEQUENCE: 155
atcatttcat agtcatttat gtttcatcgg tcctcatgtg tactagtgcg ttatttact     60 tatactcccg gatatcatat tattta                                        86

<210> SEQ ID NO 156
<211> LENGTH: 233
<212> TYPE: DNA
<213> ORGANISM: Homo sapiens

<400> SEQUENCE: 156
gaaacacaag agacttaaag gacaggagga ggagatggcc ataggagagg agggttcctc    60
ttaggtcaga tggaggttct cagagccaag tcctccctct ctactggagt ggaaggtcta   120
ttggccaaca atcctttctg cccacttccc cttcccaat tactattccc tttgacttca   180
gctgcctgaa acagccatgt ccaagttctt cacctctatc caaagaactt gat          233

<210> SEQ ID NO 157
<211> LENGTH: 146
<212> TYPE: DNA
<213> ORGANISM: Homo sapiens

<400> SEQUENCE: 157
atgttcatag gttctcaacc ctcaccccca ccacgggaga ctagagctgc aggatcccag     60

```
gggaggggtc tctcctccca ccccaaggca tcaagccctt ctccctgcac tcaataaacc    120
ctcaataaat attctcattg tcaagg                                         146

<210> SEQ ID NO 158
<211> LENGTH: 265
<212> TYPE: DNA
<213> ORGANISM: Homo sapiens

<400> SEQUENCE: 158
aacaaaatat ttctccccta gtgagagaaa gaggtcctca gagagtagca gctcacataa    60
ctgggaccag aggaagaagc aacacattgt cttctccaaa ctccaagaat gaaaaggctc    120
tgggccgcaa aataaactcc tgggaatcat caaggagtgg gcattcattc ctgagcaact    180
tgcacttgag gaatggtgaa ctggtcatcc atgaaaaagg gttttactac atctattccc    240
aaacatactt tcgatttcag gagga                                          265

<210> SEQ ID NO 159
<211> LENGTH: 186
<212> TYPE: DNA
<213> ORGANISM: Homo sapiens

<400> SEQUENCE: 159
gctgagcaaa gcagactacg agaaacacaa agtctacgcc tgcgaagtca cccatcaggg    60
cctgagctcg cccgtcacaa agagcttcaa caggggagag tgttagaggg agaagtgccc    120
ccacctgctc ctcagttcca gcctgacccc ctcccatcct ttggcctctg accctttttc    180
cacagg                                                               186

<210> SEQ ID NO 160
<211> LENGTH: 41
<212> TYPE: DNA
<213> ORGANISM: Homo sapiens

<400> SEQUENCE: 160
tacaagacca cgcctcccgt gctggactcc gacggctcct t                        41

<210> SEQ ID NO 161
<211> LENGTH: 45
<212> TYPE: DNA
<213> ORGANISM: Homo sapiens

<400> SEQUENCE: 161
aacagaaaag aaactgtaga ccttgggaca atcaacattt aaata                    45

<210> SEQ ID NO 162
<211> LENGTH: 211
<212> TYPE: DNA
<213> ORGANISM: Homo sapiens

<400> SEQUENCE: 162
gaaaaaactt tctctttgcc atttcttctt cttcttttt aactgaaagc tgaatccttc     60
catttcttct gcacatctac ttgcttaaat tgtgggcaaa agagaaaaag aaggattgat    120
cagagcattg tgcaatacag tttcattaac tccttccctc gctccccaa aaatttgaat    180 tttttttca acactcttac acctgttatg g                                    211

<210> SEQ ID NO 163
<211> LENGTH: 105
<212> TYPE: DNA
```

<213> ORGANISM: Homo sapiens

<400> SEQUENCE: 163

| ggacctgaag ggtgacatcc caggaggggc ctctgaaatt tcccacaccc cagcgcctgt | 60 |
| gctgaggact ccctccatgt ggccccaggt gccaccaata aaaat | 105 |

<210> SEQ ID NO 164
<211> LENGTH: 175
<212> TYPE: DNA
<213> ORGANISM: Homo sapiens

<400> SEQUENCE: 164

| tcatgatttg tgtagcgtgg aatgtgtttg ctcaatgtga agggttttca ttgctcaatt | 60 |
| tctctgtgta agtcttttcc ttaaggtaat aaaccatcag caaagtcaca tactggagtt | 120 |
| ggtggctttt tttgtacagg cagttgttat gagacaatga tggagcattg agcat | 175 |

<210> SEQ ID NO 165
<211> LENGTH: 65
<212> TYPE: DNA
<213> ORGANISM: Homo sapiens

<400> SEQUENCE: 165

| ttaactccat atgtgttcct cttgttttaa ttttgtcaac cagtgcaagt gaccgacaaa | 60 |
| attcc | 65 |

<210> SEQ ID NO 166
<211> LENGTH: 114
<212> TYPE: DNA
<213> ORGANISM: Homo sapiens

<400> SEQUENCE: 166

| aaggagctga cacacggaga gtcacaggct atacagctgc ttcgagcagc gggaatgttt | 60 |
| gtcttgggat tagatgctga cgtgtggtga aatgttacag agagcccaga ggaa | 114 |

<210> SEQ ID NO 167
<211> LENGTH: 100
<212> TYPE: DNA
<213> ORGANISM: Homo sapiens

<400> SEQUENCE: 167

| tgccccccctt aaggctagag gtgagcatgt ccctcacaat tgcacatgtc aagccatcag | 60 |
| caaggcgcat cacacaaaag gcaccaagac gtgaaacttt | 100 |

<210> SEQ ID NO 168
<211> LENGTH: 273
<212> TYPE: DNA
<213> ORGANISM: Homo sapiens

<400> SEQUENCE: 168

| gagtctgtga ccgatgcaat tctacagaca gaccagattt tcacagaaaa ggaaaaggag | 60 |
| attgaagtgg aatgtgtaaa agctgaatct gcacaggctt cagcaaaaat ggtggaggaa | 120 |
| atgcaaataa agtatcagca gatgatggaa gagaaagaga agagttatca agaacatgtg | 180 |
| aaacaattga ctgagaagat ggagagggag agggcccagt tgctggaaga gcaagagaag | 240 |
| accctcacta gtaaacttca ggtatccaaa tgc | 273 |

<210> SEQ ID NO 169
<211> LENGTH: 36

```
<212> TYPE: DNA
<213> ORGANISM: Homo sapiens

<400> SEQUENCE: 169
agcaggatca agggccggaa ataaaggctg ttgtaa                              36

<210> SEQ ID NO 170
<211> LENGTH: 109
<212> TYPE: DNA
<213> ORGANISM: Homo sapiens

<400> SEQUENCE: 170
agaattattg catttgagct ccgctcccct tccgaaccaa ggtataaaag taaatcaagc   60
cccttcctcg gggccgagag aattttggaa agtcaagcct tctcttggc              109

<210> SEQ ID NO 171
<211> LENGTH: 115
<212> TYPE: DNA
<213> ORGANISM: Homo sapiens

<400> SEQUENCE: 171
gcatgctcag tcttttcctc ttatctacaa tacaaagggt ttgtctgaaa agtctggttt   60
tttttctttt tacaaatgta ccttagctgc atcaacagga gtaagatgta gaaaa       115

<210> SEQ ID NO 172
<211> LENGTH: 175
<212> TYPE: DNA
<213> ORGANISM: Homo sapiens

<400> SEQUENCE: 172
atagagagta gatcagcgat tgtgaggagg taggggttaa agaaggattt tactacaaag   60
gtgcaatgca aggaagtttt ggggtgatg aactgtcctg tatcccgatt gtggtggcag   120
ttacatgaat ctatatttgt gttaagatct atagatctgt actccctcaa aaagt       175

<210> SEQ ID NO 173
<211> LENGTH: 279
<212> TYPE: DNA
<213> ORGANISM: Homo sapiens

<400> SEQUENCE: 173
gtaggtttgg gagtataacg gtcacccagg gaggggtga agacggagaa gacttacata    60
gcacggtcag gttagggctg gacagatgag gaagagctag caaaggggggc ttgaggagca  120 gtggccacta agacaggagt gtgacatttt agaagccaaa agaagaccat gtaattcaag   180
ggagaggtat gatttgctgg gtcagatcta aaaataaatc acacgttttt ttaaactgta   240
gtaattaacc actgaaaact tatgagtgat ccaatatta                         279

<210> SEQ ID NO 174
<211> LENGTH: 74
<212> TYPE: DNA
<213> ORGANISM: Homo sapiens

<400> SEQUENCE: 174
cgatatgact tccatgtaaa cgttcatcca ctctgcctgc ttacaccctg ccctcatgct    60
aatgtaataa actc                                                     74

<210> SEQ ID NO 175
<211> LENGTH: 48
<212> TYPE: DNA
```

<213> ORGANISM: Homo sapiens

<400> SEQUENCE: 175
gccgagatcg tgctagggtg actggagcaa aaccccttca agaaaaga             48

<210> SEQ ID NO 176
<211> LENGTH: 164
<212> TYPE: DNA
<213> ORGANISM: Homo sapiens

<400> SEQUENCE: 176
gtgtggatgc taaggtgttt gttttgtttt gtattttat gtagcgcgtg ggtattgtgc    60
ctagaaatga agtcattatt agggatttaa atatgcaact catggagtgg atgagaccag  120
ctagaaagat aatagagtgt gaagaggaga tcggaaattc aata                   164

<210> SEQ ID NO 177
<211> LENGTH: 34
<212> TYPE: DNA
<213> ORGANISM: Homo sapiens

<400> SEQUENCE: 177
attccaggac tttggcgcct tcaccgggag catg                               34

<210> SEQ ID NO 178
<211> LENGTH: 32
<212> TYPE: DNA
<213> ORGANISM: Homo sapiens

<400> SEQUENCE: 178
cacaaagctc tgtcaataag tgatacatgt tt                                 32

<210> SEQ ID NO 179
<211> LENGTH: 141
<212> TYPE: DNA
<213> ORGANISM: Homo sapiens

<400> SEQUENCE: 179
atttttgcct ttccgtttct gtctatgatg taggcttctg aggagaacca agaagcttgg    60
ctttagtggt agaatgacag aacttaggga tcccttgcag gctagaacaa agttctgacc  120
cttagaccaa atctttatgt t                                             141

<210> SEQ ID NO 180
<211> LENGTH: 211
<212> TYPE: DNA
<213> ORGANISM: Homo sapiens

<400> SEQUENCE: 180
gtttgtgtgg gaactttgca agtcagtttc cctgtatgaa gtgatggaga gagtgattaa    60
gatactgagc tttctctgtg ttcttgccgt taaccattgc cggtttgtgg gagattaaga  120
agtcgatgcg ttttatggag aattaattta ttttgatata gacagatgga cgggtcatga  180
aaatttgttg acatacttta ctaaactgct a                                  211

<210> SEQ ID NO 181
<211> LENGTH: 127
<212> TYPE: DNA
<213> ORGANISM: Homo sapiens

<400> SEQUENCE: 181 tttttagtt gccaacagtt gtattttgc tgattatta tgaccttaaa taatatattt     60

```
tttttttttaa gaagacattt tgttacataa ggaaaacttt tttattcaat ggaataaatt       120
atggcat                                                                 127

<210> SEQ ID NO 182
<211> LENGTH: 251
<212> TYPE: DNA
<213> ORGANISM: Homo sapiens

<400> SEQUENCE: 182
gaacaggagc aactactaaa agagggattt caaaaagaaa gcagaataat gaaaaatgag       60
atacaggatc tccagacgaa aatgagacga cgaaaggcat gtaccataag ctaaagacca      120
gagccttcct gtcaccccta accaaggcat aattgaaaca attttagaat ttggaacaag      180
cgtcactaca tttgataata attagatctt gcatcataac accaaaagtt tataaaggca      240
tgtggtacaa t                                                           251

<210> SEQ ID NO 183
<211> LENGTH: 248
<212> TYPE: DNA
<213> ORGANISM: Homo sapiens

<400> SEQUENCE: 183
gcaagcacac gcagaaggca cacagggaca ggacgcccca tggagcccg aattgaccct        60 cactgcctcc aaagcccaga gcctgcctgt cagcccagct ggagggcccg aggctgcagg      120
gtgtcctccc acagtcccgc tgtttcctgt gcattcgtga cccgcttccc tcccaccctg      180
tctcctgtct ccatcgttgg attatctttg aaccccttg tgtggatcat tttgagccgc       240
ctggcctt                                                               248

<210> SEQ ID NO 184
<211> LENGTH: 71
<212> TYPE: DNA
<213> ORGANISM: Homo sapiens

<400> SEQUENCE: 184
tattgcccgg ctcctagaat ttatttattt cctgacttac agcaagcgag ttatcgtctt       60
ctgtattttg t                                                            71

<210> SEQ ID NO 185
<211> LENGTH: 163
<212> TYPE: DNA
<213> ORGANISM: Homo sapiens

<400> SEQUENCE: 185
ctttcattgg aagttcatca ctgttaggcg ttatcttgag tattataaca aagcaaatcc       60
acaagtattc aatataagat taggaaaaaa attcctgcga tactttgttg tcaaacactt      120
gccactgata gacgttattt tagcttttaa ggcctgtcac att                        163

<210> SEQ ID NO 186
<211> LENGTH: 258
<212> TYPE: DNA
<213> ORGANISM: Homo sapiens
<220> FEATURE:
<221> NAME/KEY: modified_base
<222> LOCATION: (61)..(61)
<223> OTHER INFORMATION: a, c, t, g, unknown or other

<400> SEQUENCE: 186
```

```
atggagtata agctgtttgt agtcaggcct ggagtaatga gggtacctaa atactgaagg    60 nattttatg cagattgact gaaacctgaa tcaaattgga aggagagggc tgaattttga   120
tagactggaa gtattagaga attttctata ctttgactca aggaatggtc aacttttagg   180
aaaagcaact atattatgtc tgttaagatc atagaatctt aacctgaaag ggaccttgga   240
gactatttag tacaactc                                                 258
```

<210> SEQ ID NO 187
<211> LENGTH: 89
<212> TYPE: DNA
<213> ORGANISM: Homo sapiens

<400> SEQUENCE: 187

```
ttttgaatga actctgagtc agttgaaata gggtaccatc taggtcagtt taagaagagt    60
cagctcagag aaagcaagca taagggaaa                                      89
```

<210> SEQ ID NO 188
<211> LENGTH: 193
<212> TYPE: DNA
<213> ORGANISM: Homo sapiens
<220> FEATURE:
<221> NAME/KEY: modified_base
<222> LOCATION: (120)..(125)
<223> OTHER INFORMATION: a, c, t, g, unknown or other
<220> FEATURE:
<221> NAME/KEY: modified_base
<222> LOCATION: (127)..(127)
<223> OTHER INFORMATION: a, c, t, g, unknown or other

<400> SEQUENCE: 188

```
gaagaaagct aactcagtac actaagagtg atttacatgc ctgcaaataa tttgtgtctg    60
gggtcttgac cctccccaaa tgccttgtta tttatatctc tgcttttaga taacagatgn   120
nnnnntntct atgggcttgt accggcagag gcaacagcag gtccttaaga ctccccaggt   180
gccatgatga aaa                                                      193
```

<210> SEQ ID NO 189
<211> LENGTH: 173
<212> TYPE: DNA
<213> ORGANISM: Homo sapiens

<400> SEQUENCE: 189

```
gtaccatctt acatgcttaa ataactccac atttatttgt gtttattact ctgtgttata    60
aatatacatt tgttggtctc tctcttggat tattttgttt ctttgtcctg taactaccac   120
tgaaagggtg caatacagct ttcttgaaat gtgtattgaa cggatgaatg tat          173
```

<210> SEQ ID NO 190
<211> LENGTH: 265
<212> TYPE: DNA
<213> ORGANISM: Homo sapiens
<220> FEATURE:
<221> NAME/KEY: modified_base
<222> LOCATION: (41)..(41)
<223> OTHER INFORMATION: a, c, t, g, unknown or other

<400> SEQUENCE: 190

```
gattcggagt cttgattttg caaaggtaac aaaagacatg nttttttata agacttttca    60
tcataagttt atttattca acagaagcaa aatctaatat aatggaaaaa ataaagatct    120
gtgataaatc tgatctgtgt ggataaacac aattagaaag atttaaagat taagtattga   180
aacaaactac caaaatattt taatactgat ttgtaaaaat ttcagtacat ttttcttctt   240
```

```
tgcttaattc tactgggtcc tgttt                                          265
```

<210> SEQ ID NO 191
<211> LENGTH: 217
<212> TYPE: DNA
<213> ORGANISM: Homo sapiens

<400> SEQUENCE: 191

```
gttcccagtg acacttcaga gagctggtag ttagtagcat gttgagccag gcctgggtct     60
gtgtctcttt tctctttctc cttagtcttc tcatagcatt aactaatcta ttgggttcat    120
tattggaatt aacctggtgc tggatatttt caaattgtat ctagtgcagc tgattttaac    180
aataactact gtgttcctgg caatagtgtg ttctgat                             217
```

<210> SEQ ID NO 192
<211> LENGTH: 168
<212> TYPE: DNA
<213> ORGANISM: Homo sapiens

<400> SEQUENCE: 192

```
gatacactat acaatcctat gaccaatctc atctacaact ttattcaaat tttatagagg     60
ctgaggtgga aggatcactt gagtttgaaa ccagcctggg caacatagtg agaccccgtc    120
tctacaaaaa gtaggaaaaa aaaaatagcg aggtgttgtg gtacacgc                 168
```

<210> SEQ ID NO 193
<211> LENGTH: 115
<212> TYPE: DNA
<213> ORGANISM: Homo sapiens

<400> SEQUENCE: 193

```
ttctagtaat tatcaattgt cctggtctgg ctgcttagag tatcagtttg ctcaaaattg     60
cttgaatcat taaagcaaat actaattgtg agcattgacc agatcttaag ttaaa         115
```

<210> SEQ ID NO 194
<211> LENGTH: 193
<212> TYPE: DNA
<213> ORGANISM: Homo sapiens
<220> FEATURE:
<221> NAME/KEY: modified_base
<222> LOCATION: (147)..(147)
<223> OTHER INFORMATION: a, c, t, g, unknown or other
<220> FEATURE:
<221> NAME/KEY: modified_base
<222> LOCATION: (164)..(164)
<223> OTHER INFORMATION: a, c, t, g, unknown or other

<400> SEQUENCE: 194

```
tgtctatggc tgtttttgtg caaaatggca gagttgggtt cagagttagc aacagagagc     60
ttgtagcctg caagcctaga gtatttacta tctggatttc tacaaaaaaa aaaaaaaaaa    120
aatttggggg gggcccgtaa cccaatncgc ccctatagtg agtngtatta caatccacct    180
ggccgcgttt tac                                                       193
```

<210> SEQ ID NO 195
<211> LENGTH: 233
<212> TYPE: DNA
<213> ORGANISM: Homo sapiens
<220> FEATURE:
<221> NAME/KEY: modified_base
<222> LOCATION: (35)..(35)
<223> OTHER INFORMATION: a, c, t, g, unknown or other
<220> FEATURE:

```
<221> NAME/KEY: modified_base
<222> LOCATION: (53)..(53)
<223> OTHER INFORMATION: a, c, t, g, unknown or other
<220> FEATURE:
<221> NAME/KEY: modified_base
<222> LOCATION: (60)..(60)
<223> OTHER INFORMATION: a, c, t, g, unknown or other

<400> SEQUENCE: 195
tggagtaaca cccagatctc tgcagcagtt aagcntgggg gcctagaact agnctagagn      60
tagaagaagg gacaaatgca atccgacctt tggatctaca cattcctctt gcttcaatgg    120
gtgtcattta agaattagag gaaaatatta ggagatggag aactagagtt gaggaaacca    180
aaagaagagg agtcacagaa aaccagctct ctctgtgcaa ggcatcttga aag           233

<210> SEQ ID NO 196
<211> LENGTH: 139
<212> TYPE: DNA
<213> ORGANISM: Homo sapiens

<400> SEQUENCE: 196
caatattaaa aaaggctctg tatgcatggt ggggctatgt aagtactctt taaaactatg     60
gccctattaa tcttacaagt gttacttatg ggtcaagcaa tgtaaactgt ataaatgtaa    120
aaacaacccc tccacacac                                                 139

<210> SEQ ID NO 197
<211> LENGTH: 178
<212> TYPE: DNA
<213> ORGANISM: Homo sapiens

<400> SEQUENCE: 197
ctttggatag aggtgaagaa cttggacatg gctgtttcag gcagctgaag tcaaagggaa     60
tagtaattgg ggaaggggaa gtgggcagaa aggattgttg gccaatatac cttccactcc    120
agtagagagg gaggacttgg ctctgagaac ctccatctga cctaagagga accctcct      178

<210> SEQ ID NO 198
<211> LENGTH: 163
<212> TYPE: DNA
<213> ORGANISM: Homo sapiens

<400> SEQUENCE: 198
ctgcaaaagc cgagatgggt tccatgcagt tctccagtgg gacatcagtg cttatccgaa     60
tgtcatcaat ggcaatctct ccggaacgtc ctttccctat cactccctcg aacacaatct    120
ggtactccat gtcgtagctg ggcaggatga tccgcccgtg ctt                      163

<210> SEQ ID NO 199
<211> LENGTH: 104
<212> TYPE: DNA
<213> ORGANISM: Homo sapiens

<400> SEQUENCE: 199
ttcagcaagg actggtcttt ctatctcttg tactacactg aattcacccc cactgaaaaa     60
gatgagtatg cctgccgtgt gaaccatgtg actttgtcac agcc                     104

<210> SEQ ID NO 200
<211> LENGTH: 222
<212> TYPE: DNA
<213> ORGANISM: Homo sapiens
<220> FEATURE:
<221> NAME/KEY: modified_base
```

```
<222> LOCATION: (93)..(93)
<223> OTHER INFORMATION: a, c, t, g, unknown or other

<400> SEQUENCE: 200
tttcaaagaa ggtcaagtaa cagtcataca gctagaaaag tccctgaaaa aaagaattgt      60
taagaagtat aataacctt tcaaaaccca cantgcagct tagttttcct ttatttattt     120
gtggtcatga agactatccc catttctcca taaaatcctc cctccatact gctgcattat    180
ggcacaaaag actctaagtg ccaccagaca gaaggaccag ag                       222

<210> SEQ ID NO 201
<211> LENGTH: 267
<212> TYPE: DNA
<213> ORGANISM: Homo sapiens

<400> SEQUENCE: 201
ttgctttgta tgcactttgt ttttttcttt gggtcttgtt ttttttttcc acttagaaat      60
tgcatttcct gacagaagga ctcaggttgt ctgaagtcac tgcacagtgc atctcagccc    120
acatagtgat ggttcccctg ttcactctac ttagcatgtc cctaccgagt ctcttctcca    180
ctggatggag gaaaaccaag ccgtggcttc ccgctcagcc ctccctgccc ctcccttcaa    240
ccattcccca tgggaaatgt caacaag                                        267

<210> SEQ ID NO 202
<211> LENGTH: 108
<212> TYPE: DNA
<213> ORGANISM: Homo sapiens

<400> SEQUENCE: 202
ggtggaagac cagtaattgc tggaagactg gatttgctgg aagacttgat ttactggaag      60
acttggagct tcttggaaga catggattgt ccggaagaca tggattgt                 108

<210> SEQ ID NO 203
<211> LENGTH: 209
<212> TYPE: DNA
<213> ORGANISM: Homo sapiens

<400> SEQUENCE: 203
tgggagccgt cttcccagtc caccgtcccc atcgtgggca ttgttgctgg cctggctgtc      60
ctagcagttg tggtcatcgg agctgtggtc gctgctgtga tgtgtaggag gaagagctca    120
ggtggaaaag gagggagcta ctctcaggct gcgtgcagcg acagtgccca gggctctgat    180
gtgtctctca cagcttgaaa agcctgaga                                      209

<210> SEQ ID NO 204
<211> LENGTH: 146
<212> TYPE: DNA
<213> ORGANISM: Homo sapiens

<400> SEQUENCE: 204
gctttgatat ttcaatgtta gcctcaattt ctgaacacca taggtagaat gtaaagcttg      60
tctgatcgtt caaagcatga aatggatact tatatggaaa ttctgctcag atagaatgac    120
agtccgtcaa aacagattgt ttgcaa                                         146

<210> SEQ ID NO 205
<211> LENGTH: 48
<212> TYPE: DNA
<213> ORGANISM: Homo sapiens
```

<400> SEQUENCE: 205
agtgccaaag gatcttcccc ctgacacaac tctgctagac ctgcaaaa                48

<210> SEQ ID NO 206
<211> LENGTH: 150
<212> TYPE: DNA
<213> ORGANISM: Homo sapiens

<400> SEQUENCE: 206
gtgtcatgta agattactgc ttgcctctct aaggaaggtc gtgactgttt aaatagacgg    60
gcaaggtgga accttttgaa agatgagctt ttgaatataa gttgtctgct agatcatggt   120
ttgtattgaa ctaacaaggt ttgcagatct                                    150

<210> SEQ ID NO 207
<211> LENGTH: 186
<212> TYPE: DNA
<213> ORGANISM: Homo sapiens

<400> SEQUENCE: 207
tattcctgca ccaactgacc tgaagttcac tcaggtcaca cccacaagcc tgagcgccca    60
gtggacacca cccaatgttc agctcactgg atatcgagtg cgggtgaccc ccaaggagaa   120
gaccggacca atgaaagaag tcaaccttgc tcctgacagc tcatccgtgg ttgtatcagg   180
acttat                                                              186

<210> SEQ ID NO 208
<211> LENGTH: 276
<212> TYPE: DNA
<213> ORGANISM: Homo sapiens

<400> SEQUENCE: 208
aacaatgtca gattttaact atgaaaacga cattaccttg tgcatttttta tattgattcc    60 tatttttttt ttaagattaa agtttaaatg ttttccacta gtcatttcac ttctaacttg   120
gtataggaag cttagctctc tacatacccta tcatgtgccc tgtatcacag aagattcagg   180
aaaaatgcac ttgggaatca agaaaatgg aacttctttt tgaaaagaca agcaaccatg    240
ttaactgtat tgacacatcc tcaataaaac ctgttg                             276

<210> SEQ ID NO 209
<211> LENGTH: 158
<212> TYPE: DNA
<213> ORGANISM: Homo sapiens

<400> SEQUENCE: 209
tttgcattcc tgataattgt atgtattgta taaagaacgt ctgtacattg ggttataaca    60
ctagtatatt taaacttaca ggcttatttg taatgtaaac caccatttta atgtactgta   120
attaacatgg ttataatacg tacaatcctt ccctcatc                           158

<210> SEQ ID NO 210
<211> LENGTH: 225
<212> TYPE: DNA
<213> ORGANISM: Homo sapiens

<400> SEQUENCE: 210
tagaggcttc ttagattctc ccagcatccg cctttcccctt tagccagtct gctgtcctga    60
aacccagaag tgatgggagag aaaccaacaa gagatctcga accctgtcta gaaggaatgt   120
atttgttgct aaatttcgta gcactgtttta cagttttcct ccatgttatt tatgaatttt   180

```
atattccgtg aatgtatatt gtcttgtaat gttgcataat gttca        225
```

<210> SEQ ID NO 211
<211> LENGTH: 174
<212> TYPE: DNA
<213> ORGANISM: Homo sapiens

<400> SEQUENCE: 211

```
gatcagcaaa caggaatacg atgaagccgg gccttccatt gtccaccgca atgcttcta    60 aaacactttc ctgctcctct ctgtctctag cacacaactg tgaatgtcct gtggaattat   120
gccttcagtt cttttccaaa tcattcctag ccaaagctct gactcgttac ctat         174
```

<210> SEQ ID NO 212
<211> LENGTH: 168
<212> TYPE: DNA
<213> ORGANISM: Homo sapiens

<400> SEQUENCE: 212

```
atattttaca gggtggagtg tactatatac tattacctttt gaatgtgttt gcagagctag   60
tggatgtgtt tgtctacaag tatgattgct gttacataac accccaaatt aactcccaaa   120
ttaaaacaca gttgtgctgt caatacctca tactgcttta cctttttt               168
```

<210> SEQ ID NO 213
<211> LENGTH: 165
<212> TYPE: DNA
<213> ORGANISM: Homo sapiens

<400> SEQUENCE: 213

```
ctcagggagc gaacgtggat gaaaaccaca gggattccgg acgccagacc ccattttata    60
cttcactttt ctctacagtg ttgttttgtt gttgttggtt tttatttttt atactttggc   120
cataccacag agctagattg cccaggtctg ggctgaataa aacaa                   165
```

<210> SEQ ID NO 214
<211> LENGTH: 208
<212> TYPE: DNA
<213> ORGANISM: Homo sapiens

<400> SEQUENCE: 214

```
ccaaacactg acattaccta cacttccact acccaaagac aaaatgtgcc cactgtgtgc    60
ttttgagtgt atttctttt agtttgtttt ttgttgggtg catatttatg ataataacaa    120
tgatggactt caattgtact cactgttcta ttgttggttt taattagcag caagttgtga   180
tcactttccc aggtgaataa atcatttc                                      208
```

<210> SEQ ID NO 215
<211> LENGTH: 245
<212> TYPE: DNA
<213> ORGANISM: Homo sapiens

<400> SEQUENCE: 215

```
agatgctgtg taactaaact gaaataattc aattacttat tatttagaat gttaaagctt    60
atgatagtct tttctaattc ttaacactca tacttgaaat ctttccgagt ttccccagaa   120
gagaatatgg gatttttttt gacattttttg acccatttaa taatgctctt gtgtttacct   180
agtatatgta gactttgtct tatgtgtcaa aagtcctagg aaagtggttg atgtttctta   240
tagca                                                               245
```

<210> SEQ ID NO 216
<211> LENGTH: 257
<212> TYPE: DNA
<213> ORGANISM: Homo sapiens

<400> SEQUENCE: 216

```
ttgttactgc tgattcttgt aaatctttt gcttctactt tcatcttaaa ctaatacgtg      60
ccagatataa ctgtcttgtt tcagtgagag acgccctatt tctatgtcat ttttaatgta    120
tctatttgta caatttaaa gttcttattt tagtatacgt ataaatatca gtattctgac    180
atgtaagaaa atgttacggc atcacactta tattttatga acattgtact gttgctttaa    240
tatgagcttc aatataa                                                    257
```

<210> SEQ ID NO 217
<211> LENGTH: 174
<212> TYPE: DNA
<213> ORGANISM: Homo sapiens

<400> SEQUENCE: 217

```
tttcaaatcc ttcatcatgt cagttccaat gaggtgggga tggagaagac aattgttgct     60
tatgaaagaa agctttagct gtctctgttt tgtaagcttt aagcgcaaca tttcttggtt    120
ccaataaagc attttacaag atcttgcatg ctactcttag atagaagatg ggaa           174
```

<210> SEQ ID NO 218
<211> LENGTH: 191
<212> TYPE: DNA
<213> ORGANISM: Homo sapiens

<400> SEQUENCE: 218

```
taggtggtag atattgaggc caagaatatt gcaaaataca tgaagcttca tgcacttaaa     60
gaagtatttt tagaataaga atttgcatac ttacctagtg aaacttttct agaattattt    120
ttcactctaa gtcatgtatg tttctctttg attatttgca tgttatgttt aataagctac    180
tagcaaaata a                                                           191
```

<210> SEQ ID NO 219
<211> LENGTH: 116
<212> TYPE: DNA
<213> ORGANISM: Homo sapiens

<400> SEQUENCE: 219

```
tgctgtgaaa gaggctggct acacaatcga atggtttgag gtgatctcgc aaagttattc     60
ttccaccatg gccaacaacg aaggactttt ctccctggtg gcgaggaagc tgagca         116
```

<210> SEQ ID NO 220
<211> LENGTH: 181
<212> TYPE: DNA
<213> ORGANISM: Homo sapiens

<400> SEQUENCE: 220

```
gagttgtatc gtgtggtgta ttttttaaaa aatttgattt agcattcata ttttccatct     60
tattcccaat taaagtatg cagattattt gcccaaatct tcttcagatt cagcatttgt    120
tctttgccag tctcattttc atcttcttcc atggttccac agaagctttg tttcttgggc    180
a                                                                      181
```

<210> SEQ ID NO 221
<211> LENGTH: 248

<212> TYPE: DNA
<213> ORGANISM: Homo sapiens

<400> SEQUENCE: 221

```
tgttttcaaa ttgccattgc tactattgct tgtcggtgtt attttatttt attgttttg      60
actttggaag agatgaactg tgtatttaac ttaagctatt gctcttaaaa ccagggagtc    120
agaatatatt tgtaagttaa atcattggtg ctaataataa atgtggattt tgtattaaaa    180
tatatagaag caatttctgt ttacatgtcc ttgctacttt taaaaacttg catttattcc    240
tcagattt                                                              248
```

<210> SEQ ID NO 222
<211> LENGTH: 227
<212> TYPE: DNA
<213> ORGANISM: Homo sapiens

<400> SEQUENCE: 222

```
tatttgaact atatgttgaa gacatctacc agtttctcca aatgcctttt ttaaaactca     60
tcacagaaga ttggtgaaaa tgctgagtat gacactttc ttcttgcatg catgtcagct    120
acataaacag ttttgtacaa tgaaaattac taatttgttt gacattccat gttaaactac    180
ggtcatgttc agcttcattg catgtaatgt agacctagtc catcaga                  227
```

<210> SEQ ID NO 223
<211> LENGTH: 194
<212> TYPE: DNA
<213> ORGANISM: Homo sapiens

<400> SEQUENCE: 223

```
gaagtttaat tcatagtaat ttcactctct gcattgactt atgagataat taatgattaa     60
actattaatg ataaaaataa tgcatttgta ttgttcataa tatcatgtgc acttcaagaa    120
aatggaatgc tactcttttg tggtttacgt gtattatttt caatatctta atacccctaat    180
aaagagtcca taaa                                                       194
```

<210> SEQ ID NO 224
<211> LENGTH: 217
<212> TYPE: DNA
<213> ORGANISM: Homo sapiens

<400> SEQUENCE: 224

```
tgattagccc caagtagaaa gtcctgtggt tttatgttta atggtaatag ttgatcatat     60
atggcataat tttctatcag cttcctactc agtcactata aacacagact tgaaatagta    120
ctttaaatgt ccaaatacct aaatgtgcta aactggaggt aactatttct aggtagttga    180
attttgaaa gtcatgatca gccacacaac tgttttg                              217
```

<210> SEQ ID NO 225
<211> LENGTH: 293
<212> TYPE: DNA
<213> ORGANISM: Homo sapiens

<400> SEQUENCE: 225

```
ttgcttttca ttcagatgta tacataaact tatttaaaat gtcatttaag tgaaccattc     60
caaggcataa taaaacccga ggtagcaaat gaaaattaaa gcatttattt tggtagttct    120
tcaataatga tgcgagaaac tgaattccat ccagtagaag catctccttt tgggtaatct    180
gaacaagtgc caacccagat agcaacatcc actaatccag caccaattcc ttcacaaagt    240
```
ccttccacag aagaagtgcg atgaatatta attgttgaat tcatttcagg gct 293

<210> SEQ ID NO 226
<211> LENGTH: 95
<212> TYPE: DNA
<213> ORGANISM: Homo sapiens

<400> SEQUENCE: 226
ctgtcaggaa ctcctcactg tttaaatatt tatttattgt gacaaatgga gctggtttcc 60
tagatatgaa tgatgtttgc aatccccatt ttcct 95

<210> SEQ ID NO 227
<211> LENGTH: 210
<212> TYPE: DNA
<213> ORGANISM: Homo sapiens

<400> SEQUENCE: 227
gctgctgtag aatagcacag acgtggatga taaattatcc ccagaagcag catgacagaa 60
tgcctcgggg agcacttgga agggaaattg cagttctgtt gaaatagagg aaaatcccctt 120 ggtaaagaca cagcctgtta ggctcgtgtg ggcctccagt atgttcacca ggggaatggc 180
tgggatttct cggcactctg catcatccat 210

<210> SEQ ID NO 228
<211> LENGTH: 243
<212> TYPE: DNA
<213> ORGANISM: Homo sapiens

<400> SEQUENCE: 228
ttaatatttg ttattctctc atgaatagaa atttatgtag aagcaaacaa aatactttta 60
cccacttaaa aagagaatat aacattttat gtcactataa tcttttgttt tttaagttag 120
tgtatatttt gttgtgatta tcttttttgtg gtgtgaataa atcttttatc ttgaatgtaa 180
taagaatttg gtggtgtcaa ttgcttattt gttttcccac ggttgtccag caattaataa 240
aac 243

<210> SEQ ID NO 229
<211> LENGTH: 37
<212> TYPE: DNA
<213> ORGANISM: Homo sapiens

<400> SEQUENCE: 229
gatgcttaac aaaggttacc ataagccaca aattcat 37

<210> SEQ ID NO 230
<211> LENGTH: 264
<212> TYPE: DNA
<213> ORGANISM: Homo sapiens

<400> SEQUENCE: 230
aatgcaaact atcactgtat tttaatatatt gttattctct catgaataga aatttatgta 60
gaagcaaaca aaatactttt acccacttaa aaagagaata taacatttta tgtcactata 120
atcttttgtt ttttaagtta gtgtatattt tgttgtgatt atcttttttgt ggtgtgaata 180 aatcttttat cttgaatgta ataagaattt ggtggtgtca attgcttatt tgttttccca 240
cggttgtcca gcaattaata aaac 264

<210> SEQ ID NO 231
<211> LENGTH: 269

<212> TYPE: DNA
<213> ORGANISM: Homo sapiens

<400> SEQUENCE: 231

```
gcttatttga caacgtttca gcgactccgt tggccactcc gagaggtggg ccagtctgtg      60
gatcagagat gcaccaccaa gccaagggaa cctgtgtccg gtattcgata ctgcgacttt     120
ctgcctggag tgtatgactg cacatgactc gggggtgggg aaaggggtcg gctgaccatg     180
ctcatctgct ggtccgtggg acggtgccca agccagaggc tgggttcatt tgtgtaacga     240
caataaacgg tacttgtcat ttcgggcaa                                       269
```

<210> SEQ ID NO 232
<211> LENGTH: 179
<212> TYPE: DNA
<213> ORGANISM: Homo sapiens

<400> SEQUENCE: 232

```
agaggttata ggtcactcct ggggcctctt gggtccccca cgtgacagtg cctgggaatg      60
tattattctg cagcatgacc tgtgaccagc actgtctcag tttcactttc acatagatgt     120
ccctttcttg ccagttatc ccttcctttt agcctagttc atccaatcct cactgggtg       179
```

<210> SEQ ID NO 233
<211> LENGTH: 220
<212> TYPE: DNA
<213> ORGANISM: Homo sapiens

<400> SEQUENCE: 233

```
ctgtatcact gccttcgttt atatttttt aactgtgata atccccacag gcacattaac      60
tgttgcactt ttgaatgtcc aaaatttata ttttagaaat aataaaaaga aagatactta     120
catgttccca aaacaatggt gtggtgaatg tgtgagaaaa actaacttga tagggtctac     180
caatacaaaa tgtattacga atgcccctgt tcatgttttt                           220
```

<210> SEQ ID NO 234
<211> LENGTH: 127
<212> TYPE: DNA
<213> ORGANISM: Homo sapiens

<400> SEQUENCE: 234

```
gggcccctaa tatcccagtt taatattcca ataccctaga agaaacccg agggacagca      60
gattccacag gacacgaagg ctgcccctgt aaggtttcaa tgcatacaat aaaagagctt     120
tatccct                                                               127
```

<210> SEQ ID NO 235
<211> LENGTH: 225
<212> TYPE: DNA
<213> ORGANISM: Homo sapiens

<400> SEQUENCE: 235

```
cccaaacctg tactgtcccg gaggaggttg ggaggtggag gcccagcatc ccgcgcagat      60
gacaccatca accgccagag tcccagacac cggttttcct agaagcccct caccccact     120
ggcccactgg tggctaggtc tccccttatc cttctggtcc agcgcaagga ggggctgctt     180
ctgaggtcgg tggctgtctt tccattaaag aaacaccgtg caacg                     225
```

<210> SEQ ID NO 236
<211> LENGTH: 41
<212> TYPE: DNA

<213> ORGANISM: Homo sapiens

<400> SEQUENCE: 236

```
ttaatctatg tgcaccgttg ggaccaatgc cttaattaaa g                               41
```

<210> SEQ ID NO 237
<211> LENGTH: 160
<212> TYPE: DNA
<213> ORGANISM: Homo sapiens

<400> SEQUENCE: 237

```
cttctcactg dacagcacta gttttttgcc tgggaagtcg tggacagtaa cagtgactgg          60
aacatcccct tgcgcgtcgt gggcctccag caccatggtc tcctcgctct ccagccgcaa         120
gatgttgggg gtgatgatag agtacatggg actccccaga                               160
```

<210> SEQ ID NO 238
<211> LENGTH: 179
<212> TYPE: DNA
<213> ORGANISM: Homo sapiens

<400> SEQUENCE: 238

```
gggtcagcac agtcttctca ctggacagca ctagtttttt gcctgggaag tcgtggacag          60
taacagtgac tggaacatcc ccttgcgcgt cgtgggcctc cagcaccatg gtctcctcgc         120
tctccagccg caagatgttg ggggtgatga tagagtacat gggactcccc agagccagg         179
```

<210> SEQ ID NO 239
<211> LENGTH: 164
<212> TYPE: DNA
<213> ORGANISM: Homo sapiens

<400> SEQUENCE: 239

```
gtagtgagtt ttccttggtc ggcgtttggc tgagaaggct gcaactggcc tgagacgagt          60
ctggtcccga cgatgctgtg ctctgcctcc tcctgctgct gctgacaacc aagccctccc         120
agaatttaaa tgctgctgca gacatcctcc accaacacag ggag                          164
```

<210> SEQ ID NO 240
<211> LENGTH: 167
<212> TYPE: DNA
<213> ORGANISM: Homo sapiens

<400> SEQUENCE: 240

```
aagaaggaat gatcactctt ggagaggaag ctggtctcag aaacaccttc tgtgactgag          60
tgcccattgc tcagccatgt gatgttgacc acaggaggaa agatgttgtc cacaagacag         120
atgaggatgt tgggctgacc cagtgtcacg ggagacttgg aaaacac                       167
```

<210> SEQ ID NO 241
<211> LENGTH: 183
<212> TYPE: DNA
<213> ORGANISM: Homo sapiens

<400> SEQUENCE: 241

```
ggattataat atcctcactg gccacaatct gtaaaagtcg atactggcac ttttttttgcc         60
ccctcaaagg aaatatgcta atagacagcc cctttgcaaa tataattcct ccttcccaac        120
ccttcaaatt gctaaggccc cactggtcag caccttccct ttcgagtcca ggactactgt        180
tct                                                                      183
```

```
<210> SEQ ID NO 242
<211> LENGTH: 237
<212> TYPE: DNA
<213> ORGANISM: Homo sapiens

<400> SEQUENCE: 242
acaaaagctc ccctgatcca actagcacac tgtcaaatac agtgtcatat gagaggtcca      60
cagacggtag tttccaagac cgtttcaggg aattcgagga ttccaccttta aaacctaaca    120 gaaaaaaacc cactgaaaat attatcatag acctggacaa agaggacaag gatttaatat    180
tgacaattac agagagtacc atccttgaaa ttctacctga gctgacatcg gataaaa       237

<210> SEQ ID NO 243
<211> LENGTH: 197
<212> TYPE: DNA
<213> ORGANISM: Homo sapiens

<400> SEQUENCE: 243
agtgctaagg agtatagcag atgacttata tgtgtgttgg ctgggagaat atcatcttaa     60
agtgagagtg atgttgtgga gacagttgaa atgtcagtgc tagagcctct gtggtgtgaa   120
tgggcacgtt aggttgttgc attagaaagt gactgtttct gacagaaatt tgtagctttg   180
tgcaaactca cccacca                                                   197

<210> SEQ ID NO 244
<211> LENGTH: 131
<212> TYPE: DNA
<213> ORGANISM: Homo sapiens

<400> SEQUENCE: 244
ctacttcccc gaaccggtga cggtgtcgtg gaactcaggc gccctgacca gcggcgtgca     60
caccttcccg gctgtcctac agtcctcagg actctactcc ctcagcagcg tggtgaccgt   120
gccctccagc a                                                         131

<210> SEQ ID NO 245
<211> LENGTH: 95
<212> TYPE: DNA
<213> ORGANISM: Homo sapiens

<400> SEQUENCE: 245
ccagacctac acctgcaacg tagatcacaa gcccagcaac accaaagtgg acaagacagt     60
tgagcgcaaa tgttgtgtcg agtgcccacc gtgcc                               95

<210> SEQ ID NO 246
<211> LENGTH: 131
<212> TYPE: DNA
<213> ORGANISM: Homo sapiens

<400> SEQUENCE: 246
gtaatttgtg attgtcgagg aagaggtgtg gctgttggtg tgatagtaat actgctggtg     60
actttattgg ttgttttgtt tagtgccccg ttaattaagc cttgagttcg gttatcctgc   120
agtggtgctg a                                                         131

<210> SEQ ID NO 247
<211> LENGTH: 38
<212> TYPE: DNA
<213> ORGANISM: Homo sapiens

<400> SEQUENCE: 247
```

```
tttccccac tgtctggaca ctggtgaatg acattaga                             38
```

<210> SEQ ID NO 248
<211> LENGTH: 173
<212> TYPE: DNA
<213> ORGANISM: Homo sapiens

<400> SEQUENCE: 248

```
gaaggagaac gaatccagtg gaaagaaagc tggtgaggga aaagatgccc tgcagaaaag    60
tcccctttcc cccactgtct ggacactggt gaatgacatt agaagagacc caccccattc   120
aagtcccctc actggctcct tttctcccca ctacaccact tccaaaatct gaa          173
```

<210> SEQ ID NO 249
<211> LENGTH: 298
<212> TYPE: DNA
<213> ORGANISM: Homo sapiens

<400> SEQUENCE: 249

```
tgactttgtc acaatgacag ccaacagtga gactgataag cctgtaaaaa taaaaaaata    60
agactaatca atagacatg gcatttaat ctcaaagtgc aaaatcatct aactgaaaat    120
gacggcattg aaaaattcca gtggttaaaa atgaatcaaa acttcattac gcaggcagtg   180
gaagtgtgtt gaaagattta ccagggggtgt caagttttag acactcagaa aggcaccatt   240
ctagccatct tgattggata acatgtatat acttatgtcc ctacgatatt caaaagat     298
```

<210> SEQ ID NO 250
<211> LENGTH: 145
<212> TYPE: DNA
<213> ORGANISM: Homo sapiens

<400> SEQUENCE: 250

```
gataccgact gaccgtgggc cttacccgaa gaggacagcc catgcagtac aatgtgggtc    60
cctctgtctt caagtaccca ctgaggaatc tgcagcctgc atctgagtac accgtattcc   120
tcgtggccat aaagggcaac caaga                                        145
```

<210> SEQ ID NO 251
<211> LENGTH: 111
<212> TYPE: DNA
<213> ORGANISM: Homo sapiens

<400> SEQUENCE: 251

```
ttaagacatt ggagtgattt ctggaaatgt tttctttaag aaggctcacg tgatgtttgt    60
gtttacttgt ggttgcccta tcctatgctg cataaatcct tgaaaggaaa g            111
```

<210> SEQ ID NO 252
<211> LENGTH: 137
<212> TYPE: DNA
<213> ORGANISM: Homo sapiens

<400> SEQUENCE: 252

```
ttaagacatt ggagtgattt ctggaaatgt tttctttaag aaggctcacg tgatgtttgt    60
gtttacttgt ggttgcccta tcctatgctg cataaatcct tgaaaggaaa ggttttagtt   120
agttgctttc tttcttc                                                  137
```

<210> SEQ ID NO 253
<211> LENGTH: 203
<212> TYPE: DNA
<213> ORGANISM: Homo sapiens

<400> SEQUENCE: 253

```
tttttctttg ggctactgta ccctgcttcc agtgctgacc ccggcataag tccatctctg     60
cagaagccat ttcaggagta cctggaggct caacggcaca agcttcacca caaaagcgaa    120
atggacacac cacaggtaag actttaatcc ggtttcttct ccctctggg aagtttcggg     180
ctgaaattac attcacagct ctc                                           203
```

<210> SEQ ID NO 254
<211> LENGTH: 243
<212> TYPE: DNA
<213> ORGANISM: Homo sapiens

<400> SEQUENCE: 254

```
ttcctgcttt tcttcccaaa tgtgtctttt tctttgggct actgtaccct gcttccagtg     60
ctgaccccgg cataagtcca tctctgcaga agccatttca ggagtacctg gaggctcaac   120
ggcacaagct tcaccacaaa agcgaaatgg acacaccaca ggtaagactt taatccggtt   180
tcttctcccc tctgggaagt ttcgggctga aattacattc acagctctca ctcacatttt   240
tag                                                                 243
```

<210> SEQ ID NO 255
<211> LENGTH: 292
<212> TYPE: DNA
<213> ORGANISM: Homo sapiens

<400> SEQUENCE: 255

```
cgcggtctga gtctcgtttg aagctcgag gcataggaca gtctctgcct gggtagggaa     60
tgcagttagc tgaggaacca cggtaggttt taaaaaaaaa gactcgggga gagaaatagc   120
acattattta catgactgga caaggacaga aggtgggagg aagcccctgt cactccttgg   180
gacctgggat ctgagcacaa agctgagtgg gaaacagtgg gggctccgaa gcgcccagca   240
gggccagcgc cctcctttct agaccccgac tgcccttggt cttctgccct tt           292
```

<210> SEQ ID NO 256
<211> LENGTH: 156
<212> TYPE: DNA
<213> ORGANISM: Homo sapiens

<400> SEQUENCE: 256

```
ctgagtaaat gggactgctg tcgttggatg gcactgcgca gctcaggggt gggctctggg     60
aggcggaggc ggaggaggcc gctggagatg gtgctgagga cgaggaggcc ggtgggttgg   120
tcatgctcac taggccactg accaagctga agaggg                             156
```

<210> SEQ ID NO 257
<211> LENGTH: 249
<212> TYPE: DNA
<213> ORGANISM: Homo sapiens
<220> FEATURE:
<221> NAME/KEY: modified_base
<222> LOCATION: (142)..(142)
<223> OTHER INFORMATION: a, c, t, g, unknown or other
<220> FEATURE:
<221> NAME/KEY: modified_base
<222> LOCATION: (188)..(188)
<223> OTHER INFORMATION: a, c, t, g, unknown or other

<400> SEQUENCE: 257

```
attgatttca caagtcttca ggttgtttat agacatagct atagacaaca tctcagtttc     60
```

```
atacagaact cattcaatca tataaaaata aacacaaatt tacattgact catcaactat    120
acaatttaaa aaggcacttg anagggtat tgtattattg catttgtggt atgcatttga     180
aatagttnta agtacattaa tgaaatttgt aagaattcct cttttgcact tattcccatc    240
tttaattaa                                                            249
```

<210> SEQ ID NO 258
<211> LENGTH: 62
<212> TYPE: DNA
<213> ORGANISM: Homo sapiens

<400> SEQUENCE: 258

```
gtccccaaat gacccacatg attcaaagtg caaatttact ccaacctgca agagaaaacg    60
aa                                                                   62
```

<210> SEQ ID NO 259
<211> LENGTH: 126
<212> TYPE: DNA
<213> ORGANISM: Homo sapiens

<400> SEQUENCE: 259

```
actagtctca gtaatacatt agtaaaaatc atgtcactta attaattgtg ttagaatcaa    60
agaaacatag agttgggcaa tatacttcat cctacccatc ccacccaaat cttactctac   120
tcatct                                                              126
```

<210> SEQ ID NO 260
<211> LENGTH: 149
<212> TYPE: DNA
<213> ORGANISM: Homo sapiens

<400> SEQUENCE: 260

```
aaaaatttat ttactagtct cagtaataca ttagtaaaaa tcatgtcact taattaattg    60
tgttagaatc aaagaaacat agagttgggc aatatacttc atcctaccca tcccacccaa   120
atcttactct actcatctca ttctcatta                                     149
```

<210> SEQ ID NO 261
<211> LENGTH: 163
<212> TYPE: DNA
<213> ORGANISM: Homo sapiens

<400> SEQUENCE: 261

```
agaattaact gactatggtt ttgcaggcca gtttgatccc agtatttta tttctaaagg     60 ggttcttata gttcctctga ttgttaccat tttaaaatag agaaagtcca tagtgatgcc   120
tttcctttca gtggctgatt ggcacgacct cttgagaatg cat                     163
```

<210> SEQ ID NO 262
<211> LENGTH: 269
<212> TYPE: DNA
<213> ORGANISM: Homo sapiens

<400> SEQUENCE: 262

```
atttgcattt taccatgggt cctcaataaa taaatagaat gttgttttt gtattttaag     60 tttttttttg ttttccccct cagaggaagg atgaaaaaaa gaattaactg actatggttt   120
tgcaggccag tttgatccca gtattttat ttctaaaggg gttcttatag ttcctctgat    180
tgttaccatt ttaaaataga gaaagtccat agtgatgcct ttcctttcag tggctgattg   240
gcacgacctc ttgagaatgc atgcatgaa                                     269
```

<210> SEQ ID NO 263
<211> LENGTH: 105
<212> TYPE: DNA
<213> ORGANISM: Homo sapiens

<400> SEQUENCE: 263
atttccatca catatgtgcc aagacttgtg ttctgtatcc aggagtgtgt tagatactaa    60
catagtgttt catttacatg tgtgtgaaac ctgggtgaag agcca                  105

<210> SEQ ID NO 264
<211> LENGTH: 174
<212> TYPE: DNA
<213> ORGANISM: Homo sapiens

<400> SEQUENCE: 264
ccatcagttt ttccaatgtg aatggactgg ttcatatcac accatatttta gagatacaag    60 gtgattataa ctaacgtgtc tacaagacat actgggtcaa acaatgtgat caatccaaag   120
ggtatctttt taaaaagaat ttaagtactc agctgcaaag ataagttcac taat         174

<210> SEQ ID NO 265
<211> LENGTH: 218
<212> TYPE: DNA
<213> ORGANISM: Homo sapiens

<400> SEQUENCE: 265
gtacatggtc tggagtaacc tttatatgaa gtggctgccc aggtgtgtgg cttaggacta    60
gatctccagg ttgcacaaag ttggcattgg gtttagtttg catttttcca ttctgaagat   120
ggccctcctt ggatttcatc caggaaatcc atagctttct gttaacagga catggagtag   180
actggctgca tttgaaggac agcacagatc cctcatca                          218

<210> SEQ ID NO 266
<211> LENGTH: 103
<212> TYPE: DNA
<213> ORGANISM: Homo sapiens

<400> SEQUENCE: 266
aaaccttgtt ttattcagcc cagacctggg agatctagct ctgtggtatg gccaaagtat    60
aaaaaataaa aaccaacaac aacaaaacaa cactgtagag aaa                    103

<210> SEQ ID NO 267
<211> LENGTH: 194
<212> TYPE: DNA
<213> ORGANISM: Homo sapiens

<400> SEQUENCE: 267
tcaaactcag gtatgtgaca ctctacagtt caatgctagc acacctgtgt gaggcttaac    60
aacatgagga actgatagcc agtgatacac aaatccagca cttcctctcc atttactctg   120
tcaggctgta tatggggagc aacacatatg gctttgtggc agccagaaag tgaaggtctt   180
tttaggaggt gaca                                                    194

<210> SEQ ID NO 268
<211> LENGTH: 61
<212> TYPE: DNA
<213> ORGANISM: Homo sapiens

<400> SEQUENCE: 268

```
ttcccagcac cggaaggtct cagacttcat attccagcat aaacacagtg ctcccctccc    60
c                                                                    61

<210> SEQ ID NO 269
<211> LENGTH: 268
<212> TYPE: DNA
<213> ORGANISM: Homo sapiens

<400> SEQUENCE: 269
gtaaagcttt ggcacataca gtataaaaaa taatcaccca ccataattat accaaattcc    60
tcttatcaac tgcatactaa gtgttttcaa tacaattttt tccgtataaa aatactggga   120
aaaattgata ataacaggt aagagaaaga tatttctagg caattactag gatcatttgg    180
aaaaagtgag tactgtggat atttaaaata tcacagtaac aagatcatgc ttgttcctac   240
agtattgcgg gccagacact taagtgaa                                      268

<210> SEQ ID NO 270
<211> LENGTH: 37
<212> TYPE: DNA
<213> ORGANISM: Homo sapiens

<400> SEQUENCE: 270
tgggctggag ccgcacacgc tctcctccca tgttaaa                             37

<210> SEQ ID NO 271
<211> LENGTH: 112
<212> TYPE: DNA
<213> ORGANISM: Homo sapiens

<400> SEQUENCE: 271
atagatgaca taagttacca tactcaaatg taagataggg agaggtagaa gaaatagctg    60
agaacttgaa aagatgtact gttattgtca acaaaccaat gtcttctccc tt           112

<210> SEQ ID NO 272
<211> LENGTH: 158
<212> TYPE: DNA
<213> ORGANISM: Homo sapiens

<400> SEQUENCE: 272
ttttcgtagt ccaaaggctt tattgttctg ctgaaatgct tacaaatact gaaaaccccc    60
agcctgggcc caggcaacca agggctcaat gctgggaagg agagcagggg aggtgggctt   120
agtgttaagg cgtgaagggc gaggccagac agctggag                           158

<210> SEQ ID NO 273
<211> LENGTH: 75
<212> TYPE: DNA
<213> ORGANISM: Homo sapiens

<400> SEQUENCE: 273
catctctgac tttaatggct taagcaagaa catggtttcc gtggctcccc ctggactgaa    60
tgctggagga tatat                                                     75

<210> SEQ ID NO 274
<211> LENGTH: 182
<212> TYPE: DNA
<213> ORGANISM: Homo sapiens

<400> SEQUENCE: 274
tgagtaggtg agtttattgg gacttacaca caggtcaatc ctgggcggcg acaagacagc    60
```

```
tctagagatc tgagcttcct cccaatgcta aactgctttc atgctaattt tctgactgtt    120
tacttaccgg gtaagagcga tgggactgtt ttcattggtt ggttctcaca tactctctgg    180
ga                                                                   182

<210> SEQ ID NO 275
<211> LENGTH: 121
<212> TYPE: DNA
<213> ORGANISM: Homo sapiens

<400> SEQUENCE: 275
cctggatctc acagacgttg ggcttttcaa ctgcagactt caatgctttg tttccaggtg     60
gcaggagaaa catcacatct cattaccaac aattatttcc ctcaaaggta agtaattgta    120
t                                                                    121

<210> SEQ ID NO 276
<211> LENGTH: 177
<212> TYPE: DNA
<213> ORGANISM: Homo sapiens

<400> SEQUENCE: 276
cagtggtttg caagcatggt ttcctggatc tcacagacgt tgggcttttc aactgcagac     60
ttcaatgctt tgtttccagg tggcaggaga acatcacat ctcattacca acaattattt    120
ccctcaaagg taagtaattg tatctaactt caatattcct ttccctggcc aaaaatt       177

<210> SEQ ID NO 277
<211> LENGTH: 237
<212> TYPE: DNA
<213> ORGANISM: Homo sapiens

<400> SEQUENCE: 277
agacccctga cacagaccac tagaagattc cgggaacgtt gggagtcacc tgattctgca     60
aagataaata atatccctgc attatcaaaa taaagtagca gacctctcaa ttcacaatga    120
gttaactgat aaacaaaac agaagtcaga caatgtttta aattgaatga tcatgtaaat    180
attacacatc aaaccaatga catgggaaaa tgggagcttc taatgaggac aaacaaa      237

<210> SEQ ID NO 278
<211> LENGTH: 43
<212> TYPE: DNA
<213> ORGANISM: Homo sapiens

<400> SEQUENCE: 278
caatggttga gccctgtca agtgccagtc atgatagtag taa                        43

<210> SEQ ID NO 279
<211> LENGTH: 198
<212> TYPE: DNA
<213> ORGANISM: Homo sapiens

<400> SEQUENCE: 279
gggatttctt ggtttgtgaa aacaggagag gagaaatatc tcatacaagt gaaaggatac     60
tggagagaga aattacccat ttctaaaaaa aaaccacact ctgtcgtatc tgtgttaatg    120
ttttctagca tgtactctgg tttcaacaga cacaaattta tatgttaacc cagttttctt    180
gccgttctgt aagtgttt                                                  198

<210> SEQ ID NO 280
```

```
<211> LENGTH: 70
<212> TYPE: DNA
<213> ORGANISM: Homo sapiens

<400> SEQUENCE: 280
tgtctttgag gctaatggac ccgtggggct tgtaatctgt ctctttctac tatttacatc    60
tgatttaaat                                                            70

<210> SEQ ID NO 281
<211> LENGTH: 94
<212> TYPE: DNA
<213> ORGANISM: Homo sapiens

<400> SEQUENCE: 281
gcctcccatt caagtgaagt tataatttac actgagggtt tcaaaattcg actagaagtg    60
gagatatatt atttatttat gcactgtact gtat                                 94

<210> SEQ ID NO 282
<211> LENGTH: 165
<212> TYPE: DNA
<213> ORGANISM: Homo sapiens

<400> SEQUENCE: 282
tttcctgccc caaggcagat ccacatcacc gaagctccct agagggcaa aagatggagt     60 gagccacagg aagtttgggg cgtggtgagt tggaatgata cgtccatttc tctatgaaat   120
atttgctact agactgttca tttctctctg acatgtttgt tgaat                    165

<210> SEQ ID NO 283
<211> LENGTH: 208
<212> TYPE: DNA
<213> ORGANISM: Homo sapiens

<400> SEQUENCE: 283
catccgccag ggcccacacc cccttcctac tcccagacac ccaccctcgc ttcagccaca    60
gtttcctcat ctgtccagtg ggtaggttgg actggaaaat ctcttttga ctcttgcaat   120 ccacaatctg acattctcag gaagccccca agttgatatt tctatttcct ggaatggttg  180
gattttagtt acagctgtga tttggaag                                       208

<210> SEQ ID NO 284
<211> LENGTH: 227
<212> TYPE: DNA
<213> ORGANISM: Homo sapiens

<400> SEQUENCE: 284
agcccaactt cttacccgaa agcatcactg ccttggcccc tccctcccgg ctgcccccat    60
cacctctact gtctcctccc tgggctaagc aggggagaag cgggctgggg gtagcctgga  120
tgtgggccaa gtccactgtc ctccttggcg gcaaaagccc attgaagaag aaccagccca  180
gcctgccccc tatcttgtcc tggaatattt ttggggttgg aactcaa                  227

<210> SEQ ID NO 285
<211> LENGTH: 57
<212> TYPE: DNA
<213> ORGANISM: Homo sapiens

<400> SEQUENCE: 285
tattgaggac ccatggtaaa atgcaaatag atccggtgtc taaatgcatt catattt        57
```

```
<210> SEQ ID NO 286
<211> LENGTH: 135
<212> TYPE: DNA
<213> ORGANISM: Homo sapiens

<400> SEQUENCE: 286
tacccgggaa agtacgtcta gattgtgtgg tttgcctcat tgtgctattt gcccactttc    60
cttccctgaa gaaatatctg tgaaccttct ttctgttcag tcctaaaatt cgaaataaag   120
tgagactatg gttca                                                    135

<210> SEQ ID NO 287
<211> LENGTH: 247
<212> TYPE: DNA
<213> ORGANISM: Homo sapiens

<400> SEQUENCE: 287 caaactatt ttccacctcc aaagaaatt aacacatgga cattttaaag tctttagtat    60
aaagaaaatt tgtattcaat gtgttaagca ttaacatgta ttttatttgt gtatccactc   120
catctgattt ttctgagcca ttttgatttg ttccttcatt aaaaaaaatc tcttaaagtt   180
atttagtgtc taaaagtgac tgacttaaat tatgtggtgc caatctgtaa tgtctttgaa   240
ttcctt                                                              247

<210> SEQ ID NO 288
<211> LENGTH: 174
<212> TYPE: DNA
<213> ORGANISM: Homo sapiens

<400> SEQUENCE: 288
ttgcatggag acttgaggag ggagggcttg aggttggtga ggttaggtgc gtgtttcctg    60
tgcaagtcag gacatcagtc tgattaaagg tggtgccaat ttatttacat ttaaacttgt   120
cagggtataa aatgacatcc cattaattat attgttaatc aatcacgtgt atag         174

<210> SEQ ID NO 289
<211> LENGTH: 126
<212> TYPE: DNA
<213> ORGANISM: Homo sapiens

<400> SEQUENCE: 289
ggatccaaga gctgactatg cctgcattgc tgagaacaaa cccacctgag caccccagac    60
accttcctca acccaggcgg gtggacaggg tcccctgtg gtccagccag taaaaaccat    120
ggtccc                                                              126

<210> SEQ ID NO 290
<211> LENGTH: 132
<212> TYPE: DNA
<213> ORGANISM: Homo sapiens

<400> SEQUENCE: 290
acagcccacc cttgtgtcca ctgtgacccc tgttcccatg ctgacctgtg tttcctcccc    60
agtcatcttt cttgttccag agaggtgggg ctggatgtct ccatctctgt ctcaacttta   120
cgtgcactga gc                                                       132

<210> SEQ ID NO 291
<211> LENGTH: 173
<212> TYPE: DNA
<213> ORGANISM: Homo sapiens
```

<400> SEQUENCE: 291
aaatgctcct tgaatattaa aaggttgtaa aaatagtgca tgttatgtga tttcaatttt      60
gttttttaaa atatgggtgt atgcttgtat acgtagagca gataaaaaag acggaaggca     120
tactaaaaaa tgttgagtgg ttatctttgt atggtggaac aaagtcactg taa            173

<210> SEQ ID NO 292
<211> LENGTH: 274
<212> TYPE: DNA
<213> ORGANISM: Homo sapiens

<400> SEQUENCE: 292
ggcacgtggc ttcatgtcag taagcaagat gcttcttaat aacccacctt ctgccccact      60
ctattcctta tcctgctgcc cctgtagggg tcaagggccc tccgtctaca ccctcttctt     120
ctcctccatc ctttattcag agtcatctcg cccttcccca tgggtggggg aacctgtgtt     180
tgtttgtgtg cacatgtaaa tttaaatat tttaagcaga aagtccttac ctcctgtaac     240
acatcaataa agtacaatca ttgtgagccc tttc                                 274

<210> SEQ ID NO 293
<211> LENGTH: 185
<212> TYPE: DNA
<213> ORGANISM: Homo sapiens

<400> SEQUENCE: 293
attcactttt gttaacagta tttctctttt attctgttat atagtggatg atatacacag      60
tggcaaaaca aaagtacatt gcttaaaata tatagtgaaa aatgtcacta tatcttccca     120
tttaacattg ttttgtata ttgggtgtag atttctgaca tcaaaacttg gacccttgga     180
aaaca                                                                 185

<210> SEQ ID NO 294
<211> LENGTH: 42
<212> TYPE: DNA
<213> ORGANISM: Homo sapiens

<400> SEQUENCE: 294
tcatgacgag ttaatgcatg tccgtggttg ggtgcacctg ta                         42

<210> SEQ ID NO 295
<211> LENGTH: 250
<212> TYPE: DNA
<213> ORGANISM: Homo sapiens

<400> SEQUENCE: 295
gatttctcat gacgagttaa tgcatgtccg tggttgggtg cacctgtagt tctgtttatt      60
ggtcagtgga aatgaaaaaa aaaaaaaaaa aaagtctgcg ttcattgcag ttccagtttc     120
tcttccattc tgtgtcacag acaccaacac accactcatt ggaaaatgga aaaaaaaac     180 aaaaaaaaaa caaaaaatg tacaatggat gcattgaaat tatatgtaat tgtataaatg     240
gtgcaacagt                                                            250

<210> SEQ ID NO 296
<211> LENGTH: 247
<212> TYPE: DNA
<213> ORGANISM: Homo sapiens

<400> SEQUENCE: 296
ggcaggcttc tctgtagaac cccagggggct tcggcccaga ccacagcgtc ttgccctgag     60

```
cctagagcag ggagtcccga acttctgcat tcacagacca cctccacaat tgttataacc    120
aaaggcctcc tgttctgtta tttcacttaa atcaacatgc tattttgttt tcactcactt    180
ctgactttag cctcgtgctg agccgtgtat ccatgcagtc atgttcacgt gctagttacg    240
tttttct                                                              247
```

```
<210> SEQ ID NO 297
<211> LENGTH: 112
<212> TYPE: DNA
<213> ORGANISM: Homo sapiens

<400> SEQUENCE: 297
attttagtat ggtgtctgtt tatgtaactc tgacttgctg gaaaagttga aactccaaat    60
aatctgaaac tagaaaagaa atagcacata attactacct tccccttggc gg           112
```

```
<210> SEQ ID NO 298
<211> LENGTH: 278
<212> TYPE: DNA
<213> ORGANISM: Homo sapiens

<400> SEQUENCE: 298
aaatggcttc cgatttccag cttgggcctg gggattggag atgtccccac tgagagtagg    60
gcacaagtga ggaaatggtt tggagaggaa gatgataagt tacatcatgg atgtgctgag   120
tctgagttgc ctatgggact tggaatgggg ggtggcaaaa ggtgtgtgat cttgagcaag   180
atattcaact cttctgggcc ttggtcttct catttgtaaa acggtgataa gaatattact   240
tcccatttgt gttgctgtga atattaaatg cgctacca                           278
```

```
<210> SEQ ID NO 299
<211> LENGTH: 137
<212> TYPE: DNA
<213> ORGANISM: Homo sapiens

<400> SEQUENCE: 299
gtgggcagca cttagattcg gagccatgga tagtccggag tccaaggtct ctgggtgagc    60
agacagtcgg ccaaaggcca gcctggagtc aaagagacca gaccccctgct tagattgcca   120 tactcgcacc attccaa                                                  137
```

```
<210> SEQ ID NO 300
<211> LENGTH: 252
<212> TYPE: DNA
<213> ORGANISM: Homo sapiens

<400> SEQUENCE: 300
agttcggcaa aggtgtccta gaaatggcca gagttttga cagacagagt gtagtctcct     60
tattagaaga aaggaaaaaa aagcagaggc caaagaagtt ttgtgtttgc tgatgagagc   120
cccactcatt tgcgaaacgc acgtaaaaca aagtgaaccg tgactgttaa actagggatg   180
ggaaattttg catcttgggg ggctgtacat ttatttattt agttgaagat tcactgatcc   240
cactttgaaa ta                                                       252
```

```
<210> SEQ ID NO 301
<211> LENGTH: 106
<212> TYPE: DNA
<213> ORGANISM: Homo sapiens

<400> SEQUENCE: 301
```

```
gtgcatgtgt gtgctgtgtc tttgtgtgtg tgctgtgtgc tagtgtgtgt gctgtgtgtg      60
catgtgtgtg cgtgtgctgt gcgtttgtgt gctgtgtgct cgtgtg                    106

<210> SEQ ID NO 302
<211> LENGTH: 294
<212> TYPE: DNA
<213> ORGANISM: Homo sapiens

<400> SEQUENCE: 302
tgggaagcgg cgagatcctc gggctggggg tgcccacgtt tgctacctcc ccctgtgaaa      60
tcgctggtgc tcacaattgt ctttcacagt gtatgtgatt ttttttaagga aaaaaaaaa    120 atccctattt aagattttga aggtgctacc attattttgc cacagacttt gaagaaactt    180
ttggatgtgg ggcatcatcc gcatctttct ctctcctcca aatgacaaag tttggggaat    240
ttttgaattt tcctagcatc gcccttgtgc tcatcaggta atctgctaag gagg          294

<210> SEQ ID NO 303
<211> LENGTH: 238
<212> TYPE: DNA
<213> ORGANISM: Homo sapiens

<400> SEQUENCE: 303
acccatcctg ttcgtgaata ggtctcaggg gttggggag ggactgccag atttggacac       60
tatatttttt tttaaattca acttgaagat gtgtatttcc cctgaccttc aaaaaatgtt    120
ccaaggtaag cctcgtaaag gtcatcccac catcaccaaa gcctccgttt taacaacct     180 ccaacacgat ccattagag gccaaatgtc attctgcagg tgccttcccg atggatta       238

<210> SEQ ID NO 304
<211> LENGTH: 258
<212> TYPE: DNA
<213> ORGANISM: Homo sapiens

<400> SEQUENCE: 304
cattctttcc tccacaggat tgctttgtcc atctcctgct ttcatttcaa gtgcataaac     60
aaaacctcaa agggcctggg aaggtgaggc aggccagagt ctgtgttctg tgttgagtgt    120
caagctattt gttaagaagg tttgcaacag gcctttggtg tgggctttgc cagagactgt    180
tttgaacact ttgcttgaga tccgtgccct gtaaaatgga tatgatgttt tactgatgtc    240
tgtaatacat ttgtaaac                                                  258

<210> SEQ ID NO 305
<211> LENGTH: 85
<212> TYPE: DNA
<213> ORGANISM: Homo sapiens

<400> SEQUENCE: 305
ttaagcgcat tagaaaacaa ttgtttgtaa tggaatcaaa gtgtttccct ggacagtttg      60
atgtgcttat ggttgagatt tataa                                           85

<210> SEQ ID NO 306
<211> LENGTH: 299
<212> TYPE: DNA
<213> ORGANISM: Homo sapiens
<220> FEATURE:
<221> NAME/KEY: modified_base
<222> LOCATION: (127)..(127)
<223> OTHER INFORMATION: a, c, t, g, unknown or other
<220> FEATURE:
<221> NAME/KEY: modified_base
```

<222> LOCATION: (194)..(194)
<223> OTHER INFORMATION: a, c, t, g, unknown or other

<400> SEQUENCE: 306
atttgcaaca gcctagtgga tttggtaggg tcctgaatca tctctataag gcaaacaagg     60
aaattgtaac acaagaaat aaacatattg aatataattg ctattctgta agacatacag    120
tctgtgnaag atgtatctta tttacagaga catttttgaa aattaaaata ttaaatactt    180
tttgttatat aganacaatg atctggaagt ataaaaagaa aaatattatc ttgttgatgt    240
aaatatgata tccttatata tattagaatc caataagata tcatgggcgc aatattagc     299

<210> SEQ ID NO 307
<211> LENGTH: 229
<212> TYPE: DNA
<213> ORGANISM: Homo sapiens

<400> SEQUENCE: 307
gatggctggg agataagtcc ttgaatggag gaaccaagag gtgagttaga ggcataaact     60
aaggaatttc agttagtagg gtttaggagt gacagtctag aatgagtgga gactaggaga    120
ttcatcttga tgcaagcata cttagatcca tgttactcag gatagcatag gtgagagagg    180
agctggtaga attttaatgt catacctggg tagtacaact ggttattat                229

<210> SEQ ID NO 308
<211> LENGTH: 213
<212> TYPE: DNA
<213> ORGANISM: Homo sapiens

<400> SEQUENCE: 308
tattttccgg ttgaccccag aattcattag atttttttaa aaaacaattt caaaatagtt     60
gctgttttaa attagttgca tccagttcat atcaatgttt gcatgctttt tagtctttgt    120
tatttattga aaacctttgg tacctaaact taagtttgat tgtttcagtg tgtacttggt    180
aaatatgtca gtggccttt aactaaacat caa                                   213

<210> SEQ ID NO 309
<211> LENGTH: 174
<212> TYPE: DNA
<213> ORGANISM: Homo sapiens

<400> SEQUENCE: 309
caccccagga ctttatcaac ttgttcaagt tctgaatccc agcacatgac aacacttcag     60
aagggtcccc ctgctgactg gagagctggg aatatggcat ttggacactt catttgtaaa    120
tagtgtacat tttaaacatt ggctcgaaac ttcagagata agtcatggag agga           174

<210> SEQ ID NO 310
<211> LENGTH: 32
<212> TYPE: DNA
<213> ORGANISM: Homo sapiens

<400> SEQUENCE: 310
atggacaatt ctgtacccca ataatcagaa ca                                    32

<210> SEQ ID NO 311
<211> LENGTH: 166
<212> TYPE: DNA
<213> ORGANISM: Homo sapiens
<220> FEATURE:
<221> NAME/KEY: modified_base
<222> LOCATION: (101)..(101)

<223> OTHER INFORMATION: a, c, t, g, unknown or other

<400> SEQUENCE: 311

```
agagaggttt gtcccatata tcttgttcca gcagccatat atcttgtggt ctacagcctg    60
aagcatgatt tcccttgaag tcttggggtt gtttaaagga nagtcccttc aatataaaac   120
ctctgaaata ttagtgagaa tggctcacta atgtgaacaa tgttta                  166
```

<210> SEQ ID NO 312
<211> LENGTH: 213
<212> TYPE: DNA
<213> ORGANISM: Homo sapiens

<400> SEQUENCE: 312

```
tacaaagaat atttgggccc agtgctacag aaaaacatga actacatctt atcgtcacaa    60
aatagccatt ataaaatgaa ttttgcagcc tctgtttttt tgaactttga aataaaatgt   120
tcagacaaat attcaacttt ttaaaaacct ccattcattg atagcctgag aaatgtacaa   180
tgaacatgtt taggcagact gctagtattt tgc                                213
```

<210> SEQ ID NO 313
<211> LENGTH: 225
<212> TYPE: DNA
<213> ORGANISM: Homo sapiens

<400> SEQUENCE: 313

```
cctccaccaa tcatactttg acatttatct atttccttct ccacttatgg atgtaattgg    60
cttgctatag aaactacagt tcagatgctt tgaatgtatg aactacaatg aacaataaag   120
tcctcttctt ttgaagcata ttttggcttc agctttaaga taatcttatg acaagaaggg   180
tcacactgat tcacttaata aattccattc ttacctaaca caagg                   225
```

<210> SEQ ID NO 314
<211> LENGTH: 259
<212> TYPE: DNA
<213> ORGANISM: Homo sapiens

<400> SEQUENCE: 314

```
gctggtgtgt ggatcggatg ggcaagtccc tgccagggtc tccagatggc aatggaagct    60
cctcctgccc cactgggagt agcggctaaa gctgggggat agaggggctg cagggccact   120
ggaaggaaca tggagctgtc atcactcaac aaaaaaccga ggccctcaat ccaccttcag   180
gccccgcccc atgggcccct caccgctggt tggaaagagt gttggtgttg gctggggtgt   240
caataaagct gtgcttggg                                                259
```

<210> SEQ ID NO 315
<211> LENGTH: 217
<212> TYPE: DNA
<213> ORGANISM: Homo sapiens

<400> SEQUENCE: 315

```
gaccccagtg gaaaacaaag ccaaacaaaa ctgaaccaca aaaaaaaggc tggtgttcac    60
caaaaccaaa cttgttcatt tagataattt gaaaagttc catagaaaag gcgtgcagta   120
ctaagggaac aatccatgtg attaatgttt tcattatgtt catgtaagaa gccccttatt   180
tttagccata attttgcata ctgaaaatcc aataatc                            217
```

<210> SEQ ID NO 316
<211> LENGTH: 243

<212> TYPE: DNA
<213> ORGANISM: Homo sapiens

<400> SEQUENCE: 316

```
gagtaaaaag aacccttttgc tgagtaacca agcctttaat tttgtgtttt tatgaaagga    60
attaaaatac ccacgataaa tatttaccac aacctgtgtc agataaatgg gaaattaaac   120
acagattgta caatgtgagc ttgggagtta atggcccaga ttttactgtt aggcagtaag   180
agttggagta ggtagtcttg ttatcatgag aagaaccttg aacagataca actaattac   240
ata                                                                  243
```

<210> SEQ ID NO 317
<211> LENGTH: 172
<212> TYPE: DNA
<213> ORGANISM: Homo sapiens

<400> SEQUENCE: 317

```
aacacccata atcaatcaca gagataacca ctgttcataa ttccttccag tcttcttact    60
tggcacatat acatttgtct ttctttatat atgacatatg gatattttac aaagttagga   120
tcctactcta tgcactgctt ggtgatcgga tctattcaat gtacaaaata tt           172
```

<210> SEQ ID NO 318
<211> LENGTH: 100
<212> TYPE: DNA
<213> ORGANISM: Homo sapiens

<400> SEQUENCE: 318

```
ttttctaacc ttgattgacc atgggcaaat gaaactgcag aaagtgaaac tgcggatagg    60
ggggatgact gtattcaata gattccgaca ttatgtctgc                         100
```

<210> SEQ ID NO 319
<211> LENGTH: 32
<212> TYPE: DNA
<213> ORGANISM: Homo sapiens

<400> SEQUENCE: 319

```
ttataatgag tgcgatatat gttgtcgagg ct                                  32
```

<210> SEQ ID NO 320
<211> LENGTH: 210
<212> TYPE: DNA
<213> ORGANISM: Homo sapiens

<400> SEQUENCE: 320

```
gttttgatgc tgtgtgctt tggctgggcc tcgggctcca ggccctggga cccctttgcca   60
gggagacccc cgaacctttg tgccaggaca cctcctggtc ccctgcacct ttcctgttcg   120
gtttagaccc ccaaactgga gggggcatgg agaaccgtag agcgcaggaa cgggtgggta   180
attttagaga caaaagccaa ttaaagtcca                                    210
```

<210> SEQ ID NO 321
<211> LENGTH: 115
<212> TYPE: DNA
<213> ORGANISM: Homo sapiens

<400> SEQUENCE: 321

```
ttcattgagg ttcgtgtgtg ctgtgttcgc gtgtgtgtgc tgtgtgtgca tgtgtgtgct    60
gtgtcttagt gtgtgtgctg tgtgctagtg tgtgtgctgt ggggtaccga gctcg        115
```

<210> SEQ ID NO 322
<211> LENGTH: 241
<212> TYPE: DNA
<213> ORGANISM: Homo sapiens

<400> SEQUENCE: 322
ttcatcatat ccaagttcac tctgtcttcc tgagcagtgg aagatcatat tgctgtaact     60
tcttttaagt agttgatgtg gaaaacattt taaagtgaat ttgtcaaaat gctggttttg    120
tgttttatcc aacttttgtg catatatata aagtatgtca tggcatggtt tgcttaggag    180
ttcagagttc cttcatcatc gaaatagtga ttaagtgatc ccagaacaag gaatactaga    240
g                                                                   241

<210> SEQ ID NO 323
<211> LENGTH: 148
<212> TYPE: DNA
<213> ORGANISM: Homo sapiens
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (91)..(93)
<223> OTHER INFORMATION: a, c, t, g, unknown or other

<400> SEQUENCE: 323
gtcattgata cctgtagtaa gttgacaatg tggtgaaatt tcaaaattat atgtaacttc     60
tactagtttt actttctccc ccaagtctnt nnnaactcat gattttaca cacacaatcc    120 agaacttatt atatagcctc taagtctt                                      148

<210> SEQ ID NO 324
<211> LENGTH: 198
<212> TYPE: DNA
<213> ORGANISM: Homo sapiens

<400> SEQUENCE: 324
gattttcttt tgacacagct ccaaggccac cagctatgca aggccacaag ttatgcacta     60
tatgattaac tgcttttgtt ttacttttgt aagtccactt ataaaaaccc tgctctgtct    120
ttgtttaatg ctcagctttt tggatttgaa tccactcagc cggtgcacac cttaaaataa    180
acatcctcct gtactctc                                                 198

<210> SEQ ID NO 325
<211> LENGTH: 269
<212> TYPE: DNA
<213> ORGANISM: Homo sapiens

<400> SEQUENCE: 325
agacctagaa ggttgtagat gggaaatcag gaatgatttg aactgataaa gatttcagac     60
tcataagaac acattttata aatgttaaac acaaaaacta catgactgaa gatagaagag    120
aatgcgatgg attttattac acatggtgga agagagaaga ggcgtgtagg tttgcaaaca    180
aagttaagaa ataggaaact gaattttttca ttgtacagaa aatgtatctc ttggggaggg    240
cctgtgtacc cccattctct gattataaa                                     269

<210> SEQ ID NO 326
<211> LENGTH: 243
<212> TYPE: DNA
<213> ORGANISM: Homo sapiens

<400> SEQUENCE: 326

```
ggattttttc ccctgtagta gtgaggtaac atgcttgaat gtcactgtga tatttatttc      60
ctctttgttc agttgttttt gaattcctgt taagtacatg ttttaatact ttgagcgatt     120
taagatactt ttcttttttgc ccatcatttt ccccaaggaa tgtaattcac ataaatccaa    180
agctcatttt tttttttatt gtacacaagt agtataatgt ttgcttttcc caataaacct    240
caa                                                                   243
```

<210> SEQ ID NO 327
<211> LENGTH: 178
<212> TYPE: DNA
<213> ORGANISM: Homo sapiens
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other

<400> SEQUENCE: 327

```
gagacaagga cagacaaatt ttctggctgt ccccatttct cctggggag gggtttgggg      60
ctggtttgac tttaattggt gggngggtng tttctgccgc tctgtttgct gcagtccccg    120
tgncctgctt ggggactgag aaatttgagc caggtatcca gagccacagc ccatcttg     178
```

<210> SEQ ID NO 328
<211> LENGTH: 238
<212> TYPE: DNA
<213> ORGANISM: Homo sapiens

<400> SEQUENCE: 328

```
agttggtgcc ctgattccat ttttctcaag ttgtagaaga aacaaactaa tttacggtag      60
gagaaattca aattcagatt ctccccatcc ccaccagtta cctttggttg gtggagaggg    120
ggagaattgg caggaaaggg gcacaaagaa acttttggg gtgatggaaa tattttgtac    180
cttgctttag atgttggtca gatggaatat acgtttgtgg aaacctgcca aactgtac     238
```

<210> SEQ ID NO 329
<211> LENGTH: 155
<212> TYPE: DNA
<213> ORGANISM: Homo sapiens

<400> SEQUENCE: 329

```
aaacattacc gggcatggta gcttgcacct gcagtcccag ctacttggga gactgaggtg      60
agaggatcac ctgagtgtag gaggtgaaag cctcaccgaa ctatgactga accactgcac    120
tccagcgtgg gcacttggca ccagagcaag attct                              155
```

<210> SEQ ID NO 330
<211> LENGTH: 47
<212> TYPE: DNA
<213> ORGANISM: Homo sapiens

<400> SEQUENCE: 330

```
gggatgcata aagtatgagt gccttttagg atgggaattg agatgta                   47
```

```
<210> SEQ ID NO 331
<211> LENGTH: 235
<212> TYPE: DNA
<213> ORGANISM: Homo sapiens
<220> FEATURE:
<221> NAME/KEY: modified_base
<222> LOCATION: (157)..(157)
<223> OTHER INFORMATION: a, c, t, g, unknown or other

<400> SEQUENCE: 331
aggatttccc aaaccagccg aggccccagc acccgccgtc tccccagaag cccctcctc      60 cttccccat gggtcatatg ttgaaagtct attttaaaaa ctatgttcct tgccgtagat     120
tgcagagcta atttatcacg tttctctcct gtgagancccc ccttttata tgatatatcc    180 agaggaagtt ttgtaatata aaacaggacg cccacactga tggttttgca ctggt         235

<210> SEQ ID NO 332
<211> LENGTH: 38
<212> TYPE: DNA
<213> ORGANISM: Homo sapiens

<400> SEQUENCE: 332
tttggatttg aatccactca gccggtgcac accttaaa                              38

<210> SEQ ID NO 333
<211> LENGTH: 265
<212> TYPE: DNA
<213> ORGANISM: Homo sapiens

<400> SEQUENCE: 333
tgttttagaa ccagccgtat tttacatgaa gctgtataat taattgtcat tatttttgtt     60
agcaaagatt aaatgtgtca ttggaagcca tcccttttttt tacatttcat acaacagaaa   120
ccagaaaagc aatactgttt ccattttaag gatatgatta atattattaa tataataatg    180
atgatgatga tgatgaaaac taaggatttt tcaagagatc tttctttcca aaacattttt    240
ggacagtacc tgattgtatt ttttt                                           265

<210> SEQ ID NO 334
<211> LENGTH: 56
<212> TYPE: DNA
<213> ORGANISM: Homo sapiens

<400> SEQUENCE: 334
cacaatctga gcacgctacc aaatctcaaa atatcctaag actaacaaag gcagct          56

<210> SEQ ID NO 335
<211> LENGTH: 289
<212> TYPE: DNA
<213> ORGANISM: Homo sapiens

<400> SEQUENCE: 335
tcccaagtag tgctgactga ctctcctggt gacaggggtt tgtgtccgag ccctgcggt      60 caaggagtgt ggagcaaaac gtgggtacta gggtgggagg cggggaaagg ccacagcaca    120
ctggcgctcc agcaaagcca aatcatgtct cctctggcca ctgcggtcct ctccttggta    180
catgtcatcc cccagaggag tatccaaagc tattccacta tgcactcatc aaccctggct    240
tgtcagcctt ggggaaggtc actttattca taaaaatgcc tctttgagt                289

<210> SEQ ID NO 336
<211> LENGTH: 212
```

<212> TYPE: DNA
<213> ORGANISM: Homo sapiens

<400> SEQUENCE: 336

```
cctgagtcct gggatcagac accccttcac gtgtatcccc acacaaatgc aagctcacca    60
aggtccccttt tcagtcccct tccctacacc ctgaccggcc actgccgcac acccacccag   120
agcacgccac ccgccatggg agtgtgctca ggagtcgcgg gcagcgtgga catctgtccc   180
agaggggca gaatctccaa tagaggactg ag                                   212
```

<210> SEQ ID NO 337
<211> LENGTH: 294
<212> TYPE: DNA
<213> ORGANISM: Homo sapiens

<400> SEQUENCE: 337

```
cagggttcct ttgcctgcta acaagcccac gtggaccagt ttgaatgtct ttcctttaca    60
cctatgtttt taagtagtca aacttcaaga aacaatttaa acaagttttt gttgcatatg   120
tgtttgtgaa cttgtatttg tatttagtag gcttctatat tgcatttaac ttgttttttgt  180
aactcctgat ttttccttttt cggatactat tgatgaataa agaaattaaa gtgatagttt  240
tattggtttc ctttcccca attaaggcca aataaagtcg tgagaacatt accc           294
```

<210> SEQ ID NO 338
<211> LENGTH: 52
<212> TYPE: DNA
<213> ORGANISM: Homo sapiens

<400> SEQUENCE: 338

```
gaggccggtg ccagtgcagg tccttggtgt gctgtgtgcc ggtcccctgg gc              52
```

<210> SEQ ID NO 339
<211> LENGTH: 297
<212> TYPE: DNA
<213> ORGANISM: Homo sapiens

<400> SEQUENCE: 339

```
atggtaatgt aggatccttt cacagagtgc caggctaaag agctgaactt tgtggtggaa    60
gagacagacc cctatgtgc tctgtagaca cctgtgatga agtagaactc atgaggatat    120
gaagagaaac atttgtaatt tgagtgatta aactaggaac gaaagaggag gggagaaata   180
ggaagagaga atcaccggcc ctgttgactg atttgagctg ggaatgaaga agaaaaccct   240
gcaggtgtgg gcaccaatgt ttgaaacccc cacagtgtga gtctcaactc tgtgtga       297
```

<210> SEQ ID NO 340
<211> LENGTH: 223
<212> TYPE: DNA
<213> ORGANISM: Homo sapiens

<400> SEQUENCE: 340

```
ccatgtcagc ctggatagag gtatatgacg tgtgccaaga atttatccca gactcccctg    60
tgtgacagct tcataataaa gttacttaac tgtgcctctt cctccttcct ctccccacac   120
aggatggatg ggcatctttc tccttgacca ccctactctc ccttcctccc ctgatcacct   180
cccctccctg ctctcccctg gtgatggact tctaacatga gat                      223
```

<210> SEQ ID NO 341
<211> LENGTH: 238
<212> TYPE: DNA

<213> ORGANISM: Homo sapiens

<400> SEQUENCE: 341

| | | | | |
|---|---|---|---|---|
| actggtatat | tattgcttca | tgttttgtac | catcataaga | ttttgtgcag | attttttta | 60 |
| cagaaattat | tatttttat | gacaatatga | cacttgtaaa | ttgttgtttc | aaaatgaaca | 120 |
| gcgaagcctt | aactttaaat | gacatttgta | ttttcagaca | ctgagtagca | taaaaaccac | 180 |
| atagaactga | actgtaactt | aaattccaaa | ctatgactac | tacattccaa | agaaacag | 238 |

<210> SEQ ID NO 342
<211> LENGTH: 129
<212> TYPE: DNA
<213> ORGANISM: Homo sapiens

<400> SEQUENCE: 342

| | | | | |
|---|---|---|---|---|
| cgtccccaac | atgcatctca | ctctgggtgt | cttggtcttt | tatttttgt | aagtgtcatt | 60 |
| tgtataactc | taaacgccca | tgatagtagc | ttcaaactgg | aaatagcgaa | ataaataac | 120 |
| tcagtctgc | | | | | | 129 |

<210> SEQ ID NO 343
<211> LENGTH: 277
<212> TYPE: DNA
<213> ORGANISM: Homo sapiens

<400> SEQUENCE: 343

| | | | | |
|---|---|---|---|---|
| tggaggattc | aagatgagca | ggtatgtttt | ctgctttcaa | taactcattt | tctgctgcag | 60 |
| agatagcctt | gtaagcaagc | aaaggaaaac | tttgacattt | ctctgcaaag | ataatgcatt | 120 |
| acatataagg | gtgtgtctgg | gagggtacca | ggtgcctgtc | agcaaaagtt | gcaaaaacag | 180 |
| cttgataagg | gtattaagtg | ggcctgttgg | gaaaggcagg | agtgtcaaat | gtcggacaga | 240 |
| actccagaca | gagaaatcca | gatatccagt | aggttag | | | 277 |

<210> SEQ ID NO 344
<211> LENGTH: 231
<212> TYPE: DNA
<213> ORGANISM: Homo sapiens
<220> FEATURE:
<221> NAME/KEY: modified_base
<222> LOCATION: (92)..(92)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (160)..(160)
<223> OTHER INFORMATION: a, c, t, g, unknown or other
<220> FEATURE:
<221> NAME/KEY: modified_base
<222> LOCATION: (169)..(170)
<223> OTHER INFORMATION: a, c, t, g, unknown or other
<220> FEATURE:
<221> NAME/KEY: modified_base
<222> LOCATION: (172)..(176)
<223> OTHER INFORMATION: a, c, t, g, unknown or other
<220> FEATURE:
<221> NAME/KEY: modified_base
<222> LOCATION: (178)..(180)
<223> OTHER INFORMATION: a, c, t, g, unknown or other
<220> FEATURE:
<221> NAME/KEY: modified_base
<222> LOCATION: (182)..(182)
<223> OTHER INFORMATION: a, c, t, g, unknown or other
<220> FEATURE:
<221> NAME/KEY: modified_base

```
<222> LOCATION: (186)..(187)
<223> OTHER INFORMATION: a, c, t, g, unknown or other

<400> SEQUENCE: 344
gaatggcaaa acacaaatgg caacataaat gtccatttga cttacctaac ttcacaactt      60
tcaagttgag gatgtcattt attcttgaat tntgtttttt tactnagatg ctttcaatta    120
atagccctat attttgtgc aggcgaactg tataacaggn ataaaaaann annnnnannn     180
antgannagg aggagaaatt ctcacagaac accatatgag ctttagacca a             231

<210> SEQ ID NO 345
<211> LENGTH: 262
<212> TYPE: DNA
<213> ORGANISM: Homo sapiens

<400> SEQUENCE: 345
gaggtgtgat tttaaggcat tgttatattt tttttatt gtgagtgttt taaaattttg      60
tatttctttt aaactttta ttttagaaaa atttccaaca tatatagaag tagactattg    120
taaggaaccc ttatgtaccc tccaccagct tcaacaacta tcaacaaaag tttgatcttg    180
ttttaaccac attcctttcc aattttgtg tttaccccca gattattttg aagcaaattc    240
ctgacctcat aacattttca aa                                             262

<210> SEQ ID NO 346
<211> LENGTH: 187
<212> TYPE: DNA
<213> ORGANISM: Homo sapiens

<400> SEQUENCE: 346
ttcagtttgt cctcataggg aatcaagtat tttagctagg tgatgtcttg caagtacgtt      60
ccactttgtt acaatctact atctgtatat actatttgta tcttaattct tttatgagat    120
gttctgtaac attttctca ctttgacaaa tgtttttaga ctgtacagtc aagatctggc     180
gcttggg                                                             187

<210> SEQ ID NO 347
<211> LENGTH: 180
<212> TYPE: DNA
<213> ORGANISM: Homo sapiens

<400> SEQUENCE: 347
acagtgattc cccacgtgtg ttcatctgca cccaccgagc caggcagagg ccagccctcc      60
gtggtgcaca cagcacgcgc ctcagtccat cccattttag tctttaaacc ctcaggaagt    120
cacagtctcc ggacaccaca ccacatgagc ccaacaggtc cacgatggat ccaccagtcc    180

<210> SEQ ID NO 348
<211> LENGTH: 55
<212> TYPE: DNA
<213> ORGANISM: Homo sapiens

<400> SEQUENCE: 348
cagatcgaca cgcagctagc ctcctgcatt gtatggttat aaatagcacc ctagt           55

<210> SEQ ID NO 349
<211> LENGTH: 207
<212> TYPE: DNA
<213> ORGANISM: Homo sapiens

<400> SEQUENCE: 349
```

```
aagtgttcta caaaagaatc cctgtggtta gcttactctt aggttagatc ttctaataag    60
gctgaaattc aaaatcaaaa ccttagtgtg tccgagtcca gcctgggttc cagcattctg   120
ttcaggccac ttctgaacgg ccgaaggtgc cccattccag acctgcccat ttgatggaca   180
gagcagacag cccggaacag attcaag                                       207

<210> SEQ ID NO 350
<211> LENGTH: 241
<212> TYPE: DNA
<213> ORGANISM: Homo sapiens
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (97)..(97)
<223> OTHER INFORMATION: a, c, t, g, unknown or other

<400> SEQUENCE: 350
taagaattta tgaaactggg caagttattt cctgggactc aatggtaaag acacagcagt    60
aatccaaatt ttccatcttt gaaattttcc atncttncag tcaatattag taatacctgg   120
gtcaaggggg agagttaggc ataccaatta atgatcatca gaaatgacat agtcctacaa   180
aagcaaagaa aatttagaga cactttctta aaaatacgac tcttggtact gttgaagaaa   240
a                                                                   241

<210> SEQ ID NO 351
<211> LENGTH: 261
<212> TYPE: DNA
<213> ORGANISM: Homo sapiens

<400> SEQUENCE: 351
agccgctgcc aagtctgtat gagaagaaca taatgaagcc tgactcagct aatgtcacaa    60
catggtgcta cttcttcttc tttttgttaa cagcaacgaa ccctagaaat atatcctgtg   120
tacctcactg tccaatatga aaaccgtaaa gtgccttata ggaatttgcg taactaacac   180
accctgcttc attgacctct acttgctgaa ggagaaaaag acagcgataa gctttcaata   240
gtggcatacc aaatggcact t                                             261

<210> SEQ ID NO 352
<211> LENGTH: 274
<212> TYPE: DNA
<213> ORGANISM: Homo sapiens

<400> SEQUENCE: 352
ggttgagttt gtccattgct agggagagac ttccagtaat aaaatttact attctagatg    60
cttctactgt tatgttttat ctgcccattt atctttctta gttaccagga gaaatgtgtg   120
acacctatat tataatgaaa acaatcttat tacttatagt ttatctatat taaacaaatt   180
taattgcatt ttaaagcatt cttttgatatt gttgcttttg caataaatat ggataatctt   240
ggttataagg gagttaaaac aatgctgtaa taaa                               274

<210> SEQ ID NO 353
<211> LENGTH: 179
<212> TYPE: DNA
<213> ORGANISM: Homo sapiens

<400> SEQUENCE: 353
tcatggaatg ctacatgctt tctgtttttt tcattttgga tttctccaaa actaactgaa    60
```

```
tttaagcttc aggtcccttt gtatgcagta gaaaggaatt attaaaaaca ccaccaaga      120 aaataaatat atcctacttg aaatttactt tatggactta cccactgcta gaataaatg      179
```

<210> SEQ ID NO 354
<211> LENGTH: 249
<212> TYPE: DNA
<213> ORGANISM: Homo sapiens

<400> SEQUENCE: 354

```
cggttgttaa aactggttta gcacaattta tattttccct ctcttgcctt ttttatttgc      60
aataaaaggt attgagccat tttttaaatg acattttga taaattatgt ttgtactagt      120
tgatgaagga gttttttta acctgtttat ataatttgc agcagaagcc aaatttttg       180 tatattaaag caccaaattc atgtacagca tgcatcacgg atcaatagac tgtacttatt      240
ttccaataa                                                             249
```

<210> SEQ ID NO 355
<211> LENGTH: 64
<212> TYPE: DNA
<213> ORGANISM: Homo sapiens

<400> SEQUENCE: 355

```
ccatgaagga gcaagttttg tatttgtgac ctcagctttg ggaataaagg atcttttgaa      60
ggcc                                                                  64
```

<210> SEQ ID NO 356
<211> LENGTH: 57
<212> TYPE: DNA
<213> ORGANISM: Homo sapiens

<400> SEQUENCE: 356

```
atgaggcaga atctggttgg gtatgtttct tatatatgtt tgaagcagat ggctgac         57
```

<210> SEQ ID NO 357
<211> LENGTH: 141
<212> TYPE: DNA
<213> ORGANISM: Homo sapiens

<400> SEQUENCE: 357

```
attttgcct ttccgtttct gtctatgatg taggcttctg aggagaacca agaagcttgg      60
ctttagtggt agaatgacag aacttaggga tcccttgcag gctagaacaa agttctgacc     120
cttagaccaa atctttatgt t                                               141
```

<210> SEQ ID NO 358
<211> LENGTH: 108
<212> TYPE: DNA
<213> ORGANISM: Homo sapiens

<400> SEQUENCE: 358

```
gaggaggtgg gcctcgttag actgctcaga ttactggaac ctcgttatca catcccattc     60
tacaagtttt tcactgaatg tttcctgaca tctataaatg agggtgcc                  108
```

<210> SEQ ID NO 359
<211> LENGTH: 158
<212> TYPE: DNA
<213> ORGANISM: Homo sapiens

<400> SEQUENCE: 359

```
gttcaaatga tctacactta cattttgcaa atcttttttt ttaaattttt taaattttat    60 atttttttc cagccaactc aaggccaaaa aaaatttctt aatatagtta ttatgcgagg    120
ggaggggaag caaaggagca caggtagtcc acagaata                            158

<210> SEQ ID NO 360
<211> LENGTH: 157
<212> TYPE: DNA
<213> ORGANISM: Homo sapiens

<400> SEQUENCE: 360
aggtggtttt gataacacac ttataaggct ttctgtaaaa ggtactatag aagggcgaag    60
aatcgttcaa ctgtcaatca gcctcttgat tctttgtaaa ttgccagggt gggtgggtac   120
atatctcttc ttgattctgc atttcatact taactat                            157

<210> SEQ ID NO 361
<211> LENGTH: 273
<212> TYPE: DNA
<213> ORGANISM: Homo sapiens

<400> SEQUENCE: 361
gactgagtga gtaactgcaa gctacagggg gcagcttacg tatggcacac agggtggggc    60
tagcttggtt tcataggctc tctgtggatt ggatgattta ataattttg gtgggccctg   120 gggtttaggg actgtcccta gttgtttggt gctaggtccc aggcagatt agggcagatg   180 tgagtgtgag agcatgataa ggaaagtctt caaggtgtgg aattactcaa ctgctggaga   240
aagggaattt atcagccttt agccagggcc tca                                273

<210> SEQ ID NO 362
<211> LENGTH: 257
<212> TYPE: DNA
<213> ORGANISM: Homo sapiens

<400> SEQUENCE: 362
gaaagcctga gtttgcaacc agttgtaggg ttttttgttgt gtttttttttt tttttttgaa    60 ataaaactat aatataaatt ctcctattaa ataaaattat tttaagtttt agtgtcaaaa   120
gtgagatgct gagagtaggt gataatgtat attttacaga gtggggttg gcaggatggt   180 gacattgaac atgattgctc tctgtctctt ttttcagctt atgggtattt atcttctatt   240
agtatttgta tcttcag                                                  257

<210> SEQ ID NO 363
<211> LENGTH: 268
<212> TYPE: DNA
<213> ORGANISM: Homo sapiens

<400> SEQUENCE: 363
atgagtcaaa atccgctctc catgcttact cttgacaccc cattgaagcc actcattgtg    60
tgtgcgtctg ggtgtgaagt ccagctccgt gtggtcctgt gcttgtactg ccctgctttg   120
cagttccttt gcacttactc atcgagtgct gttttgaaat gctgacatta tataaacgta   180
aaagaaaatg taaaaaaaaa aaacccacac acaaacaaac ccatacgatc tgtatttgta   240
tatacacgtg tccgtacaag tataacta                                      268

<210> SEQ ID NO 364
<211> LENGTH: 290
<212> TYPE: DNA
<213> ORGANISM: Homo sapiens
```

<400> SEQUENCE: 364

```
gaccaaatgg attagactgt aaactgcaaa gtgctgtccg cacatgaggt catctgatta      60
ctgtcctcag atctcttttg tagaggattt caatgtattt ctttatcatt tgagtgtgtg     120
tgtgatggac gaatatgtgt gtgagtttga gaagcatatc gttcgtgtcc agttactttg     180
caaatttgtg gacatttgtg attggacaga ggggtttgtg ctgtggccta acacttgcca     240
agtgaggtgt aggttatgcc tatatgcaaa ttaaacttca cctttcttga                290
```

<210> SEQ ID NO 365
<211> LENGTH: 205
<212> TYPE: DNA
<213> ORGANISM: Homo sapiens

<400> SEQUENCE: 365

```
cctttctaag gatgagggaa tccacaacag actttctcta gaaaacacta atgatggaca      60 acttttggt gtcatcaatg agttggctac taccttgatg taaaaatttg taaggaaaat      120
tttcaccatt tcgagtgtca agtgtatttt taactgtctg gtttgtactt ttatgacttt     180
tgtactacca aagcggagtt aaaaa                                            205
```

<210> SEQ ID NO 366
<211> LENGTH: 278
<212> TYPE: DNA
<213> ORGANISM: Homo sapiens

<400> SEQUENCE: 366

```
ctatcaggta ctgtgctcat ctgaacaaca aacctcaaca acacgcaatt tatccatgta      60
attaacctgc acatgtaccc ccgaaaccta aataaaagt tcaaaaaaaa cctgtggtat      120
ttaaataggt attgtgtcta aaaatgcatg ctatctaaaa atgtagttttt attgcactgt    180 ataagaatac gagaggttta aaatagacac tctaaaagtt ataagcccta atttacatat     240
attctctagc ctttctccac cttctatcta ccaaaaaa                              278
```

<210> SEQ ID NO 367
<211> LENGTH: 41
<212> TYPE: DNA
<213> ORGANISM: Homo sapiens

<400> SEQUENCE: 367

```
tcctcatggt ggcagcgctc atagcgaaag cctactgtaa t                          41
```

<210> SEQ ID NO 368
<211> LENGTH: 133
<212> TYPE: DNA
<213> ORGANISM: Homo sapiens

<400> SEQUENCE: 368

```
aatgcagaat attcctctga acacttccct catacatcat tcaatattat aaattaaaca      60
caaagagcct ctccacttag attttatca tgcatcctac attgtaatgt ctttactctt      120
ccatagaaaa ggt                                                         133
```

<210> SEQ ID NO 369
<211> LENGTH: 74
<212> TYPE: DNA
<213> ORGANISM: Homo sapiens

<400> SEQUENCE: 369

```
ggtgcaatta ttatactgcg aaaatgaaaa tattgcatac taaacagtac ctagggtatg    60
atctcaatgt aaaa                                                      74

<210> SEQ ID NO 370
<211> LENGTH: 172
<212> TYPE: DNA
<213> ORGANISM: Homo sapiens

<400> SEQUENCE: 370
aactgtgacc gtttctgtgt gaagattttt agctgtattt gtggtctctg tatttatatt    60
tatgtttagc accgtcagtg ttcctatcca atttcaaaaa aggaaaaaaa agagggaaaa   120
ttacaaaaag agagaaaaaa agtgaatgac gtttgtttag ccagtaggag aa           172

<210> SEQ ID NO 371
<211> LENGTH: 258
<212> TYPE: DNA
<213> ORGANISM: Homo sapiens

<400> SEQUENCE: 371
actcaaggct gtgaacaaac atacgctgct ttattctttc caattttttct cttgtttttct    60 agaactctta tccatatgtt tttaaaataa gtacctaaaa gtggtttgat agtgtcctaa   120 acgactttt taacttccta aatggaaaga gcataacaat gtagttgatt ggtaagattt    180
acagggattt ggtttctgag tttgaggcac attcccagtg aataagctga gtcccatacc   240
acactcaaaa ggttttaa                                                 258

<210> SEQ ID NO 372
<211> LENGTH: 103
<212> TYPE: DNA
<213> ORGANISM: Homo sapiens

<400> SEQUENCE: 372
attaaagtac tcaagttagt tgttttgcag agatgttgcc ttcagatgtt aatcaggtct    60
ctcaagtttc atggagtcta tgctgatcct ttaattgaca aat                     103

<210> SEQ ID NO 373
<211> LENGTH: 258
<212> TYPE: DNA
<213> ORGANISM: Homo sapiens

<400> SEQUENCE: 373
ggatgaagtg gcacacactc taactgaaag cagagtatta agaacacta gacatccctt     60 tttaacatcc ttgaaatatt ccttccagac aaaagaccgt tgtgtttttg tgatggaata   120
tgttaatggg ggcgagctgt ttttccattt gtcgagagag cgggtgttct ctgaggaccg   180
cacacgtttc tatggtgcag aaattgtctc tgccttggac tatctacatt ccggaaagat   240
tgtgtaccgt gatctcaa                                                 258

<210> SEQ ID NO 374
<211> LENGTH: 252
<212> TYPE: DNA
<213> ORGANISM: Homo sapiens

<400> SEQUENCE: 374
ggttctgtaa ggtctttatt tcccataagt aaatattgcc atgggagggg ggtggaggtg    60
gcaaggaagg ggtgaagtgc tagtatgcaa gtgggcagca attattttg tgttaatcag    120 cagtacaatt tgatcgttgg catggttaaa aaatggaata taagattagc tgttttgtat   180
```

```
tttgatgacc aattacgctg tattttaaca cgatgtatgt ctgtttttgt ggtgctctag    240
tggtaaataa at                                                        252

<210> SEQ ID NO 375
<211> LENGTH: 210
<212> TYPE: DNA
<213> ORGANISM: Homo sapiens

<400> SEQUENCE: 375
tttcaagatc ttttgctcac aattcactgc aactgagggg atgtgaatat cattatgcaa    60
taaattaaga gccacagttg gctgaggtga tatgaaagcc aacctgccta agggggggtat   120 gaaagatgtg tatctttcca aacttttaaa acaacgtaag tctgagataa aacatattt    180 gatggcactg tttggaaaga ggtgtcctta                                     210

<210> SEQ ID NO 376
<211> LENGTH: 258
<212> TYPE: DNA
<213> ORGANISM: Homo sapiens

<400> SEQUENCE: 376
ctcaccagga ctcgtctctc cattcccgtc agagtttgct ttgatttccc tttcctttcc    60
ttctcgggga ccagttctta cttccttta ttttagctt tgcactccat gtggtttcag     120
ggttcagttt gatccatcaa aaggttcttt ttttataatc ccttttgaaa atgataatca   180
aaggaagaga tgtggtgttt ggtcatgtgg aaaactcaat gtataattta gacgtctgtc   240
aaaaatccga caaataaa                                                  258

<210> SEQ ID NO 377
<211> LENGTH: 218
<212> TYPE: DNA
<213> ORGANISM: Homo sapiens

<400> SEQUENCE: 377
gtttcaattg attcacaact ttaaaaaata tccacagagg cgtaagagga gatattgtat    60
tgcacccacg aaccagtttt atgctgttta agaaagggac attcaagaaa caaaaaggga   120
gctttgggaa atttgaacaa taaataatag tagaataaaa aattcagaga agtttggat    180 gataaatttg agccaatctc ccagtaagca gagcaaaa                            218

<210> SEQ ID NO 378
<211> LENGTH: 267
<212> TYPE: DNA
<213> ORGANISM: Homo sapiens

<400> SEQUENCE: 378
atgactgtgc tagagccacc ctctcacttt agcctcctga gtagctggga ctacaggtgc    60
ttcccactgt gcctggccaa ttaacaattt cattttat tttagtagag atgagatctc     120
actatgttgc ccaggctggt cctgaactcc tgagctcaag agatcctccc accttggcct   180
cccaaagtac tgggattaca aacaagagcc actgtgcctg accaggctct aagattgcta   240
atctggctat agaaggacta atgttag                                        267

<210> SEQ ID NO 379
<211> LENGTH: 230
<212> TYPE: DNA
<213> ORGANISM: Homo sapiens
```

<400> SEQUENCE: 379

```
aagccgaggg gcccgagact ctgcagcggg gccagaaaga gaagagtggg ggaggaggcc      60
gggagtggtg catggaccag ggggtagagg gaggtgggtg tggacctggg gtcgggcgcc     120
agtcagcttg cagcctatga aggacggaag ggagggctac agagataggg gaagagtggg     180
gctgaggata gccagagcgg cttggcacac agttttaggg taaaagcatc                230
```

<210> SEQ ID NO 380
<211> LENGTH: 196
<212> TYPE: DNA
<213> ORGANISM: Homo sapiens

<400> SEQUENCE: 380

```
tttatttata ccaagcctcc tcctgaaatt tctcttcctt tctttctacc tacccaagac      60
ataccacgtg cttcaataac cagtcccttc ctcctacaaa cactcaaacc tggaaagcac     120
tcttgctttt ctgaagtcct ctatacttag tgtaactctt ctgtgatgaa gattaaagtg     180
tattatggca actctc                                                    196
```

<210> SEQ ID NO 381
<211> LENGTH: 267
<212> TYPE: DNA
<213> ORGANISM: Homo sapiens

<400> SEQUENCE: 381

```
aggcattata tatactacac agagtacaat taaaccataa ttgggaatta tatttttgttt     60
ttttcttccc aggcaataca cctctgaaca tgtgtgtgat aaatgggttt gctaatgtgc    120
tgttttaaag tataaagcat aatatgttttt ggttaacaca atgtactttt tgaactataa    180
atctttatt taatatggaa atgtttggaa caggagatgc aagccactaa cagagaactt     240
taataattct accctgtatt ttataaa                                        267
```

<210> SEQ ID NO 382
<211> LENGTH: 280
<212> TYPE: DNA
<213> ORGANISM: Homo sapiens

<400> SEQUENCE: 382

```
acccacactt aaactaaagg ctaagaatat aggcttgatg ggaaattgaa ggtaggctga      60
gtattgggaa tccaaattga attttgattc tccttggcag tgaactactt tgaagaagtg    120
gtcaatgggt tgttgctgcc atgagcatgt acaacctttg gagctagaag ctcctcagga    180
aagccagttc tccaagtttt taacctgtgg cactgaaagg aatgttgagt tacctcttca    240
tgttttagac agcaaacct atccattaaa gtacttgtta                           280
```

<210> SEQ ID NO 383
<211> LENGTH: 72
<212> TYPE: DNA
<213> ORGANISM: Homo sapiens

<400> SEQUENCE: 383

```
acatgagtat ggaatggtgt tttattatga ctttagtttg cattttcctc aattctcgtt      60
aaatccttca tt                                                         72
```

<210> SEQ ID NO 384
<211> LENGTH: 260
<212> TYPE: DNA
<213> ORGANISM: Homo sapiens

<400> SEQUENCE: 384

```
gagtaggttc ggtctgaaag gtgtggcctt tatatttgat ccacacacgt tggtcttttta      60
accgtgctga gcagaaaaca aaacaggtta agaagagccg ggtggcagct gacagaggaa     120
gccgctcaaa taccttcaca ataaatagtg gcaatatata tatagtttaa gaaggctctc     180
catttggcat cgtttaattt atatgttatg ttctaagcac agctctcttc tcctattttc     240
atcctgcaag caactcaaaa                                                 260
```

<210> SEQ ID NO 385
<211> LENGTH: 222
<212> TYPE: DNA
<213> ORGANISM: Homo sapiens

<400> SEQUENCE: 385

```
atgattatag aaggctgtct tagtgcaaaa aacatactta catttcagac atatccaaag      60
ggaatactca cattttgtta agaagttgaa ctatgactgg agtaaaccat gtattccctt     120
atcttttact ttttttctgt gacatttatg tctcatgtaa tttgcattac tctggtggat     180
tgttctagta ctgtattggg cttcttcgtt aatagattat tt                        222
```

<210> SEQ ID NO 386
<211> LENGTH: 216
<212> TYPE: DNA
<213> ORGANISM: Homo sapiens

<400> SEQUENCE: 386

```
gcaatatatt tgtgattccc catgtaattc ttcaatgtta aacagtgcag tcctctttcg      60
aaagctaaga tgaccatgcg ccctttcctc tgtacatata cccttaagaa cgcccctcc     120
acacactgcc ccccagtata tgccgcattg tactgctgtg ttatatgcta tgtacatgtc     180
agaaaccatt agcattgcat gcaggtttca tattct                               216
```

<210> SEQ ID NO 387
<211> LENGTH: 35
<212> TYPE: DNA
<213> ORGANISM: Homo sapiens

<400> SEQUENCE: 387

```
ttggatagca gctatcttgt tggatgtgag gtgga                                 35
```

<210> SEQ ID NO 388
<211> LENGTH: 258
<212> TYPE: DNA
<213> ORGANISM: Homo sapiens

<400> SEQUENCE: 388

```
atgaaaggtg gaagttctac ctagatttga atgagtgttt ttttaaggga atgagaatgt      60
catggtgcta aacctgacaa ataagagatc attgaaatgc tgaaaatttt aacagttttt     120
ttaaaagtat tgaggggggca aaaattacca attatggtat acaaaaataa gcctataaat     180
gtgtttcaca ttgctaactt gagtttcagt tgattcagtt tgtaataact agtaatgagc     240
ttctgtttac aataaaaa                                                   258
```

<210> SEQ ID NO 389
<211> LENGTH: 275
<212> TYPE: DNA
<213> ORGANISM: Homo sapiens
<220> FEATURE:

```
<221> NAME/KEY: modified_base
<222> LOCATION: (195)..(195)
<223> OTHER INFORMATION: a, c, t, g, unknown or other

<400> SEQUENCE: 389
ccacagtgtt cccactaatg ctattttta atttttttaat ttagtttgtc ataatttggt    60
ttcatcaact cctttgtttt ttccttcttt tttttttttt gagatgaggt ctcactatct   120
tgcccagact ggtttcgaat tgccctccag caattctccc acctcagcct tcagagtagc   180
tggcattgtg ggtangcacc actgtgccca gctcctgttt tataataaat aagccagagc   240
tctatctcca aatggtgcaa atcatcaatg ctatt                               275

<210> SEQ ID NO 390
<211> LENGTH: 281
<212> TYPE: DNA
<213> ORGANISM: Homo sapiens

<400> SEQUENCE: 390
gggcccctgg tatttatagg gtccaagagg aggcacctgc ttttcaactg caccctcagt    60
gctgcctctt cacggcccct aaacgtttcc ctttgaggtt gtgatgctgg gaatcacaga   120
cttcactctc tgcctgcacc cttccccgag gtctcatctt ttctgggtcc cacatctttg   180
taataatgtg aaaaagcaca atttgtctga tcacccccca ggtggttccc caccttatta   240
tcactacctg atccgagtta ctgcaataag tacggtgtcg c                        281

<210> SEQ ID NO 391
<211> LENGTH: 274
<212> TYPE: DNA
<213> ORGANISM: Homo sapiens

<400> SEQUENCE: 391
tgctcagtgt catgctgtgt gtgcatgtgt gtgctgtgtg ttttgtgtgt gtgctgtgtt    60
catgtgtgct gtgcatgcgt gtgtgctgtg tgtgcctgtg tgtgcggtgt gctgtgtcct   120
tgtgtgtgct gtgtgtgcgt gtgctgtgtg catgtgtgtg ctgtgttatg tcgtgtgtgc   180
agtgtgtgct gtgtccgatg tgtgctgtgt acacatgaga gagcagagtg tacatgtgtg   240
tgctgagtct atcagaagat gtgtgtagct gcgg                                274

<210> SEQ ID NO 392
<211> LENGTH: 89
<212> TYPE: DNA
<213> ORGANISM: Homo sapiens

<400> SEQUENCE: 392
tgtgcccagc ctaagccatt tcttaaaata aaaatgctaa aggactagta agtaaaaata    60
aaacttccta tgggatttcc cagtggaaa                                      89

<210> SEQ ID NO 393
<211> LENGTH: 72
<212> TYPE: DNA
<213> ORGANISM: Homo sapiens

<400> SEQUENCE: 393
gggagattgg tggcccttgc caggaagtgt cttaacactt tgtggatact gctgcctgtt    60
gtctttaaaa gc                                                        72

<210> SEQ ID NO 394
<211> LENGTH: 177
```

```
<212> TYPE: DNA
<213> ORGANISM: Homo sapiens

<400> SEQUENCE: 394
gataacagtc ttgcatgttt atcatgttac aatttaatat tccatcctgc ccaacccttc    60
ctttcccatc ctcaaaaaag ggccatttta tgatgcattg cacaccctct ggggaaattg   120
atctttaaat tttgagacag tataaggaaa atctggttgg tgtcttacaa gtgagct     177

<210> SEQ ID NO 395
<211> LENGTH: 117
<212> TYPE: DNA
<213> ORGANISM: Homo sapiens

<400> SEQUENCE: 395
ttaaacagtc tagagtgaag ggaatgtttt aaaatccaga ggcgatcaag tgaagccaac    60
ctttggaggc ccgtagaagt catttggagg aatttggact tcgtgcagta ggaaaga     117

<210> SEQ ID NO 396
<211> LENGTH: 164
<212> TYPE: DNA
<213> ORGANISM: Homo sapiens

<400> SEQUENCE: 396
caggggggcc tgagagtaac agtgaggatt atccaggtgc cctgagtgta acagtgagga    60
ttatccaggg gggccctgag tgtaacagcg aggattatcc aggggccct gagtgcaaca   120 gtgaggatta tccagggggg cctgagtgta acagtgagga ttat                   164

<210> SEQ ID NO 397
<211> LENGTH: 259
<212> TYPE: DNA
<213> ORGANISM: Homo sapiens
<220> FEATURE:
<221> NAME/KEY: modified_base
<222> LOCATION: (139)..(139)
<223> OTHER INFORMATION: a, c, t, g, unknown or other

<400> SEQUENCE: 397
caaaaatgag tcacaactct tgattccatc cacctccaaa atccaggtat tttccttaat    60
tctcattctt tcacaactcc acatatatcc atatcctcat tatctcagga caacgtgacc   120
atttcttgcc acttcccanc acttccatgc ctaccaaaga agcctatctt ctctcaccag   180
gaccactgaa aaagtcttgc aactgatttc ccttgtcctc ttcttgcctc tctacagtca   240
attctctata caacagtca                                                259

<210> SEQ ID NO 398
<211> LENGTH: 104
<212> TYPE: DNA
<213> ORGANISM: Homo sapiens

<400> SEQUENCE: 398
tgctgcggtc gcctctctca ggctcccccg ctccccggg cctccgcttc tcagccgggt    60
gctgtgcgtt tgagtgtgtg ctgctgctcg ctgtgtgtgc tgtg                   104

<210> SEQ ID NO 399
<211> LENGTH: 147
<212> TYPE: DNA
<213> ORGANISM: Homo sapiens

<400> SEQUENCE: 399
```

| | |
|---|---|
| tatatacatg gtgctcaata gcaacatctt agcagatgaa gcagtttatg attccactcc | 60 |
| ctcctgtatg acaggtagcc actatactga atcaaggtgc tgaactcaaa tcacaaaatt | 120 |
| ctggcttacc gatacaacaa ccaatac | 147 |

<210> SEQ ID NO 400
<211> LENGTH: 208
<212> TYPE: DNA
<213> ORGANISM: Homo sapiens

<400> SEQUENCE: 400

| | |
|---|---|
| ctctgagttt tatatgctgg aatccaatgc agagttggtt tgggactgtg atcaagacac | 60 |
| cttttattaa taaagaagag acacaggtgt agatatgtat atacaaaaag atgtacggtc | 120 |
| tggccaaacc accttcccag cctttatgca aaaaaggggg agaatcaaag ctttcatttc | 180 |
| agaaatgttg cgtggaaaag tatctgta | 208 |

<210> SEQ ID NO 401
<211> LENGTH: 139
<212> TYPE: DNA
<213> ORGANISM: Homo sapiens

<400> SEQUENCE: 401

| | |
|---|---|
| aaaaagagag aatatgtcct gtgttagctt gcttaggaaa taagagagag agagagagg | 60 |
| gagggaggga aagagagaaa gagagagaga gaaagagagt gagagaaaga gagagcaaga | 120 |
| gagcaagagt aagaaagaa | 139 |

<210> SEQ ID NO 402
<211> LENGTH: 243
<212> TYPE: DNA
<213> ORGANISM: Homo sapiens

<400> SEQUENCE: 402

| | |
|---|---|
| ggcagtagat agtcaaagtc aaatcatttc taatgtttta aaaatgtgct ggtcatttc | 60 |
| tttgaaattg acttaactat tttcctttga agagtctgta gcacagaaac agtaaaaaat | 120 |
| ttaacttcat gacctaatgt aaaaaagagt gtttgaaggt ttacacaggt ccaggccttg | 180 |
| ctttgttacc attctgatgt tggactaatt gactaatcac ctacttatca gacaggaaac | 240 |
| ttg | 243 |

<210> SEQ ID NO 403
<211> LENGTH: 298
<212> TYPE: DNA
<213> ORGANISM: Homo sapiens

<400> SEQUENCE: 403

| | |
|---|---|
| agaggcccat gccaacagtc taatctaaga gattagtctt tcaaactcac catccagttg | 60 |
| cctgttacag aataactctt cttaactaaa aacctagtca acaaggaag ctgtaggtga | 120 |
| ggagatctgt ataatattct aatttaagta agtttgagtt tagtcactgc aaatttgact | 180 |
| gtgactttaa tctaaattac tatgtaaaca aaaagtagat agtttcactt tttaaaaat | 240 |
| ccattactgt tttgcatttc aaaagttgga ttaaagggtt gtaactgact acagcatg | 298 |

<210> SEQ ID NO 404
<211> LENGTH: 193
<212> TYPE: DNA
<213> ORGANISM: Homo sapiens

<400> SEQUENCE: 404

```
agagggaact gtgcagtccc caggccgccc cggctccggg ctagaggcaa taaataaacc    60
cgatcctgcc gggcacagcc gcgcccgcgc ctccggcgcc gtccccgggc tgacggggga   120
gggagcggag aagcgagcgc agattctgcg tataaatcag ctctggagca gacacagccc   180
ggctgtgaaa agc                                                     193

<210> SEQ ID NO 405
<211> LENGTH: 275
<212> TYPE: DNA
<213> ORGANISM: Homo sapiens

<400> SEQUENCE: 405
gtaggtttgg gagtataacg gtcacccagg aggggggtga agacggagaa gacttacata    60
gcacggtcag gttagggctg gacagatgag gaagagctag caaagggggc ttgaggagca   120
gtggccacta agacaggagt gtgacatttt agaagccaaa agaagaccat gtaattcaag   180
ggagaggtat gatttgctgg gtcagatcta aaaataaatc acacgttttt ttaaactgta   240
gtaattaacc actgaaaact tatgagtgat ccaat                              275

<210> SEQ ID NO 406
<211> LENGTH: 143
<212> TYPE: DNA
<213> ORGANISM: Homo sapiens

<400> SEQUENCE: 406
gtgtgagcca ctgctggcta attttttgtat tttcagtaga gacggggctt caccatattg    60
gccaggctgg tcttgaactc cttccctcgc tcccccaaaa atttgaattt ttttttcaac   120
acttttacac ctgttatgga aaa                                          143

<210> SEQ ID NO 407
<211> LENGTH: 263
<212> TYPE: DNA
<213> ORGANISM: Homo sapiens

<400> SEQUENCE: 407
gagatcactt ggtaactggt ttcatgtgta tccaaaaatc agcatttgga tttaagcttt    60
ctgaatttgg tagtttaaga aacagattta gttttcagt ggttttaact catgtgaaat   120
aatgattttc caccagcttt gatgcaaaga gatataattt taatgaacga tttatccagc   180
agtttgttcc aggggttgcc tctccttatt tacggggatt actttgtaca tgcagataag   240
ttttcgcaaa cctatttcca ttt                                          263

<210> SEQ ID NO 408
<211> LENGTH: 300
<212> TYPE: DNA
<213> ORGANISM: Homo sapiens

<400> SEQUENCE: 408
gatgataatc tttactggtg aaaaggatgg aaaaataaat caacaaatgc aaccagtttg    60
tgagaaaaaa aaaaaaaagc cgaaaaaaaa aaaaaaaaca cctgaatgcg gaagagctcg   120
gctcccgttt agcattttgt acttaaggaa ataaaaaacc aacaaggat ctcacatttt   180 cttaaaaagt gaagattgct gtatactatt tattcaactt ataatttatg ttactccttg   240
atctttgtct tttgtcatga caaagcattt atttaataaa gttatgcatt cagttcccaa   300

<210> SEQ ID NO 409
```

```
<211> LENGTH: 238
<212> TYPE: DNA
<213> ORGANISM: Homo sapiens

<400> SEQUENCE: 409
agaattccag ataaacacac agcctttccc atacctttt  ttttcttact ataaatatt      60
ataagatcca ttgatgtcca ataataccca ccgagcatct cttcacctct cctcctcttg    120
gtccacttgc taatgcccag ttttcttctc catttccact ttttcttagg ctccctattt    180
actattcatt ttgacttcct tctgttttat ttttttccct ttagcattgc atgtgaat     238

<210> SEQ ID NO 410
<211> LENGTH: 101
<212> TYPE: DNA
<213> ORGANISM: Homo sapiens

<400> SEQUENCE: 410
tgagtgtgct gtgctcgcgt gtgtgctgtg ttcatgcgtg tgctgtgtgt tgtgtgtgtg     60
tagctgcggg gatgcataaa gtatgagtgc tttttaggat g                        101

<210> SEQ ID NO 411
<211> LENGTH: 34
<212> TYPE: DNA
<213> ORGANISM: Homo sapiens

<400> SEQUENCE: 411
tttatgaaca gcagactcta tgtaaaggca tttt                                 34

<210> SEQ ID NO 412
<211> LENGTH: 168
<212> TYPE: DNA
<213> ORGANISM: Homo sapiens

<400> SEQUENCE: 412
aggagggaaa ataatagccc agtgagagct gaatgaaaag ggactgaatt taaatatttg     60
taagaacttt gtgatgatga gtaattgtca gacgtgggat agataactga gaggctcaga    120
atctttacca aggatatttt ttaggataag gtagctgcct gttcatga                 168

<210> SEQ ID NO 413
<211> LENGTH: 150
<212> TYPE: DNA
<213> ORGANISM: Homo sapiens

<400> SEQUENCE: 413
agggacccag taagaccaaa ggaggggagg acagagcatg aaaaccaaaa tccatgcaaa     60
tgaaatgtaa ttggcacgac cctcaccccc aaatcttaca tctcaattcc catcctaaaa   120
agcactcata ctttatgcat ccccgcagct                                     150

<210> SEQ ID NO 414
<211> LENGTH: 124
<212> TYPE: DNA
<213> ORGANISM: Homo sapiens

<400> SEQUENCE: 414
ggctcaggtc ctccctacaa gacctaccac tcacccatgc ctatgccact ccatctggac     60
atttaatgaa actgagagac agaggcttgt ttgctttgcc ctcttttcct ggtcaccccc    120
actc                                                                 124
```

```
<210> SEQ ID NO 415
<211> LENGTH: 93
<212> TYPE: DNA
<213> ORGANISM: Homo sapiens

<400> SEQUENCE: 415
tggagaagca ctggtgtctg cagcacccct cagttcctgt gcctcagccc acaggccact    60
gtgataatgg tctgtttagc acttctgtat tta                                 93

<210> SEQ ID NO 416
<211> LENGTH: 76
<212> TYPE: DNA
<213> ORGANISM: Homo sapiens

<400> SEQUENCE: 416
ggaggatgcg ctgtggggtt gttttttgcca taagcgaact ttgtgcctgt cctagaagtg   60
aaaattgttc agtcca                                                    76

<210> SEQ ID NO 417
<211> LENGTH: 220
<212> TYPE: DNA
<213> ORGANISM: Homo sapiens

<400> SEQUENCE: 417
tctggtagat aaagccctag accttgtcca cactctcacc cccatcccca actttccctg    60
gaccggtgcc gcccccactt gatgcttgct caaggccggg gactggagcg ggctacttgt   120
atatttcgtt gtcagtctgc agaatgtgtt tgattttat ttttccctcc ttctctgaca   180
tgtgtcaagg aataaagact ggatacaggt ccattacgtc                         220

<210> SEQ ID NO 418
<211> LENGTH: 98
<212> TYPE: DNA
<213> ORGANISM: Homo sapiens

<400> SEQUENCE: 418
tggatcgatg atgagtcccc ccaaaaaaac attccttgga aaagctgaac aaaatgagtg    60
aaaactcata ccgtcgttct cagcggaact gaggtcca                            98

<210> SEQ ID NO 419
<211> LENGTH: 97
<212> TYPE: DNA
<213> ORGANISM: Homo sapiens

<400> SEQUENCE: 419
ggccaaaaag tctacattgc gtgtgtggat ggatgaatga gcagtgggag tgcagcgcca    60
ggtgacaaga tgttgtgagg ggttttgagt catccag                             97

<210> SEQ ID NO 420
<211> LENGTH: 87
<212> TYPE: DNA
<213> ORGANISM: Homo sapiens

<400> SEQUENCE: 420
gccctgcgcc ggcaaccacc tagtggccca gggaaggccg ataatttaaa cagtctccca    60
ccacctaccc caagagatac tggttgt                                        87

<210> SEQ ID NO 421
<211> LENGTH: 36
<212> TYPE: DNA
```

<213> ORGANISM: Homo sapiens

<400> SEQUENCE: 421

| aaaaaagttc aactagtatg aaagggttat aaagta | 36 |

<210> SEQ ID NO 422
<211> LENGTH: 116
<212> TYPE: DNA
<213> ORGANISM: Homo sapiens

<400> SEQUENCE: 422

| gtgagtaaat aatgttctag tgcaacagga caaactactc tctccacagg aaacccaacc | 60 |
| acaacaggat caatagaaag aaaagagaaa acgttagccc ccaactacaa ataaat | 116 |

<210> SEQ ID NO 423
<211> LENGTH: 264
<212> TYPE: DNA
<213> ORGANISM: Homo sapiens

<400> SEQUENCE: 423

| tttcttcttt atgtccaatt ttgtgggtgg gaggaggatt tagtctcttc ctgatttcga | 60 |
| agagctcatt tactatttcg ggaaataaga tttggattgt caaccattat agctattttt | 120 |
| tacacacttt tcaactttgt ttttgttata agaatgtgta tgattgttac atgtccaagt | 180 |
| ataaccatgt tcgcttttat ggcttttgag tttcatgtca tttttggaaa gatatatata | 240 |
| ttgagtccat aaaaccttc acct | 264 |

<210> SEQ ID NO 424
<211> LENGTH: 119
<212> TYPE: DNA
<213> ORGANISM: Homo sapiens

<400> SEQUENCE: 424

| actttaataa aggttatcca taccaataaa aagtgtacaa cacagcattt tctgttaaat | 60 |
| tattattggt tttcagttgt aatttggtat ttttttctggc atgcgtttat taatttatt | 119 |

<210> SEQ ID NO 425
<211> LENGTH: 279
<212> TYPE: DNA
<213> ORGANISM: Homo sapiens

<400> SEQUENCE: 425

| gtaggtttgg gagtataacg gtcacccagg gagggggtga agacggagaa gacttacata | 60 |
| gcacggtcag gttagggctg gacagatgag gaagagctag caaggggggc ttgaggagca | 120 |
| gtggccacta agacaggagt gtgacatttt agaagccaaa agaagaccat gtaattcaag | 180 |
| ggagaggtat gatttgctgg gtcagatcta aaaataaatc acacgttttt ttaaactgta | 240 |
| gtaattaacc actgaaaact tatgagtgat ccaatatta | 279 |

<210> SEQ ID NO 426
<211> LENGTH: 130
<212> TYPE: DNA
<213> ORGANISM: Homo sapiens

<400> SEQUENCE: 426

| gggacaaggt cccttggtgc tgatggcctg aaggggcctg agctgtgggc agatgcagtt | 60 |
| ttctgtgggc ttggggaacc tctcacgttg ctgtgtcctg gtgagcagcc cgaccaataa | 120 |
| acctgctttt | 130 |

<210> SEQ ID NO 427
<211> LENGTH: 262
<212> TYPE: DNA
<213> ORGANISM: Homo sapiens

<400> SEQUENCE: 427

```
tttcactctt gctgtctgct cctctcacat catccttgcc tctgtctgtt taatcctcct    60
gtccttcatt ttccttttt gcctctgcat tcagcatttc tacttccaat ctccctcctc   120
tgctctttct tatttcctct gatctgcaga cttgcttctg tccctccctt ctgttccct   180
cctggatgtg tctttggcca acctttcctt ctctgagact tcgtgttctt gttggtagat  240
gggggctgat acttctgggt ct                                           262
```

<210> SEQ ID NO 428
<211> LENGTH: 140
<212> TYPE: DNA
<213> ORGANISM: Homo sapiens

<400> SEQUENCE: 428

```
ttattattat gaaccttcag cctactttct tgagtgccgt aaaagtgctt gtaaattttt    60
ttttttttta agaagaaaga aaaaaatggt gtttgacgtt gatggaaatt caaaatata   120
tatggaactg aaacattaac                                              140
```

<210> SEQ ID NO 429
<211> LENGTH: 143
<212> TYPE: DNA
<213> ORGANISM: Homo sapiens

<400> SEQUENCE: 429

```
cttgttctt tgaagcttgt gctgaggttt tagcttttct atgttttata tgccgctgct    60
ttgaaagaga acctagattc tatagttgta ttattgttgt ttcatacttt aaatttatat  120
ggctgtggaa aaacgaatta aaa                                          143
```

<210> SEQ ID NO 430
<211> LENGTH: 151
<212> TYPE: DNA
<213> ORGANISM: Homo sapiens

<400> SEQUENCE: 430

```
gtgtgtcaag gatttgacaa actgccattt ttctccagaa gtcaagcccc taagtgattg    60
tctagaggca agaattttt gatatgttgt ctcaacaatg cttctcactt cgtcttcagg   120
tgccccaacc cgcaagtaca catactatgt a                                 151
```

<210> SEQ ID NO 431
<211> LENGTH: 150
<212> TYPE: DNA
<213> ORGANISM: Homo sapiens

<400> SEQUENCE: 431

```
aatgttcata ggttctcaac cctcaccccc caccacggga gactagagct gcaggatccc    60
aggggagggg tctctcctcc caccccaagg catcaagccc ttctccctgc actcaataaa   120
ccctcaataa atattctcat tgtcaatcaa                                    150
```

<210> SEQ ID NO 432
<211> LENGTH: 115
<212> TYPE: DNA

<213> ORGANISM: Homo sapiens

<400> SEQUENCE: 432

```
gatgggaatt gagatgtaag atttgggggt gagggtcgtg ccaattacat ttcatttgca    60
tggattttgg ttttcatgct ctgtcctccc ctcctttggt cttactgggt ccctc        115
```

<210> SEQ ID NO 433
<211> LENGTH: 223
<212> TYPE: DNA
<213> ORGANISM: Homo sapiens

<400> SEQUENCE: 433

```
tacattgtaa gagcaacatc ctacgttaat aaatgttcta gcccggtgct tcgcgaacat    60
ttatgtgcat acaaatcacc tgggatcttg ttagaaggca gtaggtctgg ggtgggcct   120
gagattctgc atttctaacc aggtcctggg agatgctgat gctatcgagc cacaaccaca   180
ctttgagtag caagcctctg cctatcctt attgtttgtt ata                      223
```

<210> SEQ ID NO 434
<211> LENGTH: 272
<212> TYPE: DNA
<213> ORGANISM: Homo sapiens

<400> SEQUENCE: 434

```
tttcactctt gctgtctgct cctctcacat catccttgcc tctgtctgtt taatcctcct    60
gtccttcatt ttcctttttt gcctctgcat tcagcatttc tacttccaat ctccctcctc   120
tgctctttct tatttcctct gatctgcaga cttgcttctg tccctccctt ctgttcctt   180
cctggatgtg tctttggcca accttcctt ctctgagact tcgtgttctt gttggtagat   240
gggggctgat acttctgggt cttgggcatg tc                                  272
```

<210> SEQ ID NO 435
<211> LENGTH: 221
<212> TYPE: DNA
<213> ORGANISM: Homo sapiens

<400> SEQUENCE: 435

```
ttgctggggc ttgtcctaga ggctccagct ttggcacagt ggttcctggc tgctgccatg    60
tttcagatga ggagggagag aaggaggccg ccagactcga gaggtgggag gaactccttg   120
cacacaccct gagcttttgc cacttttatc attttgagc aactccctt cagctaaaag    180
gccacccctt tatcgcattg ctgtccttgg gtagaatata a                       221
```

<210> SEQ ID NO 436
<211> LENGTH: 183
<212> TYPE: DNA
<213> ORGANISM: Homo sapiens

<400> SEQUENCE: 436

```
acaaaactct ccaataatga ctctgctcag ctcaggggca gcaggagtgg agtgtcgggg    60
gcccttggtg ctgagtgaag ataaattaaa aatcccaaca agccagtgac attatgtaca   120
ggaggaaagg ggtggggctt ccaggacaga ggccgagggt ggcagggcag gacttggagt   180
ggc                                                                  183
```

<210> SEQ ID NO 437
<211> LENGTH: 237
<212> TYPE: DNA
<213> ORGANISM: Homo sapiens

<400> SEQUENCE: 437

```
cagacacatg agcaggactt tggggagtgt gttttatatc tgtcagatgc ctagaacagc    60
acctgaaata tgggactcaa tcatttagt cccttctttt ctataagtgt gtgtgtgcgg    120
atatgtgtgc tagatgttct tgctgtgtta ggaggtgata acatttgtc catgttatat    180
aggtggaaag ggtcagacta ctaaattgtg aagacatcat ctgtctgcat ttattga      237
```

<210> SEQ ID NO 438
<211> LENGTH: 189
<212> TYPE: DNA
<213> ORGANISM: Homo sapiens

<400> SEQUENCE: 438

```
tcaagttaat ggcagctaaa acgctcccag tccatttatt ggccacatga ggtggtcgtc    60
aagaaacaag ttagaaggtt atgacaggaa gtagtataat aaatgcccgg cagtacgagg    120
ggttcaacag aagtgaacaa ggcacaagaa agaggtctgt gttcaggaaa caggccagtc    180
cccacatgg                                                            189
```

<210> SEQ ID NO 439
<211> LENGTH: 246
<212> TYPE: DNA
<213> ORGANISM: Homo sapiens

<400> SEQUENCE: 439

```
tgaactaaaa ctatgagcct tattcaatat ctataattct atgattttt taaattatgg    60
gaaattaatg aaagatgttt acatgaataa tgtttgccct tactgtgtta tgaatgagtt    120
ttttgtagtg tgtctgggtg catgatgcaa gagagtagga aaatgttttt tgaaacaaaa    180
cttgacaaat atttgtaatg aaagtaaatt taaagattgc tataattgcg ctatagaaac    240
aatgca                                                               246
```

<210> SEQ ID NO 440
<211> LENGTH: 65
<212> TYPE: DNA
<213> ORGANISM: Homo sapiens

<400> SEQUENCE: 440

```
ttaacagtac atttgtgtgg ctctcaaaca tcccttttgga agggattgtg tgtactatgt    60
aatat                                                                 65
```

<210> SEQ ID NO 441
<211> LENGTH: 120
<212> TYPE: DNA
<213> ORGANISM: Homo sapiens

<400> SEQUENCE: 441

```
tacaatgatg gttgagtgaa aatacagaag gggggtttga gtattcagat ttcataaaac    60
acttccttgg aatatagctg cattaacttg gaaagaagcc tgttgggcca gaagacagaa    120
```

<210> SEQ ID NO 442
<211> LENGTH: 156
<212> TYPE: DNA
<213> ORGANISM: Homo sapiens

<400> SEQUENCE: 442

```
aactgatggg aaaggaccaa ttattatag tttcccaaca aaagttttaa gattttttac    60
```

```
ctttgcatca gtgcattttt atttatatca aaaggtgcta aaatgattca atttgcattt    120
tttgatcctg tagtgcctct atagaagtac ccacag                              156

<210> SEQ ID NO 443
<211> LENGTH: 169
<212> TYPE: DNA
<213> ORGANISM: Homo sapiens

<400> SEQUENCE: 443
tgttaaactt tggaacacct accaaaaaat aagtttgata acatttaaaa gatgggcgtt    60
tcccccaatg aaatacacaa gtaaacattc caacattgtc tttaggagtg atttgcacct    120
tgcaaaaatg gtcctggagt tggtagattg ctgttgatct tttatcaat                169

<210> SEQ ID NO 444
<211> LENGTH: 87
<212> TYPE: DNA
<213> ORGANISM: Homo sapiens

<400> SEQUENCE: 444
aaatgacttt caactaacct tgtgaatctt ttgcagtgta ctgtgtgcaa taccaagggc    60
atagctccct gtaatttggg aaataca                                        87

<210> SEQ ID NO 445
<211> LENGTH: 96
<212> TYPE: DNA
<213> ORGANISM: Homo sapiens

<400> SEQUENCE: 445
catatatttt ttgctacttt tgctgtttta tttttttaaa ttatgttcta aacctatttt    60
cagtttaggt ccctcaataa aaattgctgc tgcttc                              96

<210> SEQ ID NO 446
<211> LENGTH: 269
<212> TYPE: DNA
<213> ORGANISM: Homo sapiens

<400> SEQUENCE: 446
tgctggcact gatattatcc atcatctctt tttggacact tctgtaaatg tgattggatt    60
gtttgaaaga agatttaaag tttcaaagtt ttttgttctg ttttttgcttt gcatttggag    120 aaaatattga agcagggta tgttgtttca ttcaccttga aaaaccatg agtaaatggg     180 gatatagaat ctctgaatag ctcgctaaaa gattcaagca agggacatga attttgttcc    240
atctatcaat aaatatccaga agaacaact                                     269

<210> SEQ ID NO 447
<211> LENGTH: 188
<212> TYPE: DNA
<213> ORGANISM: Homo sapiens

<400> SEQUENCE: 447
tctgtgtgtg tcctagcatg gagagttcct tcctttttccc ttcagttagg ttgacccttt   60
ccatttgttt agtatccgtg cacatgtcgt actagacccc aatcaagttg cttatttaaa    120
attctttcag ctgtttccct attatttcct tactttgctg aacatgtccg ctgttttacc    180
tcactgct                                                             188

<210> SEQ ID NO 448
<211> LENGTH: 246
```

```
<212> TYPE: DNA
<213> ORGANISM: Homo sapiens

<400> SEQUENCE: 448
ggagccaaca attcgagtgc aaacatgatg gctcagaccc ttctctgccc tttactagcc      60
ttcatgatct gtcgggtctc agcagctcag gccacaggag gaggtgggtc tcctgactgg     120
cctgtgcatt ctcccaaaca agatgtttaa gactcttctt tatctcgtca caaacgcaca     180
ggacacacac gcacacacat gcacacacag tttacaaacg cacggtacac acacgcatga     240
cacatg                                                                246

<210> SEQ ID NO 449
<211> LENGTH: 217
<212> TYPE: DNA
<213> ORGANISM: Homo sapiens

<400> SEQUENCE: 449
agcgaaggga aggttgcggg agaaagagcg ggggccgggg ccagacgcca agaggggcgc      60
ggggagcaca gagaagcgga gggaagggcg ccacgtcgag gggccggggg aggcggtgac     120
tgggggggcgg agtggaggct gcacccggac cgcgggcgcc cagctcggtt tgggccgacg    180
gagccctctg ccgtcgcgag cccgggcctc gggaggg                              217

<210> SEQ ID NO 450
<211> LENGTH: 172
<212> TYPE: DNA
<213> ORGANISM: Homo sapiens

<400> SEQUENCE: 450
tgcagtgcta gtcccggcat cctgatggct ccgacaggcc tgctccagag cacggctgac      60
cattttgct ccgggatctc agctcccgtt ccccaagcac actcctagct gctccagtct      120
cagcctgggc agcttccccc tgccttttgc acgtttgcat ccccagcatt tc             172

<210> SEQ ID NO 451
<211> LENGTH: 188
<212> TYPE: DNA
<213> ORGANISM: Homo sapiens

<400> SEQUENCE: 451
tattcctggt agaggaattt ctgtatttga aaattctcca gaaggaataa tataaactgt      60
ggactttggg tgataatgat atgtaggttc gtcagttgtt aacaaatgta tccctctgtt    120
gggggctatt gataatgggg aaggctgtgc atgtgtggga gtaggaggtg tatgggacat    180
ctctgtac                                                              188

<210> SEQ ID NO 452
<211> LENGTH: 242
<212> TYPE: DNA
<213> ORGANISM: Homo sapiens

<400> SEQUENCE: 452
aaagagtcaa ctttccggcg gcgggggaga aatgataaaa gagagagagg agggcagatc      60
accacctaga agcacatcct tgttcgcag aggggggaga aaaagtcgga gagaaagaat     120
gaaagagggg aaaaaaggca gttcggcacc cggagaaagg aggcaattcg gggagaggag    180
gaggagaaga agaaaacaca cacgcgcgca cgcacacaca caccgcggag agaaaagaac    240
ag                                                                    242
```

<210> SEQ ID NO 453
<211> LENGTH: 33
<212> TYPE: DNA
<213> ORGANISM: Homo sapiens

<400> SEQUENCE: 453
gtgagcccat atcgtactgc tgcagtccag cct                                    33

<210> SEQ ID NO 454
<211> LENGTH: 83
<212> TYPE: DNA
<213> ORGANISM: Homo sapiens

<400> SEQUENCE: 454
taaccttagg aaaccagaat agcgtttggc agacacgacg ttttcagttt acctttgaca       60
cctgccccac tccattttgc ttt                                               83

<210> SEQ ID NO 455
<211> LENGTH: 232
<212> TYPE: DNA
<213> ORGANISM: Homo sapiens

<400> SEQUENCE: 455
tgaaccaaaa tagagtcagc tgacccagca tcagccacac tttggggttgg aaaatgtttg      60 cctgttggaa ttaatttaag cttaagtata tatcaacatt attttattgt gcaattaaaa      120
caatacaaat tcatggtttt ttaaagttaa aaattttaac cactgtaaca acagttttg       180 tgttattttc tgtattaaac atcttgttgc acgcatttga ggtcatcagg gt              232

<210> SEQ ID NO 456
<211> LENGTH: 275
<212> TYPE: DNA
<213> ORGANISM: Homo sapiens

<400> SEQUENCE: 456
acacaataca atcaggagtt ttcaaatttt tgattcagta tttgaatttc ttcttcataa       60
atgtagttgg aatttatcct agtatttttc tttacctgaa ggagggccat ttatttttaa     120
tttcactaca tttttctttg catgattatt aaaataaaaa ctgcctctgt tgtgtttctc     180
actggaggct ggaatgaatg atcactagaa cacaaaagag tgaatgatga cacttgaagt     240
caaagcagtt gtactgatca ccagaaccaa taaag                                 275

<210> SEQ ID NO 457
<211> LENGTH: 220
<212> TYPE: DNA
<213> ORGANISM: Homo sapiens

<400> SEQUENCE: 457
ctaattgatt agaactgagt cttttatatc aagctaatat ctagctttta tatcaagcta      60
atatcttgac ttctcagcat catagaaggg ggtactgatt tcctaaagtc tttcttgaat     120
ttctattatg caaaattgcc ctgaggccgg gtgtggtggc tcacacctgt aatcccagca     180
ctttgggagg ctgaggtggg aagatcccctt actgccagga                          220

<210> SEQ ID NO 458
<211> LENGTH: 187
<212> TYPE: DNA
<213> ORGANISM: Homo sapiens

<400> SEQUENCE: 458
ttctttatag tgttatgctt attttcaatt ttttttttcc tgattctgtc tggtacttag    60
aattgtagtg tcttcatcat caattaaaga aaactgtcta aatgaattca tggatgtaaa   120
tattagtggt ccttaatgtc tttgattgct ggacatgaaa caaactgcca attaaatttt   180
gcggaga                                                             187

<210> SEQ ID NO 459
<211> LENGTH: 176
<212> TYPE: DNA
<213> ORGANISM: Homo sapiens

<400> SEQUENCE: 459
tcctgcaggc atccgtgggg gaaaaaaaat ctctcagaac cctcaactat tctgttccac    60
acccaatgct gctccaccct cccccagaca cagcccaagt ccctccgcgg ctggagcgaa   120
gccttctgca gcaggaactc tggacccctg ggcctcatca cagcaatatt taacaa       176

<210> SEQ ID NO 460
<211> LENGTH: 266
<212> TYPE: DNA
<213> ORGANISM: Homo sapiens

<400> SEQUENCE: 460
aaatgtttga cattcattat cagaatgagg gaaaatttaa acaattccgt ttttctttt    60 gctagtaggc atattatgct aataaaatta ctaaattaaa agtgtgtcaa ggatttgaca   120
aactgccatt tttctccaga agtcaagccc ctaagtgatt gtctagaggc aagaattttt   180
tgatatgttg tctcaacaat gcttctcact tcgtcttcag gtgccccaac ccgcaagtac   240
acatactatg tactcacttg aaaatg                                         266

<210> SEQ ID NO 461
<211> LENGTH: 286
<212> TYPE: DNA
<213> ORGANISM: Homo sapiens

<400> SEQUENCE: 461 aactggggc tctgtggggg ctctgtatat agctatgaag aaaacacaaa gtgtataaat     60
ctgagtatat atttacatgt cttttttaaaa gggtcgttac cagagattta cccatcgggt   120
aagatgctcc tggtggctgg gaggcatcag ttgctatata ttaaaaacaa aaaagaaaaa   180
aaaggaaaat gttttaaaa aggtcatata ttttttgcta cttttgctgt tttatttttt    240
taaattatgt tctaaaccta ttttcagttt aggtccctca ataaaa                  286

<210> SEQ ID NO 462
<211> LENGTH: 278
<212> TYPE: DNA
<213> ORGANISM: Homo sapiens
<220> FEATURE:
<221> NAME/KEY: modified_base
<222> LOCATION: (214)..(214)
<223> OTHER INFORMATION: a, c, t, g, unknown or other

<400> SEQUENCE: 462
gctggtctcg ggcaacaagc agcctcctag gagcagaagg tgatggaggg ccacgggggc    60
agggaggagc agatggccat gtggctcagc ccctgcctgg gaaagcgagt ccacagttca   120
ctaacaaaca caataccatc cacaaacaag tagccacaaa gaccacagtt agcaaacaca   180
cacagtcaca cacacacaca cacacacaca catnacggga ggtgggcagg accgcagtct   240

```
gcagtggggga ggcaagtgtt agttgcatca tcaggtgg                                  278
```

<210> SEQ ID NO 463
<211> LENGTH: 122
<212> TYPE: DNA
<213> ORGANISM: Homo sapiens

<400> SEQUENCE: 463

```
aggtggtgtt ggcagaggct atcgggctgg acaaggacaa acccaaccgt gtgaccaaag           60
tggctgtgaa gatgttgaag tcggacgcaa cagagaaaga cttgtcagac ctgatctcag          120
aa                                                                        122
```

<210> SEQ ID NO 464
<211> LENGTH: 161
<212> TYPE: DNA
<213> ORGANISM: Homo sapiens

<400> SEQUENCE: 464

```
aatgaaattg ttaattggcc aggcacagtg ggaagcacct gtagtcccag ctactcagga           60
ggctaaagtg agagggtggc tctagcacag tcatcaaggc tgcaggaggc tatgatggag          120
ccactgcact ccagcctaga tgacaaggtg agacgctgtc t                              161
```

<210> SEQ ID NO 465
<211> LENGTH: 162
<212> TYPE: DNA
<213> ORGANISM: Homo sapiens

<400> SEQUENCE: 465

```
tgttttttgac atcagctgta atcattcctg tgctgtgttt tttattaccc ttggtaggta          60
ttagacttgc ccttttttaa aaaaaggttt ttgcatcgtg gaagcatttg acccagagtg         120
gaacgcgtgg cctatgcagg tggattcctt caggtctttc ct                            162
```

<210> SEQ ID NO 466
<211> LENGTH: 114
<212> TYPE: DNA
<213> ORGANISM: Homo sapiens

<400> SEQUENCE: 466

```
ttttttagtt gccaacagtt tatgtttgct gattatttat gacctgaaat tatatatttt          60 ttttttttaag aagacatttt gttacataag gatgactttt ttatacaaag gaaa              114
```

<210> SEQ ID NO 467
<211> LENGTH: 223
<212> TYPE: DNA
<213> ORGANISM: Homo sapiens

<400> SEQUENCE: 467

```
gcatttgaat tgactaggct tttcctatat aaaaaactca aaacttgtta actctgtact          60
ttaataaaat ttaaaattaa aactgtgttg ttttttttctc ttctgctaga tacatatata       120
attaaagtac tcaagttagt tgttttgcag agatgttgcc ttcagatgtt aatcaggtct       180
ctcaagtttc atggagtcta tgctgatcct ttaattgaca aat                            223
```

<210> SEQ ID NO 468
<211> LENGTH: 289
<212> TYPE: DNA
<213> ORGANISM: Homo sapiens

<400> SEQUENCE: 468

```
tatacagaat agtcactggt cttgggctaa atggtgactt caagtgtagt ggctgcatag    60
tcaaaaatga attagatgag tacaaaagtg acgaaatgaa agaatgtcaa gaatggacca   120
caaagacagt gttttatgac ctaaagatta agatttatcc atttgtgtac aattgtggac   180
tatataaaat aaaacaagac tttgacctca gtggataaga agtatttgga tgtactaatc   240 aatattttg gtctgggtca gtggtgggtt catctgtgtt tgttgtatt                289
```

<210> SEQ ID NO 469
<211> LENGTH: 36
<212> TYPE: DNA
<213> ORGANISM: Homo sapiens

<400> SEQUENCE: 469

```
agcaggatca agggccggaa ataaaggctg ttgtaa                              36
```

<210> SEQ ID NO 470
<211> LENGTH: 156
<212> TYPE: DNA
<213> ORGANISM: Homo sapiens

<400> SEQUENCE: 470

```
aatatacctg atgcgctgta gaatgaaaat gtaaagata acctgtatgt gttccgagct    60
ttaatttttt gtttacaaat tgaacagtgt tacatgggct gtccagtcct gattatagag   120
aggaagaaat ggtaacagta tggcagataa gaatta                             156
```

<210> SEQ ID NO 471
<211> LENGTH: 298
<212> TYPE: DNA
<213> ORGANISM: Homo sapiens

<400> SEQUENCE: 471

```
agcaggagta agtttctcat cccatgggcg accagggcca tctcctccca ccagtggccc    60
ccactcacag ggagctggca atgccctacc tgcctgttct ccagatggag aaacaggctc   120
tgagatttca caggtcttgc ccaaagtcat tgattttgat gattaaaaag aataaacaca   180
gtgtttcctg agtagcagtg attgttatgc cttgctattt taataaagat tctatttcg    240 tataacattg tcaagtggaa acatgctgaa atctattaaa ccatctttgt tgtggaa      298
```

<210> SEQ ID NO 472
<211> LENGTH: 98
<212> TYPE: DNA
<213> ORGANISM: Homo sapiens

<400> SEQUENCE: 472

```
aaagagtcaa ctttccggcg gcggggggaga aatgataaaa gagagagagg agggcagatc    60
accacctaga agcacatcct ttgttcgcag agggggga                            98
```

<210> SEQ ID NO 473
<211> LENGTH: 103
<212> TYPE: DNA
<213> ORGANISM: Homo sapiens

<400> SEQUENCE: 473

```
gtttgtcttg cgcagtgctt actccagctg tggcatgcag gtgtcagcaa gtatgatcag    60
caatgaggcg gtggtcaata tcctgtcgag ctcatcacca cag                     103
```

<210> SEQ ID NO 474

```
<211> LENGTH: 191
<212> TYPE: DNA
<213> ORGANISM: Homo sapiens

<400> SEQUENCE: 474
aatctctttt tttctggagg ctggcacctg attttgtatc ccctgtagc agcattactg       60 aaatacatag gcttatatac aatgcttctt tcctgtatat tctcttgtct ggctgcaccc    120
ctttttcccg cccccagatt gataagtaat gaaagtgcac tgcagtgagg gtcaaaggag    180
agtcaacata t                                                          191

<210> SEQ ID NO 475
<211> LENGTH: 220
<212> TYPE: DNA
<213> ORGANISM: Homo sapiens

<400> SEQUENCE: 475
tgcccccagt atgtttagga cgcgagcccc agaaggattt gggagtaaac ttaacattca       60
ctgtgttttt gctttgcatc cgccatttgt gtgtgttttt ggactgtggg ctgtgtgtac    120
cttggttggt gactcagtga gaagaagcag gaatgccaaa gatactatga atgttttgag    180
ttttgttgct gttgttgttg agaggttgtt tcactggtat                          220

<210> SEQ ID NO 476
<211> LENGTH: 258
<212> TYPE: DNA
<213> ORGANISM: Homo sapiens

<400> SEQUENCE: 476
gatcgtctgg taactttcta actttaaata atatgtttga gcaataattt cttgacttac       60
tgactttaca acatctttaa taattcccca ttacaaaaga taaggattta acttacacta    120
tcgccacttt cctttgtcca tctctctcca aatgtctgat agttacatca cttttttaata    180 catctattgg tttgatttta tagctttgaa caatacacta atcctctagt tcttgttcca    240
ttaactgaag atcttttc                                                  258

<210> SEQ ID NO 477
<211> LENGTH: 233
<212> TYPE: DNA
<213> ORGANISM: Homo sapiens

<400> SEQUENCE: 477
gaaacacaag agacttaaag gacaggagga ggagatggcc ataggagagg agggttcctc       60
ttaggtcaga tggaggttct cagagccaag tcctccctct ctactggagt ggaaggtcta    120
ttggccaaca atcctttctg cccacttccc cttccccaat tactattccc tttgacttca    180
gctgcctgaa acagccatgt ccaagttctt cacctctatc caaagaactt gat            233

<210> SEQ ID NO 478
<211> LENGTH: 96
<212> TYPE: DNA
<213> ORGANISM: Homo sapiens

<400> SEQUENCE: 478
ggatcgatga tgagtccccc ataaaaacat tccttggaaa agctgaacaa aatgagtgag       60
aactcatacc gtcgttctca tcggaactga ggtcca                                96

<210> SEQ ID NO 479
<211> LENGTH: 181
```

<212> TYPE: DNA
<213> ORGANISM: Homo sapiens

<400> SEQUENCE: 479

```
tggtgacaga gtttgggacc gaggtggagc ccgagtttgg gaccaaggtg gagcccgagt    60
ttgagaccca gttggagcct gagtttgaga cccagctgga acccgagttt gaggaagagg   120
aggaggagga gaaagaggag gagatagcca ctggccaggc attccccttc acaacagtag   180
a                                                                   181
```

<210> SEQ ID NO 480
<211> LENGTH: 135
<212> TYPE: DNA
<213> ORGANISM: Homo sapiens

<400> SEQUENCE: 480

```
gatatcagat cagttgagac taacagttga aagcagtaaa catattacgg acatattatt    60
gataaaagac atttatgaag aggataaaact gtgaaggtgt acagacacta aaccatagtt   120
gctaaacaca tacaa                                                    135
```

<210> SEQ ID NO 481
<211> LENGTH: 80
<212> TYPE: DNA
<213> ORGANISM: Homo sapiens

<400> SEQUENCE: 481

```
agagccagga cagtgaggtc aactttgaca attccatcca cccagaagtc ttggagctgc    60
tgcttgacta tgcgtactcc                                                80
```

<210> SEQ ID NO 482
<211> LENGTH: 96
<212> TYPE: DNA
<213> ORGANISM: Homo sapiens

<400> SEQUENCE: 482

```
ggatcgatga tgagtccccc ataaaaacat tccttggaaa agctgaacaa aatgagtgag    60
aactcatacc gtcgttctca tcagaactga ggtcca                              96
```

<210> SEQ ID NO 483
<211> LENGTH: 290
<212> TYPE: DNA
<213> ORGANISM: Homo sapiens

<400> SEQUENCE: 483

```
ttgacagtct gccttactat gaaattctag gtacaaaaat tttccttaag ctctgaagat    60
gttgatccat tgacttctgg cattcagtgt tgctgatgac aaatctgtta gcagtctatt   120
tctcatccat ttttgtgttg agctaatcgt gatgacctca tttgttttct ccctggccac   180
tttaatatct tccttctatc cttaatattc caaaatttta caatattgtg tctagatgta   240
gattgtattg ggccctctca atctggagac ttagcttgct ctgttcttca               290
```

<210> SEQ ID NO 484
<211> LENGTH: 197
<212> TYPE: DNA
<213> ORGANISM: Homo sapiens

<400> SEQUENCE: 484

```
atgtcaagaa aatgacggtc acagaccagg tgaactgccc caagctctcg taaccaggtt    60
```

```
ctacaggag gctgcaccca ctccatgtta cttctgcttc gctttcccct accccacccc    120 cccccataa agacaaacca atcaaccacg acaaaggaag ttgacctgaa catgtaacca    180
tgccctaccc tgttacc                                                 197

<210> SEQ ID NO 485
<211> LENGTH: 113
<212> TYPE: DNA
<213> ORGANISM: Homo sapiens

<400> SEQUENCE: 485
tgtcactggt gaaagacgac ttggtgccca attttaata aacacaatgc tattagcgtc     60
actccaattt agtgtctgat tgttaaatgt taatgtactg cactctacag ttt          113

<210> SEQ ID NO 486
<211> LENGTH: 183
<212> TYPE: DNA
<213> ORGANISM: Homo sapiens

<400> SEQUENCE: 486
ggattataat atcctcactg gccacaatct gtaaaagtcg atactggcac ttttttttgcc    60 ccctcaaagg aaatatgcta atagacagcc cctttgcaaa tataattcct ccttcccaac   120
ccttcaaatt gctaaggccc cactggtcag caccttccct ttcgagtcca ggactactgt   180
tct                                                                183

<210> SEQ ID NO 487
<211> LENGTH: 275
<212> TYPE: DNA
<213> ORGANISM: Homo sapiens

<400> SEQUENCE: 487
agcattaata atttccatgc atgtgtcttt ttccagtagg tatggttgaa tttatgtaaa     60
tttattgcta atcccatccc ttacgattta gagtataagc tgcgcaaggg cagaagtttt   120
tatttggttt gttcatggat gtattttaag agctgagaac agggcctgga cacaataagc   180
attcaataaa tatttactga atgaatgaac tcctacctat attcctatatt ataatttggc   240 tccactttat cctactttag ctcccattca attca                             275

<210> SEQ ID NO 488
<211> LENGTH: 123
<212> TYPE: DNA
<213> ORGANISM: Homo sapiens

<400> SEQUENCE: 488
catttaaata agaggagatc cacaaagagc aacagagata agagaagaaa ggaaataatc     60
aataaaataa ttcaagaaaa tccaaggaca tgagttttca gattgtaaga gactacttga   120
gtg                                                                123

<210> SEQ ID NO 489
<211> LENGTH: 99
<212> TYPE: DNA
<213> ORGANISM: Homo sapiens

<400> SEQUENCE: 489
aattcatatc ccctgttcgt ctcatgcgcg tcctccgtcc ccaatctaaa agcaattga      60 aaaggtctat gcaataaagg cagtcgcttc attcctctc                           99
```

```
<210> SEQ ID NO 490
<211> LENGTH: 97
<212> TYPE: DNA
<213> ORGANISM: Homo sapiens

<400> SEQUENCE: 490
tggatcgatg atgagtcctc caaaaaaaca ttccttggaa aagctgaaca aaatgagtga      60
gaactcatac cgtcgttctc atcggaactg aggtcca                              97

<210> SEQ ID NO 491
<211> LENGTH: 119
<212> TYPE: DNA
<213> ORGANISM: Homo sapiens

<400> SEQUENCE: 491
attttctatc tgtggttgga ttcagaccac atgaacactg agggctgact gtagttttga     60
atgtctgtta ctgaggaggc accagcataa agtattttat cacttcagac gctgacaat     119

<210> SEQ ID NO 492
<211> LENGTH: 121
<212> TYPE: DNA
<213> ORGANISM: Homo sapiens

<400> SEQUENCE: 492
ttatatttat gtttagcacc gtcagtgttc ctatccaatt tcaaaaagg aaaaaaaga       60 gggaaaatta caaaagaga gaaaaaaagt gaatgacgtt tgtttagcca gtaggagaaa    120
a                                                                    121

<210> SEQ ID NO 493
<211> LENGTH: 168
<212> TYPE: DNA
<213> ORGANISM: Homo sapiens

<400> SEQUENCE: 493
gtttgagcta tcgaagagta agtaaccaga aatttgagaa cagcctgggc agcatagtga    60
gaccccatct ttacaaaaac ttcacagatt agccaggtat ggtggcattt tcctgtagtc   120
ccagctactc agaatgctga ggcaggagag tggcttgtga ccaagagt                168

<210> SEQ ID NO 494
<211> LENGTH: 47
<212> TYPE: DNA
<213> ORGANISM: Homo sapiens

<400> SEQUENCE: 494
aggataaact tgtgtggtgt agagaagtta aaatcctcac gttgtac                   47

<210> SEQ ID NO 495
<211> LENGTH: 286
<212> TYPE: DNA
<213> ORGANISM: Homo sapiens

<400> SEQUENCE: 495
acttcaggga agtttcataa aaggaagaat tttaactcag cgtagaaaga tgggtaaatt     60
ttcctcatgt gaaggtgtac tgcctggggt gctgcaggct ggagatgagt attaaaatag   120
gaggagagtg agtgaaagca caggaggagg aagggtcagg caagtttggt gaacacagca   180
actggctata gaacaggagc agtgggagaa agtccagaaa ggtctgctga gcttcagttg   240
tacaaagctg tggagtttgg cctttggtca tggctagatt aggtct                  286
```

<210> SEQ ID NO 496
<211> LENGTH: 94
<212> TYPE: DNA
<213> ORGANISM: Homo sapiens

<400> SEQUENCE: 496
tggatcgatg atgacctcaa tacatgcatt ccttggaaag ctgaacaaaa tgagtgaaaa    60
ctctataccg tcgtcctcgt caaactgagg tcca    94

<210> SEQ ID NO 497
<211> LENGTH: 174
<212> TYPE: DNA
<213> ORGANISM: Homo sapiens

<400> SEQUENCE: 497
gtttgaggta tttaactgac acctaagtgg atctgttgag gaaacagttg gatatacaaa    60
tttagtgttt aaggcagact tccaggcttg aaggaaaaat ttggaagtca tcacgacata   120
tatgtggtat ttaaaattgt gaggttcaag gaccaagccc cataccattt agag         174

<210> SEQ ID NO 498
<211> LENGTH: 255
<212> TYPE: DNA
<213> ORGANISM: Homo sapiens

<400> SEQUENCE: 498
tggagatagc tcttaaagat ataaatgttt atggctgaaa tgttatggca tcttggattt    60
gctttaaaat aacccagctt gctgcaggag gtgggtattg tgtgtgtggg aaggtgggga   120
ggctgcggga ggaagagatg acccaagatt aggcagatgt tgttaactgt ggaagcaggg   180
tggtgagtgg gggctcatga cattatgctc tctactttgt gtacgtgtga acatttccgt   240
aataaaagat gcctt                                                    255

<210> SEQ ID NO 499
<211> LENGTH: 137
<212> TYPE: DNA
<213> ORGANISM: Homo sapiens

<400> SEQUENCE: 499
ggattttttc ccctgtagta gtgaggtaac atgcttgaat gtcactgtga tatttatttc    60
ctctttgttc agttgttttt gaattcctgt taagtacatg ttttaatact ttgagcgatt   120
taagatactt ttctttt                                                 137

<210> SEQ ID NO 500
<211> LENGTH: 33
<212> TYPE: DNA
<213> ORGANISM: Homo sapiens

<400> SEQUENCE: 500
aaacgatgat aatctttact ggtgaaaagg atg    33

<210> SEQ ID NO 501
<211> LENGTH: 195
<212> TYPE: DNA
<213> ORGANISM: Homo sapiens

<400> SEQUENCE: 501
tatgagttat tcaaggagga gacttttttaa agacagcaac gcaattcttg taacttgtgt    60
aaatagcccc atctttcaga gtgataccat ttctacattt gataatgcct gtattcctgt   120

```
aggatgtata tagtttaggg gatttttttt ttgtttggtt ttgttttta gaagtcaata    180 tgtctggttt tattt                                                    195

<210> SEQ ID NO 502
<211> LENGTH: 255
<212> TYPE: DNA
<213> ORGANISM: Homo sapiens

<400> SEQUENCE: 502
attattttga tagcagatgt gctatttatt tatttaatat gtataaggag cctaaacaat    60
agaaagctgt agagattggg tttcattgtt aattggtttg ggagcctcct atgtgtgact   120
tatgacttct ctgtgttctg tgtatttgtt tgaattaatg acctgggata taaagctatg   180
ctagctttca aacaggagat gcctttcaga aatttgtata ttttgcagtt gccagaccaa   240
taaaatacct ggttg                                                   255

<210> SEQ ID NO 503
<211> LENGTH: 217
<212> TYPE: DNA
<213> ORGANISM: Homo sapiens

<400> SEQUENCE: 503
gtgtgttaaa atgagggtct cactgcttta ggattgaagt ggctggaaag agtgatgcct    60
ggggaaggag atggagttat gagggtactg tggctggtac tttctgtact aaacatttcc   120
tttttctatt ttaccactaa ttttgtttta aactgtgagc cgtccaagtc agaagaagac   180
agcaaaaaaa gcaactttc caacatacaa tttactt                            217

<210> SEQ ID NO 504
<211> LENGTH: 92
<212> TYPE: DNA
<213> ORGANISM: Homo sapiens

<400> SEQUENCE: 504
cctgcctggg aaagcgagtc cacagttcac taacaaacac aataccatcc acaaacaagt    60
agccacaaag accacagtta gcaaacacac ac                                 92

<210> SEQ ID NO 505
<211> LENGTH: 251
<212> TYPE: DNA
<213> ORGANISM: Homo sapiens

<400> SEQUENCE: 505
atataattgg acaaacgctg gcaaaagaa aaaatggta agcaaaaaac ccaagataaa     60
gtttcgagga catcaggcct tttgaaatac aatgtcaaat gacacattgt acggtttcaa   120
aaaatccgct agacatgtca taagttttaa ctgtaatgcc caggaaagga tatcttaaaa   180
tattctaaac ttgtgtaaca aaggaataat taactgtaat agttttcaa taaatcgagt   240 tgggtgtttc c                                                       251

<210> SEQ ID NO 506
<211> LENGTH: 261
<212> TYPE: DNA
<213> ORGANISM: Homo sapiens

<400> SEQUENCE: 506
gaatggttac tgtttatact gtggtatgtt tttgattaca gcagataatg ctttctttc    60
```
cagtcgtctt tgagaataaa ggaaaaaaaa tcttcagatg caatggtttt gtgtagcatc    120
ttgtctatca tgttttgtaa atactggaga agctttgacc aatttgactt agagatggaa    180
tgtaactttg cttacaaaaa ttgctattaa actcctgctt aaggtgttct aattttctgt    240
gagcacacta aaagcgaaaa a                                              261

<210> SEQ ID NO 507
<211> LENGTH: 175
<212> TYPE: DNA
<213> ORGANISM: Homo sapiens

<400> SEQUENCE: 507
tatttcttgc tattgtgata tgacaagaga cttaacttat cttgctctgt tttcccctgt     60
acacgctgta tagggggtc aatgtgatgc tgctggagac gagaataaac tggactagaa    120
tagtgcattg tatttagtct gtattgatca tggatgccct ccttaatagc catat         175

<210> SEQ ID NO 508
<211> LENGTH: 251
<212> TYPE: DNA
<213> ORGANISM: Homo sapiens

<400> SEQUENCE: 508
gaaccgcaga ttatggttaa tccaattctg tgcacctgag gtccataaat aaaagaataa     60
gtattgaaat gaaagaatga cagaaagaat gaatggacac atgaacgact gaattagaaa    120
tggaaatgcc tggcacagcc aggaaggagc tgcccatggg attgtcattc atttcactct    180
gggcacctga ggtccataag cgtgaaaaga ggcaggaaga aagtgtcag ggagtcaaag     240 atagagctaa g                                                        251

<210> SEQ ID NO 509
<211> LENGTH: 237
<212> TYPE: DNA
<213> ORGANISM: Homo sapiens

<400> SEQUENCE: 509
ttattttatt tcgctatttc cagtttgaag ctactatcat gggcgtttag agttatacaa     60
atgacactta caaaaaataa aagaccaaga cacccagagt gagatgcatg ttggggacgg    120
gggaggctgg cagcaggggg gccccggcgg ctcaccccag ggctcccgga ggggctgtt    180 tccatccacc acccaaaaaa acaccacaag ggtcagtcct agcccacccg acagctt      237

<210> SEQ ID NO 510
<211> LENGTH: 133
<212> TYPE: DNA
<213> ORGANISM: Homo sapiens

<400> SEQUENCE: 510
gtatggatgg gtatgttgag actcaattac tttttttatta gcttccccgt ttggaagatc     60
ccaaacacca aagatggaag gtgaaaataa agactgcgtg accgggaaga agtttgaat    120 tactaatagt ggg                                                      133

<210> SEQ ID NO 511
<211> LENGTH: 263
<212> TYPE: DNA
<213> ORGANISM: Homo sapiens

<400> SEQUENCE: 511
aatcaaccaa tgcaaccagt ttgtgagaaa aaaaaaaaaa agccgaaaaa aaaaaaaaaa      60

```
aacacctgaa tgcggaagag ctcggctccc gtttagcatt ttgtacttaa ggaaataaaa    120
aaccaacaaa ggatttcaca ttttttttaaa aagtgaagat tgctgtatac tatttattca   180
```

```
aacacctgaa tgcggaagag ctcggctccc gtttagcatt ttgtacttaa ggaaataaaa    120
aaccaacaaa ggatttcaca tttttttaaa aagtgaagat tgctgtatac tatttattca    180
acttataatt tatgttactc cttgatcttt gtcttttgtc atgacaaagc atttatttaa    240
taaagttatg cattcagcaa ctt                                            263
```

<210> SEQ ID NO 512
<211> LENGTH: 48
<212> TYPE: DNA
<213> ORGANISM: Homo sapiens

<400> SEQUENCE: 512

```
taggttgtca acaggtacta tttgtcacat aactaacttt cgaggcac                  48
```

<210> SEQ ID NO 513
<211> LENGTH: 161
<212> TYPE: DNA
<213> ORGANISM: Homo sapiens

<400> SEQUENCE: 513

```
attagtgaac ttatctttgc agctgagtac ttaaattctt tttaaaaaga taccctttgg    60
attgatcaca ttgtttgacc cagtatgttt tgtagacacg ttagttataa tcaccttgta   120
tctctaaata tggtgtgata tgaaccagtc cattcacatt g                        161
```

<210> SEQ ID NO 514
<211> LENGTH: 286
<212> TYPE: DNA
<213> ORGANISM: Homo sapiens

<400> SEQUENCE: 514

```
gtcttcacca actaagaaag ctctgttatt ctggcctggg tgcttgctcc agactcagga    60
acatctggtc aacacaagca tcactgggct ggggaattgt gtgtgtgctg catcatctcc   120
gactctcttg tagttccttc cttccctccc tcactcttac atgcagacac agacagacac   180
agtctggttg ggacatgcag tggcagctcc tggtgtataa catctttcac acaccttgag   240
tctatctgct tgctgccttt gactgatcct gaaatggttg gccttt                   286
```

<210> SEQ ID NO 515
<211> LENGTH: 208
<212> TYPE: DNA
<213> ORGANISM: Homo sapiens

<400> SEQUENCE: 515

```
gaggccccag aggacttatc tcagctgtac atgctctgcc tgtggagaca tggcttttct    60
ttgtgctgtg gcagactggg gctttggaag tggtgtatgt ttaacttacc tgagagtgag   120
agatgtgtag gaagaatagc tggaagaaag tgaaagatga gtgccagtac ttttggcctg   180
ttatccagta gagagaaagt gacagtga                                       208
```

<210> SEQ ID NO 516
<211> LENGTH: 201
<212> TYPE: DNA
<213> ORGANISM: Homo sapiens

<400> SEQUENCE: 516

```
aactctgtaa ggaggaccat gtcagactat tgtaagctaa gcattaggac tgatacaaat    60
aatatatgct cctggcatag aaaataaaac cacagagaac gagttcaaag aatagcaaag   120
```

```
aaagaaagag gacccagtgg gcgaaagatg agagtgtact tttaccaaaa gttatctaag    180
cctgagcact tgaagtctgc a                                              201

<210> SEQ ID NO 517
<211> LENGTH: 119
<212> TYPE: DNA
<213> ORGANISM: Homo sapiens
<220> FEATURE:
<221> NAME/KEY: modified_base
<222> LOCATION: (91)..(91)
<223> OTHER INFORMATION: a, c, t, g, unknown or other

<400> SEQUENCE: 517
aaaatagaga gacatacctg gctccaaaac aaggctgtat cttctgccac tgtaataaaa    60
tagatgcaat tgaggttcat aaataaaaga ntaaatactt aaacgtgaaa ggtgactaa    119

<210> SEQ ID NO 518
<211> LENGTH: 36
<212> TYPE: DNA
<213> ORGANISM: Homo sapiens

<400> SEQUENCE: 518
ataatgaaag ttagtaacgt ccattattta ataaag                              36

<210> SEQ ID NO 519
<211> LENGTH: 91
<212> TYPE: DNA
<213> ORGANISM: Homo sapiens

<400> SEQUENCE: 519
tgtacagggt cattttgaca gtaactggta tattcctttg cattttatgt tgcattgcca    60
atttttagtg tatccagttt gaaagtataa t                                    91

<210> SEQ ID NO 520
<211> LENGTH: 178
<212> TYPE: DNA
<213> ORGANISM: Homo sapiens

<400> SEQUENCE: 520
tactgatctt tatattacag atttttttt cttttaggat tagttcagct tgccccccct    60
ttccatttcc accatttata gtgagcctct ccataattag tgccaaccat tagtttcgtt    120 catatttta caccaggagt caacaaactg tggccattgg ccaaatatgg cctcccaa      178

<210> SEQ ID NO 521
<211> LENGTH: 242
<212> TYPE: DNA
<213> ORGANISM: Homo sapiens

<400> SEQUENCE: 521
aggaagtacc cgctccataa gacccttaca tttggacagt caaggtgcac aattgtatgt    60 gaccacaac atgcaccttg gacataaatg tgtgtaactg cacatggccc atcccatctg    120
aataaggtcc tactctcaga cccctttttgc agtacagtag gtgtgctgat aaccaaggcc    180
cctcttcctg gcctgttaac gtatgtgatt atatttgtct gggttccagt gtataagaca    240
tg                                                                    242

<210> SEQ ID NO 522
<211> LENGTH: 199
<212> TYPE: DNA
<213> ORGANISM: Homo sapiens
```

<400> SEQUENCE: 522

```
gggagtcaat gaatagtacc taaaatggaa accaaacaaa acaacttcag gaagtaacaa      60
gggcttgctt agagacatga cggtaaaccc tgaaccatca gctaaaagag gtagatagca     120
gtggttgccc ctggggagag gtaaatgtga tggagaggga acaactgtgt acaaacatgt     180
gactttacgt tttgatcaa                                                  199
```

<210> SEQ ID NO 523
<211> LENGTH: 127
<212> TYPE: DNA
<213> ORGANISM: Homo sapiens

<400> SEQUENCE: 523

```
aagagttaaa cagtctagag tgaagggaat gttttaaaat ccagaggcga tcaagtgaag      60
ccaacctttg gaggcccgta gaagtcattt ggaggaattt ggacttcgtg cagtaggaaa     120
gagggaa                                                               127
```

<210> SEQ ID NO 524
<211> LENGTH: 46
<212> TYPE: DNA
<213> ORGANISM: Homo sapiens

<400> SEQUENCE: 524

```
gacaggggtt ctaattactg tctgtgagag ttactacttt gtaact                     46
```

<210> SEQ ID NO 525
<211> LENGTH: 115
<212> TYPE: DNA
<213> ORGANISM: Homo sapiens

<400> SEQUENCE: 525

```
taatattttt tgctgcctag gcaaatggct tttgtgaaaa cacttgtatg aaaagcaata      60
caccatttgt ttttacttac caatcactat cattaggttt tgatgcaaat gggaa          115
```

<210> SEQ ID NO 526
<211> LENGTH: 138
<212> TYPE: DNA
<213> ORGANISM: Homo sapiens

<400> SEQUENCE: 526

```
ttcccaagcc catgagtcct tgaaaatatt ttttatatat acagtaactt tatgtgtaaa      60
tacataagcg gcgtaagttt aaaggatgtt ggtgttccac gtgttttatt cctgtatgtt    120
gtccaattgt tgacagtt                                                   138
```

<210> SEQ ID NO 527
<211> LENGTH: 269
<212> TYPE: DNA
<213> ORGANISM: Homo sapiens

<400> SEQUENCE: 527

```
cttaggatat gaaatcttca gaggatggta gaagagaaag gtaaatgcca taagaaagta      60
gagtacttgt ggtcattgaa accatggaat ttactcaggg atagtgtata tagtgagaaa    120
tcaggtaact aagatttgag cctaaacgta atctgtaaaa ggggagctca aaggaaaagg    180
gaatgggagg accggatttt gtaaggatag tagggcaaat gttaagagag agaatgagag    240
agttgagtat ggcaaagagt gactcaatt                                      269
```

<210> SEQ ID NO 528
<211> LENGTH: 282
<212> TYPE: DNA
<213> ORGANISM: Homo sapiens

<400> SEQUENCE: 528
tcacctcctg ctggctaccg gggcaggcat gcacccggtg ccagccccgc tctgggcacc        60
acctgccttc cagcccctcc aggaccocggt cccoctgctg cccctcactt caggaggggc       120
ctggagcagg gtgaggctgg actttggggg gctgtgaggg aaatatactg gggtccccag       180
attttgcttt aaggggggcca gacccctttgc caggctggat tgtacgggcc ccaccttcgc      240
tgtgttcttg ctgcaaagtc tggtcaataa atcactgcac tg                           282

<210> SEQ ID NO 529
<211> LENGTH: 131
<212> TYPE: DNA
<213> ORGANISM: Homo sapiens

<400> SEQUENCE: 529
atacctgtta aatagatcaa ttttgattgc ctactatgtg aactcactgt taaaggcact        60
gaaaatttat catatttcat ttagccacag ccaaaaataa cgcaataccct atgttagcat      120 tttgtgaact c                                                             131

<210> SEQ ID NO 530
<211> LENGTH: 183
<212> TYPE: DNA
<213> ORGANISM: Homo sapiens

<400> SEQUENCE: 530
tcacctgagg cgttcaaaag atataaccaa ataaacaagt catccacaat caaaatacaa        60
cattcaatac ttccaggtgt gtcagacttg ggatgggacg ctgatataat agggtagaaa      120
gaagtaacac aagaagtgg tggaaatgta aaatccaagt catatggcag tgatcaatta      180
tta                                                                      183

<210> SEQ ID NO 531
<211> LENGTH: 263
<212> TYPE: DNA
<213> ORGANISM: Homo sapiens

<400> SEQUENCE: 531
ttgttggtag agacggtgat tcactatgtt ggccaggcta gtcacgaact cctgacctcg        60
tgatccgccc acctcggcct cccaaagtgc tgggattaca ggtgtgagcc accgtgcccg      120
gcctcttttt atttattcct aaaatattac cttgaggcca aattctgcgc ttaaggagaa      180
tgtgcaccaa gtgctggggt gggggctggt tataaacgag gccacaaatc atgcttgtta      240
ataaattgtg tggttcaaat ctg                                                263

<210> SEQ ID NO 532
<211> LENGTH: 140
<212> TYPE: DNA
<213> ORGANISM: Homo sapiens
<220> FEATURE:
<221> NAME/KEY: modified_base
<222> LOCATION: (71)..(71)
<223> OTHER INFORMATION: a, c, t, g, unknown or other
<220> FEATURE:
<221> NAME/KEY: modified_base
<222> LOCATION: (82)..(82)
<223> OTHER INFORMATION: a, c, t, g, unknown or other

```
<220> FEATURE:
<221> NAME/KEY: modified_base
<222> LOCATION: (94)..(94)
<223> OTHER INFORMATION: a, c, t, g, unknown or other

<400> SEQUENCE: 532
cacagccaaa acctctacat ccctacattc acacacttcc tccacacacc atcctgaagt      60
caccccaact nctaccacca anatcaccac caanccccacc agtataggaa gcagcacacc    120
catggcccac actacctcag                                                 140

<210> SEQ ID NO 533
<211> LENGTH: 134
<212> TYPE: DNA
<213> ORGANISM: Homo sapiens

<400> SEQUENCE: 533
cagaggagct ttattagagg dacagggtga aacatattta caccggccga gcagggacct      60
taagaagcag gcgtgggagc agggtcccag ctcagacgag ttccaccttg gcattggggt    120
acaccgccac cacg                                                       134

<210> SEQ ID NO 534
<211> LENGTH: 207
<212> TYPE: DNA
<213> ORGANISM: Homo sapiens

<400> SEQUENCE: 534
gagtatgagt atgcctgagt gtgaatgtgt atgagtgtga atgagtgtgt gcacatgagt      60
gcacgggtgt cagcatgtgt atataagtgt gggcatgtgt atgtgattgt gtgagtgtgg    120
gcaggtgagt gtgttgggga tgtgggttag ggtggggagt ggtgctttct ctagtgtgtc    180
ctccggaaca tcttgcctac ctagcaa                                         207

<210> SEQ ID NO 535
<211> LENGTH: 113
<212> TYPE: DNA
<213> ORGANISM: Homo sapiens

<400> SEQUENCE: 535
gaaaactgtt agatgcacac tgttgatttt catggtggat tcaagaactc cctagtgagg      60
agctgaactt gctcaatcta aggctgattg tcgtgttcct ctttaaattg ttt            113

<210> SEQ ID NO 536
<211> LENGTH: 66
<212> TYPE: DNA
<213> ORGANISM: Homo sapiens

<400> SEQUENCE: 536
gtttttatta aaacacaaac gcacacacac acaaaattag ccaggcatgg tggtccatcc      60
ctgtaa                                                                 66

<210> SEQ ID NO 537
<211> LENGTH: 66
<212> TYPE: DNA
<213> ORGANISM: Homo sapiens

<400> SEQUENCE: 537
gtcaccccag agtcattgtc acctcagagt cattgtcact ccagagtcat tgtcacctca      60
gagtca                                                                 66
```

```
<210> SEQ ID NO 538
<211> LENGTH: 128
<212> TYPE: DNA
<213> ORGANISM: Homo sapiens

<400> SEQUENCE: 538
caggctgggc cgtgagcagg tgggccgttg agttacctct gtgctggatc ccgtgccccc      60
acttgcctac cctctgtcct gccttgttat tgtaagtgcc ttcaatactt tgcattttgg     120
gataataa                                                              128

<210> SEQ ID NO 539
<211> LENGTH: 49
<212> TYPE: DNA
<213> ORGANISM: Homo sapiens

<400> SEQUENCE: 539
tgattactag tgtaaactgg ttattgagat agattatgac attggtgga                  49

<210> SEQ ID NO 540
<211> LENGTH: 209
<212> TYPE: DNA
<213> ORGANISM: Homo sapiens

<400> SEQUENCE: 540
cagagtcatt cattgtcacc ccagagtcat tgtcacccga gtcattgtca gctcagagtc      60
attgtcaccc cagagtcatt gtcaccccag agtcattgtc accccattgt caccccagag     120
tcattgtcac ctcagagtca ttgtcactcc agagtcattg tcacctcaga gtcaatgtca     180
ccccagagtc atcgtcaccc cagagacat                                       209

<210> SEQ ID NO 541
<211> LENGTH: 237
<212> TYPE: DNA
<213> ORGANISM: Homo sapiens

<400> SEQUENCE: 541
aataaatgcc tcaggcgtgc tttttgattc atttgataaa caaagcatct tttatgtgga      60 ataccatt tgggtcctg aggataagag agatgagggc attagatcac tgacagctga       120
agatagaaga acatctttgg tttgattgtt taaataatat ttcaatgcct attctttgca     180
aggtactatg tttcgtaaat taaataggtc tggcccagaa gacccactca attgcct        237

<210> SEQ ID NO 542
<211> LENGTH: 62
<212> TYPE: DNA
<213> ORGANISM: Homo sapiens

<400> SEQUENCE: 542
tatgtaatta aagatgaag cgtagtgaat tgtacagctg ttgtaataat gacctatttc      60
ta                                                                     62

<210> SEQ ID NO 543
<211> LENGTH: 277
<212> TYPE: DNA
<213> ORGANISM: Homo sapiens

<400> SEQUENCE: 543
tacccccttt tatatctaat gtagaaaaag cgaaattgaa tctggaaagc aaactgttgt      60
atatagttgc ggtaacaatc atgaagagag agccgggctg tcccctcagt aattcatttt     120
```

```
aaataacaaa ttatttaaaa ataaaattca tgccagagcc agctgaagag gccttccttc      180
atcaccactg aggccacccc caatctgggc cctctgtcca tctggcatgt ctcctcccag      240
caagattcat ctgttcaatg ccatttgcgt ttcaata                              277
```

<210> SEQ ID NO 544
<211> LENGTH: 203
<212> TYPE: DNA
<213> ORGANISM: Homo sapiens

<400> SEQUENCE: 544

```
ttttcccaac tctatagcta gatttaaaag tcccagtaaa attttgtaaa caaaatcata      60
taagaaaagg caaggctggc tcttccctat ggtcctttag tggagctata tttgcataga     120
tcctagacaa atgatgcaaa acaaattccc tccaatttcc actagcaatc tccctaattc     180
gctcaaccct tacataagca tca                                             203
```

<210> SEQ ID NO 545
<211> LENGTH: 75
<212> TYPE: DNA
<213> ORGANISM: Homo sapiens

<400> SEQUENCE: 545

```
agaacctgag tataaattta ctttctcaaa ttcttgccat gagaggttga tgagttaatt      60
aaaggagaag attcc                                                       75
```

<210> SEQ ID NO 546
<211> LENGTH: 248
<212> TYPE: DNA
<213> ORGANISM: Homo sapiens

<400> SEQUENCE: 546

```
aaaaactcaa cctatctggt gttttatttt aatggataaa aatgtaattt ttttaaggta      60
gcaacttatt tccaaattaa tatagatgaa aaatagatac caattagact aaattgaaag     120 cttttttgttc tatatttgca tagcctttga aatatttctt agtgcctagg aggtctgggg    180
attcctcttt cgtggtggtc actaaccttt acttgatgcag ataaaatcac ttgtcaatgc    240
aaaatgtg                                                              248
```

<210> SEQ ID NO 547
<211> LENGTH: 174
<212> TYPE: DNA
<213> ORGANISM: Homo sapiens
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other

<400> SEQUENCE: 547

```
acgagccctc tcacagtgga atggagngca cggtctgaat ctgcacagag caagatgctg      60
```

| | |
|---|---|
| agtggagtcg ggggcttngt gctgggcctg ctcttncttg gggccgggct gttcatctac | 120 |
| ttnaggaatc agaaaggaca ctctggactt cagccaacag gattcctgaa ctga | 174 |

<210> SEQ ID NO 548
<211> LENGTH: 251
<212> TYPE: DNA
<213> ORGANISM: Homo sapiens

<400> SEQUENCE: 548

| | |
|---|---|
| agagagtgga catttgtcgg gaaactccta acatatgccc ccattctgga gagaacacag | 60 |
| agtacgacac aatccctcac actaatagaa caatcctaaa ggaagatcca gcaaatacgg | 120 |
| tttactccac tgtggaaata ccgaaaaaga tggaaaatcc ccactcactg ctcacgatgc | 180 |
| cagacacacc aaggctattt gcctatgaga atgttatcta gacagcagtg cactgcccct | 240 |
| aagtctctgc t | 251 |

<210> SEQ ID NO 549
<211> LENGTH: 88
<212> TYPE: DNA
<213> ORGANISM: Homo sapiens

<400> SEQUENCE: 549

| | |
|---|---|
| gccctcatgg ttggcatcac atatgcctgc atgccattaa caccagctgg ccctacccct | 60 |
| ataatgatcc tgtgtcctaa attaatat | 88 |

<210> SEQ ID NO 550
<211> LENGTH: 284
<212> TYPE: DNA
<213> ORGANISM: Homo sapiens

<400> SEQUENCE: 550

| | |
|---|---|
| aactgaaatg tcaacctgtg gactgtggca ttcctgaatc cattgagaat ggtaaagttg | 60 |
| aagacccaga gagcactttg tttggttctg tcatccgcta cacttgtgag gagccatatt | 120 |
| actacatgga aaatggagga ggtggggagt atcactgtgc tggtaacggg agctgggtga | 180 |
| atgaggtgct gggcccggag ctgccgaaat gtgttccagt ctgtggagtc cccagagaac | 240 |
| cctttgaaga aaaacagagg ataattggag gatccgatgc agat | 284 |

<210> SEQ ID NO 551
<211> LENGTH: 214
<212> TYPE: DNA
<213> ORGANISM: Homo sapiens

<400> SEQUENCE: 551

| | |
|---|---|
| gacttattcc cgctgactga gttttgagg ggctaccagg aaagcgcctc caaccctagc | 60 |
| aaaagtgcaa gatggggagt gagaggctgg gaatggaggg gcagagccag gaagatcccc | 120 |
| cagaaaagaa agctacagaa gaaactgggg ctcctccagg gtggcagcaa caataaatag | 180 |
| acacgcacgg cagccacagc ttgggtgtgt gttc | 214 |

<210> SEQ ID NO 552
<211> LENGTH: 72
<212> TYPE: DNA
<213> ORGANISM: Homo sapiens

<400> SEQUENCE: 552

| | |
|---|---|
| gaatggcagt accagaaggc attggttaag tgtcccagga accacacaag cagtgactcc | 60 |
| taaagaagtt ca | 72 |

<210> SEQ ID NO 553
<211> LENGTH: 180
<212> TYPE: DNA
<213> ORGANISM: Homo sapiens

<400> SEQUENCE: 553

```
gcttccttaa aggtcagaac atcaggccaa agtacaacgt ttaatttcag aacttgcctt      60
ccaatttacg cattttcaat ttgctctccc catttgttga gtcagaagaa gcagcattgc     120
ccagaaacag gtattacgta acatgcacat actttaaaaa gtactcatcc cttgttttct     180
```

<210> SEQ ID NO 554
<211> LENGTH: 173
<212> TYPE: DNA
<213> ORGANISM: Homo sapiens

<400> SEQUENCE: 554

```
gctgagtatg ttaagctctt tatgactgtt tttgtagtgg tatagagtac tgcagaatac      60
agtaagctgc tttattgtag catttcttga tgttgcttag tcacttattt cataaacaac     120
ttaatgtttt gaataatttc ttactaaaca ttttgttatt gggcaagtga ttg            173
```

<210> SEQ ID NO 555
<211> LENGTH: 243
<212> TYPE: DNA
<213> ORGANISM: Homo sapiens

<400> SEQUENCE: 555

```
aaaacttggc acttttcgt gtggatcttg ccacatttct gatcagaggt gtacactaac       60
atttcccccg agctcttggc ctttgcattt atttatacag tgccttgctc ggcgcccacc     120
acccctcaa gccccagcag ccctcaacag gcccagggag ggaagtgtga gcgccttggt     180
atgacttaaa attggaaatg tcatctaacc attaagtcat gtgtgaacac ataaggacgt     240
gtg                                                                  243
```

<210> SEQ ID NO 556
<211> LENGTH: 201
<212> TYPE: DNA
<213> ORGANISM: Homo sapiens

<400> SEQUENCE: 556

```
ccctgctgcc tctgatcgta ggaattgagg agtgtcccgc cttgtggctg agaactggac      60
agtggcaggg gctggagatg ggtgtgtgtg tgtgtgtgtg tgtgtgtgtg tgtgtgcgcg     120
cgcgccagtg caagaccgag attgagggaa agcatgtctg ctgggtgtga ccatgttttcc    180
tctcaataaa gttccctgt g                                               201
```

<210> SEQ ID NO 557
<211> LENGTH: 174
<212> TYPE: DNA
<213> ORGANISM: Homo sapiens

<400> SEQUENCE: 557

```
tgggcgtccg ggcccccaat attcacgcac tcgcaccacg cactcatatt ccctcacccc      60
accatcacgg ccccaaagaa ggtcttccct ctcgcgaagt ccaccatatc ggggtgactg     120
atgttggacg tacaccctct cgcccctccg gagctgcacc aggccgccga accc           174
```

<210> SEQ ID NO 558

<211> LENGTH: 259
<212> TYPE: DNA
<213> ORGANISM: Homo sapiens

<400> SEQUENCE: 558

```
ctacaacagg caggtactgc tgccaggggg ctttgaacta gtgcctgcta cccaggacac    60
ccgggccatg cccctggctg ggcagcctgg cacaagtgaa gaagaaggca gtgggaaaac   120
tgggtttatt tcaaggcagc agcctgagcc caggagcaga ggacccagtt gttataaggc   180
gctgggagag gatgggcagc tcccactgcc ccagagcgga gctcgaagca cccaggttgc   240
ccacggaaaa tccaataaa                                                259
```

<210> SEQ ID NO 559
<211> LENGTH: 60
<212> TYPE: DNA
<213> ORGANISM: Homo sapiens

<400> SEQUENCE: 559

```
tttctggggt ctttgagctc caaaaaataa acacttcctt tgagggagag cccccccca    60
```

<210> SEQ ID NO 560
<211> LENGTH: 159
<212> TYPE: DNA
<213> ORGANISM: Homo sapiens

<400> SEQUENCE: 560

```
gagcttcctt cttcgttctt ggcaccatct tatgaaaagg gtccagatta agattttga    60
ctgagtcatt ctaaagtaag ttgcaagacc catgatacta gaccactaaa tacttcatca   120
cacacctcct aagaataaga accaacatta tcacaccaa                          159
```

<210> SEQ ID NO 561
<211> LENGTH: 278
<212> TYPE: DNA
<213> ORGANISM: Homo sapiens

<400> SEQUENCE: 561

```
ggaagccatt atcctaaatg aactcactca gaaacagaaa accaaatacc acatgttctc    60
acttataagt agaagctaaa cattgagtac acatggatac aaagaaggga accgcagaca   120
ctggggccta cctgaggtcg gagcatggaa ggagggtgag gatcaaaaaa ctacctatct   180
ggtactatgc tttttatctg gatgatgaaa taatctgtac aacaaaccct ggtgacatgc   240
aatttaccta tatagcaagc ctacacatgt gcccctga                           278
```

<210> SEQ ID NO 562
<211> LENGTH: 241
<212> TYPE: DNA
<213> ORGANISM: Homo sapiens

<400> SEQUENCE: 562

```
ttcccatctc gtccatgagc ctaggtcttg gagccttgtg ttggaggctg ctgtgatgtc    60
aggaacgggg atctttctag cttttggcca cttcctggga cctcacgccc ctgttgacag   120
atggagattg ggcagcaggg ccttgctgca ttgttatctg ctgttccgac ttggtttgtc   180
ttgtccaagg gtgacgaaag agccaggcac cagggtctca tgggatgagg tccaactttt   240
t                                                                   241
```

<210> SEQ ID NO 563
<211> LENGTH: 283

<212> TYPE: DNA
<213> ORGANISM: Homo sapiens

<400> SEQUENCE: 563

```
gtgagaggta acactctaaa tagcccattt catgctcaag acatccaagt caaagaaacc    60
caatagcaca ggtgagtccc ctctgttccc ccccaacacc ccactcacat cagggcccct   120
gccctggagt gtcaccttta ttagctgtga gagacacccc agagccctgg cactgtcag    180
tgattggggt agaacaaaaa caggacctgg tcagagccca cagatgtggc tagaggaact   240
gtggggtggt gagctccctc ataggctcct gaccacaata tcc                     283
```

<210> SEQ ID NO 564
<211> LENGTH: 186
<212> TYPE: DNA
<213> ORGANISM: Homo sapiens

<400> SEQUENCE: 564

```
gagacttgta tgaaagatgg ctgtgcctct gcctgtctcc cccaccgggc tgggagctct    60
gcagagcagg aaacatgact cgtatatgtc tcaggtccct gcagggccaa gcacctagcc   120
tcgctcttgg caggtactca gcgaatgaat gctgtatatg ttgggtgcaa agttccctac   180
ttcctg                                                              186
```

<210> SEQ ID NO 565
<211> LENGTH: 267
<212> TYPE: DNA
<213> ORGANISM: Homo sapiens

<400> SEQUENCE: 565

```
gcatttcaaa gtgacttcta tgaagctttt tttttaatgt gaaattttca gaatgttgtt    60
tttttcatgt agatactcca ggaagagtta agcactgctt tcagttttaa tatccacctt   120
gaggggtcgc tgcttgaggg ctcttatccc aggggacttt ttaattcgga tgttacttaa   180
tgtggcttct ctaatgtagt ttctttgatt accgactaca caattatgta ccatcacagt   240
attagtggaa aagtaccatg tgattta                                       267
```

<210> SEQ ID NO 566
<211> LENGTH: 45
<212> TYPE: DNA
<213> ORGANISM: Homo sapiens

<400> SEQUENCE: 566

```
tgcttataca cttacacttt atgcacaaaa tgtagggtta taata                    45
```

<210> SEQ ID NO 567
<211> LENGTH: 241
<212> TYPE: DNA
<213> ORGANISM: Homo sapiens

<400> SEQUENCE: 567

```
aactggaccc tgtcgttctc catcttctca gtcagttgtt tcaagtgttc ctgataactc    60
ctctccttct gttccatcat ctgctcattc tttctttgca tttcctgcaa cattttttgct  120
gaagcctgtg cagactcagc tttcacaagt tccacttcaa tctcctttct ttttcgtgtg  180
agagtctggt ctgtctggag aattgcatca gtcatagact ccttggattt caagtatgtc   240
t                                                                   241
```

<210> SEQ ID NO 568

```
<211> LENGTH: 159
<212> TYPE: DNA
<213> ORGANISM: Homo sapiens

<400> SEQUENCE: 568
gagcttcctt cttcgttctt ggcaccatct tatgaaaagg gtccagatta agatttttga    60
ctgagtcatt ctaaagtaag ttgcaagacc catgatacta gaccactaaa tacttcatca   120
cacacctcct aagaataaga accaacatta tcacaccaa                          159

<210> SEQ ID NO 569
<211> LENGTH: 107
<212> TYPE: DNA
<213> ORGANISM: Homo sapiens

<400> SEQUENCE: 569
tactcccgag gctctgtaca ttgctgccac atactcctgc cagcttgggg gagtgttcct    60
tcaccctcac agtatttatt atcctgcacc acctcactgt tccccat                 107

<210> SEQ ID NO 570
<211> LENGTH: 273
<212> TYPE: DNA
<213> ORGANISM: Homo sapiens

<400> SEQUENCE: 570
tagaagatga cctcgttccg gagctgggta tttcaaattt gctttcatcc agccactgcc    60
caaagccatt ttcctgccta ctggatgctt acagtgactg tggatacggg ggttcccttt   120
ccccattcag tgacatgtcc tctttgcttg gtgtaaacca ttcttgggag acacttttg    180 ccaatgaact ctttccccag ctgattagtg tctaaggaat gatccaatac tgttgccctt   240
ttccttgact attacactgc ctggaggata gca                                273

<210> SEQ ID NO 571
<211> LENGTH: 228
<212> TYPE: DNA
<213> ORGANISM: Homo sapiens

<400> SEQUENCE: 571
atgtaggaga acgtgcccta ttcacacttt gggaagacgc taatttgtga catttttttt    60
tcaagcctgc catcaaggac attttttaag acccaactgg catgagttgg ggtaaatttcc  120 tattattttc attttggaca actttttttaa cttatattct ttatagagga ttccccaaaa  180
tgtgctcctc attttttggcc tctcatgttc caaacctcat tgaataaa               228

<210> SEQ ID NO 572
<211> LENGTH: 286
<212> TYPE: DNA
<213> ORGANISM: Homo sapiens

<400> SEQUENCE: 572
gctgtgttgg ccctcacttg ggattctcag cagttacatg aaagttgtgc tgataatctc    60
ttctcttgta ccaatttttag tcaggcagaa aatggtaaac atgagggtgc tcttgtgact  120
taatttttgt tcaagggact aaattgctta tgtttattcc ctgtcagcgg agtgagaat    180 gtcattcatc aataaaccaa agccaatagc tggagaattg agatctggtt gaaagtggtt   240
tatggtttac atgctgtact atcctgagga attgcgagat attgct                  286

<210> SEQ ID NO 573
<211> LENGTH: 266
```

<212> TYPE: DNA
<213> ORGANISM: Homo sapiens
<220> FEATURE:
<221> NAME/KEY: modified_base
<222> LOCATION: (214)..(214)
<223> OTHER INFORMATION: a, c, t, g, unknown or other

<400> SEQUENCE: 573

| | | | | | |
|---|---|---|---|---|---|
| ccctgcgcct | atcaggtcgt | gagtccaggg | gtctacaagt | cccgggcccc | ccagttcacg | 60 |
| attctggcgc | ggacttcgct | cccccaagac | aacactcgga | agccagggcc | cgcggcctac | 120 |
| aacgtggatc | agcaccggaa | gccccgcggc | tggagtttcg | ggatccggca | ctcggactac | 180 |
| ctggccccgc | tggtgaccga | cgcggacaac | tganccgcca | ggcgggagcg | gccccacacg | 240 |
| tgtttgctta | aagtctgcga | gtccgc | | | | 266 |

<210> SEQ ID NO 574
<211> LENGTH: 270
<212> TYPE: DNA
<213> ORGANISM: Homo sapiens

<400> SEQUENCE: 574

| | | | | | |
|---|---|---|---|---|---|
| ccagggctga | gagacacgtg | aaggaagatg | atgggaggaa | aagcccagga | gaagtcccac | 60 |
| cagggaccag | cccagcctgc | atacttgcca | cttggccacc | aggactcctt | gttctgctct | 120 |
| ggcaagagac | tactctgcct | gaacactgct | tctcctggac | cctggaagca | gggactggtt | 180 |
| gagggagtgg | ggaggtggta | agaacacctg | acaacttctg | aatattggac | attttaaaca | 240 |
| cttacaaata | aatccaagac | tgtcatattt | | | | 270 |

<210> SEQ ID NO 575
<211> LENGTH: 227
<212> TYPE: DNA
<213> ORGANISM: Homo sapiens

<400> SEQUENCE: 575

| | | | | | |
|---|---|---|---|---|---|
| gaagatgaag | ccccatgctc | agtcccctcc | catccccac | gcagctccac | cccagtccca | 60 |
| agccaccagc | tgtttgctcc | tggtgggagg | tggcctcctc | agccctcct | ttctgacctt | 120 |
| taacctcact | ctcaccttgc | accgtgcacc | aacccttcac | ccctcctgga | aagcaggcct | 180 |
| gatggcttcc | cactggcctc | caccacctga | ccagagtgtt | ctcttca | | 227 |

<210> SEQ ID NO 576
<211> LENGTH: 279
<212> TYPE: DNA
<213> ORGANISM: Homo sapiens

<400> SEQUENCE: 576

| | | | | | |
|---|---|---|---|---|---|
| gcatttgctg | tgtttcgtta | gcatctggct | ccaggacaga | ccttcaactt | ccaaattgga | 60 |
| tactgctgcc | aagaagttgc | tctgaagtca | gtttctatca | ttttgctctt | tgattcaaag | 120 |
| cactgtttct | ctcactgggc | ctccaaccat | gttccctttt | ttttagcacc | acaaataatc | 180 |
| aaaacccaac | atgactgttt | gttttccttt | aaaaatatgc | accaaatcat | ctctcatcac | 240 |
| ttttctttga | gggttttagt | agacagtagg | agttaataa | | | 279 |

<210> SEQ ID NO 577
<211> LENGTH: 123
<212> TYPE: DNA
<213> ORGANISM: Homo sapiens
<220> FEATURE:
<221> NAME/KEY: modified_base
<222> LOCATION: (52)..(52)

<223> OTHER INFORMATION: a, c, t, g, unknown or other

<400> SEQUENCE: 577
gcggactcgc agactttaag caaacacgtg tggggccgct cccgcctggg tngcagttgt    60
ccgcgtcggt caccagcggg gccaggtagt ccgagtgccg gatcccgaaa ctccagccgc   120
ggg                                                                 123

<210> SEQ ID NO 578
<211> LENGTH: 82
<212> TYPE: DNA
<213> ORGANISM: Homo sapiens

<400> SEQUENCE: 578
gtgctcagta gtcagactgg atagtccgtt tttgcttatc cgttagccgt ggggatttag    60
caggaagctg tgagagcagt tt                                             82

<210> SEQ ID NO 579
<211> LENGTH: 151
<212> TYPE: DNA
<213> ORGANISM: Homo sapiens

<400> SEQUENCE: 579
acacagaaga gtgacatgtt tacaaacctc aagccagcct tgctcctggc tggggcctgt    60
tgaagatgct tgtattttac ttttccattg taattgctat cgccatcaca gctgaacttg   120
ttgagatccc cgtgttactg cctatcagca t                                  151

<210> SEQ ID NO 580
<211> LENGTH: 82
<212> TYPE: DNA
<213> ORGANISM: Homo sapiens

<400> SEQUENCE: 580
tttaaaatac tcagaggaca ggatcactgt ggaatcgaat cagaagtggt ggctggaatt    60
ccacgcaccg atcagtactg gg                                             82

<210> SEQ ID NO 581
<211> LENGTH: 109
<212> TYPE: DNA
<213> ORGANISM: Homo sapiens

<400> SEQUENCE: 581
aagagaagac tcacagtatc aggtctactg aaggagatac ggtgattcct gttcttggct    60 tgtagattc atctggtata aacagcactc ctgagttatg accttttga               109

<210> SEQ ID NO 582
<211> LENGTH: 118
<212> TYPE: DNA
<213> ORGANISM: Homo sapiens

<400> SEQUENCE: 582
tttgaagatt agaaatttag ccgtaggtaa agaatacaaa ggaaaaataa ttttaaaatc    60
atcaaccaga tcaacaaaat atatgttaat gccgagactt tgaattagag tgcgaatt    118

<210> SEQ ID NO 583
<211> LENGTH: 242
<212> TYPE: DNA
<213> ORGANISM: Homo sapiens

<400> SEQUENCE: 583

```
catcttctag cagatctttt tcagttaaga ttacttgttc ttccatgtat tcatatttag    60
ccagctcctt gatcagccgc agtatgtcac tgcagtcggc ggcagtggct gggcggatca   120
cgaatttagc cattttcgtc ttttgctttt cttcccttttg cggaccaggc ccctgtactt   180
gaacagtagg aggaggtggt tcctcattcg tctcccggga cgtcctcttc ctcagtcagg   240
ct                                                                   242
```

<210> SEQ ID NO 584
<211> LENGTH: 34
<212> TYPE: DNA
<213> ORGANISM: Homo sapiens

<400> SEQUENCE: 584

```
gaaatcattg tgggattgct agctttccct ctta                                34
```

<210> SEQ ID NO 585
<211> LENGTH: 272
<212> TYPE: DNA
<213> ORGANISM: Homo sapiens

<400> SEQUENCE: 585

```
caacctctta caacccaggc attcctttct atcgataatt actctttcaa ccaattgcca    60
atcagaaaat tgttatatct acctataatc tagaagcccc cacatcaagt tgttttgcct   120
ttctggacag gaccaatgta tatcttaaat gtatttgatt gatctctcat gtctccctaa   180
aatgtataaa accacgctgt tccccgacca cctggagcac atgttctcag ggtctcctga   240
gggctgtgtc acaggccatg ttcacttaca tt                                 272
```

<210> SEQ ID NO 586
<211> LENGTH: 189
<212> TYPE: DNA
<213> ORGANISM: Homo sapiens

<400> SEQUENCE: 586

```
ccctgcagag aatcacgtcc tggaactgca tgttcttgcg actcttggga cttcatttta    60
acttctcgct gccccagcca tgttttcaac catggcatcc ctcccccaat tagttccctg   120
tcatcctcgt caaccttctc tgtaagtgcc tggtaagctt gcccttgctt aagaactcaa   180
aacatagct                                                            189
```

<210> SEQ ID NO 587
<211> LENGTH: 163
<212> TYPE: DNA
<213> ORGANISM: Homo sapiens

<400> SEQUENCE: 587

```
tgagcagact gcaccccaag ctcccgactc caggtcccct gatcttgggg cctgtttccc    60
atgggattca agaggacag ccccagcttt gtgtgtgttt aagcttagga atcgcctttta   120 tggaaagggc tatgtgggag agtcagctat cttgtctggt ttt                     163
```

<210> SEQ ID NO 588
<211> LENGTH: 296
<212> TYPE: DNA
<213> ORGANISM: Homo sapiens
<220> FEATURE:
<221> NAME/KEY: modified_base
<222> LOCATION: (75)..(75)
<223> OTHER INFORMATION: a, c, t, g, unknown or other
<220> FEATURE:

```
<221> NAME/KEY: modified_base
<222> LOCATION: (262)..(262)
<223> OTHER INFORMATION: a, c, t, g, unknown or other

<400> SEQUENCE: 588
atgggtgtag atcaaggcag gagcaggaac caaaaagaaa ggcataaaca taagaaaaaa      60
aatggaaggg gtggnaaaca gagtacaata acatgagtaa tttgatgggg gctattatga     120
actgagaaat gaactttgaa aagtatcttg gggccaaatc atgtagactc ttgagtgatg     180
tgttaaggaa tgctatgagt gctgagaggg catcagaagt ccttgagagc ctccagagaa     240
aggctcttaa aaatgcagcg cnatctccag tgacagaaga tactgctaga aatctg         296

<210> SEQ ID NO 589
<211> LENGTH: 246
<212> TYPE: DNA
<213> ORGANISM: Homo sapiens

<400> SEQUENCE: 589
tgtacagatt caagcaatgg atgcaaggaa catgctgtat gtaatagaag aaagaagtcc      60
acgttttcgg cagaagtagt gagtcagtgt ggaagagagg tgagggtgtg ctttactttt     120
tgataaagag aaagatgttt actcataaac ccttcaaaag gtattaacaa atgtttacca     180
aacctattgc tttattttaa aaacataatt tgtgttttct atttgtaaga tctgacattt     240
cgaggc                                                                246

<210> SEQ ID NO 590
<211> LENGTH: 121
<212> TYPE: DNA
<213> ORGANISM: Homo sapiens

<400> SEQUENCE: 590
ggcagcgacc cggaaacagc gtatcactga gaccgagtcg ccttatcagg agctccaggg      60
tcagaggtcg gatgtctaca gcgacctcaa cacacagagg ccgtattaca aatgagcccg     120
a                                                                     121

<210> SEQ ID NO 591
<211> LENGTH: 262
<212> TYPE: DNA
<213> ORGANISM: Homo sapiens

<400> SEQUENCE: 591
tggtgaccag ttctcggttt catagttttt actatcagtt tgcctttggg attctttgaa      60
agctcttgag gcttttttccg cagcttctag gagatgtgtt aggtcattaa cagtaatgct     120
cctacagttt ttgttcccat ccaaccacca tttgatttca cttttgtaga cttgacctag     180
tgtatctgaa atataggaat ttttaggtgc tttcattttg gcctgacgtg cccagtccag     240
agctgtgtta aagtccttct ct                                              262

<210> SEQ ID NO 592
<211> LENGTH: 226
<212> TYPE: DNA
<213> ORGANISM: Homo sapiens

<400> SEQUENCE: 592
gtcattcaca actgatttca agagtcacct tcaccaggaa gtcttccttg accaccatca      60
ttcctgcctg attagagggc ttcctcatgg taatatgtgt tctcaagttt tcagtgtcaa     120
ggaatgccat cccagaagct cattttcaga tgcacaacag ccagaacagt ctcaagcagc     180
```

| | |
|---|---|
| attctagagc ttggaattta agaactacgc attgcctata aagtga | 226 |

<210> SEQ ID NO 593
<211> LENGTH: 272
<212> TYPE: DNA
<213> ORGANISM: Homo sapiens

<400> SEQUENCE: 593

| | |
|---|---|
| agagctcttg agtgggctag tgactccccc tgcagcctgg tggagatggt gtgaggagcg | 60 |
| aagagccctc tgctctagga tttgggttga aaaacagaga gagaagtggg gagttgccac | 120 |
| aggagctaac acgctgggag gcagttgggg gcgggtgaac tttgtgtagc cgaggccgca | 180 |
| ccctccctca ttccaggctc attcattttc atgctccatt gccagactct tgctgggagc | 240 |
| ccgtccagaa tgtcctccca ataaaactcc at | 272 |

<210> SEQ ID NO 594
<211> LENGTH: 151
<212> TYPE: DNA
<213> ORGANISM: Homo sapiens

<400> SEQUENCE: 594

| | |
|---|---|
| tagggattaa cttcctgtat gctgcaactc atgaacttgg ccattctttg ggtatgggac | 60 |
| attcctctga tcctaatgca gtgatgtatc caacctatgg aaatggagat ccccaaaatt | 120 |
| ttaaactttc ccaggatgat attaaaggca t | 151 |

<210> SEQ ID NO 595
<211> LENGTH: 243
<212> TYPE: DNA
<213> ORGANISM: Homo sapiens

<400> SEQUENCE: 595

| | |
|---|---|
| tcccctgctt gaacactgaa gggcaggtgg tgggccatgg ccatggtccc cagctgagga | 60 |
| gcaggtgtcc ctgagaaccc aaacttccca gagagtatgt gagaaccaac caatgaaaac | 120 |
| agtcccatcg ctcttacccg gtaagtaaac agtcagaaaa ttagcatgaa agcagtttag | 180 |
| cattgggagg aagctcagat ctctagagct gtcttgtcgc cgcccaggat tgacctgtgt | 240 |
| gta | 243 |

<210> SEQ ID NO 596
<211> LENGTH: 82
<212> TYPE: DNA
<213> ORGANISM: Homo sapiens

<400> SEQUENCE: 596

| | |
|---|---|
| cagatgttgg tatctgcagg gatcctggaa ccaaacccct gcagatacta agggctgacg | 60 |
| atctaggtaa gactggattt aa | 82 |

<210> SEQ ID NO 597
<211> LENGTH: 236
<212> TYPE: DNA
<213> ORGANISM: Homo sapiens

<400> SEQUENCE: 597

| | |
|---|---|
| actctcaggc tgcgtccagc gacagtgccc agggctctga tgtgtctctc acagcttgaa | 60 |
| aagcctgaga cagctgtctt gtgagggact gagatgcagg atttcttcac gcctcccctt | 120 |
| tgtgacttca agagcctctg gcatctcttt ctgcaaaggc acctgaatgt gtctgcgtcc | 180 |

```
ctgttagcat aatgtgagga ggtggagaga cagcccaccc ttgtgtccac tgtgac         236
```

<210> SEQ ID NO 598
<211> LENGTH: 119
<212> TYPE: DNA
<213> ORGANISM: Homo sapiens

<400> SEQUENCE: 598

```
gccagagaga ccaagtgtta tgtaagaagt agtgtcggct gtgtagaacc actgactaca    60
caggccgaag ttactgagaa cttggacaga aaaaatagcc agcaagtgtt caaactact   119
```

<210> SEQ ID NO 599
<211> LENGTH: 264
<212> TYPE: DNA
<213> ORGANISM: Homo sapiens

<400> SEQUENCE: 599

```
gccaacagca tcttttccgg gttcctgctc tttccagata tggaggcctg acctgtgggc    60
tgcttcacat ccaccccggc tcccctgcc agcaacgctc actctacccc caacaccacc   120
ccttgcccag ccaatgcaca cagtagggct tggtgaatgc tgctgagtga atgagtaaat  180
aaacttttca aggccaaggg acagtggttt aattcaactc tgtgtcccag cacctggcac  240
accagaagtg ccatgctcag aaat                                         264
```

<210> SEQ ID NO 600
<211> LENGTH: 273
<212> TYPE: DNA
<213> ORGANISM: Homo sapiens

<400> SEQUENCE: 600

```
ttcaaactca atgatgctac catgcctctc caacattttc aaccccctga cattatcttg    60
gatcctatgg tttctccatc caattctttg aatttcccag tctcccctat gtaaaactta   120
gcaacttggg ggacctcatt cctgggacta tgctgtaacc aaattattgt ccaaggctat  180
attttgggga tgaatataat ttgaggaagg gagttaaaga ccctcctggg gctctcagtg   240
tgccatagag gacagcaact ggtgattgtt tca                                273
```

<210> SEQ ID NO 601
<211> LENGTH: 275
<212> TYPE: DNA
<213> ORGANISM: Homo sapiens

<400> SEQUENCE: 601

```
acttacatac tagcttccaa ggacaggtgg aggtagggcc agcctggcgg gagtggagaa    60
gcccagtctg tcctatgtaa gggacaaagc caggtttaat ggtactgggt aggggggcact  120
gccaagacaa taagctaggc tactgggtcc agctactact ttggtgggat tcaggtgagt   180
ctccatgcac ttcacatgtt acccagtgtt cttgttactt ccaaggagaa ccaagaatgg   240
ctctgtcaca ctcgaagcca ggtttgatca ataaa                              275
```

<210> SEQ ID NO 602
<211> LENGTH: 261
<212> TYPE: DNA
<213> ORGANISM: Homo sapiens

<400> SEQUENCE: 602

```
tcactcccac ctgttactgc tgggagtcaa gtcagctagg aaggaagcag acatttttt    60
caaacagcaa gtggggccca tggaactgaa tctttactcc ttggtgcacc gcttttgtcg   120
```
tgcgttgcct tgctccgttt ttcccaaaaa gcactggctt catcaaggcc accgacgatt      180
tcctgagtgc actgggaaat ttgggtatag gtcaggcttg gcagccttga tcccaggaga      240
gtactaatgg taacaagtca a                                                261

<210> SEQ ID NO 603
<211> LENGTH: 241
<212> TYPE: DNA
<213> ORGANISM: Homo sapiens

<400> SEQUENCE: 603
ttgttcccga ctagctgcct tgcacattat tttcattttc ctggaatttg atacagagag      60
caatttatag ccaattgata gcttatgctg tttcaatgta aattcgtggt aaataactta     120
ggaactgcct tttcttttc tttgaaaacc tacttataac tgttgctaat aagaatgtgt      180
attgttcagg acaacttgtc tccatacagt tgggttgtaa ccctcatgct tggcccaaat    240
a                                                                      241

<210> SEQ ID NO 604
<211> LENGTH: 107
<212> TYPE: DNA
<213> ORGANISM: Homo sapiens

<400> SEQUENCE: 604
taaatataat atcgacacag tgctttccgt ggcactgcat acaatctgag gcctcctctc      60
tcagttttta tatagatggc gagaacctaa gtttcagttg attttac                    107

<210> SEQ ID NO 605
<211> LENGTH: 252
<212> TYPE: DNA
<213> ORGANISM: Homo sapiens
<220> FEATURE:
<221> NAME/KEY: modified_base
<222> LOCATION: (180)..(182)
<223> OTHER INFORMATION: a, c, t, g, unknown or other

<400> SEQUENCE: 605
gtggagcagt tggactgctc tctctgctct caggatgata ctgtgagaac aatttaaata      60
tgctaagcac atgtcaggaa acagttttgt ggtctttgga cactcgctgt agccattccg     120
ttccatttca ggtgattta ttcatttcat ttgtagaata aaataatcc atttcacacn       180 nncacacaca cacacacaca cacacacaca caccctctat acaccactaa agcctcccat     240
taaacccata ga                                                         252

<210> SEQ ID NO 606
<211> LENGTH: 96
<212> TYPE: DNA
<213> ORGANISM: Homo sapiens

<400> SEQUENCE: 606
tcgacacagt gctttccgtg gcactgcata caatctgagg cctcctctct cagttttat      60 atagatggcg agaacctaag tttcagttga ttttac                               96

<210> SEQ ID NO 607
<211> LENGTH: 181
<212> TYPE: DNA
<213> ORGANISM: Homo sapiens
<220> FEATURE:
<221> NAME/KEY: modified_base
<222> LOCATION: (43)..(44)

```
<223> OTHER INFORMATION: a, c, t, g, unknown or other
<220> FEATURE:
<221> NAME/KEY: modified_base
<222> LOCATION: (78)..(79)
<223> OTHER INFORMATION: a, c, t, g, unknown or other
<220> FEATURE:
<221> NAME/KEY: modified_base
<222> LOCATION: (99)..(99)
<223> OTHER INFORMATION: a, c, t, g, unknown or other
<220> FEATURE:
<221> NAME/KEY: modified_base
<222> LOCATION: (110)..(110)
<223> OTHER INFORMATION: a, c, t, g, unknown or other

<400> SEQUENCE: 607
gccagagaag cgattagaaa ccctgaggg ccgattactg acnncataaa tcatgagttt    60
gggggctttg cctgggtnnt gttggtacca ggagacatng ttataaccan caacgtcact    120
gctggttcca gtgcaggaga tggtgatcga ctgtccagga gacccagaca cggaggcagg    180
c                                                                    181

<210> SEQ ID NO 608
<211> LENGTH: 115
<212> TYPE: DNA
<213> ORGANISM: Homo sapiens

<400> SEQUENCE: 608
aggagctgag gtgctacccg gagccccatt cacccccacc tgcccacttg ggaatctgag    60
gcagaggagg gtgaggcctg tgtgccaacc ttgttcacat accaccttcg tcccc         115

<210> SEQ ID NO 609
<211> LENGTH: 53
<212> TYPE: DNA
<213> ORGANISM: Homo sapiens

<400> SEQUENCE: 609
aagcaagata tcaatgtagc agaattgcac ttgtgcctca cgaacataca taa            53

<210> SEQ ID NO 610
<211> LENGTH: 155
<212> TYPE: DNA
<213> ORGANISM: Homo sapiens

<400> SEQUENCE: 610
gttgttgatc atggatcata ctccccttgt ttctttgggt gagaagggat cgcagtttgg    60
aaactccggc ggctgcgtgc ggggtttcag tcccagctgt aggcttgtaa atacccgccc    120
cgccaaaccg catagagaac gtggcagcaa gctga                                155

<210> SEQ ID NO 611
<211> LENGTH: 190
<212> TYPE: DNA
<213> ORGANISM: Homo sapiens

<400> SEQUENCE: 611
cacagggaaa tcagggttac aaatcttctt gatccacttc tctcaggatc ccctctcttc    60
ctacccttcc tcaccacttc cctcagtccc aactcctttt ccctatttcc ttctcctcct    120
gtctttaaag cctgcctctt ccaggaagac cccctattg ctgctggggc tcccatttg     180 cttactttgc                                                           190

<210> SEQ ID NO 612
<211> LENGTH: 63
```

<212> TYPE: DNA
<213> ORGANISM: Homo sapiens

<400> SEQUENCE: 612
attagaacct tagtataaat ttactttctc aaattcttgc catgagaggt tgatgagtta    60
att                                                                 63

<210> SEQ ID NO 613
<211> LENGTH: 281
<212> TYPE: DNA
<213> ORGANISM: Homo sapiens

<400> SEQUENCE: 613
ggagacagat ggagggtacc ctatttacaa ctgagtcagc caagccactg atgggaatat    60
acagatttag gtgctaaacc atttattttc cacggatgag tcacaatttg aagaatcaaa   120
cttccatcct gaaaatttat atgtttcaaa accacttgcc atcctgttag attgccagtt   180
cctgggacca ggcctcagac tgtgaagtat atatcctcca gcattcagtc caggggagc   240 cacggaaacc atgttttgc ttaagccatt aaagtcagag a                       281

<210> SEQ ID NO 614
<211> LENGTH: 239
<212> TYPE: DNA
<213> ORGANISM: Homo sapiens

<400> SEQUENCE: 614
agatgcgctc gagacccacg ggccttccac ctccctcagc ttcctgcatg gacccacctt    60
actggccagt ctgcatcctt gcctagacca ttctcccctc cagggagccc accctgaccc   120
acccccactg cacccctcc ccatgggttc tctccttcct ctgaacttct ttaggagtca   180
ctgcttgtgt ggttcctggg acacttaacc aatgccttct ggtactgcca ttctttttt    239

<210> SEQ ID NO 615
<211> LENGTH: 196
<212> TYPE: DNA
<213> ORGANISM: Homo sapiens

<400> SEQUENCE: 615
gcctttaaga taccttgatg aagacctgga ctattgaatg gagcagaaat tcacctctct    60
cactgactat tacagttgca tttttatgga gttcttcttc tcctaggatt cctaagactg   120
ctgctgaatt tataaaaatt aagtttgtga atgtgactac ttagtggtgt atatgagact   180
ttcaagggaa ttaaat                                                   196

<210> SEQ ID NO 616
<211> LENGTH: 38
<212> TYPE: DNA
<213> ORGANISM: Homo sapiens

<400> SEQUENCE: 616
agtctgccta tgatctttga atgagctttt taaggaag                           38

<210> SEQ ID NO 617
<211> LENGTH: 110
<212> TYPE: DNA
<213> ORGANISM: Homo sapiens

<400> SEQUENCE: 617
tttaacttga gggtgtagag gtcctccacg cttgtttgcc tgaaagtaat ataatgatgc    60
tgtctgaaca ggttttactg cttgctttcc aagtaaaggt taattatgat    110

<210> SEQ ID NO 618
<211> LENGTH: 173
<212> TYPE: DNA
<213> ORGANISM: Homo sapiens

<400> SEQUENCE: 618
tattttccct ctttcgaaca aagacattgg tttgcccaag gactacaaat aaaccaacgg    60 gaaaaagaa aggttccagt tttgtctgaa aattctgatt aagcctctgg gccctacagc    120
ctggagaacc tggagaatcc tacacccaca gaacccggct ttgtccccaa aga    173

<210> SEQ ID NO 619
<211> LENGTH: 82
<212> TYPE: DNA
<213> ORGANISM: Homo sapiens

<400> SEQUENCE: 619
gttatttaag atggctatcc agataatcct gaacactgtg tatttatttt atttagacta    60
ccagcaaaga ttaaagcatg aa    82

<210> SEQ ID NO 620
<211> LENGTH: 266
<212> TYPE: DNA
<213> ORGANISM: Homo sapiens

<400> SEQUENCE: 620
gcttggggaa caatgatggt gcacaaaggc ttagatttgc cttgtctcaa aataaggaat    60
tttgtagtgg ttttcaaaaa taattcaaca agaaacaat acaaaaagtg ggtagaatta    120
cctatcacat ttcccaatct tgactattca gaatgctgtt tatttagtga tgaggattag    180
cacttgattg aagattcttt taaaatacta tcagttaaac atttaatatg attatgatta    240
atgtattcat tatgctacag aactga    266

<210> SEQ ID NO 621
<211> LENGTH: 115
<212> TYPE: DNA
<213> ORGANISM: Homo sapiens

<400> SEQUENCE: 621
cagaaagcca agtggactca acggagaggc cagcaagttt caggaaatgg tgcatttggt    60
gaacaaggag tcgtcagaaa ctccagacca gtttatgaca gctgatgaga caagg    115

<210> SEQ ID NO 622
<211> LENGTH: 262
<212> TYPE: DNA
<213> ORGANISM: Homo sapiens

<400> SEQUENCE: 622
gttcacccgg tgaactattt atgagttctt ttggtgtgaa gaaagggctc atgttgcatt    60
tccagccatt gctacaaaga acctttattt gttcagtaac ggtagaaaat ccttcccgat    120
taaaaacttc agacttgctg aatatcctgc aatgtcaaga tgaccgatgt tgagttgggt    180
ggatttgcta acgagtcaga tttgaacatg aggctattgg aacccaatag gcgtcattga    240
tggcggcaag ccatagcttt ca    262

<210> SEQ ID NO 623
<211> LENGTH: 94

```
<212> TYPE: DNA
<213> ORGANISM: Homo sapiens

<400> SEQUENCE: 623
ggggagccag gcttccctca cgcagcctgt ggtggatgtg ggaaggagat caacttctcc      60
tcactctggg acagacgatg tatggaaact aaaa                                  94

<210> SEQ ID NO 624
<211> LENGTH: 114
<212> TYPE: DNA
<213> ORGANISM: Homo sapiens

<400> SEQUENCE: 624
ctgcacagct cagcacaaca ttccaagctc aaaatagaag ccttctcagt gagctccagc      60
acgcccagag gactgttaat aacgatgatc catgtgtttt actctaaagt gcta           114

<210> SEQ ID NO 625
<211> LENGTH: 37
<212> TYPE: DNA
<213> ORGANISM: Homo sapiens

<400> SEQUENCE: 625
cagggactgg ctatcccaag acctggcaga tgtggct                               37

<210> SEQ ID NO 626
<211> LENGTH: 74
<212> TYPE: DNA
<213> ORGANISM: Homo sapiens

<400> SEQUENCE: 626
gtgaaaggga agtagaaccg aaacaagatt agtcctgagt taacaatggc tgcaagctgg      60
atacatggaa ttca                                                        74

<210> SEQ ID NO 627
<211> LENGTH: 201
<212> TYPE: DNA
<213> ORGANISM: Homo sapiens

<400> SEQUENCE: 627
tggtgaatgc gtgctgccca ggaccagtga agacagacat ggatgggaaa gacagcatca      60
ggactgtgga ggagggggct gagacccctg tctacttggc cctcttgcct ccagatgcca     120
ctgagccaca aggccagttg gtccatgaca agttgtgca aaactggtaa acgtctgctt      180
cggagcttgc tgcttaataa a                                               201

<210> SEQ ID NO 628
<211> LENGTH: 217
<212> TYPE: DNA
<213> ORGANISM: Homo sapiens

<400> SEQUENCE: 628
atgctgtggt tggatcaagg actcattcct gccttggaga aaatacttca accagagcag      60
ggagcctggg ggtgtcgggg caggaggctg gggatggggg tgggatatga gggtggcatg     120
cagctgaggg cagggccagg gctggtgtcc ctaaggttgt acagactctt gtgaatattt     180
gtattttcca gatggaataa aaaggcccgt gtaatta                              217

<210> SEQ ID NO 629
<211> LENGTH: 33
<212> TYPE: DNA
```

<213> ORGANISM: Homo sapiens

<400> SEQUENCE: 629
ttctgtgcct cagccgttct tgacatcaag aat                         33

<210> SEQ ID NO 630
<211> LENGTH: 222
<212> TYPE: DNA
<213> ORGANISM: Homo sapiens

<400> SEQUENCE: 630
gacacagtcg ggttgaccca gggctgtctc cctccagagc ctccctccgg acaatgagtc      60 cccctcttg tctcccaccc tgagattggg catggggtgc ggtgtggggg gcatgtgctg     120
cctgttgtta tgggtttttt ttgcgggggg ggttgctttt ttctggggtc tttgagctcc    180
aaaaaataaa cacttccttt gagggagagc acaccttccc aa                      222

<210> SEQ ID NO 631
<211> LENGTH: 278
<212> TYPE: DNA
<213> ORGANISM: Homo sapiens

<400> SEQUENCE: 631
tgagaggcaa gagttgttcc tgcccttccc tttgtgactt gaagaacccct gactttgttt    60 ctgcaaaggc acctgcatgt gtctgtgttc gtgtaggcat aatgtgagga ggtggggaga   120
gcaccccacc cccatgtcca ccatgaccct cttcccacgc tgacctgtgc tccctctcca   180
atcatctttc ctgttccaga gaggtggggc tgaggtgtct ccatctctgt ctcaacttca   240
tggtgcactg agctgtaact tcttccttcc ctattaaa                           278

<210> SEQ ID NO 632
<211> LENGTH: 90
<212> TYPE: DNA
<213> ORGANISM: Homo sapiens

<400> SEQUENCE: 632
aaattaaagc taaagtatct gtattgcatt aaatataata tcgacacagt gctttccgtg     60
gcactgcata caatctgagg cctcctctct                                     90

<210> SEQ ID NO 633
<211> LENGTH: 198
<212> TYPE: DNA
<213> ORGANISM: Homo sapiens

<400> SEQUENCE: 633
accgcaggat cctttgctct gcacgagtta cctgttaaac tttggaacac ctaccaaaaa     60
ataagtttga taacatttaa aagatgggcg tttccccccaa tgaaatacac aagtaaacat   120
tccaacattg tctttaggag tgatttgcac cttgcaaaaa tggtcctgga gttggtagat   180
tgctgttgat cttttatc                                                  198

<210> SEQ ID NO 634
<211> LENGTH: 243
<212> TYPE: DNA
<213> ORGANISM: Homo sapiens

<400> SEQUENCE: 634
ttcatgctgg acctcaggta caaaaggtta agaacttctc agttcattat atgatcatca     60
ttggtgcctc cgagctctct ctctctccct tgatttattt ggtcccttttt atctccagtc   120

```
cttactccca tatctaacct cttaccccta cctcataggt aaacattttta atgaatttga      180 tgtttccttt tatttgcata gatcctctgt aatatgtagt agtgtccagt gtacatgtat      240
ttt                                                                    243
```

<210> SEQ ID NO 635
<211> LENGTH: 211
<212> TYPE: DNA
<213> ORGANISM: Homo sapiens
<220> FEATURE:
<221> NAME/KEY: modified_base
<222> LOCATION: (140)..(140)
<223> OTHER INFORMATION: a, c, t, g, unknown or other

<400> SEQUENCE: 635

```
ggtgagctac catactgctg acagtaatac actgcaaaat cttcaggctc cagtctgctg       60
atggtgagag tgaagtctgt cccagaccca ctgccactga acctgtctgg gatgccagtg      120
gccctgctgg atgcaccatn gatgaggagc ctgggagcct ggccaggttt ctgctggtac      180
caggctaagt agctgctgct aacactctga c                                     211
```

<210> SEQ ID NO 636
<211> LENGTH: 256
<212> TYPE: DNA
<213> ORGANISM: Homo sapiens

<400> SEQUENCE: 636

```
agagagtgga catttgtcgg gaaactccta acatatgccc ccattctgga gagaacacag       60
agtacgacac aatccctcac actaatagaa caatcctaaa ggaagatcca gcaaatacgg      120
tttactccac tgtggaaata ccgaaaaaga tggaaaatcc ccactcactg ctcacgatgc      180
cagacacacc aaggctattt gcctatgaga atgttatcta gacagcagtg cactgcccct      240
aagtctctgc tcaaaa                                                      256
```

<210> SEQ ID NO 637
<211> LENGTH: 239
<212> TYPE: DNA
<213> ORGANISM: Homo sapiens
<220> FEATURE:
<221> NAME/KEY: modified_base
<222> LOCATION: (138)..(138)
<223> OTHER INFORMATION: a, c, t, g, unknown or other

<400> SEQUENCE: 637

```
gaagggtaaa tgaagctatc gtagcttcac ttgggaaaag ggagagaaca gatgaccagc       60
accaaggata gaagagggat ttcttacttt aaaaaaaatg gtccaaagaa taaacaaact      120
gaaaacagcc aaaagagnaa ggaagaattt gttagaatag gcaagactaa aggacagag      180 taagggtgct ggccgccacc tgactcaagt tcaagtcgag ctgccactgt tgaaatttc      239
```

<210> SEQ ID NO 638
<211> LENGTH: 204
<212> TYPE: DNA
<213> ORGANISM: Homo sapiens
<220> FEATURE:
<221> NAME/KEY: modified_base
<222> LOCATION: (63)..(63)
<223> OTHER INFORMATION: a, c, t, g, unknown or other

<400> SEQUENCE: 638

```
attttatgac atttcgaagt ttctgtgtct taactctttt taattaattt tctgcacgtt       60
```

```
gcnttttttc tctttgtttt taattccata cagagtattc aattcttgaa acacattaaa      120
ataatttgct tgctagggta tggtttattt tataattaca ttcctagtct tgtgtggtta      180
ttgtaatgat gtctggtcct aatt                                             204

<210> SEQ ID NO 639
<211> LENGTH: 231
<212> TYPE: DNA
<213> ORGANISM: Homo sapiens

<400> SEQUENCE: 639
tgtctcccgg cctgatacca gatacaggtt gttgatttca tcgtgggtag caagctagta       60
ataaatttca aagtgctttc tcttttcatg cttttttgcca ataactgtta ccgccgttct     120
tattctctcc cttaactcat tgtctttggg ggagttagac accaggaggt gccttgtcgg     180
tcatattttt cagcacgtca tcaatcctat catcttcaat aacaacccgc t              231

<210> SEQ ID NO 640
<211> LENGTH: 237
<212> TYPE: DNA
<213> ORGANISM: Homo sapiens

<400> SEQUENCE: 640
gcatggcatc aaaaggtagg tcaacatatt aataattcc atgtattgaa atatccagaa        60
aatatataga cagatctata gagatagaaa ctggtctgcc caggactagg ggttgtctaa      120
ggataaggag cttctttttt ggatggtgaa ataacctaaa atatattgtg ccattgtttg      180
cacaactttg tgaatatatt aaaaacctgt taattgtact cactaaatgt cctcctt        237

<210> SEQ ID NO 641
<211> LENGTH: 228
<212> TYPE: DNA
<213> ORGANISM: Homo sapiens

<400> SEQUENCE: 641
attgatagtg cttcttacca ggtgaaggga agggctactt tttcctaaag gagaaaaaag       60 cttttcagaca aagctcgtac caaccccctga actgcaaatt tgctcaagtg accgtgcata    120
cttatattcc taatttaaat gattatttat gtcaaacgct cattgtgaaa cttgaaaatg      180
ttgtattaca ttcatcaaa taaagtttac ttgtagcaga cagaaaga                   228

<210> SEQ ID NO 642
<211> LENGTH: 188
<212> TYPE: DNA
<213> ORGANISM: Homo sapiens

<400> SEQUENCE: 642
gaagcagcca acaaaaacgt aattagtaac taggacttcc tcatgggata gaccaaataa       60
ggcaactgta taactgtgta actgtataac tgtaaccaat gaaatattat ctttgctttt     120
atctatttgt cctaaaaagc ctcctcctca tgttctctct ggggagctcc ctagccactt     180
ctggcttg                                                               188

<210> SEQ ID NO 643
<211> LENGTH: 259
<212> TYPE: DNA
<213> ORGANISM: Homo sapiens

<400> SEQUENCE: 643
gactggacca aagagcatgt gaaaaaatgg gtaaatgaag accttaagat taatgagcaa       60
```

```
tacgggcaaa ttctgctcag tgaagaagta acaggattag tcctgcagga attaactgag      120
aaggaccttg tagaaatggg gctaccatgg ggtccagcac ttttgataaa acgttcatac      180
aacaaattga atagtaagtc ccctgaaagt gacaatcatg atccgggaca attagataat      240
tcaaaaccgt ccaaaacag                                                   259

<210> SEQ ID NO 644
<211> LENGTH: 242
<212> TYPE: DNA
<213> ORGANISM: Homo sapiens

<400> SEQUENCE: 644
tgttctagag agctcatgta caccatggtg accatagtta ataatactgg attgtatgct      60
taaaatttgc taagagagta gatcttaagt catcaccaaa aaagtaaact gtaagatgat      120
ggagatgtgt taattagctt gacggtggta atcacaatat atgtgtatat caaaacatca      180
cattatacac cttaaatgta tataatattt gtcaattata cctcagtaaa gccaaaaaga      240
aa                                                                      242

<210> SEQ ID NO 645
<211> LENGTH: 205
<212> TYPE: DNA
<213> ORGANISM: Homo sapiens

<400> SEQUENCE: 645
ataggcagga accaatttgc atttaagtag tatgggaagc ctcgagtatg ttttcttgtc      60
cagagtgaag caaccaagaa agtaagatgc tggagatatc ttagactcaa gagatagaaa      120
gcaagaccct aggggagata agtaggagca ggatttcaag gacggaatta gtattgcaca      180
gagattaggg acacttcttc cttgg                                            205

<210> SEQ ID NO 646
<211> LENGTH: 217
<212> TYPE: DNA
<213> ORGANISM: Homo sapiens

<400> SEQUENCE: 646
aaaggcaaaa cactccagga cctctcccgg atctgtctcc tcctctagcc agcagtatgg      60
acagctggac ccctgaactt cctctcctct tacctgggca gagtgttgtc tctccccaaa      120
tttataaaaa ctaaaatgca ttccattcct ctgaaagcaa aacaaattca taattgagtg      180
atattaaata gagaggtttt cggaagcaga tctgtga                               217

<210> SEQ ID NO 647
<211> LENGTH: 253
<212> TYPE: DNA
<213> ORGANISM: Homo sapiens
<220> FEATURE:
<221> NAME/KEY: modified_base
<222> LOCATION: (208)..(208)
<223> OTHER INFORMATION: a, c, t, g, unknown or other

<400> SEQUENCE: 647
aaagctgaac tgcaaatctc aacgaaggaa gaggccattt taaagaaact aaagtcaatt      60
gagcggacaa cagaagacat tataagatct gtgaaagtgg aaagagaaga aagagcagaa      120
gagtcaattg aggacatcta tgctaatatc cctgaccttc caagtcccta catacccttct     180 aggttaagga aggagataaa tgaagaanaa gaagatgatg aacaaaatag gaaagcttta     240
```
tatgccatgg aaa 253

<210> SEQ ID NO 648
<211> LENGTH: 249
<212> TYPE: DNA
<213> ORGANISM: Homo sapiens

<400> SEQUENCE: 648
aggaggtaga cccctttagct cccttccaat taaaggagtc cccaattctg gcacctgaga 60
gtcccctggg tctaacagct atgatattta tgtagtgtgt tgcttaccta aatgaataca 120
atttccttcc agacacgtga cactgatatt aaagtgctaa tgagagggat ctatttcttc 180
ttgtacgcta aaagagaaac agcagttcag atttcccatc agaagtccga ggactttgtt 240
cttgataac 249

<210> SEQ ID NO 649
<211> LENGTH: 185
<212> TYPE: DNA
<213> ORGANISM: Homo sapiens

<400> SEQUENCE: 649
ttgatattct cttttggttt tattgttgtg gttcattgaa aaaaaagat aattttttt 60
tctgatccgg ggagctgtat ccccagtaga aaaacattt taatcactct aatataactc 120
tggatgaaac acacctttt ttttaataag aaaagagaat taactgcttc agaaatgact 180
aataa 185

<210> SEQ ID NO 650
<211> LENGTH: 234
<212> TYPE: DNA
<213> ORGANISM: Homo sapiens

<400> SEQUENCE: 650
atcaacctgg ttgacctgtc atggccgcct gtgccctgcc tccaccccca tcctacactc 60
ccccagggcg tgcggggctg tgcagactgg ggtgccaggc atctcctccc cacccggggt 120
gtccccacat gcagtactgt ataccccca tccctccctc ggtccactga acttcagagc 180
agttcccatt cctgccccgc ccatcttttt gtgtctcgct gtgatagatc aata 234

<210> SEQ ID NO 651
<211> LENGTH: 270
<212> TYPE: DNA
<213> ORGANISM: Homo sapiens

<400> SEQUENCE: 651
ggattttgat ccaagctggt ccactcagtc catagcagag aatgaaaggg cccagagagg 60
gtggtgacct ctgcctgaag tcacacagtg agtcgaggac agggaggtga ccccaggttt 120
ctatgtgtag ggcgggagga tgttctggga cacagttcaa ttctcatttg tcacacactt 180
tggctattag agatcaaccc cttcgctcct gtgtcttgca atggcagcct tggcaaacgc 240
taaatgaaaa tcgtgacaac acttgtgtta 270

<210> SEQ ID NO 652
<211> LENGTH: 37
<212> TYPE: DNA
<213> ORGANISM: Homo sapiens

<400> SEQUENCE: 652
cccaaattat ccccaattat ccccacacat aaaaaaa 37

<210> SEQ ID NO 653
<211> LENGTH: 173
<212> TYPE: DNA
<213> ORGANISM: Homo sapiens

<400> SEQUENCE: 653

```
gttggtgttt catgacatgt ggacttcttt tgaaatagca agtcaaatgt agtgaccaaa    60
ttgtggaaga gatttctgtc aaataggaaa tgtgtaagtt cgtctaaaag ctgatggtta   120
tgtaagttgc tcagcactca gatgacagca gattctgggt tctgggagtg ttc          173
```

<210> SEQ ID NO 654
<211> LENGTH: 236
<212> TYPE: DNA
<213> ORGANISM: Homo sapiens

<400> SEQUENCE: 654

```
gaaaccatgg gcaggagtag gaattgagtg ataaacaatt gggctaatga agaaaacttc    60
tcttattgtt cagttcatcc agattataac ttcaatggga cactttagac cattagacaa   120
ttgacactgg gattaaacaa attcacataa tgccaaatac acaatgtatt tatagcaacg   180
tataatttgc aaagatggac tttaaaagga tgctgtgtaa ctaaactgaa ataatt       236
```

<210> SEQ ID NO 655
<211> LENGTH: 187
<212> TYPE: DNA
<213> ORGANISM: Homo sapiens

<400> SEQUENCE: 655

```
taatccacta aactggtctt cttcaagaga gctaagtata cactatctgg tgaaacttgg    60
attctttcct ataaaagtgg gaccaagcaa tgatgatctt ctgtggtgct taaggaaact   120
tactagagct ccactaacag tctcataagg aggcagccat cataaccatt gaatagcatg   180
caagggt                                                             187
```

<210> SEQ ID NO 656
<211> LENGTH: 79
<212> TYPE: DNA
<213> ORGANISM: Homo sapiens

<400> SEQUENCE: 656

```
ctcagttctg gtccttcaag cctgtatggt ttggattttc agtaggggac agttgatgtg    60
gagtcaatct ctttggtac                                                 79
```

<210> SEQ ID NO 657
<211> LENGTH: 94
<212> TYPE: DNA
<213> ORGANISM: Homo sapiens

<400> SEQUENCE: 657

```
taacaaatca tcaacttcca ctggtcaata tatagatttt gggtgtctga ggccccaaga    60
ttagatgcca ctaatctcca aagattccct ccaa                                94
```

<210> SEQ ID NO 658
<211> LENGTH: 246
<212> TYPE: DNA
<213> ORGANISM: Homo sapiens

<400> SEQUENCE: 658

```
gaggcttggc cttctttgtg aggcagtgtg agcagaagct gatgccagca tgtcactggt    60
tttgaaggga tgagcccaga cttgatgttt tgggattgtc cttattttaa cctcaaggtc   120
tcgcatggtg gggcccctga ccaacctaca caagttccct cccacaagtg gacatcagtg   180
tcttctctgt gaggcatctg gccattcgc actccctggt gtggtcagcc tctctcacac    240
aaggag                                                              246

<210> SEQ ID NO 659
<211> LENGTH: 270
<212> TYPE: DNA
<213> ORGANISM: Homo sapiens

<400> SEQUENCE: 659
tttgtgccag gcctatagca gtgttgggag cgaaactcta gcaggatcct tcttacatgc    60
agaaaaggtt cattttacac ttgccaatag gaatgaaact atttcgctgc cacaatagct   120
aactgttttt ctaaatggcc tatttcgtca caacaatca ggaaagtgta ggaaggtaca    180
atctctaatg attgtagccc gtgcttaagg tgaggaaaaa agtcaaaaaa ttacacatga    240
gaaacctgaa tccaggcaga tcttacccaa                                   270

<210> SEQ ID NO 660
<211> LENGTH: 195
<212> TYPE: DNA
<213> ORGANISM: Homo sapiens

<400> SEQUENCE: 660
aagagtatga tacaacatta gagaaagaaa gatacaaagg ctttattcat gtgtgatagt    60
aaaaatcagg atgagtctta gatatacaaa agataaatgg atatttaaaa tagttatata   120
tgctttttta gcaaaatatt cacgtgttaa gtatttctgg atcttaaaat acaaaatcca   180
cttattttat tagtt                                                   195

<210> SEQ ID NO 661
<211> LENGTH: 147
<212> TYPE: DNA
<213> ORGANISM: Homo sapiens

<400> SEQUENCE: 661
gagaggccgc gctctcaggt gaaattaaaa ttggaggtca gttcccggat ccgattctct    60
cggttcattt tcttgagttt cattctgcga ttttgaaacc agattttgac ttgtctgtct   120
gtaaggttaa tggtcctgct tatctcc                                      147

<210> SEQ ID NO 662
<211> LENGTH: 106
<212> TYPE: DNA
<213> ORGANISM: Homo sapiens

<400> SEQUENCE: 662
gaaagatcca gtaagttcag tttctctatg aactaatcat tcaagtcaaa ggcacactga    60
tgcaaaatca gtatatggac cccggtgtct gattagcaag gttttc                 106

<210> SEQ ID NO 663
<211> LENGTH: 268
<212> TYPE: DNA
<213> ORGANISM: Homo sapiens

<400> SEQUENCE: 663
gataggattg atgacgtgct gaaaaatatg accgacaagg cacctcctgg tgtctaactc    60
```

```
ccccaaagac aatgagttaa gggagagaat aagaacggcg gtaacagtta ttggcaaaaa    120
gcatgaaaag agaaagcact ttgaaattta ttactagctt gctacccacg atgaaatcaa    180
caacctgtat ctggtatcag gccgggagac agatgaggcg agaggaggag gaggaggagg    240
agaaggctct gggctcctct gcaaaaaa                                       268
```

<210> SEQ ID NO 664
<211> LENGTH: 160
<212> TYPE: DNA
<213> ORGANISM: Homo sapiens

<400> SEQUENCE: 664

```
accagcaaag caatgcactc ctgaccaagt agattctttt aaaaattaga gtgcattact     60
ttgaatcaaa aatttattta tatttcaaga ataaagtact aagattgtgc tcaatacaca    120
gaaaagtttc aaacctacta atccagcgac aatttgaatc                          160
```

<210> SEQ ID NO 665
<211> LENGTH: 239
<212> TYPE: DNA
<213> ORGANISM: Homo sapiens

<400> SEQUENCE: 665

```
agtcccgaga ctgggttcaa gtagagggca gatctagatg ggggaggact aggactgact     60
cctatgggga tggaaaaggg actcctgggt gtctttgtga ctgtttagtg tgttctgtga    120
atgtgcgggc aggtatttt gcccacatct gtatatttgt ctattaatgt gatgtatttg    180
agtattgttg tggggcggg tatgtctgta tataaatctg tgcagccact agtcaacaa     239
```

<210> SEQ ID NO 666
<211> LENGTH: 259
<212> TYPE: DNA
<213> ORGANISM: Homo sapiens

<400> SEQUENCE: 666

```
gaagaaagct ataccattac cataatacat ttttcatctc atggctacaa tggaattctt     60
gaaaaggaaa aaaaatccta tctacatata aaaacctgca tgaatgaatc actacatatg    120
cttataatga ggaagagtta tgggtcctga gtgtaatttt ttatcctttc ttaaaaagtt    180
tctgtattat gcattttgat aacactctg atgatccttc cacttatatt tgaaatgtta     240
tgtaccacat ttgcacaat                                                 259
```

<210> SEQ ID NO 667
<211> LENGTH: 234
<212> TYPE: DNA
<213> ORGANISM: Homo sapiens

<400> SEQUENCE: 667

```
ggctactctg aaatgttgca gtgtggaaca atggaaagag cctgggtgtt tgggtcagat     60
aaatgaagat caaactccag ctccagcctc atttgcttga ctttgtgt gtatggggga     120 cttgtatgta tgggagtgag gagtttcagg gccattgcaa acatagctgt gcccttgaag    180
agaatagtaa tgatgggaat ttagaggttt atgactgaat tcccttgac atta          234
```

<210> SEQ ID NO 668
<211> LENGTH: 294
<212> TYPE: DNA
<213> ORGANISM: Homo sapiens
<400> SEQUENCE: 668

```
ctcgattatt ccctgtacaa tatttaaaat ttattgcttg atactttga caacaaatta      60
ggttttgtac aattgaactt aaataaatgt cattaaaata aataaatgca atatgtatta     120
atattcattg tataaaaata gaagaataca aacatatttg ttaaatattt acatatgaaa     180
tttaatatag ctatttttat ggaattttc attgatatga aaaatatgat attgcatatg     240
catagttccc atgttaaatc ccattcataa ctttcattaa agcatttact ttga            294
```

<210> SEQ ID NO 669
<211> LENGTH: 265
<212> TYPE: DNA
<213> ORGANISM: Homo sapiens
<400> SEQUENCE: 669

```
atatggctgt ggaaaaacga attaaaatgt tttgaggaga aagactttt cacttctttg      60
ttgctttctt ttctattgag tctgggcttg tttgtgttac tgcatactgt gattagcata    120
ataattgttt ctttgaggtc atctaaatat ttttttccta aaggaataaa gggtgaggaa    180
agaaaaatat taaaaagct aatatttgat actgtgcttg ctgtcagtat gcattacatt    240
taaattattc tctattcaag tggga                                           265
```

<210> SEQ ID NO 670
<211> LENGTH: 190
<212> TYPE: DNA
<213> ORGANISM: Homo sapiens
<400> SEQUENCE: 670

```
ggaagatggt ttctatctca tgaccccac tccctgtgag agggaatggg ggaagcctga      60
tgaccctcag ctgttccaat ctagtatttt ttttctttt taaaattact gtatttatta    120
tgacgatggt gactccccag tgcaaggggg ggccagattc tgtgtgtttc tctaacctct    180
ttgtaaataa                                                            190
```

<210> SEQ ID NO 671
<211> LENGTH: 138
<212> TYPE: DNA
<213> ORGANISM: Homo sapiens
<400> SEQUENCE: 671

```
aagaattaca gggatgtttt taatcccact atggactcag tctcctggaa ataggtctgt      60
ccactcctgg tcattggtgg atgttaaacc catattcctt tcaactgctg cctgctaggg    120
aaaactgctc ctcattat                                                   138
```

<210> SEQ ID NO 672
<211> LENGTH: 257
<212> TYPE: DNA
<213> ORGANISM: Homo sapiens
<400> SEQUENCE: 672

```
actctggctc cgaaaaactt tgttatatat atcaaggatg ttctggcttt acattttatt      60
tattagctgt aaatacatgt gtggatgtgt aaatggagct tgtacatatt ggaaaggtca    120
ttgtggctat ctgcatttat aaatgtgtgg tgctaactgt atgtgtcttt atcagtgatg    180
gtctcacaga gccaactcac tcttatgaaa tgggctttaa caaaacaaga aagaaacgta    240
cttaactgtg tgaagaa                                                    257
```

<210> SEQ ID NO 673
<211> LENGTH: 231
<212> TYPE: DNA
<213> ORGANISM: Homo sapiens

<400> SEQUENCE: 673

| | | | | | |
|---|---|---|---|---|---|
| accatgtaca | gagaaatttt | aggccaaact | taaaatatgt | aaggaggcag | ctttaggcta | 60 |
| aacttgattt | aacagcacca | ataccccta | cctttagtga | gcacatctgc | acattccaat | 120 |
| tttaatgaca | gctccttaga | atttcttatc | aacgaagaca | ctaacaaaga | atggcgcatt | 180 |
| cctccttctc | ctttctgagg | atgccctacc | ctgtaacaaa | gtcgtttcta a | | 231 |

<210> SEQ ID NO 674
<211> LENGTH: 132
<212> TYPE: DNA
<213> ORGANISM: Homo sapiens

<400> SEQUENCE: 674

| | | | | | |
|---|---|---|---|---|---|
| gtgagcctgc | cagcgtttgc | gacgtccccg | cacgacaggc | tcatactttc | tgaggatcgt | 60 |
| gcatagcata | ggacgtctga | acctttgtac | aaatgtgtag | atgacatctt | gctacagctt | 120 |
| ttatttgtga | at | | | | | 132 |

<210> SEQ ID NO 675
<211> LENGTH: 283
<212> TYPE: DNA
<213> ORGANISM: Homo sapiens

<400> SEQUENCE: 675

| | | | | | |
|---|---|---|---|---|---|
| aattccagtg | cttgtcctag | taccttagca | catggttgct | gaatacatga | atgaagagtg | 60 |
| agaaaccaga | agctctgata | tttaactgcc | gtgataatga | attcaatgtg | caactatggg | 120 |
| caaattgtat | ttaatagtaa | ttgcatattg | tacatatttt | tcattcttat | taacactgat | 180 |
| aaactttca | acttatactg | actttaataa | aattgtatta | ctaggctatt | aacatgatat | 240 |
| tttgtttccc | attaaatgtg | acatgcaaag | acgtttatta | aat | | 283 |

<210> SEQ ID NO 676
<211> LENGTH: 229
<212> TYPE: DNA
<213> ORGANISM: Homo sapiens

<400> SEQUENCE: 676

| | | | | | |
|---|---|---|---|---|---|
| actgtacaaa | gtataagtct | tagatgtata | tatttcctat | attgttttca | gtgtacatgg | 60 |
| aataacatgt | aattaagtac | tatgtatcaa | tgagtaacag | gaaaattta | aaatacaga | 120 |
| tagatatatg | ctctgcatgt | tacataagat | aaatgtgctg | aatggttttc | aaataaaaat | 180 |
| gaggtactct | cctggaaata | ttaagaaaga | ctatctaaat | gttgaaaga | | 229 |

<210> SEQ ID NO 677
<211> LENGTH: 39
<212> TYPE: DNA
<213> ORGANISM: Homo sapiens

<400> SEQUENCE: 677
gttgctgacc tgctgtgctc gcagtagatt ccaaaaaaa          39

<210> SEQ ID NO 678
<211> LENGTH: 259
<212> TYPE: DNA
<213> ORGANISM: Homo sapiens

<400> SEQUENCE: 678

```
gacatcccca ctcacgaata ttatgcccag tttctgcctc tgagggaaag cccagaaaag    60
gacagaaacg aagtagaaag gggcccagtc ctggcctggc ttctcctttg aagtgaggc    120
attgcacggg gagacgtacg tatcagcggc cccttgactc tggggactcc gggtttgaga   180
tggacacact ggtgtggatt aacctgccag ggagacagag ctcacaataa aaatggctca   240
gatgccactt caaagaaaa                                                 259
```

<210> SEQ ID NO 679
<211> LENGTH: 236
<212> TYPE: DNA
<213> ORGANISM: Homo sapiens

<400> SEQUENCE: 679

```
gacagtccgt caaaacagat tgtttgcaaa ggggaggcat cagtgtcctt ggcaggctga    60
tttctaggta ggaaatgtgg tagcctcact tttaatgaac aaatggcctt tattaaaaac   120
tgagtgactc tatatagctg atcagttttt tcacctggaa gcatttgttt ctactttgat   180
atgactgttt ttcggacagt ttatttgttg agagtgtgac caaaagttac atgttt        236
```

<210> SEQ ID NO 680
<211> LENGTH: 280
<212> TYPE: DNA
<213> ORGANISM: Homo sapiens

<400> SEQUENCE: 680

```
tctgaactct caaaagtcta tttttttaac tgaaaatgta aatttataaa tatattcagg    60
agttggaatg ttgtagttac ctactgagta ggcggcgatt tttgtatgtt atgaacatgc   120
agttcattat tttgtggttc tattttactt tgtacttgtg tttgcttaaa caaagtgact   180
gtttggctta taaacacatt gaatgcgctt tattgcccat gggatatgtg gtgtatatcc   240
ttccaaaaaa ttaaaacgaa aataaagtag ctgcgattgg                          280
```

<210> SEQ ID NO 681
<211> LENGTH: 215
<212> TYPE: DNA
<213> ORGANISM: Homo sapiens

<400> SEQUENCE: 681

```
caaacttgga gcaggtgtcc atcccagccc tgtgtagtta gagcaggaat caagatctca    60
acacaaatgt ggctgccaag cactcagccc cggggcgagg ggtcaagttc ttctcagaga   120
aagaggaata agttggttct cagaagacat cacaagatac gtgtgtaccc aacaatctct   180
gatctctgct gatcttttgc ttagacgtta acttg                               215
```

<210> SEQ ID NO 682
<211> LENGTH: 258
<212> TYPE: DNA
<213> ORGANISM: Homo sapiens

<400> SEQUENCE: 682

```
aggcgcctgg agaagtgctc agctacttct cctgcacttt gaaagacccc tcccactcct    60
ggcctcacat ttctctgtgt gatcccccac ttctgggctc tgccacccca cagtgggaaa   120
ggccacccta gaaagaagtc cgctggcacc cataggaagg ggcctcagga gcaggaaggg   180
ccaggaccag aaccttgccc acggcaactg ccttcctgcc tctcccttc ctcctctgct    240
cttgatctgt gtttcaat                                                  258
```

<210> SEQ ID NO 683
<211> LENGTH: 248
<212> TYPE: DNA
<213> ORGANISM: Homo sapiens

<400> SEQUENCE: 683

| | |
|---|---|
| gaaactccct agttccttca tgtaacttcc ctgaaaaatc taagtgtttc ataaatttga | 60 |
| gagtctgtga cccacttacc ttgcatctca caggtagaca gtatataact aacaaccaaa | 120 |
| gactacatat tgtcactgac acacacgtta taatcattta tcatatatat acatacatgc | 180 |
| atacactctc aaagcaaata attttttcact tcaaaacagt attgacttgt ataccttgta | 240 |
| atttgaaa | 248 |

<210> SEQ ID NO 684
<211> LENGTH: 39
<212> TYPE: DNA
<213> ORGANISM: Homo sapiens

<400> SEQUENCE: 684

| | |
|---|---|
| ggtaggttga agggacctct ctcttaccag taccagaaa | 39 |

<210> SEQ ID NO 685
<211> LENGTH: 72
<212> TYPE: DNA
<213> ORGANISM: Homo sapiens

<400> SEQUENCE: 685

| | |
|---|---|
| tctatttatt tattgaggac ccatggtaaa atgcaaatag atccggtgtc taaatgcatt | 60 |
| catatttta tg | 72 |

<210> SEQ ID NO 686
<211> LENGTH: 241
<212> TYPE: DNA
<213> ORGANISM: Homo sapiens

<400> SEQUENCE: 686

| | |
|---|---|
| atgtgtgcaa aagcccaaag gttcctaagc ctggctgcaa agaagaatca acagggacac | 60 |
| tttttaaaaa cactcttatc agcctgggca acacagtgag actccatctc ttaaaaaaaa | 120 |
| aattagctgg gtatagtggt atgtgcctgt agtcccaggt actcaggagg ctgaggcagg | 180 |
| aggattgcct gagcccagga ggtggaaact gcagagagtc atgatcatgt ccttacactc | 240 |
| c | 241 |

<210> SEQ ID NO 687
<211> LENGTH: 278
<212> TYPE: DNA
<213> ORGANISM: Homo sapiens

<400> SEQUENCE: 687

| | |
|---|---|
| gtaataaact ctctagggcc aaaacctggt atggtcattg ggaaatgagt gctcagggag | 60 |
| atggagctta ggggaggtgg gtgcttccct cctagatgtc agcatacact ctttcttctt | 120 |
| ttgtcccagg tctaaaacat cttttcctaga gaaaacaaaa gggactaaac tagaaatata | 180 |
| aagagcccta tacatgacag gtgatcacgt actgaatgat tttgaagtag tacaaacaat | 240 |
| aaaaattctc attccgcatc atcatgcggt ccatgatg | 278 |

<210> SEQ ID NO 688

<211> LENGTH: 244
<212> TYPE: DNA
<213> ORGANISM: Homo sapiens

<400> SEQUENCE: 688

| | | | | | |
|---|---|---|---|---|---|
| aaaagcttcc | ccaactaaag | cctagaagag | cttctgaggc | gctgctttgt | caaaaggaag | 60 |
| tctctaggtt | ctgagctctg | gctttgcctt | ggctttgcca | gggctctgtg | accaggaagg | 120 |
| aagtcagcat | gcctctagag | gcaaggaggg | gaggaacact | gcactcttaa | gcttccgccg | 180 |
| tctcaacccc | tcacaggagc | ttactggcaa | acatgaaaaa | tcggcttacc | attaaagttc | 240 |
| tcaa | | | | | | 244 |

<210> SEQ ID NO 689
<211> LENGTH: 118
<212> TYPE: DNA
<213> ORGANISM: Homo sapiens

<400> SEQUENCE: 689

| | | | | | |
|---|---|---|---|---|---|
| ccagcactct | gaaactgaga | aatgttcaga | atgtacggaa | agatgatcag | ctattttcaa | 60 |
| cataactgaa | ggcatatgct | ggcccataaa | caccctgtag | gttcttgata | tttataat | 118 |

<210> SEQ ID NO 690
<211> LENGTH: 264
<212> TYPE: DNA
<213> ORGANISM: Homo sapiens

<400> SEQUENCE: 690

| | | | | | |
|---|---|---|---|---|---|
| aatacccatt | atattcctgt | aagtaaatga | ctatttttcc | cttaactcag | tgattagaca | 60 |
| ggaaggaaga | cattagtgat | tagacaggag | ggaagatatt | agtgattaga | cagcagggaa | 120 |
| gatattagtg | gtaaagagtg | aatgatagta | gtgaatataa | atggggctga | ggaaactta | 180 |
| agcataaaag | attcctgaga | tgactttaca | agtctgtacg | aatctgcctt | gactgtatat | 240 |
| ttcatactgc | ccaacaaaac | aata | | | | 264 |

<210> SEQ ID NO 691
<211> LENGTH: 270
<212> TYPE: DNA
<213> ORGANISM: Homo sapiens

<400> SEQUENCE: 691

| | | | | | |
|---|---|---|---|---|---|
| gttcctattc | ttccattgta | cgataatgtc | tttaatatga | aatgctacat | tatttataat | 60 |
| tggtagagtt | attgtatctt | tttatagttg | taagtacaca | gaggtggtat | atttaaactt | 120 |
| ctgtaatata | ctgtatttag | aaatggaaat | atatatagtg | ttaggtttca | cttcttttaa | 180 |
| ggtttacccc | tgtggtgtgg | tttaaaaatc | tataggcctg | ggaattccga | tcctagctgc | 240 |
| agatcgcatc | ccacaatgcg | agaatgataa | | | | 270 |

<210> SEQ ID NO 692
<211> LENGTH: 187
<212> TYPE: DNA
<213> ORGANISM: Homo sapiens

<400> SEQUENCE: 692

| | | | | | |
|---|---|---|---|---|---|
| aattcatagt | aatttcactc | tctgcattga | cttatgagat | aattaatgat | taaactatta | 60 |
| atgataaaaa | taatgcattt | gtattgttca | taatatcatg | tgcacttcaa | gaaaatggaa | 120 |
| tgctactctt | ttgtggttta | cgtgtattat | tttcaatatc | ttaataccct | aataagagt | 180 |
| ccataaa | | | | | | 187 |

<210> SEQ ID NO 693
<211> LENGTH: 249
<212> TYPE: DNA
<213> ORGANISM: Homo sapiens

<400> SEQUENCE: 693

| | | | | |
|---|---|---|---|---|
| tcaccacaac agaacatgca gtactaaagc aatatatttg tgattcccca tgtaattctt | | | | 60 |
| caatgttaaa cagtgcagtc ctctttcgaa agctaagatg accatgcgcc ctttcctctg | | | | 120 |
| tacatatacc cttaagaacg ccccctccac acactgcccc ccagtatatg ccgcattgta | | | | 180 |
| ctgctgtgtt atatgctatg tacatgtcag aaaccattag cattgcatgc aggtttcata | | | | 240 |
| ttctttcta | | | | 249 |

<210> SEQ ID NO 694
<211> LENGTH: 199
<212> TYPE: DNA
<213> ORGANISM: Homo sapiens

<400> SEQUENCE: 694

| | | | | |
|---|---|---|---|---|
| gttgagccaa ctatagctct gtgttcctac tgggctttcc ctaatgtggt tgggagttat | | | | 60 |
| gccctagact aactgtattg tcctagtcac agctccttgc tttgatttca tccttgataa | | | | 120 |
| aatgaagatg aaacttacac tacttctcca agccttttgc tgtcttaaga ataagacctg | | | | 180 |
| agattaacac taaccctag | | | | 199 |

<210> SEQ ID NO 695
<211> LENGTH: 190
<212> TYPE: DNA
<213> ORGANISM: Homo sapiens

<400> SEQUENCE: 695

| | | | | |
|---|---|---|---|---|
| ttcacttaca agctctatga tcttaaataa tttacttaat gtattttggt gtattttcct | | | | 60 |
| caaattaata ttggtgttca agactatatc taattcctct gatcactttg agaaacaaac | | | | 120 |
| ttttattaaa tgtaaggcac ttttctatga attttaaata taaaaataaa tattgttctg | | | | 180 |
| attattactg | | | | 190 |

<210> SEQ ID NO 696
<211> LENGTH: 235
<212> TYPE: DNA
<213> ORGANISM: Homo sapiens

<400> SEQUENCE: 696

| | | | | |
|---|---|---|---|---|
| gttttgctgg agaaacatca ggtttgtagg agactgagtt gttagcaggt gtgcttagct | | | | 60 |
| cttgatagtg aacgtgtacc ttgggaactg gctcacccac ctgctaatag caccatcgtc | | | | 120 |
| actattaagc agacatttca gttggtagaa tccatgtaga agtcatggac ttttctggga | | | | 180 |
| aatgactttt ctgggaaatg acagtttctt tgacatattt tctttgccca cttta | | | | 235 |

<210> SEQ ID NO 697
<211> LENGTH: 243
<212> TYPE: DNA
<213> ORGANISM: Homo sapiens

<400> SEQUENCE: 697

| | | | | |
|---|---|---|---|---|
| gactgaggga tcgtagattt ttacaatctg tatctttgac aattctgggt gcgagtgtga | | | | 60 |
| gagtgtgagc agggcttgct cctgccaacc acaattcaat gaatcccga ccccctacc | | | | 120 |

```
ccatgctgta cttgtggttc tctttttgta ttttgcatct gaccccgggg ggctgggaca      180
gattggcaat gggccgtccc ctctcccctt ggttctgcac tgttgccaat aaaaagctct      240
taa                                                                    243

<210> SEQ ID NO 698
<211> LENGTH: 192
<212> TYPE: DNA
<213> ORGANISM: Homo sapiens

<400> SEQUENCE: 698
gctgtttgtt ctcctggggc gctccctcca acttttgcag attcttgcaa cctcctcctg      60
agccgggatt gtccaattac taaaatgtaa ataatcacgt attgtgggga ggggagttcc      120
aagtgtgccc tcctctcttc tcctgcctgg attatttaaa aagccatgtg tggaaaccca      180
ctatttaata aa                                                          192

<210> SEQ ID NO 699
<211> LENGTH: 114
<212> TYPE: DNA
<213> ORGANISM: Homo sapiens

<400> SEQUENCE: 699
agcaagtgta gacaccttcg agggcagaga tcgggagatt taagatgtta cagcatattt      60 tttttcttg ttttacagta ttcaattttg tgttgattca gctaaattat gaaa             114

<210> SEQ ID NO 700
<211> LENGTH: 123
<212> TYPE: DNA
<213> ORGANISM: Homo sapiens

<400> SEQUENCE: 700
tgtggggagc caggcttccc tcacgcagcc tgtggtggat gtgggaagga gatcaacttc      60
tcctcactct gggacagacg atgtatggaa actaaaaaga acatgcggca ccttaaaaaa      120
aaa                                                                    123

<210> SEQ ID NO 701
<211> LENGTH: 158
<212> TYPE: DNA
<213> ORGANISM: Homo sapiens

<400> SEQUENCE: 701
cagccccacc cctgtaaatg gaatttacca gatgaaggga atgaagtccc tcactgagcc      60
tcagatttcc tcacctgtga aatgggctga ggcaggaaat gggaaaaagt gttagtgctt      120
ccaggcggca ctgacagcct cagtaacaat aaaaacaa                              158

<210> SEQ ID NO 702
<211> LENGTH: 206
<212> TYPE: DNA
<213> ORGANISM: Homo sapiens

<400> SEQUENCE: 702
agtattatac aactgctgtg accagacttg tatactggct gaatatcagt gctgtttgta      60 attttttcact ttgagaacca acattaattc catatgaatc aagtgttttg taactgctat     120
tcatttattc agcaaatatt tattgatcat ctcttctcca taagatagtg tgataaacac      180
agtcatgaat aaagttattt tccaca                                           206
```

-continued

```
<210> SEQ ID NO 703
<211> LENGTH: 252
<212> TYPE: DNA
<213> ORGANISM: Homo sapiens

<400> SEQUENCE: 703
tggcagactc cttgttgctt aagagtggct ttctaggcag gccactggca tctgaattca      60
tcattgacaa taaatgtaag aaattggaat aaaaaagaga gacctgctgt tattcgcttt     120
tgttctccag tgatttgatt aactcagggc aaggctgaat atcagagtgt atcgcactga     180
agaataataa tccattcagt aatgttatag ttatcctcaa tctaaatatg tcaactgtca     240
ttttgctgct tt                                                          252

<210> SEQ ID NO 704
<211> LENGTH: 227
<212> TYPE: DNA
<213> ORGANISM: Homo sapiens

<400> SEQUENCE: 704
ctaaggtagc aacttatttc caaattaata tagatgaaaa atagatacca attagactaa      60
attgaaagct ttttgttcta tatttgcata gcctttgaaa tatttcttag tgcctaggag     120
gtctggggat tcctctttcg tggtggtcac taaccttact tgatgcagat aaaatcactt     180
gtcaatgcaa aatgtgttag aacttgataa agctttgagt ttgagaa                   227

<210> SEQ ID NO 705
<211> LENGTH: 262
<212> TYPE: DNA
<213> ORGANISM: Homo sapiens
<220> FEATURE:
<221> NAME/KEY: modified_base
<222> LOCATION: (77)..(117)
<223> OTHER INFORMATION: a, c, t, g, unknown or other

<400> SEQUENCE: 705
taaaaacgac cattacagtg ccaatatcgc taatatgatc cctggatgga attggttatt      60
ctgagctgtg acaaggnnnn nnnnnnnnnn nnnnnnnnnn nnnnnnnaag                120
ggcaagtgct gttttcctgt tttcttcctt atcttagttg taatgaatca cttttataac     180
ttgtacctgc tacactaagt attgtctcag caaagtcatt cattttactg gtaacaaaag     240
ccaggaataa cgtgctatgg aa                                              262

<210> SEQ ID NO 706
<211> LENGTH: 275
<212> TYPE: DNA
<213> ORGANISM: Homo sapiens

<400> SEQUENCE: 706
gcctggatag aggtatatga tcgtgtgcca agaatttatc ccagactccc ctgtgtgaca      60
gcttcataat aaagttactt aactgtgcct cttcctcctt cctctcccca cacaggatgg     120
atgggcatct ttctccttga ccaccctact ctcccttcct cccctgatca cctcccctcc     180
ctgctcttcc ctggtgatgg acttctaaca tgagattttt ttaaaaaatt tctatttctt     240
ttataatttt gctgagtttt cagggtttct tctgt                                275

<210> SEQ ID NO 707
<211> LENGTH: 81
<212> TYPE: DNA
<213> ORGANISM: Homo sapiens
```

-continued

<400> SEQUENCE: 707
agctatctga gccttgacgc tgagcaagtg gaagtcccac agaagctaca agttgccagg    60
tcaacgcatg aagggagcca c                                              81

<210> SEQ ID NO 708
<211> LENGTH: 147
<212> TYPE: DNA
<213> ORGANISM: Homo sapiens

<400> SEQUENCE: 708
cagtatgtca tgtttgctgt agtgctcata tttattgttg tttttgtttt agtactcact    60
tgtttcataa tatcaagatt actaaaaatg ggggaaagga cttctaatct tttttttcata  120 atatctttga cacatattac agaagaa                                       147

<210> SEQ ID NO 709
<211> LENGTH: 47
<212> TYPE: DNA
<213> ORGANISM: Homo sapiens

<400> SEQUENCE: 709
acacagtgct ttccgtggca ctgcatacaa tctgaggcct cctctct                  47

<210> SEQ ID NO 710
<211> LENGTH: 52
<212> TYPE: DNA
<213> ORGANISM: Homo sapiens

<400> SEQUENCE: 710
taaatatcca cagtactcac tttttccaaa tgatcctagt aattgcctag aa             52

<210> SEQ ID NO 711
<211> LENGTH: 222
<212> TYPE: DNA
<213> ORGANISM: Homo sapiens

<400> SEQUENCE: 711
ggtgttggca ctaacgctgc ttgtttggca aatcatcatc actgaggtat tccacccaga    60 gacttttttca aaaaagtcaa ctaaagtgct aagtcataag aggagagcca ttatacccgt  120 tgtcttttctg ggctccttga gtttatctgg attccaacag cacttggaaa gtaccgccct  180
ccactacctc aaatgcaaac acaatctctg ccagtagaca tt                      222

<210> SEQ ID NO 712
<211> LENGTH: 284
<212> TYPE: DNA
<213> ORGANISM: Homo sapiens
<220> FEATURE:
<221> NAME/KEY: modified_base
<222> LOCATION: (33)..(33)
<223> OTHER INFORMATION: a, c, t, g, unknown or other

<400> SEQUENCE: 712
acaagcccaa atttgatata cttttttatat ttnaaaaatt atattcactg cccccataag    60
agcaatcaag gcatgtcttt aaattctata catagatata gccaaaaata gtgcatttag   120
taacattctt ttccaaaact atattcttgg gaatgaatat ctgtttcttc taacagtttg   180
agtgataatc tatacctgta gatataagtt attttgcata taaaattaat cttaatcttt   240
tatggaatgt tctctgtctg tggcattaaa tgaaccttaa gaac                    284

```
<210> SEQ ID NO 713
<211> LENGTH: 224
<212> TYPE: DNA
<213> ORGANISM: Homo sapiens
<220> FEATURE:
<221> NAME/KEY: modified_base
<222> LOCATION: (144)..(144)
<223> OTHER INFORMATION: a, c, t, g, unknown or other

<400> SEQUENCE: 713
tgtgcccagc tgacatattc tcacttaata gaattataga gaaattttc atgtttttct      60 ttttctctcc cactttttca tattcctctt tttcattttt gccttccgt ttctgtctat     120 gatgtaggct tctgaggaga accnagaagc ttggctttag tggtagaatg acagaactta    180 gggatcccctt gcaggctaga acaaagttct gacccttaga ccaa                    224

<210> SEQ ID NO 714
<211> LENGTH: 224
<212> TYPE: DNA
<213> ORGANISM: Homo sapiens

<400> SEQUENCE: 714
gaaattgcat caagcgtccg aacatgctgc ttacaacttt agaaacgcaa aatgcgttgt     60
tgtgggagtt gtgtaatttt tagtaggtgc tcaaatactt gctgaacttg gtgtctattt   120
ttaagtcttg cccattgatg taaactgtcc ctaggtcacg tgtatcttga ggtctaaaag   180
attatttatg caataaattg aaattcccat agccaattaa agat                     224

<210> SEQ ID NO 715
<211> LENGTH: 194
<212> TYPE: DNA
<213> ORGANISM: Homo sapiens

<400> SEQUENCE: 715
tggtgggctg aggatgtctt cttcctgtcc aggatgcaat atggtcaagg atgaaaggaa     60
agagatgctg ggagcaagtc tgcattgaag atgtatttct gttgctttac taccaaccct   120
ggttataaat gatgaaacta taatgggtct gtaatagcta ctttcccata tagctcttgt   180
ctgtacatac ataa                                                      194

<210> SEQ ID NO 716
<211> LENGTH: 227
<212> TYPE: DNA
<213> ORGANISM: Homo sapiens
<220> FEATURE:
<221> NAME/KEY: modified_base
<222> LOCATION: (71)..(72)
<223> OTHER INFORMATION: a, c, t, g, unknown or other
<220> FEATURE:
<221> NAME/KEY: modified_base
<222> LOCATION: (185)..(187)
<223> OTHER INFORMATION: a, c, t, g, unknown or other
<220> FEATURE:
<221> NAME/KEY: modified_base
<222> LOCATION: (189)..(191)
<223> OTHER INFORMATION: a, c, t, g, unknown or other
<220> FEATURE:
<221> NAME/KEY: modified_base
<222> LOCATION: (193)..(195)
<223> OTHER INFORMATION: a, c, t, g, unknown or other
<220> FEATURE:
<221> NAME/KEY: modified_base
<222> LOCATION: (199)..(199)
<223> OTHER INFORMATION: a, c, t, g, unknown or other
<220> FEATURE:
<221> NAME/KEY: modified_base
<222> LOCATION: (201)..(202)
```

<223> OTHER INFORMATION: a, c, t, g, unknown or other

<400> SEQUENCE: 716

```
attgtgctta ggtgatttgt aactcaggta tagggtattt aaatagtagg cacccttttt    60
gcaccatgtg nnttttttt tttatctagt tcttgtatac tacagataat atttgaactt   120
tgtcatctca ctgtaaaact tttgttcatt tctcattatg gtaataaata gctattataa   180
ccaannnann nannnaaana nnttatttcc ctaagtgtta ttttgac                 227
```

<210> SEQ ID NO 717
<211> LENGTH: 183
<212> TYPE: DNA
<213> ORGANISM: Homo sapiens
<220> FEATURE:
<221> NAME/KEY: modified_base
<222> LOCATION: (126)..(127)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other

<400> SEQUENCE: 717

```
agtgccattt cattatttga ttatcaccaa attatctgga aataattggg acattgtaac    60
ttatctattt atagttatga gattaagact ggagtgccat caccgcgggt gatgatttag   120
cttttnntgt gtgtntgngt gtgtgccttc caaatcatgc cataattgta atgttgaatc   180
gga                                                                 183
```

<210> SEQ ID NO 718
<211> LENGTH: 288
<212> TYPE: DNA
<213> ORGANISM: Homo sapiens

<400> SEQUENCE: 718

```
tgtgcccaac cattgtaata tgcgtattga cgtatatgat aggagaaaac actagcattt    60
tgagttaata agtaggtcag tttggattaa tggaaagttt gaagcttaga gtgtttaaat   120
aatgatttta ttctttcaa tacacaagtg gaaatgtttc tccagtctaa attcccccta   180
gtattctcct gaaacaaaat ttttatatgc agatatttgc ttcttttgca agtttgagaa   240
tttcacagta acttctggtt accctgggtt gtgtcttgca gttaccaa                288
```

<210> SEQ ID NO 719
<211> LENGTH: 183
<212> TYPE: DNA
<213> ORGANISM: Homo sapiens

<400> SEQUENCE: 719

```
ttctgtgtct gaagtgtaag tgaacacaga agagtgacat gtttacaaac ctcaagccag    60
ccttgctcct ggctggggcc tgttgaagat gcttgtattt tacttttcca ttgtaattgc   120
tatcgccatc acagctgaac ttgttgagat ccccgtgtta ctgcctatca gcattttact   180
act                                                                 183
```

<210> SEQ ID NO 720
<211> LENGTH: 205
<212> TYPE: DNA
<213> ORGANISM: Homo sapiens

<400> SEQUENCE: 720

```
gctgcttcct cctggaaatt gacgaggggt gtcttgggca gagctggctc tgagcgcctc    60
catccaaggc caggttctcc gttagctcct gtggccccac cctgggccct gggctggaat   120
caggaatatt ttccaaagag tgatagtctt ttgcttttgg caaaactcta cttaatccaa   180
tgggtttttc cctgtacagt agatt                                         205
```

<210> SEQ ID NO 721
<211> LENGTH: 189
<212> TYPE: DNA
<213> ORGANISM: Homo sapiens

<400> SEQUENCE: 721

```
gcccacctga agcagcaagt gagcgggctg gagggtgtgc aggacgacct gttctggctg    60
accttcgagg ggaagcccct ggaggaccag ctcccgctgg gggagtacgg cctcaagccc   120
ctgagcaccg tgttcatgaa tctgcgcctg cggggaggcg gcacagagcc tggcgggcgg   180
agctaaggg                                                           189
```

<210> SEQ ID NO 722
<211> LENGTH: 191
<212> TYPE: DNA
<213> ORGANISM: Homo sapiens

<400> SEQUENCE: 722

```
caaacagagt gaactttctg ccaagatgcg ggagtggttt tcagagacat ttcagaaagt    60
gaaggagaaa ctcaagattg actcatgagg acctgaaggg tgacatccca ggaggggcct   120
ctgaaatttc ccacacccca gcgcctgtgc tgaggactcc ctccatgtgg ccccaggtgc   180
caccaataaa a                                                        191
```

<210> SEQ ID NO 723
<211> LENGTH: 217
<212> TYPE: DNA
<213> ORGANISM: Homo sapiens

<400> SEQUENCE: 723

```
aggttagatt ctcattcacg ggactagtta gctttaagca ccctagagga ctagggtaat    60
ctgacttctc acttcctaag ttcccttcta tatcctcaag gtagaaatgt ctatgttttc   120
tactccaatt cataaatcta ttcataagtc tttggtacaa gtttacatga taaaagaaa   180
tgtgatttgt cttcccttct ttgcacttt gaaataa                            217
```

<210> SEQ ID NO 724
<211> LENGTH: 233
<212> TYPE: DNA
<213> ORGANISM: Homo sapiens

<400> SEQUENCE: 724

```
ggagagtaga acattttcc tcattttatc aaatcctctc ttgccctccc tcaattcccc    60
tgtaacattc ctgaagctgt tcccactccc agatggtttt atcaatagcc tagaggtaaa   120
gaactgtctt tttctctgat tctttaataa attatcttta tagaatatgc acaagttttt   180
ctacactcag tgttaaagta tttattaatg ggaagtcaac ttaatgtttt gaa          233
```

<210> SEQ ID NO 725
<211> LENGTH: 250
<212> TYPE: DNA

<213> ORGANISM: Homo sapiens

<400> SEQUENCE: 725

| | |
|---|---|
| ttgcatttca tgtttaacct ccggctggaa atagaaagca ttcccttaga gatgaggata | 60 |
| aaagaaagtt tcagattcaa caggggaag aaaatggaga tttaatccta aaactgtgac | 120 |
| ttggggaggt cagtcattta cagttagtcc tgtgtctttc gacttctgtg attattaacc | 180 |
| ccactcacta ccctgtttca gatgcatttg gaataccaaa gattaaatcc ttgacataag | 240 |
| atctcatttg | 250 |

<210> SEQ ID NO 726
<211> LENGTH: 183
<212> TYPE: DNA
<213> ORGANISM: Homo sapiens

<400> SEQUENCE: 726

| | |
|---|---|
| ggagtggtgg cctctctgag atttcctaaa gttgctcaac agcccctgat caactaagtt | 60 |
| ttgtggtact tcaccctctt ctgccctcat ttcatgtgac agccattgtg agactgatgc | 120 |
| acaaactgtc acttggttaa tttaagcact tctgttttcg tgaatttact tgattgtttc | 180 |
| ttc | 183 |

<210> SEQ ID NO 727
<211> LENGTH: 77
<212> TYPE: DNA
<213> ORGANISM: Homo sapiens

<400> SEQUENCE: 727

| | |
|---|---|
| accaccacca gaatgcagtt ccagcttagg aagccacaaa caagccaccc aggaggaaca | 60 |
| aaacaccgcc agcgtgg | 77 |

<210> SEQ ID NO 728
<211> LENGTH: 231
<212> TYPE: DNA
<213> ORGANISM: Homo sapiens

<400> SEQUENCE: 728

| | |
|---|---|
| aataattcct ttctactgca tacaaaggga cctgaagctt aaattcagtt agttttggag | 60 |
| aaatccaaaa tgagaaaaac agaaagcatg tagcattcca tgaagcaaga acagcgtgca | 120 |
| tatgctattc ctgaaatac tgaagtgtcc gaatttcatg cctaaaaagt ctggaaatca | 180 |
| cactgaatca gttgctggtt tctgatgtct ctgggatgtg ctattacaaa c | 231 |

<210> SEQ ID NO 729
<211> LENGTH: 77
<212> TYPE: DNA
<213> ORGANISM: Homo sapiens

<400> SEQUENCE: 729

| | |
|---|---|
| attcagcaaa aactcagcca gctctttcta tggggcagtt gctaatttag ttctaggcaa | 60 |
| acgtggacac attaaat | 77 |

<210> SEQ ID NO 730
<211> LENGTH: 269
<212> TYPE: DNA
<213> ORGANISM: Homo sapiens

<400> SEQUENCE: 730

| | |
|---|---|
| ttccttcttg gcctaactct tccagttagg atctagaact ttgcctttt tttttttttt | 60 |

```
tttttttttga gatgggttct cactatattg tccaggctag agtgcagtgg ctattcacag      120
atgcgaacat agtacactgc agcctccaac tcctagcctc aagtgatcct cctgtctcaa      180
cctcccaagt aggattacaa gcatgcgccg acgatgccca gaatccagaa ctttgtctat      240
cactctcccc aacaacctag atgtgaaaa                                        269

<210> SEQ ID NO 731
<211> LENGTH: 229
<212> TYPE: DNA
<213> ORGANISM: Homo sapiens

<400> SEQUENCE: 731
aaatatgttt acagaccaaa gtgtgatttc acactgtttt taaatctagc attattcatt      60
ttgcttcaat caaagtggt ttcaatattt tttttagttg gttagaatac tttcttcata      120
gtcacattct ctcaacctat aatttggaat attgttgtgg tcttttgttt tttctcttag      180
tatagcattt ttaaaaaaat ataaaagcta ccaatctttg tacaatttg                 229

<210> SEQ ID NO 732
<211> LENGTH: 216
<212> TYPE: DNA
<213> ORGANISM: Homo sapiens

<400> SEQUENCE: 732
gtgatctggc aatgctatcc agcatctttg gagaccaatg gtcagtcttt tcctggccag      60
aggaaagatt gatggccctc ccacttgaac tgacagcctg tgagccccctt ggggcatag      120 actgccttcc ttggacccctt ccaaagtgtg tggtacgggg ctcagtgcac agagtattca     180
cccagcatca tgaatcaact tgggaggagt caacca                                216

<210> SEQ ID NO 733
<211> LENGTH: 165
<212> TYPE: DNA
<213> ORGANISM: Homo sapiens

<400> SEQUENCE: 733
gggacatgaa gagcggcgca cgagtgggac tggcgcgcgc tcgccctcgc ggagcggacc      60
tgggaaggcg cgagaccgcg caggcgcagt accgcgggtg ccgcccaggt gatgcgcatg     120
cgcaccgggt agcagagcta gcgctactca gtaaaaatcc aatat                    165

<210> SEQ ID NO 734
<211> LENGTH: 124
<212> TYPE: DNA
<213> ORGANISM: Homo sapiens

<400> SEQUENCE: 734
gacctgggcc tgacgggccc ttctcagccc gttttgagga cagacagtcc cccgaggtag      60
gctacatccc cccaccccag ctggtctgct tggatttcct acagccccccg tgggcatgga    120 ccac                                                                 124

<210> SEQ ID NO 735
<211> LENGTH: 156
<212> TYPE: DNA
<213> ORGANISM: Homo sapiens

<400> SEQUENCE: 735
gttataattt acactgaggg tttcaaaatt cgactagaag tggagatata ttatttattt      60
```

```
atgcactgta ctgtattttt atattgctgt ttaaaacttt taagctgtgc ctcacttatt    120
aaagcacaaa atgttttacc tactccttat ttacga                             156

<210> SEQ ID NO 736
<211> LENGTH: 276
<212> TYPE: DNA
<213> ORGANISM: Homo sapiens

<400> SEQUENCE: 736
gagtaagctc tagtccctct gtcctgtaga aagagccctg aagaatcagc aattttgttg    60
ctttattgtg gcatctgttc gaggtttgct tcctctttaa gtctgtttct tcattagcaa    120
tcatatcagt tttaatgcta ctactaacaa tgaacagtaa caataatatc cccctcaatt    180
aatagagtgc tttctatgtg caaggcactt ttcacgtgtc acctatttta accttttccaa    240 ccacataaat aaaaaaggcc attattagtt gaatct                              276

<210> SEQ ID NO 737
<211> LENGTH: 257
<212> TYPE: DNA
<213> ORGANISM: Homo sapiens

<400> SEQUENCE: 737
gcctctggct tctcaggcct ctgctctccg acctctctcc tctgaaaccc tcctccacag    60
ctgcagccca tcctcccggc tccctcctag tctgtcctgc gtcctctgtc cccgggtttc    120
agagacaact tcccaaagca caaagcagtt tttcccccta ggggtgggag aagcaaaag     180 actctgtacc tattttgtat gtgtataata atttgagatg ttttttaatta ttttgattgc   240 tggaataaag catgtgg                                                   257

<210> SEQ ID NO 738
<211> LENGTH: 283
<212> TYPE: DNA
<213> ORGANISM: Homo sapiens

<400> SEQUENCE: 738
cgcatgttat ggtgctaatg tactttcact tttaaactct agatcagaat tgttgacttg    60
cattcagaac ataaatgcac aaaatctgta catgtctccc atcagaaaga ttcattggca    120
tgccacaggg gattctcctc cttcatcctg taaaggtcaa caataaaaac caaattatgg    180
ggctgctttt gtcacactag catagagaat gtgttgaaat ttaactttgt aagcttgtat    240
gtggttgttg atcttttttt tccttacaga cacccataat aaa                     283

<210> SEQ ID NO 739
<211> LENGTH: 254
<212> TYPE: DNA
<213> ORGANISM: Homo sapiens

<400> SEQUENCE: 739
aattcagtgg tgtgagtata ttcataagat ttatacttgg tgtctattca taagacttat    60
atccagcata ttcataacta gagccatatc acagatgcat tcatcataat aattccagac    120
attttcatca ccctaaaagg aaaccctgaa acccattagc agtcattccc cattcctcca    180
acccattctc tccctaatcc ctagaaacca ccaatctgct gtgtatttca tctattgcca    240
acatttcata taaa                                                      254

<210> SEQ ID NO 740
<211> LENGTH: 217
```

```
<212> TYPE: DNA
<213> ORGANISM: Homo sapiens

<400> SEQUENCE: 740 tattttgag atatccctt ggaagacctt gcttggaaga gcctggacac taacaattct       60
acaccaaatt gtctcttcaa atacgtatgg actggataac tctgagaaac acatctagta    120
taactgaata agcagagcat caaattaaac agacagaaac cgaaagctct atataaatgc    180
tcagagttct ttatgtattt cttattggca ttcaaca                             217

<210> SEQ ID NO 741
<211> LENGTH: 171
<212> TYPE: DNA
<213> ORGANISM: Homo sapiens

<400> SEQUENCE: 741
atcgctggtc accatggtga tcaaggtgct cctggctccg tgggtcctgc tggtcctagg     60
ggccctgctg gtccttctgg ccctgctgga aagatggtc gcactggaca tcctggtaca    120
gttggacctg ctggcattcg aggccctcag ggtcaccaag gccctgctgg c            171

<210> SEQ ID NO 742
<211> LENGTH: 289
<212> TYPE: DNA
<213> ORGANISM: Homo sapiens

<400> SEQUENCE: 742
aaaccctcag gaaactccca gggtgatgct tggagaagct gtgagttgag ctgaagctgg     60
agaacttcct ccagagcaaa gggcttaaga aagaaagaag aactctaagc tgggtctgct    120
aacatcactc cagtttagat ggatcttggc agagagacat gcttgttcct ctggattgga    180
aagatgattt actctcggga atcttctctg tcagcctgta catctaaagg catgaagcac    240
tcaattgggc aattaacatt agtgtttgtt ctctgatggt atctctgag                289

<210> SEQ ID NO 743
<211> LENGTH: 271
<212> TYPE: DNA
<213> ORGANISM: Homo sapiens

<400> SEQUENCE: 743
gtggtcatgc ggaacactct gttatttaag atggctatcc agataatcct gaacactgtg     60
tatttatttt atttagacta ccagcaaaga ttaaagcatg aaatgtaaaa catctgataa    120
aacttacagc cccctacacc aagagtgtat ctgtgaaaga gctcctacac tttgaaaact    180
taagaatccc ttatcatgaa gtttgcctgt tctagaattg taagattgtt aatttccttc    240
aatctctagt gacaacactt aatttctttt c                                   271

<210> SEQ ID NO 744
<211> LENGTH: 193
<212> TYPE: DNA
<213> ORGANISM: Homo sapiens

<400> SEQUENCE: 744
cacctggctt catgttcccg gtattagtac aatgccaaaa tatttaaaat tcttaaaggt     60
taactcaaat atcttaagtt ttacttcact tacaatttca ataatgctga aattttgatt    120
gaatattgtg tttgtagtgc tacctctttt tcgttcataa gaacaaaagc ctatcattct    180
cttagtttct aaa                                                      193
```

<210> SEQ ID NO 745
<211> LENGTH: 206
<212> TYPE: DNA
<213> ORGANISM: Homo sapiens

<400> SEQUENCE: 745

```
cctgtaactc tttaaaactt ggctataggc tgtttagcac agtacagatt aaagatacag      60
ttacgtaaac agcaaagtaa ttttatagtg cttcatccat ttatcatgct ttggtttgct     120
aatttttca catacctttt tctatcacag tctgttgctt ttgtacacat ttctcatatt     180
ggggttcgac aggtaaacac aaactg                                          206
```

<210> SEQ ID NO 746
<211> LENGTH: 242
<212> TYPE: DNA
<213> ORGANISM: Homo sapiens

<400> SEQUENCE: 746

```
gtgctataat ccctatttag ttcaaaatta accagaattc ttccatgtga aatggaccaa      60
actcatatta ttgttatgta aatacagagt tttaatgcag tatgcatcc cacaggggaa     120
aagaatgtct gtagtgggtg actgttatca aatattttat agaatacaat gaacggtgaa     180
cagactggta acttgtttga gttcccatga cagatttgag acttgtcaat agcaaatcat     240
tt                                                                    242
```

<210> SEQ ID NO 747
<211> LENGTH: 266
<212> TYPE: DNA
<213> ORGANISM: Homo sapiens

<400> SEQUENCE: 747

```
ttatcaactg tgcacaagga aaaaaataga tatgtgaaag gttcacgtaa atttcctcac      60
atcacagaag attaaaattc agaaggaga aaacacagac caaagagaag tatctaagac     120
caaagggatg tgttttatta atgtctagga tgaagaaatg catagaacat tgtagtactt     180
gtaaataact agaaataaca tgatttagtc ataattgtga aaaataataa taatttttct     240
tggatttatg ttctgtatct gtgaaa                                          266
```

<210> SEQ ID NO 748
<211> LENGTH: 202
<212> TYPE: DNA
<213> ORGANISM: Homo sapiens

<400> SEQUENCE: 748

```
gtggaggata ttgcaactgg agttcagaca ctgtactcga agtggaagga ctttcatttt      60
gagaagatac catttgatcc agcagaaatg tccaaatgat atcaggtcct caatcttcag     120
ctacagggaa tgagtaactt tgagtggaga agaaacaaac atagtgggta taatcatgga     180
tcgcttgtac ccctgtgaaa at                                              202
```

<210> SEQ ID NO 749
<211> LENGTH: 208
<212> TYPE: DNA
<213> ORGANISM: Homo sapiens
<220> FEATURE:
<221> NAME/KEY: modified_base
<222> LOCATION: (124)..(124)
<223> OTHER INFORMATION: a, c, t, g, unknown or other

<400> SEQUENCE: 749

```
gaatatgtgg cagagctcct ggaaatgatg cagattaggt ggcattttg tcagctctgt      60 ggtttattgt tgggactatt ctttaaaata tccattgttc actacagtga agatctctga    120
tttnaccgtg tactatccac atgcattaca aacatttcgc agagctgctt agtatataag    180
cgtacaatgt atgtaataac catctcat                                        208

<210> SEQ ID NO 750
<211> LENGTH: 150
<212> TYPE: DNA
<213> ORGANISM: Homo sapiens

<400> SEQUENCE: 750
gctgataaat agcattaggg ttctttgcaa tgtggtatct agctgtatta ttggttttat     60
ttactttaaa cattttgaaa agcttatact ggcagcctag aaaaacaaac aattaatgta    120
tctttatgtc cctggcacat gaataaactt                                      150

<210> SEQ ID NO 751
<211> LENGTH: 97
<212> TYPE: DNA
<213> ORGANISM: Homo sapiens

<400> SEQUENCE: 751
caaattcaag tcactagact tcagagttca acacctggac atgagaagat attatattat     60
gtaccataaa tatttcctgt atctgactgc ctgaaca                               97

<210> SEQ ID NO 752
<211> LENGTH: 237
<212> TYPE: DNA
<213> ORGANISM: Homo sapiens

<400> SEQUENCE: 752
agcaagactt gctgcctaaa ggagcccacc attttacttt tcacatttaa tctgccacgt     60
tgaatcaatt ggaataaaac ctgactcgca ggtgactgga caggaaatcc caaagttcca    120
ccatttctat gcttaatttt aacgtccccc cgcttttttt tttgtagaaa ataaaaacaa    180
gaaaatcgtt ccaatgtaag atgtttgtta tagaaacttt aggcaataca ggtgtgt       237

<210> SEQ ID NO 753
<211> LENGTH: 292
<212> TYPE: DNA
<213> ORGANISM: Homo sapiens
<220> FEATURE:
<221> NAME/KEY: modified_base
<222> LOCATION: (54)..(55)
<223> OTHER INFORMATION: a, c, t, g, unknown or other

<400> SEQUENCE: 753
ttgcaagtca attaggtgtc ttgtgaacaa ggaaatacta atctctaagc tgcnnnggtc     60
tttttgtgtg aatatttaat ggtgctccat gactgttgag ttttaaaaac ctcgttaaat    120
tttgccaaat cagttgcccc caaaagggaa tatgcttttc cttattttt tttctaaaat     180 gctatttatc tctaaggaaa aaaaaaaaag actattactc atttaacatt gtttaagcag    240
gttgagctag ctgtgaaaat agcttttgtg agccttctaa ttcctaaacg tc            292

<210> SEQ ID NO 754
<211> LENGTH: 243
<212> TYPE: DNA
<213> ORGANISM: Homo sapiens
```

-continued

<400> SEQUENCE: 754
gttaacactg tggatcacct tcggccaagg gacacgactg gagattaaac gtaagtaatt    60
tttcactatt gtcttctgaa atttgggtct gatggccagt attgactttt agaggcttaa   120
ataggagttt ggtaaagatt ggtaaatgag ggcatttaag atttgccatg ggttgcaaaa   180
gttaaactca gcttcaaaaa tggatttgga gaaaaaaga ttaaattgct ctaaactgaa    240
tga                                                                 243

<210> SEQ ID NO 755
<211> LENGTH: 120
<212> TYPE: DNA
<213> ORGANISM: Homo sapiens

<400> SEQUENCE: 755
tcattctcat ccatccagga tgtactaaaa cagtgtgttt aataaattgt aattattttg    60
tgtacagttc tatactgtta tctgtgtcca tttccaaaac ttgcacgtgt ccctgaattc   120

<210> SEQ ID NO 756
<211> LENGTH: 185
<212> TYPE: DNA
<213> ORGANISM: Homo sapiens

<400> SEQUENCE: 756
aaggtttggc agaaattgtt ttttgagtgg ctcaccagag tacccagaag aatcagtatg    60
gaattagagg acagtggcct accctaaata agacatgag tgatgtataa agtctagtgt   120
caatttattc agaaaatatc aaaattattc tgggagctat gggtcaaagt tgataggcac   180
aaaca                                                              185

<210> SEQ ID NO 757
<211> LENGTH: 130
<212> TYPE: DNA
<213> ORGANISM: Homo sapiens

<400> SEQUENCE: 757
atcccaatag atatccccct atgtgcatgc acacctgcac actcacggct gaaatctccc    60
taacccaggg ggaccttagc atgcctaagt gactaaacca ataaaaatgt tctggtctgg   120
cctgaaaaaa                                                          130

<210> SEQ ID NO 758
<211> LENGTH: 86
<212> TYPE: DNA
<213> ORGANISM: Homo sapiens

<400> SEQUENCE: 758
aagcagacta cgagaaacac aaagtctacg cctgcgaagt cacccatcag ggcctgagct    60
cgcccgtcac aaagagcttc aacagg                                         86

<210> SEQ ID NO 759
<211> LENGTH: 264
<212> TYPE: DNA
<213> ORGANISM: Homo sapiens

<400> SEQUENCE: 759
ggtacacaaa tctggttctc aatggtgagg tgggatcaga gatattctcc ctgttgttca    60
gaggaacaat aattcggatg tttctctcca caatgtcctc attaggatct tcggaagaac   120
ggatgatcct ggaagtaatc cgggcacact tacatttgtt gtcaacaaga acaatccttt   180

```
catcttcttg ggctttcaca tgaacagcct taataaaaac cgccaggact ccccagaaaa    240
gcaaatggtt cttcatcttg accc                                          264

<210> SEQ ID NO 760
<211> LENGTH: 101
<212> TYPE: DNA
<213> ORGANISM: Homo sapiens

<400> SEQUENCE: 760
ttgataggga tagcattgaa ctatttgctc aactcaacat tttaggaatt tatttctgct    60
gtctagtgct caaaacttgc agctagaatt gagggaagag a                       101

<210> SEQ ID NO 761
<211> LENGTH: 233
<212> TYPE: DNA
<213> ORGANISM: Homo sapiens

<400> SEQUENCE: 761
tgcttatccg ttagccgtgg tgatttagca ggaagctgtg agagcagttt ggtttctagc    60
atgaagacag agccccaccc tcagatgcac atgagctggc gggattgaaa gatgctgtct   120
tcgtactggg aaagggattt tcagccctca gaatcgctcc accttgcagc tctcccttc    180 tctgtattcc tagaaactga cacatgctga acatcacagc ttatttcctc att          233

<210> SEQ ID NO 762
<211> LENGTH: 256
<212> TYPE: DNA
<213> ORGANISM: Homo sapiens

<400> SEQUENCE: 762
ctgaggtgct atgttcttag tggatgttct gaccctgctt caaatatttc cctcaccttt    60
cccatcttcc aagggtataa ggaatctttc tgctttgggg tttatcagaa ttctcagaat   120
ctcaaataac taaaaggtat gcaatcaaat ctgcttttta aagaatgctc tttacttcat   180
ggacttccac tgccatcctc ccaaggggcc caaattcttt cagtggctac ctacatacaa   240 ttccaaaacac atacag                                                  256

<210> SEQ ID NO 763
<211> LENGTH: 259
<212> TYPE: DNA
<213> ORGANISM: Homo sapiens

<400> SEQUENCE: 763
acagaagcca ttgcctccct tgtttacctt gggtccacct ccaccaaaac ccaacagacc    60
accaaatgtt gacctgacga aattccacaa aacctcttct ggaaacagta ctagcaaagg   120
ccagacgtct tactcaacaa cttccctgcc accacctcca ccatcccatc cggccagcca   180
accaccattg ccagcatctc acccatcaca accaccagtc ccaagcctac ctcccagaaa   240
cattaaacct ccgtttgac                                                259

<210> SEQ ID NO 764
<211> LENGTH: 114
<212> TYPE: DNA
<213> ORGANISM: Homo sapiens

<400> SEQUENCE: 764
ggacctgtac accacgagca gccagctgac cctgccggcc acacagtgcc tagccggcaa    60
```
gtccgtgaca tgccacgtga agcactacac gaatcccagc caggatgtga ctgt       114

<210> SEQ ID NO 765
<211> LENGTH: 265
<212> TYPE: DNA
<213> ORGANISM: Homo sapiens

<400> SEQUENCE: 765
ggatttctcc aaaactaact gaatttaagc ttcaggtccc tttgtatgca gtagaaagga   60
attattaaaa acaccaccaa agaaaataaa tatatcctac ttgaaattta ctctatggac  120
ttacccactg ctagaataaa tgtatcaaat cttatttgta aattctcaat tttgatatat  180
atatgtatat atgcatatac atatccacac ttgtctgcaa gaatattgat taaaattgct  240
aaatttgtac ttgttcacca gaaaa                                        265

<210> SEQ ID NO 766
<211> LENGTH: 198
<212> TYPE: DNA
<213> ORGANISM: Homo sapiens

<400> SEQUENCE: 766
gcacagctca gcacaacatt ccaagctcaa aatagaagcc ttctcagtga gctccagcac   60
gcccagagga ctgttaataa cgatgatcca tgtgttttac tctaaagtgc taaatatggg  120
agtttccttt ttttactctt tgtcactgat gacacaacag aaaagaaact gtagaccttg  180
ggacaatcaa catttaaa                                                198

<210> SEQ ID NO 767
<211> LENGTH: 162
<212> TYPE: DNA
<213> ORGANISM: Homo sapiens

<400> SEQUENCE: 767
atgttcatac tctaagtatc aaaatcttcc aattatcatg ctcacctgaa agaggtatgc   60
tctcttagga atacagtttc tagcattaaa caaataaaca aggggagaaa ataaaactca  120
aggagtgaaa atcaggaggt gtaataaaat gttcctcgca tt                     162

<210> SEQ ID NO 768
<211> LENGTH: 256
<212> TYPE: DNA
<213> ORGANISM: Homo sapiens

<400> SEQUENCE: 768
tcctgtttac ccttcaagtt tcaagttcat gtcactgtct cagagaggtt ttcctgtgct   60
cgccctgttt ctctcaggaa gccttgctct tttccatcat gcctctaatc acagcttata  120
atcggatatt tatttctgtg tctacagtct tgccctgcca gactgtatgc cccatgtggg  180
caggcgctca tgattgtttc tgattgtttc acgcatgctg ctaacccaga gcctgggccc  240
aaagctagtt agtact                                                  256

<210> SEQ ID NO 769
<211> LENGTH: 294
<212> TYPE: DNA
<213> ORGANISM: Homo sapiens

<400> SEQUENCE: 769
caaagggtga gagggcttcc ttctcaccct tctctccata agtatcttga agatccatgg   60
tttgttttgc tctattgttt agttttttact tgggtgcaat gtgtacgtca aaagttttta  120

```
ttttgatatt tgaaagagac caaatcaggc ccagaccgcc tctctggaag gtgttgtagg      180
ccattcaaaa cgcctccgga gtgtcgcaaa ccaagtgcgg aggggccctg aggttgtact      240
gtaaacatca tagtgacttg tcttttcaaa tatattccca ctattttcgc agaa            294
```

<210> SEQ ID NO 770
<211> LENGTH: 221
<212> TYPE: DNA
<213> ORGANISM: Homo sapiens

<400> SEQUENCE: 770

```
tgctggactc cgacggctcc ttcttcctct acagcaagct caccgtggac aagagcaggt      60
ggcagcaggg gaacatcttc tcatgctccg tgatgcatga ggctctgcac aaccgcttca      120
cgcagaagag cctctccctg tctccgggta aatgagtgcg acggccggca agcccccgct      180
ccccgggctc tcgggtcgc gcgaggatgc ttggcacgta c                          221
```

<210> SEQ ID NO 771
<211> LENGTH: 239
<212> TYPE: DNA
<213> ORGANISM: Homo sapiens

<400> SEQUENCE: 771

```
ggagaggcag cattgcacag tgaaagaatt ctggatatct caggagcccc gaaattctag      60
ctctgacttt gctgtttcca gtggtatgac cttggagaag tcacttatcc tcttggagcc      120
tcagtttcct catctgcaga ataatgactg acttgtctaa ttcgtaggga tgtgaggttc      180
tgctgaggaa atgggtatga atgtgccttg aacacaaagc tctgtcaata agtgataca      239
```

<210> SEQ ID NO 772
<211> LENGTH: 181
<212> TYPE: DNA
<213> ORGANISM: Homo sapiens

<400> SEQUENCE: 772

```
gaggaccgag cacagaaatc ttagagattt cttgtcccct ctcaggtcat gtgtagatgc      60
gataaatcaa gtgattggtg tgcctgggtc tcactacaag cagcctatct gcttaagaga      120
ctctggagtt tcttatgtgc cctggtggac acttgcccac catcctgtga gtaaaagtga      180
a                                                                     181
```

<210> SEQ ID NO 773
<211> LENGTH: 228
<212> TYPE: DNA
<213> ORGANISM: Homo sapiens

<400> SEQUENCE: 773

```
gggatgacat gcactcagct cttggctcca ctgggatggg aggagaggac aagggaaatg      60 tcagggggcgg ggagggtgac agtggccgcc caaggcccac gagcttgttc tttgttcttt     120
gtcacaggga ctgaaaacct ctcctcatgt tctgctttcg attcgttaag agagcaacat      180
tttacccaca cacagataaa gttttcccctt gaggaaacaa cagcttta                  228
```

<210> SEQ ID NO 774
<211> LENGTH: 136
<212> TYPE: DNA
<213> ORGANISM: Homo sapiens

<400> SEQUENCE: 774

```
caggacccat cacgcctgtg cagtggcccc cacagaaaga ctgagctcaa ggtgggaacc    60
acgtctgcta acttggagcc ccagtgccaa gcacagtgcc tgcatgtatt tatccaataa   120
atgtgaaatt ctgtcc                                                   136

<210> SEQ ID NO 775
<211> LENGTH: 193
<212> TYPE: DNA
<213> ORGANISM: Homo sapiens

<400> SEQUENCE: 775
gcagtctact agattgtgat cccttgagat atggaaggat gccttttttt ctctgcattt    60
aaaaaaatcc cccagcactt cccacagtgc ctattgatac ttggggaggg tgcttggcac   120
ttattgaata tatgatcggc catcaaggga agaactattg tgctcagaga cactgttgat   180
aaaaactcag gca                                                      193

<210> SEQ ID NO 776
<211> LENGTH: 175
<212> TYPE: DNA
<213> ORGANISM: Homo sapiens

<400> SEQUENCE: 776
aaatttaatt ttctacgcct ctggggatat ctgctcagcc aatggaaaat ctgggttcaa    60
ccagcccctg ccatttctta agactttctg ctgcactcac aggatcctga gctgcactta   120
cctgtgagag tcttcaaact tttaaacctt gccagtcagg acttttgcta ttgca         175

<210> SEQ ID NO 777
<211> LENGTH: 183
<212> TYPE: DNA
<213> ORGANISM: Homo sapiens

<400> SEQUENCE: 777
taaatattga gcagatctat aggaagattg aacctgaata ttgccattat gcttgacatg    60
gtttccaaaa aatggtactc cacatacttc agtgagggta agtattttcc tgttgtcaag   120
aatagcattg taaagcattt tgtaataat aaagaatagc tttaatgata tgcttgtaac   180
taa                                                                 183

<210> SEQ ID NO 778
<211> LENGTH: 235
<212> TYPE: DNA
<213> ORGANISM: Homo sapiens

<400> SEQUENCE: 778
taactttttc tcaaagtcac tgatgtttgt tcctgttaaa tgtatagcat tgtaatgaga    60
gcccatcaaa tcctgagtgt cagtttgttg tccctattgt agatgaaata gtgatgtagc   120
aaaaacctag taaattctga atgcttttcc acgtagactt atctggaatg tgaacacaac   180
tctttggtta atagtaaatg cttaactgta gtcctgagta ggtgcatttc tgtct         235

<210> SEQ ID NO 779
<211> LENGTH: 154
<212> TYPE: DNA
<213> ORGANISM: Homo sapiens

<400> SEQUENCE: 779
agtatatttt ctatcttctg gtgacttgag cttgagctct gacaggcatg ggcctctccg    60
accttcatca ctattcttag gataatgctg gcgggcagag atgatcaatc atcatattaa   120
```

```
atcataatga gcttataatc ctcccactgg aaaa                              154
```

<210> SEQ ID NO 780
<211> LENGTH: 280
<212> TYPE: DNA
<213> ORGANISM: Homo sapiens

<400> SEQUENCE: 780

```
atcagaaagg gcaacttact cttcctggca tcttattgta ttggagggtg accaccctgg   60
gcatggggtg ttggcagggg tcaaaaagct tatttctttt aatctcttac tcaacgaaca  120
catcttctga tgatttccca aaattaatga gaatgagatg agtagagtaa gatttggggtg 180
ggatgggtag gatgaagtat attgcccaac tctatgtttc tttgattcta acacaattaa  240
ttaagtgaca tgattttttac taatgtatta ctgagactag                       280
```

<210> SEQ ID NO 781
<211> LENGTH: 206
<212> TYPE: DNA
<213> ORGANISM: Homo sapiens

<400> SEQUENCE: 781

```
tattcttcta taacactcta tatagagcta tgtgagtact aatcacattg aataatagtt   60
ataaaattat tgtatagaca tctgcttctt aaacagattg tgagttcttt gagaaacagc  120
gtggatttta cttatctgtg tattcacaga gcttagcaca gtgcctggta atgagcaagc  180
atacttgcca ttacttttcc ttccca                                       206
```

<210> SEQ ID NO 782
<211> LENGTH: 247
<212> TYPE: DNA
<213> ORGANISM: Homo sapiens

<400> SEQUENCE: 782

```
gctgaaattg tatctctcag taattttaga tgtcttttaa aaaattgaaa aacaaagtgt   60
tagactgtgt gcgtgtgcgt tgatgggcac tcaagagtcc cgtgagtcat ccagccctgc  120
cttcccctg cgcccccatc ctctcacgtc ccgcctgcc tccacttggg gaccctgcct   180
cgtgtcgtct ttatctgcct attactcagc ctaaggaaac aagtacactc cacacatgca  240
taaagga                                                            247
```

<210> SEQ ID NO 783
<211> LENGTH: 190
<212> TYPE: DNA
<213> ORGANISM: Homo sapiens

<400> SEQUENCE: 783

```
gtggagaacc acagctgcag agtaggcagc tgcctccagg atgagttact gaaatttgc    60
cttgagtgtg ttacctcctt tccaagctcc tcgtgataat gcagacttcc tggagtacaa  120
acacaggatt tgtaattcct tactgtaacg gagtttagag ccagggctga tgctttggtg  180
tggccagcac                                                         190
```

<210> SEQ ID NO 784
<211> LENGTH: 165
<212> TYPE: DNA
<213> ORGANISM: Homo sapiens

<400> SEQUENCE: 784

```
cccattgaaa agaccgagcc ttgtatgtat gttatggata cataaaatgc acgcaagcca    60
ttatctctcc atgggaagct aagttataaa aataggtgct tggtgtacaa aacttttat   120 atcaaaaggc tttgccattt ctatatgagt gggtttactg gtaaa                  165

<210> SEQ ID NO 785
<211> LENGTH: 260
<212> TYPE: DNA
<213> ORGANISM: Homo sapiens

<400> SEQUENCE: 785
gaacagagag aaagtgctcc gtaaaagtga gctgcgatgc ggaggtgggc aagctcttcc    60
ctggaggggg aagagctctc aacccagagg gatctgacca ggaaggttca ccccccctcc  120
acccaggaag cccctgcaga cagtatgtgt tttaggcttt gctggccaaa tggtctctgc  180
cgtgactact cagctctgcc attgtggctg cagagtgacc atagaccttc tgaaagtgaa  240
tgagtatgac tgtgttccaa                                              260

<210> SEQ ID NO 786
<211> LENGTH: 197
<212> TYPE: DNA
<213> ORGANISM: Homo sapiens

<400> SEQUENCE: 786
aaatggtaaa catgagggtg ctcttgtgac ttaattttg ttcaagggac taaattgctt    60
atgtttattc cctgtcagcg gagtggagaa tgtcattcat caataaacca aagccaatag  120
ctggagaatt gagatctggt tgaaagtggt ttatggttta catgctgtac tatcctgagg  180
aattgcgaga tattgct                                                 197

<210> SEQ ID NO 787
<211> LENGTH: 187
<212> TYPE: DNA
<213> ORGANISM: Homo sapiens

<400> SEQUENCE: 787
aaaacatctg gttcaattac gctgaactct gactacatgt gggccagtaa taatatgaat    60
tggacttaag aataaaacctt gtgtttaatc tctttttttc cttaaaattt taatgtgagt  120
tttctgttac gcaaattatc catgttagca catttggaac aaatgtataa atgtactttc  180
tgaataa                                                            187

<210> SEQ ID NO 788
<211> LENGTH: 228
<212> TYPE: DNA
<213> ORGANISM: Homo sapiens

<400> SEQUENCE: 788
gggatgacat gcactcagct cttggctcca ctgggatggg aggagaggac aagggaaatg    60 tcagggggcgg ggagggtgac agtggccgcc caaggcccac gagcttgttc tttgttcttt  120
gtcacaggga ctgaaaaacct ctcctcatgt tctgctttcg attcgttaag agagcaacat  180
tttacccaca cacagataaa gttttcccctt gaggaaacaa cagcttta               228

<210> SEQ ID NO 789
<211> LENGTH: 213
<212> TYPE: DNA
<213> ORGANISM: Homo sapiens

<400> SEQUENCE: 789
```

```
actctccgga ttgaccaagt tcatcctggg ctccattggg tctgccattg cggctgtcat    60
tgcgaggttc tactagctcc ctgcccctcg ccctgcagag aagagaacca tgccagggga   120
gaaggcaccc agccatcctg acccagcgag gagccaacta tcccaaatat acctggggtg   180
aaatatacca aattctgcat ctccagagga aaa                                 213

<210> SEQ ID NO 790
<211> LENGTH: 104
<212> TYPE: DNA
<213> ORGANISM: Homo sapiens

<400> SEQUENCE: 790
gttggtgtgc tgaggtgtta gagagggacc atgtgtcact tgtgctttgc tcttgtccca    60
cgtgtcttcc actttgcata tgagccgtga actgtgcata gtgc                    104

<210> SEQ ID NO 791
<211> LENGTH: 132
<212> TYPE: DNA
<213> ORGANISM: Homo sapiens

<400> SEQUENCE: 791
acattgattc cccatcgctg aaggacagaa ttcattgtgt ggcatttgta tttgatgcca    60
gctctattca atacttctcc tctcagatga tagtaaagat caaaagaatt cgaagggagt   120
tggtaaacgc tg                                                       132

<210> SEQ ID NO 792
<211> LENGTH: 281
<212> TYPE: DNA
<213> ORGANISM: Homo sapiens

<400> SEQUENCE: 792
gttattaaca gtcctctggg cgtgctggag ctcactgaga aggcttctat tttgagcttg    60
gaatgttgtg ctgagctgtg cagcctgttc ctgcatctgt tgttcctgca ttttctgttg   120
ctctgccagc caattttgtt tggctatctc catttaactc acttgttcct gatggagtct   180
ctccctctcc tgcatcattt gctcgttctg cctttgaatc gccgcaacc tttgcgcttc   240 agccttttca gcttctgctt tcacttgtgc ctctgaggag a                      281

<210> SEQ ID NO 793
<211> LENGTH: 239
<212> TYPE: DNA
<213> ORGANISM: Homo sapiens

<400> SEQUENCE: 793
gggagggtaa cctcactctt ctccaggcca ggcctccttg gactcccctg ggggtgtccc    60
actcttcttc cctctaaact gccccacctc ctaacctaat cccccgccc cgctgccttt   120 cccaggctcc cctcacccca gcgggtaatg agccttaat cgctgcctct agggagctg   180 attgtagcag cctcgttagt gtcaccccct cctccctgat ctgtcagggc cacttagtg   239

<210> SEQ ID NO 794
<211> LENGTH: 174
<212> TYPE: DNA
<213> ORGANISM: Homo sapiens

<400> SEQUENCE: 794
ggtcctgtag ccctaagtgg tactaacttt ccttcattca acccacctgc gtctcatact    60
```

```
cacctcaccc cactgtggct gatttggaat tttgtgcccc catgtaagca ccccttcatt      120
tggcattccc cacttgagaa ttaccctttt gccccgaaca tgttttctt ctcc              174

<210> SEQ ID NO 795
<211> LENGTH: 270
<212> TYPE: DNA
<213> ORGANISM: Homo sapiens

<400> SEQUENCE: 795
aaataaccac ttttgttgg gcaatatgaa attttaaag gagtagaata ccaaatgata         60
gaaacagact gcctgaattg agaattttga tttcttaaag tgtgtttctt tctaaattgc     120
tgttccttaa tttgattaat ttaattcatg tattatgatt aaatctgagg cagatgagct     180
tacaagtatt gaataatta ctaattaatc acaaatgtga agttatgcat gatgtaaaaa       240
atacaaacat tctaattaaa ggctttgcaa                                        270

<210> SEQ ID NO 796
<211> LENGTH: 276
<212> TYPE: DNA
<213> ORGANISM: Homo sapiens

<400> SEQUENCE: 796
gagtaagctc tagtccctct gtcctgtaga aagagccctg aagaatcagc aattttgttg       60
ctttattgtg gcatctgttc gaggtttgct tcctctttaa gtctgtttct tcattagcaa     120
tcatatcagt tttaatgcta ctactaacaa tgaacagtaa caataatatc cccctcaatt     180
aatagagtgc tttctatgtg caaggcactt ttcacgtgtc acctatttta accttttccaa    240 ccacataaat aaaaaaggcc attattagtt gaatct                                 276

<210> SEQ ID NO 797
<211> LENGTH: 264
<212> TYPE: DNA
<213> ORGANISM: Homo sapiens

<400> SEQUENCE: 797 taacttttc tcaaagtcac tgatgtttgt tcctgttaaa tgtatagcat tgtaatgaga        60
gcccatcaaa tcctgagtgt cagtttgttg tccctattgt agatgaaata gtgatgtagc     120
aaaaacctag taaattctga atgcttttcc acgtagactt atctgaatg tgaacacaac     180 tctttggtta atagtaaatg cttaactgta gtcctgagta ggtgcatttc tgtctgtctc     240 aataaattt actttgtctg caaa                                               264

<210> SEQ ID NO 798
<211> LENGTH: 275
<212> TYPE: DNA
<213> ORGANISM: Homo sapiens

<400> SEQUENCE: 798
tattccatct actttctat cgccgtcccc ttttgcagcc ctctctgggg atggactggg       60
taaatgttga cagaggccct gccccgttca cagatcctgg ccctgagcca gccctgtgct     120
cctccctccc ccaacactcc ctaccaaccc cctaatcccc tactccctcc accccccctc     180
cactgtaggc cactggatgg tcatttgcat ctccgtaaat gtgctctgct cctcagctga    240
gagagaaaaa aataaactgt atttggctgc aagaa                                  275

<210> SEQ ID NO 799
<211> LENGTH: 210
```

<212> TYPE: DNA
<213> ORGANISM: Homo sapiens

<400> SEQUENCE: 799

```
agaggctctt ctgcgtgtag tggttgtgca gagcctcatg catcacggag catgagaaga    60
cgttcccctg ctgccacctg ctcttgtcca cggtgagctt gctatagagg aagaaggagc   120
cgtcggagtc cagcacggga ggcgtggtct tgtagttgtt ctccggctgc ccattgctct   180
cccactccac ggcgatgtcg ctgggataga                                    210
```

<210> SEQ ID NO 800
<211> LENGTH: 235
<212> TYPE: DNA
<213> ORGANISM: Homo sapiens

<400> SEQUENCE: 800

```
gagtgtctca gaagtgtgct cctctggcct cagttctcct cttttggaac aacataaaac    60
aaatttaatt ttctacgcct ctggggatat ctgctcagcc aatggaaaat ctgggttcaa   120
ccagcccctg ccatttctta agactttctg ctccactcac aggatcctga gctgcactta   180
cctgtgagag tcttcaaact tttaaacctt gccagtcagg acttttgcta ttgca        235
```

<210> SEQ ID NO 801
<211> LENGTH: 162
<212> TYPE: DNA
<213> ORGANISM: Homo sapiens

<400> SEQUENCE: 801

```
ggacataaca gacttggaag cagatgatac agacttcttt ttttcataat caggttagtg    60
taagaaattg ccatttgaaa caatccattt tgtaactgaa ccttatgaaa tatatgtatt   120
tcatggtacg tattctctag cacagtctga gcaattaaat ag                      162
```

<210> SEQ ID NO 802
<211> LENGTH: 249
<212> TYPE: DNA
<213> ORGANISM: Homo sapiens

<400> SEQUENCE: 802

```
aggccctctt gagagtctat ccagggaccc attgttttac tttaacagac cagaaaagat    60
gtttgttttc catgtcatta cccccagggg ataccgaatg tgtgggtaga aatttctctg   120
tagattaaaa atcagatttt tacatggatt caacaaagga gcgtcacttg gattttttgtt  180
ttcatccatg aatgtagctg cttctgtgta aatgccatt tgctattaa aaatcaattc     240
acgctggaa                                                           249
```

<210> SEQ ID NO 803
<211> LENGTH: 200
<212> TYPE: DNA
<213> ORGANISM: Homo sapiens

<400> SEQUENCE: 803

```
aagtgtttgc tgaggacatt gctcctctga ctcccatctc actttgtcca tcgcagcctt    60
ttgttgggag atgacactgt cagtcagccc atgatgtctg ttcacacgag atgctttttt   120
aatagaattg accaatgttt tgctgccact gattaaagta ttatttatac taattgttgc   180
ttgtagtttt gatgtaattc                                               200
```

<210> SEQ ID NO 804

```
<211> LENGTH: 150
<212> TYPE: DNA
<213> ORGANISM: Homo sapiens

<400> SEQUENCE: 804
ctagttactg tggtatggct aatacctgtc aacatttgga ggcaatccta ccttgctttt      60
gcttctagag cttagcatat ctgattgttg tcaggccata ttatcaatgt ttactttttt     120
ggtactataa aagctttctg ccacccctaa                                       150

<210> SEQ ID NO 805
<211> LENGTH: 142
<212> TYPE: DNA
<213> ORGANISM: Homo sapiens

<400> SEQUENCE: 805
tgtggcatgc ttttctgagc cttcctactt taaagcatgg aacatgcagg tgatttggga      60
agtgtagaaa gacctgagaa aacgagcctg tttcagagga acatcgtcac aacgaatact     120
tctggaagct taacaaaact aa                                               142

<210> SEQ ID NO 806
<211> LENGTH: 224
<212> TYPE: DNA
<213> ORGANISM: Homo sapiens

<400> SEQUENCE: 806
tgtagcagct tgtgttgtca cgcttcttct tttgagcaac tttcttacac tgaagaaagg      60
cagaatgagt gcttcagaat gtgatttcct actaacctgt tccttggata ggcttttttag    120
tatagtattt ttttttttgtc attttctcca tcagcaacca gggagactgc acctgatgga    180
aaagatatat gactgcttca tgacattcct aaactatctt tttt                       224

<210> SEQ ID NO 807
<211> LENGTH: 176
<212> TYPE: DNA
<213> ORGANISM: Homo sapiens

<400> SEQUENCE: 807
ggctgagcaa ggcacatagt ctactcagtc tattcctaag tcctaactcc tccttgtggt      60
gttggatttg taaggcactt tatccctttt gtctcatgtt tcatcgtaaa tggcataggc     120
agagatgata cctaattctg catttgattg tcactttttg tacctgcatt aattta          176

<210> SEQ ID NO 808
<211> LENGTH: 250
<212> TYPE: DNA
<213> ORGANISM: Homo sapiens
<220> FEATURE:
<221> NAME/KEY: modified_base
<222> LOCATION: (221)..(221)
<223> OTHER INFORMATION: a, c, t, g, unknown or other

<400> SEQUENCE: 808
tagaacagga tggagggcaa gacctgtgta agaagaagtc ttaaactgta aacatgggtg      60
tagtgagggt agtgtggcta agaggaaatg gatccagatg gcttgatgg ggagcagatg     120
ggcaggcacg atggcagggg tgcatcggct cactgggggct gcatctgagg taaatggaaa    180
taaaggaggt gaggaaatga ggaagagaag gaagtggcgg nactggctgt ggagttttgt    240
gggagccttc                                                             250
```

```
<210> SEQ ID NO 809
<211> LENGTH: 178
<212> TYPE: DNA
<213> ORGANISM: Homo sapiens

<400> SEQUENCE: 809
taccagaata ggagttttcc tctgtggacc tgaagccttg gctgaaaccc tgagtaaaca      60
aagcatctcc aactctgagt ctggccctcg gggagtgcat ttcattttca acaaggaaaa    120
cttctaactt gtctcttcca tgaggaaata aatgtgggtt gtgctgccaa atgctcaa     178

<210> SEQ ID NO 810
<211> LENGTH: 229
<212> TYPE: DNA
<213> ORGANISM: Homo sapiens
<220> FEATURE:
<221> NAME/KEY: modified_base
<222> LOCATION: (48)..(48)
<223> OTHER INFORMATION: a, c, t, g, unknown or other

<400> SEQUENCE: 810
gtagttagaa aaagcctcct aggtgatttt gatgaatccc agtctcanat ttcttcattt      60
ggaaatgata atgtaggcca cacgtattac tggagaaaaa tgtgctcccg agactttcca    120
gagcagcaga gctgggacta gcaggtgag gcagctacgt gcaagtgtag ccctgagaat     180
gagcacctct ttaaagaatg taccttgcgt tagttctgtg cctgtttaa                 229

<210> SEQ ID NO 811
<211> LENGTH: 278
<212> TYPE: DNA
<213> ORGANISM: Homo sapiens
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (230)..(230)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other

<400> SEQUENCE: 811
gaaagttggc tcgtaatatg atttaatatt caaagtagag tcatctacct attagcttgc      60
tggcgtggtc ctagtttatg cctgtttcag catgattgtt gagtaccctg tttcatcctt    120 agcatttct tgattttgtt gttaaatgat gtataccctt atttccattg aatctgtgct    180 tccaccccc caactgaagt tgtnttccct ttgcttggcc acccttacan cctnttggat    240
ggtgtatcct acagtgtaag cactaaactg aagaggca                            278

<210> SEQ ID NO 812
<211> LENGTH: 243
<212> TYPE: DNA
<213> ORGANISM: Homo sapiens

<400> SEQUENCE: 812
atcatagctc actgagattg ccaggttcga caaagaggaa tttataggat ggggatatag      60
ggtagacttg actctgcttt atccgggaaa gcttttaaaa ctctgagcca gttaactttg    120
agtaagcata aaacatactg tattggtgtt tgtatttttc atgccacaat attaaaatgg    180
aattttaaat gtagattatt ataatctata aaagataagt atgcatgtat taggatactg    240
``` gaa                                                                    243

<210> SEQ ID NO 813
<211> LENGTH: 151
<212> TYPE: DNA
<213> ORGANISM: Homo sapiens

<400> SEQUENCE: 813
aaatttgtaa atgggattga gtccctaaaa cctggaaaaa ctgacatggg ctagctattt      60
attcactcat cgagttactt attccttcgt aaaaaaaaaa aaaaaaaaat catttgagat     120
gataaaaatg gtagggtata gtttaagatg a                                   151

<210> SEQ ID NO 814
<211> LENGTH: 84
<212> TYPE: DNA
<213> ORGANISM: Homo sapiens

<400> SEQUENCE: 814
cgcccgggca ggtactggat gtcaggtctg cgaaacttct tagattttga cctcagtcca      60
taaaccacac tatcacctcg gccg                                            84

<210> SEQ ID NO 815
<211> LENGTH: 252
<212> TYPE: DNA
<213> ORGANISM: Homo sapiens

<400> SEQUENCE: 815
tgagcttccc ttggacacta actcttccca gatgatgaca atgaaattag tgcctgtttt      60
cttgcaaatt tagcacttgg aacatttaaa gaaaggtcta tgctgtcata tggggtttat     120
tgggaactat cctcctggcc ccaccctgcc ccttcttttt ggttttgaca tcattcattt     180
ccacctggga atttctggtg ccatgccaga agaatgagg aacctgtatt cctcttcttc     240
gtgataatat aa                                                        252

<210> SEQ ID NO 816
<211> LENGTH: 272
<212> TYPE: DNA
<213> ORGANISM: Homo sapiens

<400> SEQUENCE: 816
aatgttgtgt gtggtgattg ttcaggtcga atctgttgta tccagtacag ctttaggtct      60
tcagctgccc ttctggcgag tacatgcaca ggattgtaaa tgagaaatgc agtcatattt     120
ccagtctgcc tctatgatga tgttaaatta ttgctgttta gctgtgaaca agggatgtac     180
cactggagga atagagtatc cttttgtaca cattttgaaa tgcttcttct gtagtgatag     240
aacaaataaa tgcaacgaat actctgtcaa aa                                  272

<210> SEQ ID NO 817
<211> LENGTH: 185
<212> TYPE: DNA
<213> ORGANISM: Homo sapiens

<400> SEQUENCE: 817
gccacaagct gtccagtcta atcgacagga ttccgattcc tgaacagtgt cattcgaatc      60
agaatgtcag agctgagtct gctgttctga cttaaggaac aacttgactc agtctcttga     120
tggctggaga atgcacatcc tagctgtcac tggggctaca ggcaggtcag tgagcacgct     180
aaaat                                                                185

<210> SEQ ID NO 818
<211> LENGTH: 256
<212> TYPE: DNA
<213> ORGANISM: Homo sapiens

<400> SEQUENCE: 818

```
gcagcaagat ggtgttgcag acccaggtct tcatttctct gttgctctgg atctctggtg      60
cctacgggga catcgtgatg acccagtctc cagactccct ggctgtgtct ctgggcgaga     120
gggccaccat caagtgcaag tccagccaga gtatttata taggtccaac aacaagaact     180
acttagcttg gtaccagcag aaagcaggac agcctcctaa attgttcatt tactgggcat     240
ctaccccggga atccgg                                                     256
```

<210> SEQ ID NO 819
<211> LENGTH: 146
<212> TYPE: DNA
<213> ORGANISM: Homo sapiens

<400> SEQUENCE: 819

```
aggtcgggc actctgagtc ccagttccca gtgcagctgt aggtcgtcat cacctaacca       60
cacgtgcaat aaagtcctcg tgcctgctgc tcacagcccc cgagagcccc tcctcctgga     120
gaataaaacc tttggcagct gccctt                                           146
```

<210> SEQ ID NO 820
<211> LENGTH: 122
<212> TYPE: DNA
<213> ORGANISM: Homo sapiens

<400> SEQUENCE: 820

```
ccagacgtca accaggaaca tgtaacttgg agagggacga agaaagggtc tgataaacac       60
agaggtttta aacagtccct accattggcc tgcatcatga caaagttaca aattcaagga     120
ga                                                                     122
```

<210> SEQ ID NO 821
<211> LENGTH: 225
<212> TYPE: DNA
<213> ORGANISM: Homo sapiens

<400> SEQUENCE: 821

```
gaagagtctg ttgccgagct ggactggaaa gccccaaaat cccaggattt cttcttcttt       60
tcttcttcca gctccttctc tctgaccttc tgcaatgcac cctgtatac ctggtcctgg     120
cagtagacaa tctgttccat ctggaagtgg aggcggatca gcttctcacc ttctctctct     180
tgttctgctc taatgtcttc aattttggac ttggcggttc tgtgg                     225
```

<210> SEQ ID NO 822
<211> LENGTH: 274
<212> TYPE: DNA
<213> ORGANISM: Homo sapiens

<400> SEQUENCE: 822

```
ggattatacc cgtcttagtc tcgatcattg ctttcacttg tgccactgag ctggaccttc       60
gcacctggag gaggtgcctc tttgcctcat cacctgactc cacaagaaac aagggcagct     120
cctcatcact gggcttcacc actttcaggg taaggtggat ggtcttctct ttgtcaatgc     180
cataagatga gaggcttctc cgtggcttta agatcttgga gcccagcaaa agaacctggt     240
```
cctgcacagg aaccttggta gtagaccgga ccca                                   274

<210> SEQ ID NO 823
<211> LENGTH: 256
<212> TYPE: DNA
<213> ORGANISM: Homo sapiens
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (206)..(206)
<223> OTHER INFORMATION: a, c, t, g, unknown or other
<220> FEATURE:
<221> NAME/KEY: modified_base
<222> LOCATION: (221)..(221)
<223> OTHER INFORMATION: a, c, t, g, unknown or other

<400> SEQUENCE: 823
ttgctgataa ttcaaattct gtactttggc aagcaaaaga ggtacaacat caccttggag     60
ttttacaatt taataatgca tactttaaaa ttcatgataa atcatggaac cccactatac   120
tcactaattc aactattgat ttcttttga gcaactgact ttatgattta tccttaaaag    180
taaggaagta taccagaagg ncaaanggat aaatccaccc ntaaatacta gagtctaagt   240
tattttcctg aaaagg                                                   256

<210> SEQ ID NO 824
<211> LENGTH: 143
<212> TYPE: DNA
<213> ORGANISM: Homo sapiens

<400> SEQUENCE: 824
gttgtcccca cagtagacac atatgatggc cgaggtgata gtgtggttta tggactgagg    60
tcaaaatcta agaagtttcg cagacctgac atccagtacc ctgatgctac agacgaggac   120
atcacctcac acatggaaag cga                                           143

<210> SEQ ID NO 825
<211> LENGTH: 199
<212> TYPE: DNA
<213> ORGANISM: Homo sapiens

<400> SEQUENCE: 825
gcacagctca gcacaacatt ccaagctcaa aatagaagcc ttctcagtga gctccagcac    60
gcccagagga ctgttaataa cgatgatcca tgtgttttac tctaaagtgc taaatatggg   120
agtttccttt ttttactct tgtcactga tgacacaaca gaaaagaaac tgtagacctt    180
gggacaatca acatttaaa                                                199

<210> SEQ ID NO 826
<211> LENGTH: 224
<212> TYPE: DNA
<213> ORGANISM: Homo sapiens

<400> SEQUENCE: 826
ccttgacccc agtacgaagt ctatgccctg aatcccaga gtagcccttc ctggtgccca     60
actggcctgg ggacaaacag cgtccactac atctaggact gccggctaag tggacacact   120
tcttgacctc ctaccaggaa cttggtaaa agctagcttt ggggaagggg ttgggtgtaa   180
atatgagagg gtggagggag accagctggt agcaataaac atgg                    224

```
<210> SEQ ID NO 827
<211> LENGTH: 263
<212> TYPE: DNA
<213> ORGANISM: Homo sapiens

<400> SEQUENCE: 827
gagatcactt ggtaactggt ttcatgtgta tccaaaaatc agcatttgga tttaagcttt    60
ctgaatttgg tagtttaaga aacagattta gttttcaat ggttttaact catgtgaaat   120
aatgattttc caccagctct gatgcaaaga gatataattt taatgaacga tttatccagc   180
agtgtgttcc aggggttgcc tctccttatc tacggggatt actttgtaca tgcagataag   240
ttttcgcaaa cctatttcca ttt                                          263

<210> SEQ ID NO 828
<211> LENGTH: 252
<212> TYPE: DNA
<213> ORGANISM: Homo sapiens

<400> SEQUENCE: 828
cactgtgtat gactgaaatt tctggaataa ctgtaaatgg ttatgttaat ggaataaaac    60
acaaatgttg aaaaatgtaa aatatatata catagattca aatccttata tatgtatgct   120
tgttttgtgt acaggatttt gttttttctt tttaagtaca ggttcctagt gttttactat   180
aactgtcact atgtatgtaa ctgacatata taaatagtca tttataaatg accgtattat   240
aacatttgaa aa                                                       252

<210> SEQ ID NO 829
<211> LENGTH: 226
<212> TYPE: DNA
<213> ORGANISM: Homo sapiens

<400> SEQUENCE: 829
agatccactg aacatctgtg tctttatttt gctgcttgta tttattgtag tcaaatgctt    60
tacatcagaa tgatgaaaat aggcttgcca ctttctctta ttttaattcc atggtagtca   120
atgaactggc tgccacttta atataactga aaattcattt tgagaccaag caggatcaag   180
tttgtagaat aaacactggt ttcctagcca tcctctgaaa acagta                  226

<210> SEQ ID NO 830
<211> LENGTH: 100
<212> TYPE: DNA
<213> ORGANISM: Homo sapiens

<400> SEQUENCE: 830
tagaattacc tatcacattt cccaatcttg actattcaga atgctgttta tttagtgatg    60
aggattagca cttgattgaa gattctttta aaatactatc                         100

<210> SEQ ID NO 831
<211> LENGTH: 239
<212> TYPE: DNA
<213> ORGANISM: Homo sapiens

<400> SEQUENCE: 831
ttctttgagg gctcgcatcc aaaagaatat aacactccaa gcatgaaaga gtggcagcaa    60
atttcatcac tgtatacttt caatccgaag ggccagtact acagcatgtt gcacaaatat   120
gtcaacagaa aagagaagac tcacagtatc aggtctactg aaggagatac ggtgattcct   180
gttcttggct ttgtagattc atctggtata aacagcactc ctgagttatg accttttga   239
```

<210> SEQ ID NO 832
<211> LENGTH: 292
<212> TYPE: DNA
<213> ORGANISM: Homo sapiens

<400> SEQUENCE: 832
catcttagtg cctttatctg tctttatgtc ttggggttgg ggtaggtaga taccaaatga     60
aacactttca ggaccttcct tcctcttgca gttgttcttt aatctccttt actagaggag    120
ataaatattt tgcatataat gaagaaattt ttctagtata taacgcaggc cttttatttt    180
ctaaaatgat gatagtataa aaatgttagg ataacagaat gattttagat tttccagaga    240
atattataaa gtgctttagg tatgaaaata aatcatcttt gtctgattaa aa            292

<210> SEQ ID NO 833
<211> LENGTH: 207
<212> TYPE: DNA
<213> ORGANISM: Homo sapiens

<400> SEQUENCE: 833
atatttccgg tcatctctgg tggtgagagg ctggtgttct gttttgagga tatcccttta     60
aatctcccaa atgactgtct ctatcttcat gagtgtgact tgaggtgttg ggatgggtga    120
gggagcttct ctaaagagga aagtgagtgg attaacccct gcttctcttc ttgttccctg    180
ttatcattcc tccccaacat aataata                                        207

<210> SEQ ID NO 834
<211> LENGTH: 183
<212> TYPE: DNA
<213> ORGANISM: Homo sapiens

<400> SEQUENCE: 834
aaaatctgat tttgcagcga tcacttttaa accctgtagt gatgtaagac taaaatataa     60
ttgctaagat tttgttggtt aatgtaaaga tatgactttt ctgcactgta ctctcttcat    120
aggattgtaa aggtgttcta atccaattgc atgatgtagt aagcctctta aatatgtgtg    180
tta                                                                  183

<210> SEQ ID NO 835
<211> LENGTH: 151
<212> TYPE: DNA
<213> ORGANISM: Homo sapiens

<400> SEQUENCE: 835
gtcttttgcg aaagggattg caggttcaga aggcatctta ccatggctgg ggaattgtct     60
ggtggtgggg ggcaggggac agaggccatg aaggagcaag ttttgtattt gtgacctcag    120
ctttgggaat aaaggatctt ttgaaggcca a                                   151

<210> SEQ ID NO 836
<211> LENGTH: 233
<212> TYPE: DNA
<213> ORGANISM: Homo sapiens

<400> SEQUENCE: 836
ttggcttcct tcctggcaag gaccaggcag tggggaagga ggaggtcctc cgtggtacat     60
actgggtcag gcactagcat ggaggagggt cacagagtgg ggcacgtgag gacccatgga    120
accgtcctgg tgcccaggcc ctcacaagta ccaaagccag caccaaagga gtcagggaag    180
gggttggctg agtcaaggga ccccagaggg caccaggaat aaaatcttct tga            233

<210> SEQ ID NO 837
<211> LENGTH: 211
<212> TYPE: DNA
<213> ORGANISM: Homo sapiens

<400> SEQUENCE: 837

| | | | | | |
|---|---|---|---|---|---|
| aaatcggggt | ccaggaaatc | ctcaccagaa | tctggcactg | cagccaaagg cgatacttcc | 60 |
| agagttctag | taggctgcta | tggaatttct | ggcatgaaaa | ttcttgaccc ctcacacttt | 120 |
| acccccctgta | cagcacaggc | ataccatgga | gatattacag | gatcagttcc agaccaccat | 180 |
| aataaagtgg | atatcgcaat | aaagtgagtc | a | | 211 |

<210> SEQ ID NO 838
<211> LENGTH: 270
<212> TYPE: DNA
<213> ORGANISM: Homo sapiens

<400> SEQUENCE: 838

| | | | | | |
|---|---|---|---|---|---|
| ctttaaaggt | gggtttttgc | tgtgataaat | gaatacggta | ctctgaagga gaaaaaagtt | 60 |
| tctcaaatga | gcttaaactg | caagtgattt | aaaaattaga | gaatataatt cttaaagcta | 120 |
| ttgaaagttt | caaccagaaa | acctcaagtg | aattttgtat | gtaaatgaaa tcttgaatgt | 180 |
| aagttctgtg | attctttaag | caaacaatta | gctgaaaact | tggtattgtt gtagtttatg | 240 |
| tagtaagtga | cttggcaccc | atcagaaaat | | | 270 |

<210> SEQ ID NO 839
<211> LENGTH: 253
<212> TYPE: DNA
<213> ORGANISM: Homo sapiens

<400> SEQUENCE: 839

| | | | | | |
|---|---|---|---|---|---|
| gctttgtaaa | gtgcatgtgg | aattaatggg | acagtgtgcc | ctttgtgtta gatgttagag | 60 |
| caaaagaaag | ggcttatagt | gttagtattg | gagcactttg | aagatagata ttttcagaaa | 120 |
| agatgtagga | tttaaaagtt | aaattttaaa | ttttagaaaa | agatatgatg gcaattggaa | 180 |
| atagtcacaa | tgaagttctt | catccagtag | gtgtttaaca | gtgttatttt gccactggta | 240 |
| atgtgtaaac | tgt | | | | 253 |

<210> SEQ ID NO 840
<211> LENGTH: 194
<212> TYPE: DNA
<213> ORGANISM: Homo sapiens

<400> SEQUENCE: 840

| | | | | | |
|---|---|---|---|---|---|
| ctaggcctgg | catggcacct | gtcgcccagt | gccctggggc | tgatctcagg gaagcccagc | 60 |
| tccagggcca | gatgagcaga | agctctcgat | ggacaatgaa | cggccttgct gggggccgcc | 120 |
| ctgtaccctc | tttcaccttt | ccctaaagac | cctaaatctg | aggaatcaac agggcagcag | 180 |
| atctgtatat | tttt | | | | 194 |

<210> SEQ ID NO 841
<211> LENGTH: 217
<212> TYPE: DNA
<213> ORGANISM: Homo sapiens

<400> SEQUENCE: 841

| | | | | | |
|---|---|---|---|---|---|
| aaactggtgg | tggaatgcgt | catgaaaggc | gtcacttcca | cgagagttta tgagagagca | 60 |

```
taagccaagg gacgttgacc tggactgaag ttcgcattga actctacaac attctgtggg    120
atatattgtt caaaagata ttgttgtttt ccctgattta gcaagcaagt aattttctcc    180
caagctgatt ttattcaata tggttacgtt ggttaaa                              217

<210> SEQ ID NO 842
<211> LENGTH: 180
<212> TYPE: DNA
<213> ORGANISM: Homo sapiens

<400> SEQUENCE: 842
tcctgacttc taataacatt gatgtcaaga aaatgacggt cacagaccag gtgaactgcc     60
ccaagctctc gtaaccaggt tctacaggga ggctgcaccc actccatgtt acttctgctt   120
cgctttcccc tacccaccc cccccccata aagacaaacc aatcaaccac gacaaaggaa    180

<210> SEQ ID NO 843
<211> LENGTH: 262
<212> TYPE: DNA
<213> ORGANISM: Homo sapiens

<400> SEQUENCE: 843
gtattttcct tacatgtaca gtagacgttc tctattctat cagccttcta tggtacctttt  60 ttgtcaggac aattaggatt gtaatgctaa tgcaaaggca gcaattcaaa gatcttctag   120
tgcctcatga ataagttga gatttaaaat ttgtaacatt gatggaacag ctgggaggtt    180
agaccaatca ttaaggaatg tatgccatag ctttctttgc taccataaac attttggagg   240
tgcatctgct atgtgacatg gt                                             262

<210> SEQ ID NO 844
<211> LENGTH: 274
<212> TYPE: DNA
<213> ORGANISM: Homo sapiens

<400> SEQUENCE: 844
ttccttttct tcgtggccaa tgccataatc cacctcttct gcttcagttg aggtgacacg     60
tctcagcctt agccctgtgc ccctgaaac agctgccacc atcactcgca agagaatccc    120
ctccatcttt ggaggggtt gatgccagac atcaccaggt tgtagaagtt gacaggcagt    180
gccatggggg caacagccaa ataggggg aatgatgta ggggccaagc agtgcccagc      240
tgggggtcaa taaagttacc cttgtacttg caaa                                274

<210> SEQ ID NO 845
<211> LENGTH: 289
<212> TYPE: DNA
<213> ORGANISM: Homo sapiens

<400> SEQUENCE: 845
ttcatgtggc tgtagatccc aagatgactg gggtgggagg tcttgctaga atgggaaggg    60
tcatagaaag ggccttgaca tcagttcctt tgtgtgtact cactgaagcc tgcgttggtc   120
cagagcggag gctgtgtgcc tggggagtt ttcctctata catctctccc caaccctagg    180
ttccctgttc ttcctccagc tgcaccagag caacctctca ctcccatgc cacgttccac     240 agttgccacc acctctgtgg cattgaaatg agcacctcca ttaaagtct                289

<210> SEQ ID NO 846
<211> LENGTH: 255
<212> TYPE: DNA
<213> ORGANISM: Homo sapiens
```

<400> SEQUENCE: 846

```
aaccagccgt attttacatg aagctgtata attaattgtc attattttttg ttagcaaaga        60 ttaaatgtgt cattggaagc catccctttt tttacatttc atacaacaga aaccagaaaa       120
gcaatactgt ttccatttta aggatatgat taatattatt aatataataa tgatgatgat       180
gatgatgaaa actaaggatt tttcaagaga tctttctttc caaaacattt ctggacagta       240
cctgattgta ttttt                                                        255
```

<210> SEQ ID NO 847
<211> LENGTH: 166
<212> TYPE: DNA
<213> ORGANISM: Homo sapiens

<400> SEQUENCE: 847

```
attcctgtca ttacccattg taacagagcc acaaactaat actatgcaat gttttaccaa        60
taatgcaata caaagacct caaaatacct gtgcatttct gtaggaaaa caacaaaagg        120 taattatgtg taattatact agaagttttg taatctgtat cttatc                     166
```

<210> SEQ ID NO 848
<211> LENGTH: 198
<212> TYPE: DNA
<213> ORGANISM: Homo sapiens

<400> SEQUENCE: 848

```
gcactggcga ggagagggcg ctcctctctg cacacctact agtcaccaga gactttaggg        60
ggtgggattc cactcgtgtg tttctatttt ttgaaaagca gacattttaa aaaatggtca       120
cgtttggtgc ttctcagatt tctgaggaaa ttgctttgta ttgtatatta caatgatcac       180
cgactgaaaa tattgttt                                                    198
```

<210> SEQ ID NO 849
<211> LENGTH: 187
<212> TYPE: DNA
<213> ORGANISM: Homo sapiens

<400> SEQUENCE: 849

```
atccggagaa ttgcctctac ctggaccttt tgtctcacac agcagtaccc tgacctgctg        60
tgcaccttac attcctagag agcagaaata aaaagcatga ctatttccac catcaaatgc       120
tgtagaatgc ttggcactcc ctaaccaaat gctgtctcca taatgccact ggtgttaaga       180
tatattt                                                                187
```

<210> SEQ ID NO 850
<211> LENGTH: 93
<212> TYPE: DNA
<213> ORGANISM: Homo sapiens

<400> SEQUENCE: 850

```
atatcttgtt ttctgccaat agatttttta aaatgtagtc agcaaaatgg gggtggggaa        60
gcagagcatg tcctagttca atgttgactt ttt                                    93
```

<210> SEQ ID NO 851
<211> LENGTH: 257
<212> TYPE: DNA
<213> ORGANISM: Homo sapiens

<400> SEQUENCE: 851

```
aaaagcttcc ccaactaaag cctagaagag cttctgaggc gctgctttgt caaaaggaag    60
tctctaggtt ctgagctctg gctttgcctt ggctttgcca gggctctgtg accaggaagg   120
aagtcagcat gcctctagag gcaaggaggg gaggaacact gcactcttaa gcttccgccg   180
tctcaacccc tcacaggagc ttactggcaa acatgaaaaa tcggcttacc attaaagttc   240
tcaatgcaac cataaaa                                                  257
```

<210> SEQ ID NO 852
<211> LENGTH: 197
<212> TYPE: DNA
<213> ORGANISM: Homo sapiens

<400> SEQUENCE: 852

```
ccacagcagg ccaggtccag agagaccgag gagggagagt ctcccaggga gcatgagagg    60
aggcagcagg actgtcccct tgaaggagaa tcatcaggac cctggacctg atacggctcc   120
ccagtacacc ccacctcttc cttgtaaata tgatttatac ctaactgaat aaaaagctgt   180
tctgtcttcc cacccaa                                                  197
```

<210> SEQ ID NO 853
<211> LENGTH: 151
<212> TYPE: DNA
<213> ORGANISM: Homo sapiens

<400> SEQUENCE: 853

```
ataaaaaacc aacaaaggat ctcacatttt cttaaaaagt gaagattgct gtatactatt    60
tattcaactt ataatttatg ttactccttg atctttgtct tttgtcatga caaagcattt   120
atttaataaa gttatgcatt cagttaaaaa a                                  151
```

<210> SEQ ID NO 854
<211> LENGTH: 273
<212> TYPE: DNA
<213> ORGANISM: Homo sapiens

<400> SEQUENCE: 854

```
tgtctgacct ccgtgcctag tcgtggctct ccatcttgtc tcctcccgt gtccccaatg     60 tcttcagtgg ggggccccct cttgggtccc ctcctctgcc atcacctgaa gaccccacg    120 ccaaacactg aatgtcacct gtgcctgccg ccttcggtcca ccttgcggcc cgtgtttgac  180
tcaactcaac tcctttaacg ctaatatttc cggcaaaatc ccatgcttgg gttttgtctt   240
taaccttgta acgcttgcaa tcccaataaa gca                                273
```

<210> SEQ ID NO 855
<211> LENGTH: 284
<212> TYPE: DNA
<213> ORGANISM: Homo sapiens

<400> SEQUENCE: 855

```
catctctttg atgtcatatg gaagagttaa aacaggtgga gaaattcctt gattcacaat    60
gaaatgctct cctttcccct gcccccagac cttttatcca cttacctaga ttctacatat   120
tctttaaatt tcatctcagg cctccctcaa ccccaccact tcttttataa ctagtccttt   180
actaatccaa cccatgatga gctcctcttc ctggcttctt actgaaaggt taccctgtaa   240
catgcaattt tgcatttgaa taaagcctgc ttttaagtg ttaa                     284
```

<210> SEQ ID NO 856
<211> LENGTH: 245

<212> TYPE: DNA
<213> ORGANISM: Homo sapiens

<400> SEQUENCE: 856

```
ggtgaaattc ttcaccaaca tttcatttgc tcctttgtca tattgtaatg ccaatataat        60
atagttaatg aaaacagcat ttttaaaaac cgaaatattg aaatggtgta atgttgtacc       120
atttgcactg tgagcaaatg ctaatacagt aaatatattg tgtttgctga caatcagccg       180
gcctataaat ctccttattt tatttcttgt ttttatagca taaagcttta gtttggcctg       240
aaaaa                                                                    245
```

<210> SEQ ID NO 857
<211> LENGTH: 268
<212> TYPE: DNA
<213> ORGANISM: Homo sapiens

<400> SEQUENCE: 857

```
attgccactc tgctccttgc tttgggagtc ttctgctttg ctggacatga gactggaagg        60
ctgtctgggg ctgccgacac acaagctctg ttgaggaatg accaggtcta tcagcccctc       120
cgagatcgag atgatgctca gtacagccac cttggaggaa actgggctcg gaacaagtga       180
acctgagact ggtggcttct agaagcagcc attaccaact gtaccttccc ttcttgctca       240
gccaataaat atatcctctt tcactcag                                          268
```

<210> SEQ ID NO 858
<211> LENGTH: 251
<212> TYPE: DNA
<213> ORGANISM: Homo sapiens

<400> SEQUENCE: 858

```
tgggccatga ttatcttaaa ggcattattc tccagcctta agatcttagg acgtttcctt        60
tgctatgatt tgtacttgct tgagtcccat gactgtttct cttcctctct ttcttccttt       120
tggaatagta atatccatcc tatgtttgtc ccactattgt attttggaag cacataactt       180
gtttggtttc acaggttcac agttaagaag gaattttgcc tctgaataaa tagaatcttg       240
agtctcatgc a                                                            251
```

<210> SEQ ID NO 859
<211> LENGTH: 32
<212> TYPE: DNA
<213> ORGANISM: Homo sapiens

<400> SEQUENCE: 859

```
ctcagcccaa cttcttaccc gaaagcatca ct                                      32
```

<210> SEQ ID NO 860
<211> LENGTH: 268
<212> TYPE: DNA
<213> ORGANISM: Homo sapiens

<400> SEQUENCE: 860

```
aatggacatc attttagcac actagcggtt tatattttaa ggaccttcat tctctgttct        60
gcacctcttc tggaaattga gtaaattttg ctttttttt tttactcagt tgcaacttac       120
gcttggcatc ttcagaatgc ttttctagca ttaagagatg taaatgataa aggaattatt       180
gtatgaaata ttacaaagcg tagactatgc attgttattc attataatat tttttgctgt       240
cataatcgcc tcataaagac aggtttca                                          268
```

<210> SEQ ID NO 861
<211> LENGTH: 259
<212> TYPE: DNA
<213> ORGANISM: Homo sapiens

<400> SEQUENCE: 861

```
cttggagata gctcttaaag atataaatgt ttatggctga aatgttatgg catcttggat    60
ttgctttaaa ataacccagc ttgctgcagg aggtgggtat tgtgtgtgtg ggaaggtggg   120
gaggctgcgg gaggaagaga tgacccaaga ttaggcagat gttgttaact gtggaagcag   180
ggtggtgagt gggggctcat gacattatgc tctctacttt gtgtacgtgt gaacatttcc   240
gtaataaaag atgccttca                                                259
```

<210> SEQ ID NO 862
<211> LENGTH: 166
<212> TYPE: DNA
<213> ORGANISM: Homo sapiens

<400> SEQUENCE: 862

```
gattttgcaa ttgtggtaaa tagcaaataa caatcttgta ttctaacata atctgcagtt    60
gtctgtatgt gttttaacta ttacagtgca tgttagggag aaatttcctg aatttcttta   120
gttttgtatt caaacaatta tgccactcga tgcaacaaac ataata                  166
```

<210> SEQ ID NO 863
<211> LENGTH: 158
<212> TYPE: DNA
<213> ORGANISM: Homo sapiens

<400> SEQUENCE: 863

```
aatctaacta actaactcat ttatttctat taaaaggta ttgtccttta ggcggggaat    60
gggaatcctt gctgcactgt tgcagtcatt ctgaaaggac ctttccctgt acttaccttt   120
caacatgctt caatcttatc aacgctacat tttgtatt                           158
```

<210> SEQ ID NO 864
<211> LENGTH: 88
<212> TYPE: DNA
<213> ORGANISM: Homo sapiens

<400> SEQUENCE: 864

```
tgtgtgtcac tatctccgtt tgctctcggt tcccttcaat aacaatgaat ggtgctttct    60
tctgaaagac tcagcctaat taaaggat                                       88
```

<210> SEQ ID NO 865
<211> LENGTH: 168
<212> TYPE: DNA
<213> ORGANISM: Homo sapiens

<400> SEQUENCE: 865

```
gcaatgttta gtatattcag ctgtatctgt agaaactctt tgacgaacct caatttaacc    60
aatttgatga atacccagtt ctcttctttt ctagagaaag atagttgcaa cctcacctcc   120
ctcactcaac actttgaata cttattgttt ggcaggtcat ccacacac                168
```

<210> SEQ ID NO 866
<211> LENGTH: 237
<212> TYPE: DNA
<213> ORGANISM: Homo sapiens

<400> SEQUENCE: 866

```
taagccacac agtgaatcct gtccttcaga gatggagagg tgataaaagt agaatgctca      60
ggtgtaattg gtttacggga attaaactgt tataaaaaca taaggtaaca ttcagaaatc     120
agagagcctc tgtttaaccc ttaaagacac aattaatgct tctaatactg taactactga     180
tctccctctt tctcctcagc tactctttcc ccaaacagta gcacctcctc tttactt        237
```

<210> SEQ ID NO 867
<211> LENGTH: 277
<212> TYPE: DNA
<213> ORGANISM: Homo sapiens

<400> SEQUENCE: 867

```
gagaaaaagc ctttagggac cctgaaccaa tgaatctgaa attccccaac tgccagatgt      60
atcttcattt tcatttttcc gggagatgta atatgtccta aaaatcacag tcgctagatt     120
gaaatcaacc ttaaaaatca tctagtccaa tgtctactcc cagtccacta cttgaatccc     180
ctgtgtcccc tcccagtagt cgtcttgaca acctccactg aaaggcaatt tctacactcc     240
atccacccca ccaccaaccc atggttcatg atctctt                              277
```

<210> SEQ ID NO 868
<211> LENGTH: 280
<212> TYPE: DNA
<213> ORGANISM: Homo sapiens
<220> FEATURE:
<221> NAME/KEY: modified_base
<222> LOCATION: (55)..(63)
<223> OTHER INFORMATION: a, c, t, g, unknown or other

<400> SEQUENCE: 868

```
gatcttcata agagcacctg gaggagggggg gtggggtgtt tgtgtttgtt taaannnnnn      60
nnngtgaaaa aaatgaagat aggcattttg tagacaatct ggaagttctg gaccggaatc     120
catgatgtag tcagggaaga aatgacccgt gtccagtaac cccaggcctc gagtgtgtgg     180
tgtatttttc tacataattg taatcattct atacatacaa attcatgtct tgaccatcat     240
attaatattt ggtaagtttc tctctcttta gagactccac                           280
```

<210> SEQ ID NO 869
<211> LENGTH: 89
<212> TYPE: DNA
<213> ORGANISM: Homo sapiens

<400> SEQUENCE: 869

```
ggttgctatg cgaaagcaag actgtggttt cattccaatt tcctgtatat cggaatcatc      60
accatctgtg tatgtgtgat tgaggtgtt                                        89
```

<210> SEQ ID NO 870
<211> LENGTH: 274
<212> TYPE: DNA
<213> ORGANISM: Homo sapiens

<400> SEQUENCE: 870

```
cccttactta catactagct tccaaggaca ggtggaggta gggccagcct ggcgggagtg      60
gagaagccca gtctgtccta tgtaagggac aaagccaggt ctaatggtac tgggtagggg     120
gcactgccaa gacaataagc taggctactg gtccagcta ctactttggt gggattcagg      180
tgagtctcca tgcacttcac atgttaccca gtgttcttgt tacttccaag gagaaccaag     240
aatggctctg tcacactcga agccaggttt gatc                                 274
```

<210> SEQ ID NO 871
<211> LENGTH: 135
<212> TYPE: DNA
<213> ORGANISM: Homo sapiens

<400> SEQUENCE: 871
tggtatttgc cgctgtgttt ttaaataact ttgtctatct gtcttgactt cttagctttg    60
gattttgaga actgacttcc cgccctggtt gaggattcag ctttcttact gtgccttcct   120
catgcacatg tgcct                                                    135

<210> SEQ ID NO 872
<211> LENGTH: 221
<212> TYPE: DNA
<213> ORGANISM: Homo sapiens

<400> SEQUENCE: 872
gtaagccttc tataaccaag acattataaa tccaaggtag gtggttggtt gttttgggtg    60
tataattcag aggttcaaaa tggaaatgac cttgctctaa tgaaactctg ttcccatcac   120
ataattgata ggcaatgttt ctcaccattt atatgatacg gactaaaaca aggaatggaa   180
ttgatattga acccttggca aaaataacat tcatccatag g                       221

<210> SEQ ID NO 873
<211> LENGTH: 245
<212> TYPE: DNA
<213> ORGANISM: Homo sapiens

<400> SEQUENCE: 873
gctggtacca agctaagtag ttcttattgt tggagctgta taaaacactc tggctggact    60
tgcagttgat ggtggccctc tcgcccagag acacagccag ggagtctgga gactgggtca   120
tcacgatgtc cccgtaggca ccagagatcc agagcaacag agaaatgaag acctgggtct   180
gcaacaccat cttgctgccc ctgcctgcct gttgtagctc agttcacaat gcaaacggcc   240
cgttt                                                               245

<210> SEQ ID NO 874
<211> LENGTH: 292
<212> TYPE: DNA
<213> ORGANISM: Homo sapiens

<400> SEQUENCE: 874 atttccatttt acctcagatg cagccccagt gagccgatgc acccctgcca tcgtgcctgc    60
ccatctgctc ccatcaagc ccatctggat ccatttcctc ttagccacac tacccctcact   120 acacccatgt ttacagttta agacttcttc ttacacaggt cttgccctcc atcctgttct   180
acctttcctc ctctcttgct ctctaccttg cgtcttccaa acatgaagcc ctcatcccag   240
cacccgacac cctgaccctc tccaaactct gggcatactc tctcccactg gg           292

<210> SEQ ID NO 875
<211> LENGTH: 292
<212> TYPE: DNA
<213> ORGANISM: Homo sapiens

<400> SEQUENCE: 875
tctggaagtg actatgcctg agtcccaggg tgcggcaggt aggaaacatt cacagatgaa    60
gacagcagat tccccacatt ctcatctttg gcctgttcaa tgaaaccatt gtttgcccat   120
ctcttcttag tggaacttta ggtctctttt caagtctcct cagtcatcaa tagttcctgg   180

```
ggaaaaacag agctggtaga cttgaagagg agcattgatg ttgggtggct tttgttcttt    240
cactgagaaa ttcggaatac atttgtctca cccctgatat tggttcctga tg           292
```

<210> SEQ ID NO 876
<211> LENGTH: 90
<212> TYPE: DNA
<213> ORGANISM: Homo sapiens

<400> SEQUENCE: 876

```
actgtaggaa caagcatgat cttgttactg tgatattta aatatccaca gtactcactt     60
tttccaaatg atcctagtaa ttgcctagaa                                     90
```

<210> SEQ ID NO 877
<211> LENGTH: 75
<212> TYPE: DNA
<213> ORGANISM: Homo sapiens

<400> SEQUENCE: 877

```
ctttatgaga attctcaggc tgaactatag gccattgttc ccaggcaaat caatacatca    60
atgcatcctc aaaaa                                                     75
```

<210> SEQ ID NO 878
<211> LENGTH: 208
<212> TYPE: DNA
<213> ORGANISM: Homo sapiens

<400> SEQUENCE: 878

```
tttccccatg tgctttagtg ggctttggtt ttcttttgt gcgagtgtgt gtgagaatgg     60
ctgtgtggtg agtgtgaact ttgttctgtg atcatagaaa gggtatttta ggctgcaggg   120
gagggcaggg ctggggaccg aagggggacaa gttccccttt catcctttgg tgctgagttt   180
tctgtaaccc ttggttgcca gagataaa                                      208
```

<210> SEQ ID NO 879
<211> LENGTH: 148
<212> TYPE: DNA
<213> ORGANISM: Homo sapiens

<400> SEQUENCE: 879

```
accagaattt atggatgaac tgattgctta tattttagtc agggtttata aatgtagatg     60
gtcaaattta cattgcctag tgatggaaaa ttcaactttt tttgattttt ttttccaata   120
ttaaaaaagg ctctgtatgc atggtggg                                      148
```

<210> SEQ ID NO 880
<211> LENGTH: 207
<212> TYPE: DNA
<213> ORGANISM: Homo sapiens
<220> FEATURE:
<221> NAME/KEY: modified_base
<222> LOCATION: (182)..(182)
<223> OTHER INFORMATION: a, c, t, g, unknown or other

<400> SEQUENCE: 880

```
ctgcaaaagc cgagatgggt tccatgcagt tctccagtgg gacatcagtg cttatccgaa     60
tgtcatcaat ggcaatctct ccggaacgtc ctttccctat cactccctcg aacacaatct   120
ggtactccat gtcgtagctg ggcaggatga tccgcccgtg cttccactcg ccgccctggt   180
cntcacggat gacccacagc aacttgc                                       207
```

<210> SEQ ID NO 881
<211> LENGTH: 233
<212> TYPE: DNA
<213> ORGANISM: Homo sapiens

<400> SEQUENCE: 881

| | | | | | |
|---|---|---|---|---|---|
| ggtggtttgg | cctctaattt | aattctgatt | cagactctcc | tgtcaggact | caagaaaatt | 60 |
| taattaatta | ccaaggatta | agtcttctgg | ttaaggtttc | tgggaaaaaa | aaatagcaaa | 120 |
| gatgttgatt | tcttggaatc | cttttacagg | ttcataacag | aaaaatcttc | attccctgta | 180 |
| ggcatttaat | taaacctagt | tgagaagtgt | gtgggattcc | tcaattatga | aca | 233 |

<210> SEQ ID NO 882
<211> LENGTH: 254
<212> TYPE: DNA
<213> ORGANISM: Homo sapiens

<400> SEQUENCE: 882

| | | | | | |
|---|---|---|---|---|---|
| gaagcaatgt | gccaaaggtc | atgattctta | tcacggatgg | gaaatcatca | gatgctttca | 60 |
| gagatcctgc | gataaaactg | aggaattcag | atgttgaaat | ctttgcagtt | ggtgtgaagg | 120 |
| atgccgttcg | ctcagaattg | gaagctattg | cctctcctcc | tgcagagacc | catgtgttca | 180 |
| cagtggaaga | ttttgatgct | tttcagagga | tatcttttga | actcacacag | tctatctgcc | 240 |
| ttagaattga | gcaa | | | | | 254 |

<210> SEQ ID NO 883
<211> LENGTH: 244
<212> TYPE: DNA
<213> ORGANISM: Homo sapiens

<400> SEQUENCE: 883

| | | | | | |
|---|---|---|---|---|---|
| aatgcccta | atgtgagggt | tgtaatggt | gcttattaag | accaaagact | tgttaaatgt | 60 |
| atacaccaag | tggtaatgaa | atttcgtgac | tggcccacac | gtgcatagag | gtctgggagg | 120 |
| accaggaaac | agcctcagtg | ccagaggat | caccagtgca | tccttcatca | cagcatgtgc | 180 |
| aatatgccaa | gattaccctc | ggtcattcct | gtcaacaagg | ggtcaatgtc | ataaatgtca | 240 |
| caat | | | | | | 244 |

<210> SEQ ID NO 884
<211> LENGTH: 291
<212> TYPE: DNA
<213> ORGANISM: Homo sapiens

<400> SEQUENCE: 884

| | | | | | |
|---|---|---|---|---|---|
| gaagcatagc | acctttcagt | atctaaaata | taaacaagaa | tagtaagtcc | atcccagctt | 60 |
| ctagagatga | ggtagctcat | gctaagaaat | gttgggtcat | ttttcctatg | aaagttcaaa | 120 |
| ggccaaatgg | tctaattcca | atcatcacat | ttgattagag | tcagctccac | aactcagttt | 180 |
| ctagatcttt | ttcttcatta | taggcttcag | gatgatgaga | ttgtacatgt | ggaagagtct | 240 |
| caatttagag | tccttggaca | tatgtttgta | aagttctata | tgtcacctcg | t | 291 |

<210> SEQ ID NO 885
<211> LENGTH: 191
<212> TYPE: DNA
<213> ORGANISM: Homo sapiens

<400> SEQUENCE: 885

| | | | | | |
|---|---|---|---|---|---|
| caaacagagt | gaactttctg | ccaagatgcg | ggagtggttt | tcagagacat | ttcagaaagt | 60 |

| | |
|---|---|
| gaaggagaaa ctcaagattg actcatgagg acctgaaggg tgacatccca ggagggcct | 120 |
| ctgaaatttc ccacacccca gcgcctgtgc tgaggactcc ctccatgtgg ccccaggtgc | 180 |
| caccaataaa a | 191 |

<210> SEQ ID NO 886
<211> LENGTH: 238
<212> TYPE: DNA
<213> ORGANISM: Homo sapiens
<220> FEATURE:
<221> NAME/KEY: modified_base
<222> LOCATION: (194)..(206)
<223> OTHER INFORMATION: a, c, t, g, unknown or other

<400> SEQUENCE: 886

| | |
|---|---|
| aagatggcta gaatggtgcc tttctgagtg tctaaaactt gacaccctg gtaaatcttt | 60 |
| caacacactt ccactgcctg cgtaatgaag ttttgattca ttttaacca ctggaatttt | 120 |
| tcaatgccgt cattttcagt tagatgattt tgcactttga gattaaaatg ccatgtctat | 180 |
| ttgattagtc ttannnnnnn nnnnnnacag gcttatcatt ctcactgttg gctgtcat | 238 |

<210> SEQ ID NO 887
<211> LENGTH: 188
<212> TYPE: DNA
<213> ORGANISM: Homo sapiens

<400> SEQUENCE: 887

| | |
|---|---|
| gcacaccaga ttcagggaga ctgaccacca agggatagtg taaaaggaca ttttctcagt | 60 |
| tgggtccatc agcagttttt cttcctgcat ttattgttga aaactattgt ttcatttctt | 120 |
| cttttatagg ccttattact gcttaatcca aatgtgtacc attggtgaga cacatacaat | 180 |
| gctctgaa | 188 |

<210> SEQ ID NO 888
<211> LENGTH: 191
<212> TYPE: DNA
<213> ORGANISM: Homo sapiens
<220> FEATURE:
<221> NAME/KEY: modified_base
<222> LOCATION: (38)..(51)
<223> OTHER INFORMATION: a, c, t, g, unknown or other

<400> SEQUENCE: 888

| | |
|---|---|
| gaggtgtcaa acagcagagt gtactttcca aagaacannn nnnnnnnnnn nacacagcaa | 60 |
| atcccaagcc ttcccagtct cacacctttc cacccattca taaaaaaaca cacgaatttc | 120 |
| tcgcaagttc caatatcact gtctctttat catctaaata gggccagttg gacacctcat | 180 |
| tgaaacaaaa a | 191 |

<210> SEQ ID NO 889
<211> LENGTH: 288
<212> TYPE: DNA
<213> ORGANISM: Homo sapiens
<220> FEATURE:
<221> NAME/KEY: modified_base
<222> LOCATION: (114)..(145)
<223> OTHER INFORMATION: a, c, t, g, unknown or other
<220> FEATURE:
<221> NAME/KEY: modified_base
<222> LOCATION: (219)..(232)
<223> OTHER INFORMATION: a, c, t, g, unknown or other

<400> SEQUENCE: 889

```
tatatttcca tgtctgctgt aatgtatcca agtcttgtaa agaccaataa tttattaatt      60
ttaataagac agaaagtatt tctccttcta gtctcatcgt ctgatttgaa aggnnnnnnn     120
nnnnnnnnnn nnnnnnnnnn nnnngtgag ttccaggaag aaatgttttt ctttttttcat     180 ataaaatggt agctgtatgt atgtaactct gaattaaann nnnnnnnnnn nncagtcact     240
ctggttctaa atccttattg ggcaagctgg agttttgaag tgacccaa                  288
```

<210> SEQ ID NO 890
<211> LENGTH: 189
<212> TYPE: DNA
<213> ORGANISM: Homo sapiens

<400> SEQUENCE: 890

```
accacacaag cagtgactcc taaagaagtt cagaggaagg agagaaccca tggggagggg      60
gtgcagtggg ggtgggtcag ggtgggctcc ctggaggga aattggtcta ggcaaggatg     120
cagactggcc agtaaggtgg gtccatgcag gaagctgagg gaggtggaag gcccgtgggt    180
ctcgagcgc                                                             189
```

<210> SEQ ID NO 891
<211> LENGTH: 269
<212> TYPE: DNA
<213> ORGANISM: Homo sapiens

<400> SEQUENCE: 891

```
ttccttcttg gcctaactct tccagttagg atctagaact ttgcctttt tttttttttt      60 tttttttga gatgggttct cactatattg tccaggctag agtgcagtgg ctattcacag    120
atgcgaacat agtacactgc agcctccaac tcctagcctc aagtgatcct cctgtctcaa   180
cctcccaagt aggattacaa gcatgcgccg acgatgccca gaatccagaa ctttgtctat   240
cactctcccc aacaacctag atgtgaaaa                                      269
```

<210> SEQ ID NO 892
<211> LENGTH: 183
<212> TYPE: DNA
<213> ORGANISM: Homo sapiens

<400> SEQUENCE: 892

```
gagagttcaa ctaagaaagg tcacatatgt gaaagcccaa ggacactgtt tgatatacag     60
caggtattca atcagtgtta tttgaaacca aatctgaatt tgaagtttga atcttctgag   120
ttggaatgaa ttttttttcta gctgagggaa actgtatttt ctttccccca aagaggaatg  180
taa                                                                   183
```

<210> SEQ ID NO 893
<211> LENGTH: 187
<212> TYPE: DNA
<213> ORGANISM: Homo sapiens

<400> SEQUENCE: 893

```
ccttcatgct gccttcaaag ctagatcatg tttgccttgc ttagagaatt actgcaaatc     60
agccccagtg cttggcgatg catttacaga tttctaggcc ctcagggttt tgtagagtgt   120
gagccctggt gggcagggtt gggggtctg tcttctgctg gatgctgctt gtaatccatt    180
tggtgta                                                               187
```

<210> SEQ ID NO 894
<211> LENGTH: 183

<212> TYPE: DNA
<213> ORGANISM: Homo sapiens

<400> SEQUENCE: 894

```
ttctgtgtct gaagtgtaag tgaacacaga agagtgacat gtttacaaac ctcaagccag     60
ccttgctcct ggctggggcc tgttgaagat gcttgtattt tacttttcca ttgtaattgc    120
tatcgccatc acagctgaac ttgttgagat ccccgtgtta ctgcctatca gcattttact    180
act                                                                  183
```

<210> SEQ ID NO 895
<211> LENGTH: 272
<212> TYPE: DNA
<213> ORGANISM: Homo sapiens

<400> SEQUENCE: 895

```
tcctcacccc ggtatgaatg tgtttcctcc acattgtata tccttccacc ctctggctgc     60
ctagatcagt aaataaaatt gatgtaatat aatttataag taacactgtt gaaaccctga    120
tcccagtgga ggctgtaacc cacctgcccc cgcaccaccc ccctgacccc tgttaccgca    180
tttgtgtgta ttaatgctga agaattaaat gtttaaagag tttaaatttt gaaggcgttt    240
gctatataca gttgtcctgc attattataa ag                                  272
```

<210> SEQ ID NO 896
<211> LENGTH: 224
<212> TYPE: DNA
<213> ORGANISM: Homo sapiens

<400> SEQUENCE: 896

```
aggccattct gagccacact gaaaaggaaa atgggaattt ataacccagt gagttcagcc     60
tttaagatac cttgatgaag acctggacta ttgaatggag cagaaattca cctctctcac    120
tgactattac agttgcattt ttatggagtt cttcttctcc taggattcct aagactgctg    180
ctgaatttat aaaaattaag tttgtgaatg tgactactta gtgg                     224
```

<210> SEQ ID NO 897
<211> LENGTH: 191
<212> TYPE: DNA
<213> ORGANISM: Homo sapiens

<400> SEQUENCE: 897

```
caaacagagt gaactttctg ccaagatgcg ggagtggttt tcagagacat ttcagaaagt     60
gaaggagaaa ctcaagattg actcatgagg acctgaaggg tgacatccca ggaggggcct    120
ctgaaatttc ccacacccca gcgcctgtgc tgaggactcc ctccatgtgg ccccaggtgc    180
caccaataaa a                                                         191
```

<210> SEQ ID NO 898
<211> LENGTH: 217
<212> TYPE: DNA
<213> ORGANISM: Homo sapiens

<400> SEQUENCE: 898

```
aggttagatt ctcattcacg ggactagtta gctttaagca ccctagagga ctagggtaat     60
ctgacttctc acttcctaag ttcccttcta tatcctcaag gtagaaatgt ctatgttttc    120
tactccaatt cataaatcta ttcataagtc tttggtacaa gtttacatga taaaagaaa     180
tgtgatttgt cttcccttct ttgcactttt gaaataa                             217
```

<210> SEQ ID NO 899
<211> LENGTH: 174
<212> TYPE: DNA
<213> ORGANISM: Homo sapiens

<400> SEQUENCE: 899
tccccagagt tcttgcaccc tcattccctc gggaccctcc cagtgagaag ggcctgctct    60
gcttttcctg tctgtatata acttatttgc cctaagaact ttgagaatcc caattattta   120
ttttaatgta ttttttagac cctctattta cctgcgaact tgtgtttata ataa         174

<210> SEQ ID NO 900
<211> LENGTH: 269
<212> TYPE: DNA
<213> ORGANISM: Homo sapiens

<400> SEQUENCE: 900
ttccttcttg gcctaactct tccagttagg atctagaact ttgccttttt tttttttttt    60
ttttttttga gatgggttct cactatattg tccaggctag agtgcagtgg ctattcacag   120
atgcgaacat agtacactgc agcctccaac tcctagcctc aagtgatcct cctgtctcaa   180
cctcccaagt aggattacaa gcatgcgccg acgatgccca gaatccagaa ctttgtctat   240
cactctcccc aacaacctag atgtgaaaa                                    269

<210> SEQ ID NO 901
<211> LENGTH: 231
<212> TYPE: DNA
<213> ORGANISM: Homo sapiens

<400> SEQUENCE: 901
aaaacttggc acttttttcgt gtggatcttg ccacatttct gatcagaggt gtacactaac    60
atttcccccg agctcttggc cttttgcattt atttatacag tgccttgctc ggggcccacc   120
accccctcaa gccccagcag ccctcaacag gcccagggag ggaagtgtga gcgccttggt   180
atgacttaaa attggaaatg tcatctaacc attaagtcat gtgtgaacac a             231

<210> SEQ ID NO 902
<211> LENGTH: 186
<212> TYPE: DNA
<213> ORGANISM: Homo sapiens

<400> SEQUENCE: 902
taggtggtag atattgaggc caagaatatt gcaaaataca tgaagcttca tgcacttaaa    60
gaagtatttt tagaataaga atttgcatac ttacctagtg aaacttttct agaattattt   120
ttcactctaa gtcatgtatg tttctctttg attatttgca tgttatgttt aataagctac   180
tagcaa                                                             186

<210> SEQ ID NO 903
<211> LENGTH: 159
<212> TYPE: DNA
<213> ORGANISM: Homo sapiens

<400> SEQUENCE: 903
caccctcaga tgcacatgag ctggcgggat tgaaggatgc tgtcttcgta ctgggaaagg    60
gattttcagc cctcagaatc gctccacctt gcagctctcc ccttctctgt attcctagaa   120
actgacacat gctgaacatc acagcttatt tcctcattt                         159

<210> SEQ ID NO 904
<211> LENGTH: 295
<212> TYPE: DNA
<213> ORGANISM: Homo sapiens

<400> SEQUENCE: 904
aggatccatc ctattgtcaa tgagatgttc tcatccagaa gccatagaat cctgaataat    60
aattctaaaa gaaacttcta gagatcatct ggcaatcgct tttaaagact cggctcaccg   120
tgagaaagag tcactcacat ccattcttcc cttgatggtc cctattcctc cttcccttgc   180
ttcttggact tcttgaaatc aatcaagact gcaaacccct tcataaagtc ttgccttgct   240
gaactccctc tctgcaggca gcctgccttt aaaaatagtt gctgtcatcc acttt         295

<210> SEQ ID NO 905
<211> LENGTH: 175
<212> TYPE: DNA
<213> ORGANISM: Homo sapiens

<400> SEQUENCE: 905
ccccacgtga cagtgcctgg gaatgtatta ttctgcagca tgacctgtga ccagcactgt    60
ctcagtttca cttttcacata gatgtcccctt tcttggccag ttatcccttc cttttagcct   120
agttcatcca atcctcactg ggtggggtga ggaccactcc tgtacactga atatt         175

<210> SEQ ID NO 906
<211> LENGTH: 228
<212> TYPE: DNA
<213> ORGANISM: Homo sapiens

<400> SEQUENCE: 906
gttgtggggt caaccgtaca atggtgtggg agtgacgatg atgtgaatat ttagaatgta    60
ccatattttt tgtaaattat ttatgttttt ctaaacaaat ttatcgtata ggttgatgaa   120
acgtcatgtg ttttgccaaa gactgtaaat atttatttat gtgttcacat ggtcaaaatt   180
tcaccactga aaccctgcac ttagctagaa cctcatttttt aaagatta                228

<210> SEQ ID NO 907
<211> LENGTH: 293
<212> TYPE: DNA
<213> ORGANISM: Homo sapiens

<400> SEQUENCE: 907
agaggtcttt aatcattggt tcggctgctt ttatgtagtt taggctggaa atggtttcac    60
ttgctctttg actgtcagca agactgaaga tggcttttcc tggacagcta gaaaacacaa   120
aatcttgtag gtcattgcac ctatctcagc cataggtgca gtttgcttct acatgatgct   180
aaaggctgcg aatgggatcc tgatggaact aaggactcca atgtcgaact cttctttgct   240
gcattccttt tcttcactt acaagaaagg cctgaatgga ggacttttct gta            293

<210> SEQ ID NO 908
<211> LENGTH: 137
<212> TYPE: DNA
<213> ORGANISM: Homo sapiens

<400> SEQUENCE: 908
gtcagacaga tgtggttgca tcctaactcc atgtctctga gcattagatt tctcatttgc    60
caataataat acctccctta gaagtttgtt gtgaggatta ataatgtaa ataaagaact    120 agcataacac tcaaaaa                                                   137

<210> SEQ ID NO 909
<211> LENGTH: 267
<212> TYPE: DNA
<213> ORGANISM: Homo sapiens

<400> SEQUENCE: 909
gccttctggc tgacaatcct ggaaatctgt tctccagaat ccaggccaaa aagttcacag        60
tcaaatgggg aggggtattc ttcatgcagg agacccagg ccctggaggc tgcaacatac       120
ctcaatcctg tcccaggccg atcctcctg aagcccttttt cgcagcactg ctatcctcca     180
aagccattgt aaatgtgtgt acagtgtgta taaaccttct tcttcttttt ttttttttaa      240
actgaggatt gtcattaaac acagttg                                            267

<210> SEQ ID NO 910
<211> LENGTH: 254
<212> TYPE: DNA
<213> ORGANISM: Homo sapiens

<400> SEQUENCE: 910
aattcagtgg tgtgagtata ttcataagat ttatacttgg tgtctattca taagacttat        60
atccagcata ttcataacta gagccatatc acagatgcat tcatcataat aattccagac       120 atttttcatca ccctaaaagg aaaccctgaa acccattagc agtcattccc cattcctcca       180
acccattctc tccctaatcc ctagaaacca ccaatctgct gtgtatttca tctattgcca       240
acatttcata taaa                                                           254

<210> SEQ ID NO 911
<211> LENGTH: 162
<212> TYPE: DNA
<213> ORGANISM: Homo sapiens

<400> SEQUENCE: 911
tacgttatgt atttgacaag tggtggtgaa acaaaatcaa aacagatttg atttgtgttt        60
ttgaaatgtc agtacatttt gtgccactaa cactgtgatg tataaaagag ctgtttgaat       120
gccttttaat gttgtgtttt gtactctgga atcatatgga aa                          162

<210> SEQ ID NO 912
<211> LENGTH: 254
<212> TYPE: DNA
<213> ORGANISM: Homo sapiens

<400> SEQUENCE: 912
aaagattaaa ttgctattgc tgtagtaaga gaagctcttt gtatctgaac atagttgtat        60
ttgaaatttg tggttttttta atttatttaa aattgggggg agggcatggg aaggattaa       120 caccgatata ttgttaccgc tgaaaatgaa ctttatgaac cttttccaag ttgatctatc       180
cagtgacgtg gcctggtggg cgtttcttct tgtacttatg tggttttttg gcttttaata      240
cagacatttt cctc                                                           254

<210> SEQ ID NO 913
<211> LENGTH: 83
<212> TYPE: DNA
<213> ORGANISM: Homo sapiens

<400> SEQUENCE: 913
tctgctgaac atgagcttca gttgctactc ggagcattga gagggaggcc taagaataat        60
aacaatccag tgcttaagag tca                                                83

```
<210> SEQ ID NO 914
<211> LENGTH: 296
<212> TYPE: DNA
<213> ORGANISM: Homo sapiens

<400> SEQUENCE: 914
gccacaagag aagagctcta gtcctggact ctaccctcct ctgaaagaag ctggggcttg    60
ctctgacggt ctccactccc gtctgcaggc agccaggagg gcaggaagcc cttgctctgt   120
gctgccatcc tgcctccctc ctccagcctc agggcactcg ggcctgggtg ggagtcaacg   180
ccttcccctc tggactcaaa taaaacccag tgacctcact tctttctct gcaaaaggtg    240
cttgtggggc tgggagtgca gacattggtg tttctgctga tgtcccttgt gaaaaa       296

<210> SEQ ID NO 915
<211> LENGTH: 244
<212> TYPE: DNA
<213> ORGANISM: Homo sapiens

<400> SEQUENCE: 915
atttacctat atagcaagcc tacacatgtg cccctgaacc taaaaaaaaa gttaaaagaa    60
aaacgtttgg attattttcc ctctttcgaa caaagacatt ggtttgccca aggactacaa   120
ataaaccaac gggaaaaaag aaaggttcca gttttgtctg aaaattctga ttaagcctct   180
gggccctaca gcctggagaa cctggagaat cctacaccca cagaacccgg ctttgtcccc   240
aaag                                                                244

<210> SEQ ID NO 916
<211> LENGTH: 253
<212> TYPE: DNA
<213> ORGANISM: Homo sapiens

<400> SEQUENCE: 916
gaaacaagat tagtcctgag ttaacaatgg ctgcaagctg gatacatgga attcagcaca    60
cttttctccc tcttactgat tatgcttttg aaattttctc ttgtaaaaca tttagaaaac   120
aaaaacaaaa aaaatgtgat tgtttctgt cttcaaaatc tcattagaat ttttcactg     180
gaggaagatt ttcccttgct tctgcataaa attttaactc cataacttat aagctcactc   240
tttattgtta ctt                                                      253

<210> SEQ ID NO 917
<211> LENGTH: 74
<212> TYPE: DNA
<213> ORGANISM: Homo sapiens

<400> SEQUENCE: 917
aaaaatttaa ctcccatatg tgttcctctt gttcctaatc ttgtcaaccc agtgcaagtg    60
accgacaaaa ttcc                                                     74

<210> SEQ ID NO 918
<211> LENGTH: 294
<212> TYPE: DNA
<213> ORGANISM: Homo sapiens

<400> SEQUENCE: 918
actccacagt ttccattgtg aatggcttct ttggtgcaga gttccaaaaa ttatgtagcc    60
cagctcttta attttgtaac atctaatgat atcaccgcct tgaagtgatt aaagtagatt   120
```

| | |
|---|---:|
| gcttaaagaa ttaaagcttt aaagatgaaa gatgttattg cttttgctgg acatgaggaa | 180 |
| cagttgtaaa gtttccaggt ctacaataac tttctggaac cctctcagtg aactgtttct | 240 |
| tgtaaaagtt ttccctaaga taaaagctca atcccattgt ttccacactc aaaa | 294 |

<210> SEQ ID NO 919
<211> LENGTH: 153
<212> TYPE: DNA
<213> ORGANISM: Homo sapiens

<400> SEQUENCE: 919

| | |
|---|---:|
| gggcatgtgg gctgttgtga gtgaagccac ttcagacgtt tgcgtgcagg tttggtgggg | 60 |
| acgtgcagtt tcatttcttt tgagagtggg attgctggag cctatgttaa gggtacgttc | 120 |
| aactcatcag ctcaactgtc ttccaaatgg cag | 153 |

<210> SEQ ID NO 920
<211> LENGTH: 266
<212> TYPE: DNA
<213> ORGANISM: Homo sapiens

<400> SEQUENCE: 920

| | |
|---|---:|
| ttatcaactg tgcacaagga aaaaataga tatgtgaaag gttcacgtaa atttcctcac | 60 |
| atcacagaag attaaaattc agaaggaga aaacacagac caaagagaag tatctaagac | 120 |
| caaagggatg tgttttatta atgtctagga tgaagaaatg catagaacat tgtagtactt | 180 |
| gtaaataact agaaataaca tgatttagtc ataattgtga aaaataataa taattttct | 240 |
| tggatttatg ttctgtatct gtgaaa | 266 |

<210> SEQ ID NO 921
<211> LENGTH: 202
<212> TYPE: DNA
<213> ORGANISM: Homo sapiens

<400> SEQUENCE: 921

| | |
|---|---:|
| gtggaggata ttgcaactgg agttcagaca ctgtactcga agtggaagga ctttcatttt | 60 |
| gagaagatac catttgatcc agcagaaatg tccaaatgat atcaggtcct caatcttcag | 120 |
| ctacagggaa tgagtaactt tgagtggaga agaaacaaac atagtgggta taatcatgga | 180 |
| tcgcttgtac ccctgtgaaa at | 202 |

<210> SEQ ID NO 922
<211> LENGTH: 208
<212> TYPE: DNA
<213> ORGANISM: Homo sapiens
<220> FEATURE:
<221> NAME/KEY: modified_base
<222> LOCATION: (124)..(124)
<223> OTHER INFORMATION: a, c, t, g, unknown or other

<400> SEQUENCE: 922

| | |
|---|---:|
| gaatatgtgg cagagctcct ggaaatgatg cagattaggt ggcattttg tcagctctgt | 60 |
| ggtttattgt tgggactatt ctttaaaata tccattgttc actacagtga agatctctga | 120 |
| tttnaccgtg tactatccac atgcattaca aacatttcgc agagctgctt agtatataag | 180 |
| cgtacaatgt atgtaataac catctcat | 208 |

<210> SEQ ID NO 923
<211> LENGTH: 150
<212> TYPE: DNA
<213> ORGANISM: Homo sapiens

```
<400> SEQUENCE: 923
gctgataaat agcattaggg ttctttgcaa tgtggtatct agctgtatta ttggttttat      60
ttactttaaa cattttgaaa agcttatact ggcagcctag aaaaacaaac aattaatgta     120
tctttatgtc cctggcacat gaataaactt                                      150

<210> SEQ ID NO 924
<211> LENGTH: 97
<212> TYPE: DNA
<213> ORGANISM: Homo sapiens

<400> SEQUENCE: 924
caaattcaag tcactagact tcagagttca acacctggac atgagaagat attatattat      60
gtaccataaa tatttcctgt atctgactgc ctgaaca                               97

<210> SEQ ID NO 925
<211> LENGTH: 237
<212> TYPE: DNA
<213> ORGANISM: Homo sapiens

<400> SEQUENCE: 925
agcaagactt gctgcctaaa ggagcccacc attttacttt tcacatttaa tctgccacgt      60
tgaatcaatt ggaataaaac ctgactcgca ggtgactgga caggaaatcc caaagttcca     120
ccatttctat gcttaatttt aacgtccccc cgcttttttt tttgtagaaa ataaaaacaa     180
gaaaatcgtt ccaatgtaag atgtttgtta tagaaacttt aggcaataca ggtgtgt       237

<210> SEQ ID NO 926
<211> LENGTH: 292
<212> TYPE: DNA
<213> ORGANISM: Homo sapiens
<220> FEATURE:
<221> NAME/KEY: modified_base
<222> LOCATION: (54)..(55)
<223> OTHER INFORMATION: a, c, t, g, unknown or other

<400> SEQUENCE: 926
ttgcaagtca attaggtgtc ttgtgaacaa ggaaatacta atctctaagc tgcnnggatc      60
tttttgtgtg aatatttaat ggtgctccat gactgttgag ttttaaaaac ctcgttaaat     120
tttgccaaat cagttgcccc caaaagggaa tatgcttttc cttattttt tttctaaaat     180 gctatttatc tctaaggaaa aaaaaaaag actattactc atttaacatt gtttaagcag     240
gttgagctag ctgtgaaaat agcttttgtg agccttctaa ttcctaaacg tc             292

<210> SEQ ID NO 927
<211> LENGTH: 243
<212> TYPE: DNA
<213> ORGANISM: Homo sapiens

<400> SEQUENCE: 927
gttaacactg tggatcacct tcggccaagg gacacgactg gagattaaac gtaagtaatt      60
tttcactatt gtcttctgaa atttgggtct gatggccagt attgactttt agaggcttaa     120
ataggagttt ggtaaagatt ggtaaatgag ggcatttaag atttgccatg ggttgcaaaa     180
gttaaactca gcttcaaaaa tggatttgga gaaaaaaaga ttaaattgct ctaaactgaa     240
tga                                                                  243

<210> SEQ ID NO 928
```

```
<211> LENGTH: 120
<212> TYPE: DNA
<213> ORGANISM: Homo sapiens

<400> SEQUENCE: 928
tcattctcat ccatccagga tgtactaaaa cagtgtgttt aataaattgt aattattttg      60
tgtacagttc tatactgtta tctgtgtcca tttccaaaac ttgcacgtgt ccctgaattc     120

<210> SEQ ID NO 929
<211> LENGTH: 185
<212> TYPE: DNA
<213> ORGANISM: Homo sapiens

<400> SEQUENCE: 929
aaggtttggc agaaattgtt ttttgagtgg ctcaccagag tacccagaag aatcagtatg      60
gaattagagg acagtggcct accctaaata aagcatgag tgatgtataa agtctagtgt     120
caatttattc agaaaatatc aaaattattc tgggagctat gggtcaaagt tgataggcac     180
aaaca                                                                 185

<210> SEQ ID NO 930
<211> LENGTH: 130
<212> TYPE: DNA
<213> ORGANISM: Homo sapiens

<400> SEQUENCE: 930
atcccaatag atatccccct atgtgcatgc acacctgcac actcacggct gaaatctccc      60
taacccaggg ggaccttagc atgcctaagt gactaaacca ataaaaatgt tctggtctgg     120
cctgaaaaaa                                                            130

<210> SEQ ID NO 931
<211> LENGTH: 86
<212> TYPE: DNA
<213> ORGANISM: Homo sapiens

<400> SEQUENCE: 931
aagcagacta cgagaaacac aaagtctacg cctgcgaagt cacccatcag ggcctgagct      60
cgcccgtcac aaagagcttc aacagg                                          86

<210> SEQ ID NO 932
<211> LENGTH: 264
<212> TYPE: DNA
<213> ORGANISM: Homo sapiens

<400> SEQUENCE: 932
ggtacacaaa tctggttctc aatggtgagg tgggatcaga gatattctcc ctgttgttca      60
gaggaacaat aattcggatg tttctctcca caatgtcctc attaggatct tcggaagaac     120
ggatgatcct ggaagtaatc cgggcacact tacatttgtt gtcaacaaga acaatccttt     180
catcttcttg ggctttcaca tgaacagcct taataaaaac cgccaggact ccccagaaaa     240
gcaaatggtt cttcatcttg accc                                            264

<210> SEQ ID NO 933
<211> LENGTH: 101
<212> TYPE: DNA
<213> ORGANISM: Homo sapiens

<400> SEQUENCE: 933 ttgatagggga tagcattgaa ctatttgctc aactcaacat tttaggaatt tatttctgct      60
```

```
gtctagtgct caaaacttgc agctagaatt gagggaagag a                101
```

<210> SEQ ID NO 934
<211> LENGTH: 233
<212> TYPE: DNA
<213> ORGANISM: Homo sapiens

<400> SEQUENCE: 934

```
tgcttatccg ttagccgtgg tgatttagca ggaagctgtg agagcagttt ggtttctagc    60
atgaagacag agccccaccc tcagatgcac atgagctggc gggattgaaa gatgctgtct   120
tcgtactggg aaagggattt tcagccctca gaatcgctcc accttgcagc tctcccttc    180
tctgtattcc tagaaactga cacatgctga acatcacagc ttatttcctc att          233
```

<210> SEQ ID NO 935
<211> LENGTH: 256
<212> TYPE: DNA
<213> ORGANISM: Homo sapiens

<400> SEQUENCE: 935

```
ctgaggtgct atgttcttag tggatgttct gaccctgctt caaatatttc cctcacctt     60
cccatcttcc aagggtataa ggaatctttc tgctttgggg tttatcagaa ttctcagaat   120
ctcaaataac taaaggtat gcaatcaaat ctgcttttta aagaatgctc tttacttcat    180
ggacttccac tgccatcctc ccaaggggcc caaattcttt cagtggctac ctacatacaa   240
ttccaaacac atacag                                                   256
```

<210> SEQ ID NO 936
<211> LENGTH: 259
<212> TYPE: DNA
<213> ORGANISM: Homo sapiens

<400> SEQUENCE: 936

```
acagaagcca ttgcctccct tgtttacctt gggtccacct ccaccaaaac ccaacagacc    60
accaaatgtt gacctgacga aattccacaa aacctcttct ggaaacagta ctagcaaagg   120
ccagacgtct tactcaacaa cttccctgcc accacctcca ccatcccatc cggccagcca   180
accaccattg ccagcatctc acccatcaca accaccagtc ccaagcctac ctcccagaaa   240
cattaaacct ccgtttgac                                                259
```

<210> SEQ ID NO 937
<211> LENGTH: 114
<212> TYPE: DNA
<213> ORGANISM: Homo sapiens

<400> SEQUENCE: 937

```
ggacctgtac accacgagca gccagctgac cctgccggcc acacagtgcc tagccggcaa    60
gtccgtgaca tgccacgtga agcactacac gaatcccagc caggatgtga ctgt          114
```

<210> SEQ ID NO 938
<211> LENGTH: 265
<212> TYPE: DNA
<213> ORGANISM: Homo sapiens

<400> SEQUENCE: 938

```
ggatttctcc aaaactaact gaatttaagc ttcaggtccc tttgtatgca gtagaaagga    60
attattaaaa acaccaccaa agaaaataaa tatatcctac ttgaaattta ctctatggac   120
```

```
ttacccactg ctagaataaa tgtatcaaat cttatttgta aattctcaat tttgatatat    180
atatgtatat atgcatatac atatccacac ttgtctgcaa gaatattgat taaaattgct    240
aaatttgtac ttgttcacca gaaaa                                          265

<210> SEQ ID NO 939
<211> LENGTH: 198
<212> TYPE: DNA
<213> ORGANISM: Homo sapiens

<400> SEQUENCE: 939
gcacagctca gcacaacatt ccaagctcaa aatagaagcc ttctcagtga gctccagcac     60
gcccagagga ctgttaataa cgatgatcca tgtgttttac tctaaagtgc taaatatggg    120
agtttccttt ttttactctt tgtcactgat gacacaacag aaaagaaact gtagaccttg    180
ggacaatcaa catttaaa                                                  198

<210> SEQ ID NO 940
<211> LENGTH: 162
<212> TYPE: DNA
<213> ORGANISM: Homo sapiens

<400> SEQUENCE: 940
atgttcatac tctaagtatc aaaatcttcc aattatcatg ctcacctgaa agaggtatgc     60
tctcttagga atacagtttc tagcattaaa caaataaaca aggggagaaa ataaaactca    120
aggagtgaaa atcaggaggt gtaataaaat gttcctcgca tt                       162

<210> SEQ ID NO 941
<211> LENGTH: 256
<212> TYPE: DNA
<213> ORGANISM: Homo sapiens

<400> SEQUENCE: 941
tcctgtttac ccttcaagtt tcaagttcat gtcactgtct cagagaggtt ttcctgtgct     60
cgccctgttt ctctcaggaa gccttgctct tttccatcat gcctctaatc acagcttata    120
atcggatatt tatttctgtg tctacagtct tgccctgcca gactgtatgc cccatgtggg    180
caggcgctca tgattgtttc tgattgtttc acgcatgctg ctaacccaga gcctgggccc    240
aaagctagtt agtact                                                    256

<210> SEQ ID NO 942
<211> LENGTH: 294
<212> TYPE: DNA
<213> ORGANISM: Homo sapiens

<400> SEQUENCE: 942
caaagggtga gagggcttcc ttctcaccct tctctccata agtatcttga agatccatgg     60
tttgttttgc tctattgttt agttttttact tgggtgcaat gtgtacgtca aaagttttta    120
ttttgatatt tgaaagagac caaatcaggc ccagaccgcc tctctggaag gtgttgtagg    180
ccattcaaaa cgcctccgga gtgtcgcaaa ccaagtgcgg aggggccctg aggttgtact    240
gtaaacatca tagtgacttg tcttttcaaa tatattccca ctattttcgc agaa          294

<210> SEQ ID NO 943
<211> LENGTH: 221
<212> TYPE: DNA
<213> ORGANISM: Homo sapiens

<400> SEQUENCE: 943
```

```
tgctggactc cgacggctcc ttcttcctct acagcaagct caccgtggac aagagcaggt    60
ggcagcaggg gaacatcttc tcatgctccg tgatgcatga ggctctgcac aaccgcttca   120
cgcagaagag cctctccctg tctccgggta aatgagtgcg acggccggca agcccccgct   180
ccccgggctc tcgggtcgc gcgaggatgc ttggcacgta c                       221
```

<210> SEQ ID NO 944
<211> LENGTH: 239
<212> TYPE: DNA
<213> ORGANISM: Homo sapiens

<400> SEQUENCE: 944

```
ggagaggcag cattgcacag tgaaagaatt ctggatatct caggagcccc gaaattctag    60
ctctgacttt gctgtttcca gtggtatgac cttggagaag tcacttatcc tcttggagcc   120
tcagtttcct catctgcaga ataatgactg acttgtctaa ttcgtaggga tgtgaggttc   180
tgctgaggaa atgggtatga atgtgccttg aacacaaagc tctgtcaata agtgataca   239
```

<210> SEQ ID NO 945
<211> LENGTH: 181
<212> TYPE: DNA
<213> ORGANISM: Homo sapiens

<400> SEQUENCE: 945

```
gaggaccgag cacagaaatc ttagagattt cttgtcccct ctcaggtcat gtgtagatgc    60
gataaatcaa gtgattggtg tgcctgggtc tcactacaag cagcctatct gcttaagaga   120
ctctggagtt tcttatgtgc cctggtggac acttgcccac catcctgtga gtaaaagtga   180
a                                                                   181
```

<210> SEQ ID NO 946
<211> LENGTH: 228
<212> TYPE: DNA
<213> ORGANISM: Homo sapiens

<400> SEQUENCE: 946

```
gggatgacat gcactcagct cttggctcca ctgggatggg aggagaggac aagggaaatg    60
tcaggggcgg ggagggtgac agtggccgcc caaggcccac gagcttgttc tttgttcttt   120
gtcacaggga ctgaaaacct ctcctcatgt tctgctttcg attcgttaag agagcaacat   180
tttacccaca cacagataaa gttttcccctt gaggaaacaa cagctttta              228
```

<210> SEQ ID NO 947
<211> LENGTH: 136
<212> TYPE: DNA
<213> ORGANISM: Homo sapiens

<400> SEQUENCE: 947

```
caggacccat cacgcctgtg cagtggcccc cacagaaaga ctgagctcaa ggtgggaacc    60
acgtctgcta acttggagcc ccagtgccaa gcacagtgcc tgcatgtatt tatccaataa   120
atgtgaaatt ctgtcc                                                   136
```

<210> SEQ ID NO 948
<211> LENGTH: 193
<212> TYPE: DNA
<213> ORGANISM: Homo sapiens

<400> SEQUENCE: 948

```
gcagtctact agattgtgat cccttgagat atggaaggat gccttttttt ctctgcattt      60
aaaaaaatcc cccagcactt cccacagtgc ctattgatac ttggggaggg tgcttggcac     120
ttattgaata tatgatcggc catcaaggga agaactattg tgctcagaga cactgttgat     180
aaaaactcag gca                                                         193

<210> SEQ ID NO 949
<211> LENGTH: 175
<212> TYPE: DNA
<213> ORGANISM: Homo sapiens

<400> SEQUENCE: 949
aaatttaatt ttctacgcct ctggggatat ctgctcagcc aatggaaaat ctgggttcaa      60 ccagccctg ccatttctta agactttctg ctgcactcac aggatcctga gctgcactta     120
cctgtgagag tcttcaaact tttaaacctt gccagtcagg acttttgcta ttgca          175

<210> SEQ ID NO 950
<211> LENGTH: 183
<212> TYPE: DNA
<213> ORGANISM: Homo sapiens

<400> SEQUENCE: 950
taaatattga gcagatctat aggaagattg aacctgaata ttgccattat gcttgacatg      60
gtttccaaaa aatggtactc cacatacttc agtgagggta agtattttcc tgttgtcaag     120
aatagcattg taaaagcatt ttgtaataat aaagaatagc tttaatgata tgcttgtaac     180
taa                                                                    183

<210> SEQ ID NO 951
<211> LENGTH: 235
<212> TYPE: DNA
<213> ORGANISM: Homo sapiens

<400> SEQUENCE: 951 taacttttc tcaaagtcac tgatgtttgt tcctgttaaa tgtatagcat tgtaatgaga       60
gcccatcaaa tcctgagtgt cagtttgttg tccctattgt agatgaaata gtgatgtagc     120
aaaaacctag taaattctga atgcttttcc acgtagactt atctggaatg tgaacacaac     180
tctttggtta atagtaaatg cttaactgta gtcctgagta ggtgcatttc tgtct          235

<210> SEQ ID NO 952
<211> LENGTH: 154
<212> TYPE: DNA
<213> ORGANISM: Homo sapiens

<400> SEQUENCE: 952
agtatatttt ctatcttctg gtgacttgag cttgagctct gacaggcatg ggcctctccg      60
accttcatca ctattcttag gataatgctg gcgggcagag atgatcaatc atcatattaa     120
atcataatga gcttataatc ctcccactgg aaaa                                 154

<210> SEQ ID NO 953
<211> LENGTH: 280
<212> TYPE: DNA
<213> ORGANISM: Homo sapiens

<400> SEQUENCE: 953
atcagaaagg gcaacttact cttcctggca tcttattgta ttggagggtg accaccctgg      60
gcatggggtg ttggcagggg tcaaaaagct tatttctttt aatctcttac tcaacgaaca     120
```

```
catcttctga tgatttccca aaattaatga gaatgagatg agtagagtaa gatttgggtg    180
ggatgggtag gatgaagtat attgcccaac tctatgtttc tttgattcta acacaattaa    240
ttaagtgaca tgattttac taatgtatta ctgagactag                           280
```

<210> SEQ ID NO 954
<211> LENGTH: 206
<212> TYPE: DNA
<213> ORGANISM: Homo sapiens

<400> SEQUENCE: 954

```
tattcttcta taacactcta tatagagcta tgtgagtact aatcacattg aataatagtt    60
ataaaattat tgtatagaca tctgcttctt aaacagattg tgagttcttt gagaaacagc    120
gtggatttta cttatctgtg tattcacaga gcttagcaca gtgcctggta atgagcaagc    180
atacttgcca ttacttttcc ttccca                                          206
```

<210> SEQ ID NO 955
<211> LENGTH: 247
<212> TYPE: DNA
<213> ORGANISM: Homo sapiens

<400> SEQUENCE: 955

```
gctgaaattg tatctctcag taattttaga tgtcttttaa aaaattgaaa aacaaagtgt    60
tagactgtgt gcgtgtgcgt tgatgggcac tcaagagtcc cgtgagtcat ccagccctgc    120
ctttcccctg cgcccccatc ctctcacgtc ccgccctgcc tccacttggg gaccctgcct    180
cgtgtcgtct ttatctgcct attactcagc ctaaggaaac aagtacactc cacacatgca    240
taaagga                                                               247
```

<210> SEQ ID NO 956
<211> LENGTH: 190
<212> TYPE: DNA
<213> ORGANISM: Homo sapiens

<400> SEQUENCE: 956

```
gtggagaacc acagctgcag agtaggcagc tgcctccagg atgagttact tgaaatttgc    60
cttgagtgtg ttacctcctt tccaagctcc tcgtgataat gcagacttcc tggagtacaa    120
acacaggatt tgtaattcct tactgtaacg gagtttagag ccagggctga tgctttggtg    180
tggccagcac                                                            190
```

<210> SEQ ID NO 957
<211> LENGTH: 165
<212> TYPE: DNA
<213> ORGANISM: Homo sapiens

<400> SEQUENCE: 957

```
cccattgaaa agaccgagcc ttgtatgtat gttatggata cataaaatgc acgcaagcca    60
ttatctctcc atgggaagct aagttataaa aataggtgct tggtgtacaa aacttttat    120 atcaaaaggc tttgccattt ctatatgagt gggtttactg gtaaa                   165
```

<210> SEQ ID NO 958
<211> LENGTH: 260
<212> TYPE: DNA
<213> ORGANISM: Homo sapiens

<400> SEQUENCE: 958

```
gaacagagag aaagtgctcc gtaaaagtga gctgcgatgc ggaggtgggc aagctcttcc      60 ctggagggg aagagctctc aacccagagg gatctgacca ggaaggttca cccccctcc      120 acccaggaag cccctgcaga cagtatgtgt tttaggcttt gctggccaaa tggtctctgc     180
cgtgactact cagctctgcc attgtggctg cagagtgacc atagaccttc tgaaagtgaa     240
tgagtatgac tgtgttccaa                                                 260

<210> SEQ ID NO 959
<211> LENGTH: 197
<212> TYPE: DNA
<213> ORGANISM: Homo sapiens

<400> SEQUENCE: 959
aaatggtaaa catgagggtg ctcttgtgac ttaatttttg ttcaagggac taaattgctt      60
atgtttattc cctgtcagcg gagtggagaa tgtcattcat caataaacca aagccaatag    120
ctggagaatt gagatctggt tgaaagtggt ttatggttta catgctgtac tatcctgagg    180
aattgcgaga tattgct                                                    197

<210> SEQ ID NO 960
<211> LENGTH: 187
<212> TYPE: DNA
<213> ORGANISM: Homo sapiens

<400> SEQUENCE: 960
aaaacatctg gttcaattac gctgaactct gactacatgt gggccagtaa taatatgaat      60
tggacttaag aataaaacctt gtgtttaatc tcttttttc cttaaaattt taatgtgagt    120
tttctgttac gcaaattatc catgttagca catttggaac aaatgtataa atgtactttc    180
tgaataa                                                               187

<210> SEQ ID NO 961
<211> LENGTH: 228
<212> TYPE: DNA
<213> ORGANISM: Homo sapiens

<400> SEQUENCE: 961
gggatgacat gcactcagct cttggctcca ctgggatggg aggagaggac aagggaaatg      60 tcagggggcgg ggagggtgac agtggccgcc caaggcccac gagcttgttc tttgttcttt    120
gtcacaggga ctgaaaacct ctcctcatgt tctgctttcg attcgttaag agagcaacat    180
tttacccaca cacagataaa gttttcccctt gaggaaacaa cagcttta                228

<210> SEQ ID NO 962
<211> LENGTH: 213
<212> TYPE: DNA
<213> ORGANISM: Homo sapiens

<400> SEQUENCE: 962
actctccgga ttgaccaagt tcatcctggg ctccattggg tctgccattg cggctgtcat      60
tgcgaggttc tactagctcc ctgcccctcg ccctgcagag aagagaacca tgccagggga    120
gaaggcaccc agccatcctg acccagcgag gagccaacta tcccaaatat acctggggtg    180
aaatatacca aattctgcat ctccagagga aaa                                  213

<210> SEQ ID NO 963
<211> LENGTH: 104
<212> TYPE: DNA
<213> ORGANISM: Homo sapiens
```

<400> SEQUENCE: 963
gttggtgtgc tgaggtgtta gagagggacc atgtgtcact tgtgctttgc tcttgtccca     60
cgtgtcttcc actttgcata tgagccgtga actgtgcata gtgc                     104

<210> SEQ ID NO 964
<211> LENGTH: 132
<212> TYPE: DNA
<213> ORGANISM: Homo sapiens

<400> SEQUENCE: 964
acattgattc cccatcgctg aaggacagaa ttcattgtgt ggcatttgta tttgatgcca     60
gctctattca atacttctcc tctcagatga tagtaaagat caaaagaatt cgaagggagt    120
tggtaaacgc tg                                                        132

<210> SEQ ID NO 965
<211> LENGTH: 281
<212> TYPE: DNA
<213> ORGANISM: Homo sapiens

<400> SEQUENCE: 965
gttattaaca gtcctctggg cgtgctggag ctcactgaga aggcttctat tttgagcttg     60
gaatgttgtg ctgagctgtg cagcctgttc ctgcatctgt tgttcctgca ttttctgttg    120
ctctgccagc caattttgtt tggctatctc catttaactc acttgttcct gatggagtct    180
ctccctctcc tgcatcattt gctcgttctg cctttgaatc gccgccaacc tttgcgcttc    240
agccttttca gcttctgctt tcacttgtgc ctctgaggag a                        281

<210> SEQ ID NO 966
<211> LENGTH: 239
<212> TYPE: DNA
<213> ORGANISM: Homo sapiens

<400> SEQUENCE: 966
gggagggtaa cctcactctt ctccaggcca ggcctccttg gactcccctg ggggtgtccc     60
actcttcttc cctctaaact gccccacctc ctaacctaat cccccgccc cgctgccttt    120 cccaggctcc cctcacccca gcgggtaatg agcccttaat cgctgcctct aggggagctg    180
attgtagcag cctcgttagt gtcacccccct cctccctgat ctgtcagggc cacttagtg    239

<210> SEQ ID NO 967
<211> LENGTH: 174
<212> TYPE: DNA
<213> ORGANISM: Homo sapiens

<400> SEQUENCE: 967
ggtcctgtag ccctaagtgg tactaacttt ccttcattca acccacctgc gtctcatact     60
cacctcaccc cactgtggct gatttggaat tttgtgcccc catgtaagca ccccttcatt    120
tggcattccc cacttgagaa ttaccctttt gccccgaaca tgttttttctt ctcc         174

<210> SEQ ID NO 968
<211> LENGTH: 270
<212> TYPE: DNA
<213> ORGANISM: Homo sapiens

<400> SEQUENCE: 968
aaataaccac tttttgttgg gcaatatgaa attttttaaag gagtagaata ccaaatgata    60

```
gaaacagact gcctgaattg agaattttga tttcttaaag tgtgtttctt tctaaattgc    120
tgttccttaa tttgattaat ttaattcatg tattatgatt aaatctgagg cagatgagct    180
tacaagtatt gaaataatta ctaattaatc acaaatgtga agttatgcat gatgtaaaaa    240
atacaaacat tctaattaaa ggctttgcaa                                    270
```

<210> SEQ ID NO 969
<211> LENGTH: 276
<212> TYPE: DNA
<213> ORGANISM: Homo sapiens

<400> SEQUENCE: 969

```
gagtaagctc tagtccctct gtcctgtaga aagagccctg aagaatcagc aattttgttg    60
ctttattgtg gcatctgttc gaggtttgct tcctctttaa gtctgtttct tcattagcaa    120
tcatatcagt tttaatgcta ctactaacaa tgaacagtaa caataatatc cccctcaatt    180
aatagagtgc tttctatgtg caaggcactt ttcacgtgtc acctatttta acctttccaa    240
ccacataaat aaaaaaggcc attattagtt gaatct                             276
```

<210> SEQ ID NO 970
<211> LENGTH: 264
<212> TYPE: DNA
<213> ORGANISM: Homo sapiens

<400> SEQUENCE: 970

```
taacttttttc tcaaagtcac tgatgttttgt tcctgttaaa tgtatagcat tgtaatgaga    60
gcccatcaaa tcctgagtgt cagtttgttg tccctattgt agatgaaaata gtgatgtagc    120 aaaaacctag taaattctga atgcttttcc acgtagactt atctggaatg tgaacacaac    180
tctttggtta atagtaaatg cttaactgta gtcctgagta ggtgcatttc tgtctgtctc    240
aataaatttt actttgtctg caaa                                          264
```

<210> SEQ ID NO 971
<211> LENGTH: 275
<212> TYPE: DNA
<213> ORGANISM: Homo sapiens

<400> SEQUENCE: 971

```
tattccatct acttttctat cgccgtcccc ttttgcagcc ctctctgggg atggactggg    60
taaatgttga cagaggccct gccccgttca cagatcctgg ccctgagcca gccctgtgct    120
cctccctccc ccaacactcc ctaccaaccc cctaatcccc tactccctcc accccccctc    180
cactgtaggc cactggatgg tcatttgcat ctccgtaaat gtgctctgct cctcagctga    240
gagagaaaaa aataaactgt atttggctgc aagaa                              275
```

<210> SEQ ID NO 972
<211> LENGTH: 210
<212> TYPE: DNA
<213> ORGANISM: Homo sapiens

<400> SEQUENCE: 972

```
agaggctctt ctgcgtgtag tggttgtgca gagcctcatg catcacggag catgagaaga    60
cgttcccctg ctgccacctg ctcttgtcca cggtgagctt gctatagagg aagaaggagc    120
cgtcggagtc cagcacggga ggcgtggtct tgtagttgtt ctccggctgc ccattgctct    180
cccactccac ggcgatgtcg ctgggataga                                    210
```

```
<210> SEQ ID NO 973
<211> LENGTH: 235
<212> TYPE: DNA
<213> ORGANISM: Homo sapiens

<400> SEQUENCE: 973
gagtgtctca gaagtgtgct cctctggcct cagttctcct cttttggaac aacataaaac      60
aaatttaatt ttctacgcct ctggggatat ctgctcagcc aatggaaaat ctgggttcaa     120
ccagcccctg ccatttctta agactttctg ctccactcac aggatcctga gctgcactta     180
cctgtgagag tcttcaaact tttaaacctt gccagtcagg acttttgcta ttgca          235

<210> SEQ ID NO 974
<211> LENGTH: 162
<212> TYPE: DNA
<213> ORGANISM: Homo sapiens

<400> SEQUENCE: 974
ggacataaca gacttggaag cagatgatac agacttcttt ttttcataat caggttagtg      60
taagaaattg ccatttgaaa caatccattt tgtaactgaa ccttatgaaa tatatgtatt     120
tcatggtacg tattctctag cacagtctga gcaattaaat ag                         162

<210> SEQ ID NO 975
<211> LENGTH: 249
<212> TYPE: DNA
<213> ORGANISM: Homo sapiens

<400> SEQUENCE: 975
aggccctctt gagagtctat ccagggaccc attgttttac tttaacagac cagaaaagat      60
gtttgttttc catgtcatta cccccagggg ataccgaatg tgtgggtaga aatttctctg     120
tagattaaaa atcagatttt tacatggatt caacaaagga gcgtcacttg gatttttgtt     180
ttcatccatg aatgtagctg cttctgtgta aaatgccatt ttgctattaa aaatcaattc     240
acgctggaa                                                              249
```

MOLECULAR DIAGNOSTIC TEST FOR CANCER

CROSS REFERENCE TO RELATED PATENT APPLICATIONS

This application is a national phase of International Application No. PCT/GB2013/053202, filed on Dec. 3, 2013, and claims the benefit of U.S. Provisional Application No. 61/732,761 entitled "Molecular Diagnostic Test for Cancer" filed on Dec. 3, 2012, which are both incorporated herein in their entirety by reference.

SEQUENCE LISTING

The instant application contains a Sequence Listing which has been submitted electronically in ASCII format and is hereby incorporated by reference in its entirety. Said ASCII copy, created on Sep. 9, 2015, is named 12970.0008 SL.txt and is 348,753 bytes in size.

FIELD OF THE INVENTION

The present invention relates to a molecular diagnostic test useful for diagnosing cancers from different anatomical sites that includes the use of a common subtype related to angiogenesis. The invention includes the derivation of a gene classification model from gene expression levels. One application is the stratification of response to and selection of patients for cancer therapeutic drug classes and thus guide patient treatment selection. Another application is the stratification of cancer patients into those that respond and those that do not respond to anti-angiogenic therapeutics. The present invention provides a test that can guide therapy selection as well as selecting patient groups for enrichment strategies during clinical trial evaluation of novel therapeutics. The invention can be used as a prognostic indicator for certain cancers including ovarian cancer, breast cancer, colon, prostate, lung and glioblastoma. The angiogenesis subtype can be identified from fresh/frozen (FF) or formalin fixed paraffin embedded FFPE patient samples.

BACKGROUND

The pharmaceutical industry continuously pursues new drug treatment options that are more effective, more specific or have fewer adverse side effects than currently administered drugs. Drug therapy alternatives are constantly being developed because genetic variability within the human population results in substantial differences in the effectiveness of many established drugs. Therefore, although a wide variety of drug therapy options are currently available, more therapies are always needed in the event that a patient fails to respond.

Traditionally, the treatment paradigm used by physicians has been to prescribe a first-line drug therapy that results in the highest success rate possible for treating a disease. Alternative drug therapies are then prescribed if the first is ineffective. This paradigm is clearly not the best treatment method for certain diseases. For example, in diseases such as cancer, the first treatment is often the most important and offers the best opportunity for successful therapy, so there exists a heightened need to choose an initial drug that will be the most effective against that particular patient's disease.

Ovarian cancer is the leading cause of death among all gynecological cancers in western countries. This high death rate is due to the diagnosis at an advanced stage in most patients. Epithelial ovarian cancer (EOC) constitutes 90% of ovarian malignancies and is classified into distinct histologic categories including serous, mucinous, endometrioid, clear cell, transitional, mixed, and undifferentiated subtypes. There is increasing evidence that these differed histologies arise from different aetiologies. There have been recent advances in the methodology used to classify epithelial ovarian cancer (McCluggage, W. G. "Morphological subtypes of ovarian carcinoma: a review with emphasis on new developments and pathogenesis," PATHOLOGY 2011 August; 43(5):420-32). One of the consequences of this is that many tumors that would previously been classified as endometrioid are now being classified as serous.

The current standard treatment for ovarian cancer is debulking surgery and standard platinum taxane based cytotoxic chemotherapy. However, not all patients respond to this, and of those that do, approximately 70% will experience a recurrence. Specific targeted therapies for ovarian cancer based on histological or molecular classification have not yet reached the marketplace. Similarly for other types of cancer, there is still no accurate way of selecting appropriate cytotoxic chemotherapeutic agents.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genetic information, thereby providing a genetic fingerprint of an individual. There is much enthusiasm that this technology will ultimately provide the necessary tools for custom-made drug treatment regimens.

Currently, healthcare professionals have few mechanisms to help them identify cancer patients who will benefit from chemotherapeutic agents. Identification of the optimal first-line drug has been difficult because methods are not available for accurately predicting which drug treatment would be the most effective for a particular cancer's physiology. This deficiency results in relatively poor single agent response rates and increased cancer morbidity and death. Furthermore, patients often needlessly undergo ineffective, toxic drug therapy.

Angiogenesis is a key component of neo-vascularisation of tumors and essential to tumorigenesis and metastatsis. As such, it is a key area for therapeutic intervention and has been correlated to poor prognosis and reduced survival. This has promoted the development of a number of agents that target angiogenesis related processes and pathways, including the market leader and first FDA-approved anti-angiogenic, bevacizumab (Avastin), produced by Genentech/Roche.

Treatment regimens that include bevacizumab have demonstrated broad clinical activity[1-10]. However, no overall survival (OS) benefit has been shown after the addition of bevacizumab to cytotoxic chemotherapy in most cancers[8, 12-13]. This suggests that a substantial proportion of tumours are either initially resistant or quickly develop resistance to VEGF blockade (the mechanism of action of bevacizumab). In fact, 21% of ovarian, 10% of renal and 33% of rectal cancer patients show partial regression when receiving bevacizumab monotherapy, suggesting that bevacizumab may be active in small subgroups of patients, but that such incremental benefits do not reach significance in unselected patients. As such, the use of a biomarker of response to bevacizumab would improve assessment of treatment outcomes and thus enable the identification of patient subgroups that would receive the most clinical benefit from bevacizumab treatment. This would be particularly relevant in the case of metastatic breast cancer, where the absence of a clinically beneficial biomarker has undermined the use of bevacizumab. Thus far, no such biomarker has been clinically validated to predict bevacizumab efficacy. Hypertension and VEGF polymorphisms are so far the only biomarkers to show potential, but important questions remain about their use in a clinical setting.

Another approach to anti-angiogenic therapy is simultaneous targeting of multiple angiogenic pathways rather than selective targeting of the VEGF pathway. Theoretically, multitargeted anti-angiogenic agents should more completely inhibit angiogenesis than agents such as bevacizumab and thus may produce greater therapeutic benefit. It has been postulated that in some tumors, angiogenesis may require VEGF only in the early stages of disease but is driven by additional angiogenic pathways as the disease progresses. Therefore, by targeting multiple pathways, it may be possible to counteract compensatory escape mechanisms that could lead to resistance to VEGF inhibition.

As for other types of cancer there is still no accurate way of selecting which patients will or will not respond to standard of care with an anti-angiogenic therapeutic or single agent anti-angiogenic therapy.

What is therefore needed is a molecular diagnostic test that would facilitate the stratification of patients based upon their predicted response to anti-angiogenic therapeutics, either in combination with standard of care or as a single-agent therapeutic. This would allow for the rapid identification of those patients who should receive alternative therapies. Such a molecular diagnostic test should be predictive of therapeutic responsiveness across different cancer types with sufficient accuracy.

SUMMARY OF THE INVENTION

Disclosed are methods of using a collection of biomarkers expressed in cancer such that when some or all of the transcripts are under-expressed, they identify a subtype of cancer that has an up-regulation or down-regulation in molecular signaling relating to angiogenesis. The collection of biomarkers may be defined by an expression signature, and the expression signature is used to assign a cumulative score to the measured expression values of the collection of biomarkers. The invention also provides methods for indicating responsiveness or non-responsiveness to anti-angiogenic agents as well as identifying patients with a good or poor prognosis, using the collection of biomarkers and expression signatures disclosed herein. In different aspects, the biomarkers and expression signatures may form the basis of a single parameter or multiparametric predictive test that could be delivered using methods known in the art such as microarray, Q-PCR, immunohistochemistry, ELISA or other technologies that can quantify mRNA or protein expression.

In one example embodiments, the present invention provides an expression signature defining a cancer subtype associated with up-regulation of angiogenesis related biomarkers ("angiogeneis"). In another example embodiment, the present invention provides an expression signature defining a cancer subtype association with down-regulation of angiogenesis related biomarkers ("non-angiogenesis"). In addition, the cancer subtypes described herein are common to many types of cancer and are not limited to a single cancer disease type. Accordingly, the expression signatures of the present invention are not limited to a single cancer type. In certain exemplary embodiments, the expression signature comprises two or more biomarkers selected from the biomarkers listed in Tables 1A-1C. In another exemplary embodiment, the angiogenesis expression signature comprises two or more biomarkers selected from the biomarkers listed in Tables 2A or 2B. In another exemplary embodiment, the non-angiogenesis expression signature comprises two or more biomarkers listed in Table 2C. In another exemplary embodiment, the angiogenesis expression signature comprises the biomarkers listed in Table 2A or 2B and their corresponding weights as determined using a PLS classifier. I another exemplary embodiment, the non-angiogenesis signature comprises the biomarkers listed in Table 2C and their corresponding weights as determined using a PLS classifier.

In one embodiment of the invention, the expression signatures are useful for evaluating a cancer tumor's responsiveness to anti-angiogenic therapeutics. The use of the invention to determine a tumor's responsiveness to anti-angiogeneic therapeutics is not limited to a single cancer type. In one example embodiment, the cancer may be ovarian cancer, breast cancer, colon cancer, colorectal cancer, lung cancer, prostate cancer, or glioblastoma. The present invention relates to prediction of response to drugs using at least or up to different 10 classifications of response, such as overall survival, progression free survival, radiological response, as defined by RECIST, complete response, partial response, stable disease and serological markers such as, but not limited to, PSA, CEA, CA125, CA15-3 and CA19-9. The invention described herein is not limited to any one drug; it can be used to identify responders and non responders to any of a range of drugs currently in use, under development and novel, that directly or indirectly affect or target angiogeneic processes. In one embodiment, the present invention may be used to evaluate adjuvant or neoadjuvant bevacizumab or dasatanib, either as single agents, or in combination with standard of care therapy. In another embodiment, the present invention may be used to evaluate Avastin, VEGF-TRAP, treatment in ovarian cancer.

In another embodiment of the invention, the expression signatures disclosed herein may be used to determine a patient's clinical prognosis. For example, patients identified as having a cancer subtype associated with down-regulation of angiogenesis related biomarkers may exhibit a longer survival rate than a cancer subtype related to up-regulation of angiogenesis related biomarkers. The use of the invention to determine an individual's clinical prognosis is not limited to a single cancer type. In one example embodiment, the cancer may be ovarian cancer, colon cancer, colorectal cancer, breast cancer, lung cancer, prostate cancer, or glioblastoma. The present invention relates to prediction of clinical prognosis using at least progression free survival. Additional prognostic factors that may be considered are ethnicity and race, age, stage of disease, histology, tumor grade, tumor makers (for example, CA125), site-specific surgical treatment, size of residual disease, and tumor response.

The predictive and prognostic uses of the expression signatures disclosed herein may be achieved using a single expression signature or multiple expression signatures. For example, one expression signature may be a non-angiogenesis signature and a second expression signature may be an angiogenesis signature. In one example embodiment, a non-angiogenesis expression signature is used to determine a patient's clinical prognosis and an angiogenesis signature is used to determine a patient's predicted responsiveness to a given class of therapeutic agent or treatment regimen. In one example embodiment, the angiogenesis signature comprises one or more biomarkers from Table 2A or Table 2B, and the non-angiogenesis signature comprises one or more biomarkers from Table 2C. In another example embodiment, the angiogenesis signature comprises the biomarkers in Table 2A or Table 2B, and the non-angiogenesis signature comprises the biomarkers in Table 2A.

In another aspect, the present invention relates to kits for conventional diagnostic uses listed above such as qPCR, microarray, and immunoassays such as immunohistochemistry, ELISA, Western blot and the like. Such kits include appropriate reagents and directions to assay the expression of the genes or gene products and quantify mRNA or protein expression.

Also disclosed are methods for identifying human tumors with or without the non-angiogenesis phenotype. In certain exemplary embodiments, such methods may be used to identify patients that are sensitive to and respond to drugs that inhibit, either directly or indirectly, processes relating to angiogenesis. In certain other exemplary embodiments, such methods may be used to identify patients that are resistant to or do not respond to drugs that inhibit, either directly or indirectly, processes relating to angiogenesis.

This invention also relates to guiding effective treatment of patients. Further, methods relating to selection of patient treatment regimens and selecting patients for clinical trials of current, or developmental stage drugs that directly or indirectly affect angiogenesis are provided.

In addition, methods that accommodate the use of archived formalin fixed paraffin-embedded (FFPE) biopsy material, as well as fresh/frozen (FF) tissue, for assay of all transcripts, and are therefore compatible with the most widely available type of biopsy material, are described herein. A biomarker expression level may be determined using RNA obtained from FFPE tissue, fresh frozen tissue or fresh tissue that has been stored in solutions such as RNAlater®.

BRIEF DESCRIPTION OF DRAWINGS

FIG. 2A shows a histogram representing the significance of the top 10 enriched Gene Ontology Biological processes. Red bars indicate significance of a process at a p-value of 0.05 after false discovery rate correction. FIG. 2B represents the subset of the Gene Ontology Biological processes tree where processes include one or more genes encoded by the probe sets in cluster 3. Red coloured processes indicate significance of that process at a p-value of 0.05 after false discovery rate correction. Black coloured processes include one or more genes encoded by the probe sets in angiogenesis probe set cluster, but are not significant.

FIG. 7A shows a histogram representing the significance of the top 10 enriched Gene Ontology biological processes. Red bars indicate significance of a process at a p-value of 0.05 after False Discovery Rate correction. FIG. 7B represents the subset of the Gene Ontology Biological processes tree where processes include one or more genes encoded by the probe sets in cluster 2 (angiogenesis probe set cluster). Red coloured processes indicate significance of that process at a p-value of 0.05 after false discovery rate correction. Black coloured processes include one or more genes encoded by the probe sets in the angiogenesis cluster, but are not significant.

DETAILED DESCRIPTION OF THE INVENTION

Figure 1:
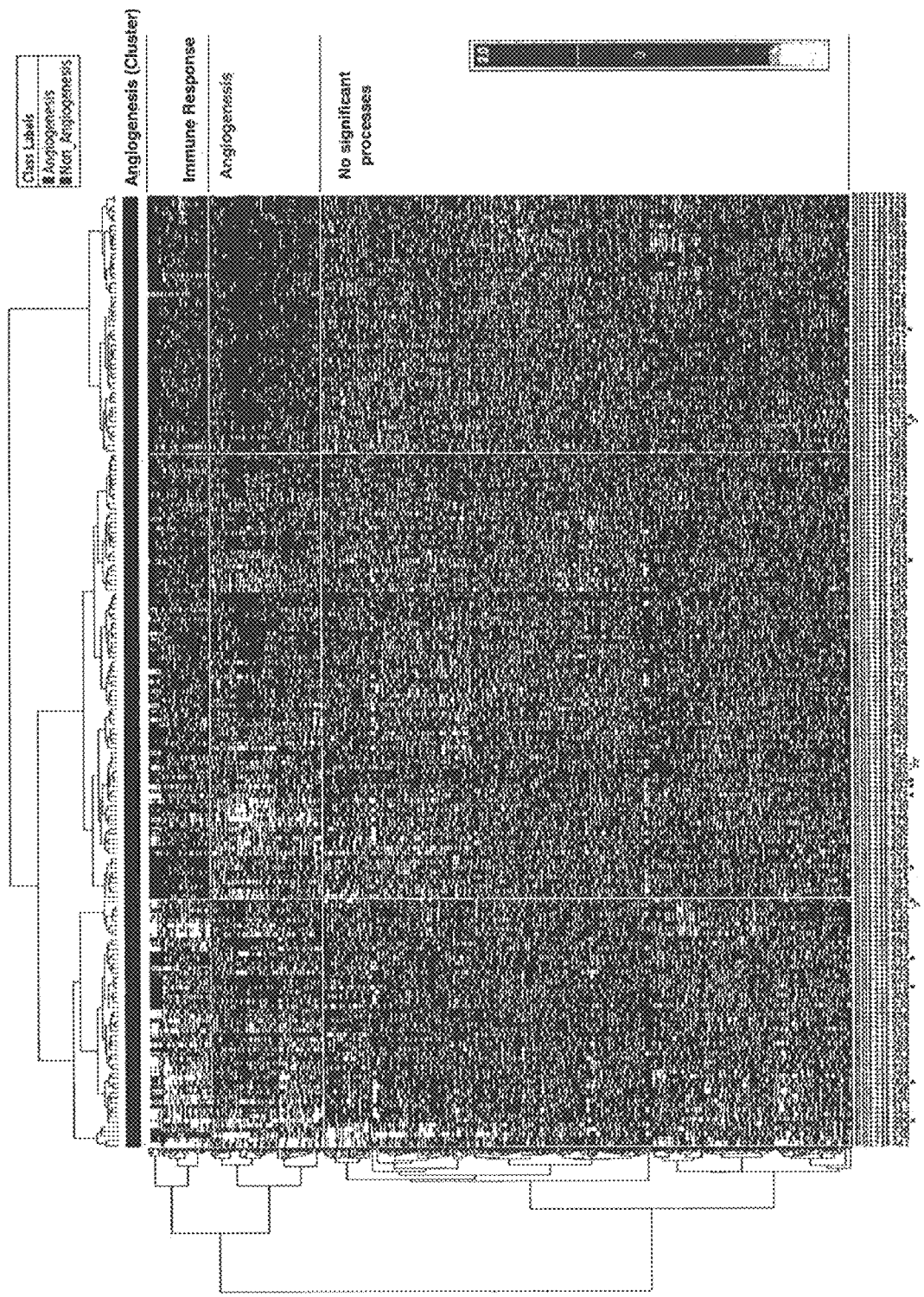
FIG. 1 provides a heatmap representing the hierarchical agglomerative clustering analysis of the most variable probe sets across 199 serous samples of the Almac Diagnostics' epithelial ovarian cancer sample set. The functional analysis of the probe set clusters is summarized on the right hand side of the image. The legend across the top of the image indicates the classifier group each sample was assigned to for classifier generation (i.e. Class labels).

Unless defined otherwise, technical and scientific terms used herein have the same meaning as commonly understood by one of ordinary skill in the art to which this disclosure belongs. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

As used herein terms "marker panel," "expression classifier," "classifier," "expression signature," or "signature" may be used interchangeably.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

A major goal of current research efforts in cancer is to increase the efficacy of perioperative systemic therapy in patients by incorporating molecular parameters into clinical therapeutic decisions. Pharmacogenetics/genomics is the study of genetic/genomic factors involved in an individuals' response to a foreign compound or drug. Agents or modulators which have a stimulatory or inhibitory effect on expression of a biomarker of the invention can be administered to individuals to treat (prophylactically or therapeutically) cancer in the patient. It is ideal to also consider the pharmacogenomics of the individual in conjunction with such treatment. Differences in metabolism of therapeutics may possibly lead to severe toxicity or therapeutic failure by altering the relationship between dose and blood concentration of the pharmacologically active drug. Thus, understanding the pharmacogenomics of an individual permits the selection of effective agents (e.g., drugs) for prophylactic or therapeutic treatments. Such pharmacogenomics can further be used to determine appropriate dosages and therapeutic regimens. Accordingly, the level of expression of a biomarker of the invention in an individual can be determined to thereby select appropriate agent(s) for therapeutic or prophylactic treatment of the individual.

The present invention relates to a molecular diagnostic tests useful for diagnosing cancers from different anatomical sites that includes the use of one or more common subtypes related to angiogenesis. The invention includes expression signatures that identify a subject as responsive or non-responsive to anti-angiogenic therapeutics and/or having a good or poor clinical prognosis. The expression signature is derived by obtaining the expression profiles of samples from a sample set of known pathology and/or clinical outcome. The samples may originate from the same sample tissue type or different tissue types. As used herein an "expression profile" comprises a set of values representing the expression level for each biomarker analyzed from a given sample.

The expression profiles from the sample set are then analyzed using a mathematical model. Different mathematical models may be applied and include, but are not limited to, models from the fields of pattern recognition (Duda et al.

Pattern Classification, $2^{nd}$ ed., John Wiley, New York 2001), machine learning (Schölkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998). The mathematical model identifies one or more biomarkers expressed in the sample set that are most predictive of a given disease phenotype. These one or more biomarkers define an expression signature. Accordingly, an expression signature includes the biomarkers identified as most predictive of a given disease phenotype. In certain exemplary embodiments, the mathematical model defines a variable, such as a weight, for each identified biomarker. In certain exemplary embodiments, the mathematical model defines a decision function. The decision function may further define a threshold score which separates the sample set into two disease phenotypes such as, but not limited to, samples that are responsive and non-responsive to anti-angiogenic therapeutics. In one exemplary embodiment, the decision function and expression signature are defined using a linear classifier.

To classify new samples using a defined expression signature, the biomarkers defined by the expression signature are isolated and an expression profile of the biomarker(s) determined. The new sample biomarker expression profile is analyzed with the same mathematical model used to define the expression signature. In certain exemplary embodiments, the mathematical model defines an expression score for the new sample. The expression score may be determined by combining the expression values of the biomarkers with corresponding scalar weights using non-linear, algebraic, trigonometric or correlative means to derive a single scalar value. The expression score is compared to the threshold score and the sample classified based on whether the expression score is greater than, or equal to, or less than the threshold score. In one exemplary embodiment, a sample expression value greater than the reference expression value indicates a patient will be responsive to an anti-angiogenic therapeutic. In another exemplary embodiment, a sample expression score below the threshold score indicates the patient will not be responsive to an anti-angiogenic therapeutic. In another exemplary embodiment, a sample expression score below the threshold expression score indicates the patient has a cancer type, or is at risk of developing a cancer type, that is not responsive to an anti-angiogenic therapeutic. In another exemplary embodiment, a sample expression score above the reference expression score indicates the patient has a cancer type, or is at risk of developing a cancer type, that is responsive to an anti-angiogenic therapeutic. In another example embodiment, a sample expression score above the threshold score indicates the patient has a cancer sub-type with a good clinical prognosis. In another example embodiment, a sample expression score below the threshold score indicates a patient with a cancer subtype with a poor clinical prognosis. Where an expression signature is derived from a tissue sample set comprising one type of cancer tissue, the expression signature is not limited to identifying the same cancer sub-type only in tissues of the same cancer type, but may be used with other cancer types that share the same cancer sub-type. For example, where an expression signature is derived from ovarian cancer samples, the expression signature may be used to identify a similar angiogenesis sub-type in different cancers such as glioblastoma, breast cancer, lung cancer, colon cancer, or prostate cancer.

One application of the expression signatures disclosed herein is the identification of patients with good and poor prognosis. By examining the expression of a collection of the identified biomarkers in a tumor, it is possible to determine the likely clinical outcomes of a patient. By examining the expression of a collection of biomarkers, it is therefore possible to identify those patients in most need of more aggressive therapeutic regimens and likewise eliminate unnecessary therapeutic treatments or those unlikely to significantly improve a patient's clinical outcome.

A patient may be considered to have a "good prognosis" where, for example, the survival rate associated with the cancer subtype is greater than a survival rate associated with other related cancer subtypes. In certain embodiments, a "good prognosis" indicates at least an increased expected survival time. This may be based upon a classification as responsive to an anti-angiogenic therapeutic agent as described herein. The increased expected survival time may be as compared to classification as non-responsive to the anti-angiogenic therapeutic agent.

A patient may be considered to have a "poor prognosis" or "bad prognosis" where, for example, the survival rate associated with the cancer subtype is less than the survival rate associated with other related cancer subtypes.

Another application of the expression signatures disclosed herein is the stratification of response to, and selection of patients for therapeutic drug classes that encompass anti-angiogenic therapies. By examining the expression of a collection of the identified biomarkers in a tumor, it is possible to determine which therapeutic agent or combination of agents will be most likely to reduce the growth rate of a cancer. It is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued. The present invention provides a test that can guide therapy selection as well as selecting patient groups for enrichment strategies during clinical trial evaluation of novel therapeutics. For example, when evaluating a putative anti-angiogeneic agent or treatment regime, the expression signatures and methods disclosed herein may be used to select individuals for clinical trials that have cancer subtypes that are responsive to anti-angiogenic agents.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways. For instance, the size of a tumor or measuring the expression of tumor markers appropriate for that tumor type.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or measuring the expression of tumor markers appropriate for that tumor type. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor such as, but not limited to, patient quality of life, and degree of metastases.

Another application of the expression signatures disclosed herein is the combined identification of prognosis of a patient along with identification of a predicted responsiveness of the patient to a given therapeutic. In certain example embodiments, a non-angiogenesis expression signature defined below is used to identify patients with a good prognosis from those with a poor prognosis, and an angiogenesis expression signature is used to predict the patient's response to a given therapeutic class of drugs.

The angiogenesis subtype can be identified from a fresh/frozen (FF) or formalin fixed paraffin embedded (FFPE) patient sample. In one exemplary embodiment, the cancer type is ovarian cancer, breast cancer, colon cancer, colorectal cancer, lung cancer, prostate cancer, or glioblastoma. In another exemplary embodiment, the cancer type is a ovarian cancer. In a further exemplary embodiment, the cancer type is breast cancer. In another exemplary embodiment, the cancer type is lung cancer. In another exemplary embodiment, the cancer type is colon cancer. In another exemplary embodiment, the cancer type is prostate cancer. In another exemplary embodiment, the cancer type is glioblastoma Identifying Expression Signatures The expression signatures of the present invention are identified by analyzing the expression profiles of certain biomarkers in a patient sample set. Biomarkers suitable for use in the present invention include DNA, RNA, and proteins. The biomarkers are isolated from a patient sample and their expression levels determined to derive a set of expression profiles for each sample analyzed in the patient sample set. In certain example embodiments the expression signature is an angiogenesis expression signature. An angiogenesis expression signature relates to an angiogenesis phenotype obversed in cancer tissues, the phenotype characterized by an up-regulation of biomarkers associated with angiogenesis and vascular development. In certain other example embodiments, the expression signature is a non-angiogenesis expression signature. A non-angiogenesis expression signature relates to a phenotype observed in cancer tissues, the phenotype characterized by a down-regulation of biomarkers associated with angiongenesis and vascular development.

a. Expression Profiles

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic or prognostic methods is one that is a nucleic acid sample. The nucleic acid sample includes a population of nucleic acids that includes the expression information of the phenotype determinative biomarkers of the cell or tissue being analyzed. In some embodiments, the nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as isolated, amplified, or employed to prepare cDNA, cRNA, etc., as is known in the field of differential gene expression. Accordingly, determining the level of mRNA in a sample includes preparing cDNA or cRNA from the mRNA and subsequently measuring the cDNA or cRNA. The sample is typically prepared from a cell or tissue harvested from a subject in need of treatment, e.g., via biopsy of tissue, using standard protocols, where cell types or tissues from which such nucleic acids may be generated include any tissue in which the expression pattern of the to be determined phenotype exists, including, but not limited to, disease cells or tissue, body fluids, etc.

The expression profile may be generated from the initial nucleic acid sample using any convenient protocol. While a variety of different manners of generating expression profiles are known, such as those employed in the field of differential gene expression/biomarker analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

b. Diseases and Sample Tissue Sources

In certain exemplary embodiments, the patient sample set comprises cancer tissue samples, such as archived samples. The patient sample set is preferably derived from cancer tissue samples having been characterized by prognosis, likelihood of recurrence, long term survival, clinical outcome, treatment response, diagnosis, cancer classification, or personalized genomics profile. As used herein cancer includes, but is not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, and the like. As used herein, colorectal cancer encompasses cancers that may involve cancer in tissues of both the rectum and other portions of the colon as well as cancers that may be individually classified as either colon cancer or rectal cancer. In one embodiment, the methods described herein refer to cancers that are treated with anti-angiogenic agents, anti-angiogenic targeted therapies, inhibitors of angiogenesis signaling, but not limited to these classes. These cancers also include subclasses and subtypes of these cancers at various stages of pathogenesis. In certain exemplary embodiments, the patient sample set comprises ovarian cancer samples. In another exemplary embodiment, the patient sample set comprises breast cancer samples. In yet another exemplary embodiment, the patient sample set comprises glioblastoma samples.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual, for example, fresh frozen or formalin fixed and/or paraffin embedded. The methods of the invention as defined herein may begin with an obtained sample and thus do not necessarily incorporate the step of obtaining the sample from the patient. The methods may be in vitro methods performed on an isolated sample.

As used herein, the term "patient" includes human and non-human animals. The preferred patient for treatment is a human. "Patient," "individual" and "subject" are used interchangeably herein.

c. Biomarkers

As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. When a biomarker indicates or is a sign of an abnormal process, disease or other condition in an individual, that biomarker is generally described as being either over-expressed or under-expressed as compared to an expression level or value of the biomarker that indicates or is a sign of a normal process, an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The terms "differential biomarker expression" and "differential expression" are used interchangeably to refer to a biomarker whose expression is activated to a higher or lower level in a subject suffering from a specific disease, relative to its expression in a normal subject, or relative to its expression in a patient that responds differently to a particular therapy or has a different prognosis. The terms also include biomarkers whose expression is activated to a higher or lower level at different stages of the same disease. It is also understood that a differentially expressed biomarker may be either activated or inhibited at the nucleic acid level or protein level, or may be subject to alternative splicing to result in a different polypeptide product. Such differences may be evidenced by a variety of changes including mRNA levels, miRNA levels, antisense transcript levels, or protein surface expression, secretion or other partitioning of a polypeptide. Differential biomarker expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a biomarker among, for example, normal and diseased cells, or among cells which have undergone different disease events or disease stages.

In certain exemplary embodiments, the biomarker is an RNA transcript. As used herein "RNA transcript" refers to both coding and non-coding RNA, including messenger RNAs (mRNA), alternatively spliced mRNAs, ribosomal RNA (rRNA), transfer RNA (tRNA), small nuclear RNAs (snRNA), and antisense RNA. Measuring mRNA in a biological sample may be used as a surrogate for detection of the level of the corresponding protein and gene in the biological sample. Thus, any of the biomarkers or biomarker panels described herein can also be detected by detecting the appropriate RNA. Methods of biomarker expression profiling include, but are not limited to quantitative PCR, NGS, northern blots, southern blots, microarrays, SAGE, immunoassays (ELISA, EIA, agglutination, nephelometry, turbidimetry, Western blot, immunoprecipitation, immunocytochemistry, flow cytometry, Luminex assay), and mass spectrometry. The overall expression data for a given sample may be normalized using methods known to those skilled in the art in order to correct for differing amounts of starting material, varying efficiencies of the extraction and amplification reactions.

In certain exemplary embodiments, biomarkers useful for distinguishing between cancer types that are responsive and non-responsive to anti-angiogenic therapeutics can be determined by identifying biomarkers exhibiting the highest degree of variability between samples in the patient data set as determined using the expression detection methods and patient sample sets discussed above. Standard statistical methods known in the art for identifying highly variable data points in expression data may be used to identify the highly variable biomarkers. For example, a combined background and variance filter to the patient data set. The background filter is based on the selection of probe sets with expression E and expression variance $var_E$ above the thresholds defined by background standard deviation $\sigma Bg$ (from the Expression Console software) and quantile of the standard normal distribution $z_a$ at a specified significance a probe sets were kept if:

$$E > \log_2((z_a \sigma B_g)); \log_2((var_E) > 2[\log_2(\sigma_{Bg}) - E - \log_2(\log(2))]$$

where a defines a significance threshold. In certain exemplary embodiment, the significance threshold is $6.3 \cdot 10^{-5}$. In another exemplary embodiment, the significance threshold may be between $1.0 \cdot 10^{-7}$ to $1.0 \cdot 10^{-3}$.

In certain exemplary embodiments, the highly variable biomarkers may be further analyzed to group samples in the patient data set into subtypes or clusters based on similar gene expression profiles. For examples, biomarkers may be clustered based on how highly correlated the up-regulation or down-regulation of their expression is to one another. Various clustering analysis techniques known in the art may be used. In one exemplary embodiment, hierarchical agglomerative clustering is used to identify the cancer subtypes. To determine the biological relevance of each subtype, the biomarkers within each cluster may be further mapped to their corresponding genes and annotated by cross-reference to one or more gene ontology databases containing information on biological activity and biological pathways associated with the gene. In one exemplary embodiment, biomarker in clusters enriched for angiogenesis, vasculature development and immune response general functional terms are grouped into a putative angiogenesis sample group and used for expression signature generation. In another exemplary embodiment, biomarkers in clusters that are up regulated and enriched for angiogeneis, vasculature development and immune response general functional terms are grouped into a putative angiongenesis sample group and used for expression signature generation. In another exemplary embodiment, biomarkers in clusters that are down regulated and enriched for angiogenesis, vasculature development and immune response general functional terms are grouped into a putative angiongenesis sample group and used for expression signature generation. Further details for conducting functional analysis of biomarker clusters is provided in the Examples section below.

In one exemplary embodiment, the biomarkers useful in deriving an expression signature for use in the present invention are those biomarkers listed in Table 1A, Table 1B, Table 1C, or a combination thereof. These biomarkers are identified as having predictive value to determine a patient response to a therapeutic agent and/or a prognostice value in identifying individuals with a good or poor clinical prognosis.

In certain example embodiments, their expression correlates with the response, or lack thereof, to an agent, and more specifically, an anti-angiogenic therapeutic agent. By examining the expression of a collection of the identified biomarkers in a tumor, it is possible to determine which therapeutic agent or combination of agents will be most likely to reduce the growth rate of a cancer. By examining a collection of identified biomarkers in a tumor, it is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued.

In certain other example embodiments, the expression of the biomarkers disclosed herein correlated with a patient's overall clinical prognosis. By examining the expression of a collection of biomarkers identified in a tumor, it is possible to determine whether the individual has a cancer subtype associated with good clinical prognosis or poor clinical prognosis. Importantly, in certain embodiments, these determinations can be made on a patient-by-patient basis. Thus, one of ordinary skill in the art can use predicted prognosis to help select appropriate treatment regimens to treat the underlying disease while eliminating those treatment regimens most likely to produce undesired or medically unwarranted adverse side effects.

The SEQ ID NOs listed in Table 1A, Table 1B, and Table 1C refer to probe set identifiers used to measure the expression levels of the genes on an exemplary transcriptome array. Expression signatures of the present invention have been cross-validated using expression data from different arrays with different probe sets as detailed further in the Examples section below. Accordingly, the expression signatures and methods disclosed herein are not limited to expression values measured using the probe sets disclosed herein.

TABLE 1A

Genes in Clusters of FIG. 1

| SEQ NO: | Orientation | Gene Symbol |
|---|---|---|
| 1 | Sense | STAT1 |
| 2 | Sense | PDGFC |
| 3 | Sense | TGFB3 |
| 4 | Sense | RAC2 |
| 5 | Sense | MARCKS |
| 6 | Sense | ALOX5 |
| 7 | Sense | COL8A1 |
| 8 | Sense | CTSS |

TABLE 1A-continued

Genes in Clusters of FIG. 1

| SEQ NO: | Orientation | Gene Symbol |
|---|---|---|
| 9 | Sense | HAVCR2 |
| 10 | Sense | RAB31 |
| 11 | Sense | KCNAB2 |
| 12 | Sense | THBS1 |
| 13 | Sense | SH3BP4 |
| 14 | Sense | CTGF |
| 15 | Sense | CTGF |
| 16 | Sense | VCAN |
| 17 | Sense | IGKC |
| 18 | Sense | IGKC |
| 19 | Sense | IGKC |
| 20 | Sense | SGK1 |
| 21 | Sense | NFATC1 |
| 22 | Sense | HMHA1 |
| 23 | Sense | FCGR1C /// FCGR1A /// FCGR1B |
| 24 | Sense | EDA2R |
| 25 | Sense | COL8A1 |
| 26 | Sense | COL12A1 |
| 27 | Sense | HLA-B |
| 28 | Sense | HLA-F |
| 29 | Sense | HLA-C |
| 30 | Sense | SPP1 |
| 31 | Sense | MYO1F |
| 32 | Sense | SPARC |
| 33 | Sense | SPARC |
| 34 | Sense | UBD /// GABBR1 |
| 35 | Sense | CCND1 |
| 36 | Sense | COL1A1 |
| 37 | Sense | EGR1 |
| 38 | Sense | EGR1 |
| 39 | Sense | TNFSF10 |
| 40 | Sense | SULF2 |
| 41 | Sense | CERCAM |
| 42 | Sense | ATF3 |
| 43 | Sense | MIR21 |
| 44 | Sense | BASP1 |
| 45 | Sense | IFIT2 |
| 46 | Sense | SULF1 |
| 47 | Sense | IGLC2 /// IGLC3 |
| 48 | Sense | IGLC2 /// IGLC3 |
| 49 | Sense (Fully0Exonic) | IGLC2 /// IGLC3 |
| 50 | Sense | IGLC2 /// IGLC3 |
| 51 | Sense | IGLC2 /// IGLC3 |
| 52 | Sense | IGLC1 |
| 53 | Sense | IGLC1 |
| 54 | Sense | IGLC2 /// IGLC3 |
| 55 | Sense | ANGPTL2 |
| 56 | Sense | COL5A2 |
| 57 | Sense | IGJ |
| 58 | Sense | THY1 |
| 59 | Sense | NDN |
| 60 | Sense | RGS2 |
| 61 | Sense | MEIS3P1 /// MEIS3P2 |
| 62 | Sense | GBP2 |
| 63 | Sense | CSF1R |
| 64 | Sense | C1R |
| 65 | Sense | FAT1 |
| 66 | Sense | COL1A1 |
| 67 | Sense | RHOB |
| 68 | Sense | MMP11 |
| 69 | Sense | GADD45B |
| 70 | Sense | MMP14 |
| 71 | Sense | MMP14 |
| 72 | Sense | IGHG4 |
| 73 | Sense | DDX60L |
| 74 | Sense | SPP1 |
| 75 | Sense | ROR2 |
| 76 | Sense | CTSK |
| 77 | Sense | FCGR2B |
| 78 | Sense | PTAFR |
| 79 | Sense | ICAM1 |
| 80 | Sense | HCLS1 |
| 81 | No Transcript Match | — |
| 82 | Sense | SLFN11 |
| 83 | No Transcript Match | — |
| 84 | Sense | JAM3 |
| 85 | Sense | TMEM49 |
| 86 | Sense | TMEM49 |
| 87 | Sense | LTBP2 |
| 88 | Sense | IRS1 |
| 89 | Sense | COL5A2 |
| 90 | Sense | C17orf91 |
| 91 | Sense | GPNMB |
| 92 | Sense | FAM198B |
| 93 | Sense | MICAL2 |
| 94 | Sense | TMEM2 |
| 95 | Sense | CHST15 |
| 96 | Sense | SECTM1 |
| 97 | Sense | DCN |
| 98 | Sense | VCAM1 |
| 99 | Sense | TNFAIP3 |
| 100 | Sense | C1QA |
| 101 | Sense | C1QA |
| 102 | Sense | FBXO32 |
| 103 | Sense | COL12A1 |
| 104 | Sense | CPE |
| 105 | Sense | CIITA |
| 106 | Sense | GAS7 |
| 107 | Sense | COL3A1 |
| 108 | Sense | FN1 |
| 109 | Sense | IFI30 |
| 110 | Sense | ITGB2 |
| 111 | Sense | ELN |
| 112 | Sense | CMTM3 |
| 113 | Sense | ANTXR1 |
| 114 | Sense | ARHGDIB |
| 115 | Sense | LAPTM5 |
| 116 | Sense | SOX4 |
| 117 | Sense | IFI44L |
| 118 | Sense | IL4I1 |
| 119 | Sense | ANTXR2 |
| 120 | Sense | IGLC2 /// IGLC3 |
| 121 | Sense | EPSTI1 |
| 122 | Sense | BIRC3 |
| 123 | Sense | IGLC2 /// IGLC3 |
| 124 | Sense | BST2 |
| 125 | Sense | TNFSF10 |
| 126 | Sense | COL10A1 |
| 127 | Sense | IGLC2 /// IGLC3 |
| 128 | Sense | FBP1 |
| 129 | Sense | RHOBTB3 |
| 130 | Sense | CDK6 |
| 131 | Sense | CD74 |
| 132 | Sense | ISM1 |
| 133 | Sense | C1QC |
| 134 | Sense | BIN2 |
| 135 | Sense | CSRNP1 |
| 136 | Sense | TYROBP |
| 137 | Sense | C1QTNF3 |
| 138 | Sense | DCN |
| 139 | Sense | IGFBP4 |
| 140 | Sense | AOAH |
| 141 | Sense | SIRPA |
| 142 | Sense | FOSB |
| 143 | Sense | CCDC80 |
| 144 | Sense | IGLC1 |
| 145 | Sense | HCST |
| 146 | Sense | IFI35 |
| 147 | Sense | BIRC3 |
| 148 | Sense | COL3A1 |
| 149 | Sense | IFITM2 |
| 150 | Sense | ZFP36 |
| 151 | Sense | MMP11 |
| 152 | Sense | COL1A2 |
| 153 | Sense | HLA-DPA1 |
| 154 | Sense | TWIST1 |
| 155 | Sense | ZNF154 |
| 156 | Sense | EGR1 |
| 157 | Sense | IGLC2 /// IGLC3 |
| 158 | Sense | TNFSF10 |

TABLE 1A-continued

Genes in Clusters of FIG. 1

| SEQ NO: | Orientation | Gene Symbol |
|---|---|---|
| 159 | Sense | IGKC |
| 160 | Sense | IGHG1 /// IGHG4 |
| 161 | Sense | GBP5 |
| 162 | Sense | COL1A2 |
| 163 | Sense | APOC1 |
| 164 | No Transcript Match | — |
| 165 | Sense | COL3A1 |
| 166 | AntiSense | PXDN |
| 167 | AntiSense | EGR1 |
| 168 | Sense | GBP3 |
| 169 | Sense | ISG15 |
| 170 | Sense | — |
| 171 | Sense | KIAA0146 |
| 172 | Sense | CMAH |
| 173 | Sense | APBB2 |
| 174 | Sense | TPM1 |
| 175 | No Transcript Match | — |
| 176 | Sense | DMD |
| 177 | No Genome Match | — |
| 178 | Sense | IL10RA |
| 179 | Sense | — |
| 180 | No Transcript Match | — |
| 181 | Sense | DUSP1 |
| 182 | Sense | GBP1 |
| 183 | Sense | PARVG |
| 184 | Sense | MAFF |
| 185 | Sense | PDGFC |
| 186 | Sense | MSN |
| 187 | Sense | RSAD2 |
| 188 | Sense | TPM1 |
| 189 | Sense | EMB |
| 190 | Sense | C6orf155 |
| 191 | Sense | FOS |
| 192 | Sense | DEXI |
| 193 | Sense | RNF19A |
| 194 | Sense | FBXO32 |
| 195 | Sense | DPYSL3 |
| 196 | Sense | PRICKLE1 |
| 197 | AntiSense | EGR1 |
| 198 | AntiSense | NRP2 |
| 199 | Sense | B2M |
| 200 | AntiSense | MIR21 |
| 201 | Sense | MMP2 |
| 202 | Sense | CDR1 |
| 203 | Sense | HLA-B |
| 204 | Sense | CTGF |
| 205 | Sense | DCN |
| 206 | Sense | SOD2 |
| 207 | Sense | FN1 |
| 208 | Sense | COL8A2 |
| 209 | Sense | SGK1 |
| 210 | Sense | TIMP3 |
| 211 | Sense | ACTA2 |
| 212 | Sense | SRGN |
| 213 | Sense | LOXL1 |
| 214 | Sense | CCR1 |
| 215 | Sense | GBP1 |
| 216 | Sense | CDH11 |
| 217 | Sense | FCGR3A |
| 218 | Sense | LUM |
| 219 | Sense | NNMT |
| 220 | Sense | COL1A2 |
| 221 | Sense | RGS1 |
| 222 | Sense | GJA1 |
| 223 | Sense | SPARCL1 |
| 224 | Sense | DAB2 |
| 225 | AntiSense | CTHRC1 |
| 226 | Sense | RGS16 |
| 227 | Sense | FBLN1 |
| 228 | Sense | SPP1 |
| 229 | Sense | CTSB |
| 230 | Sense | SPP1 |
| 231 | Sense | SDC1 |
| 232 | Sense | PLAU |
| 233 | Sense | PDGFRA |
| 234 | Sense | SERPINF1 |
| 235 | Sense | BGN |
| 236 | Sense | COL6A3 |
| 237 | AntiSense | C3 |
| 238 | AntiSense | C3 |
| 239 | AntiSense | SPP1 |
| 240 | AntiSense | HLA-DQA1 |
| 241 | AntiSense | GAS1 |
| 242 | Sense | VCAN |
| 243 | AntiSense | — |
| 244 | Sense | IGHG4 /// IGHG2 /// IGHG1 /// IGHGP |
| 245 | Sense | IGHG2 |
| 246 | Sense | C3orf26 |
| 247 | AntiSense | ATF3 |
| 248 | AntiSense | ATF3 |
| 249 | AntiSense | SULF1 |
| 250 | Sense | FN1 |
| 251 | AntiSense | CALD1 |
| 252 | AntiSense | CALD1 |
| 253 | Sense | TMEM49 |
| 254 | Sense | TMEM49 |
| 255 | Sense | CHD5 |
| 256 | AntiSense | EGR1 |
| 257 | AntiSense | SNAI2 |
| 258 | AntiSense | ITPRIPL2 |
| 259 | AntiSense | GABBR1 /// UBD |
| 260 | AntiSense | GABBR1 /// UBD |
| 261 | AntiSense | TWIST1 |
| 262 | AntiSense | TWIST1 |
| 263 | AntiSense | BATF2 |
| 264 | AntiSense | NFKBIZ |
| 265 | Sense | C3orf26 |
| 266 | AntiSense | LOXL1 |
| 267 | Sense | — |
| 268 | AntiSense | TIMP2 |
| 269 | AntiSense | FN1 |
| 270 | AntiSense | COL1A1 |
| 271 | AntiSense | DCN |
| 272 | Sense | TREH |
| 273 | AntiSense | UBE2L6 |
| 274 | AntiSense | APOL1 |
| 275 | AntiSense | BIRC3 |
| 276 | AntiSense | BIRC3 |
| 277 | Sense | LILRB4 |
| 278 | Sense | FGD2 |
| 279 | Sense | TMEM49 |
| 280 | Sense | NCF4 |
| 281 | Sense | COL10A1 |
| 282 | Sense | GAL3ST4 |
| 283 | Sense | HCK |
| 284 | Sense | TAGLN |
| 285 | Sense | TWIST1 |
| 286 | Sense | HCLS1 |
| 287 | Sense | LPAR6 |
| 288 | Sense | ITGB2 |
| 289 | Sense | LST1 |
| 290 | Sense | HLA-B |
| 291 | Sense | C17orf91 |
| 292 | Sense | ZC3H12A |
| 293 | Sense | KLF10 |
| 294 | Sense | BASP1 |
| 295 | Sense | BASP1 |

TABLE 1B

Figure 6:
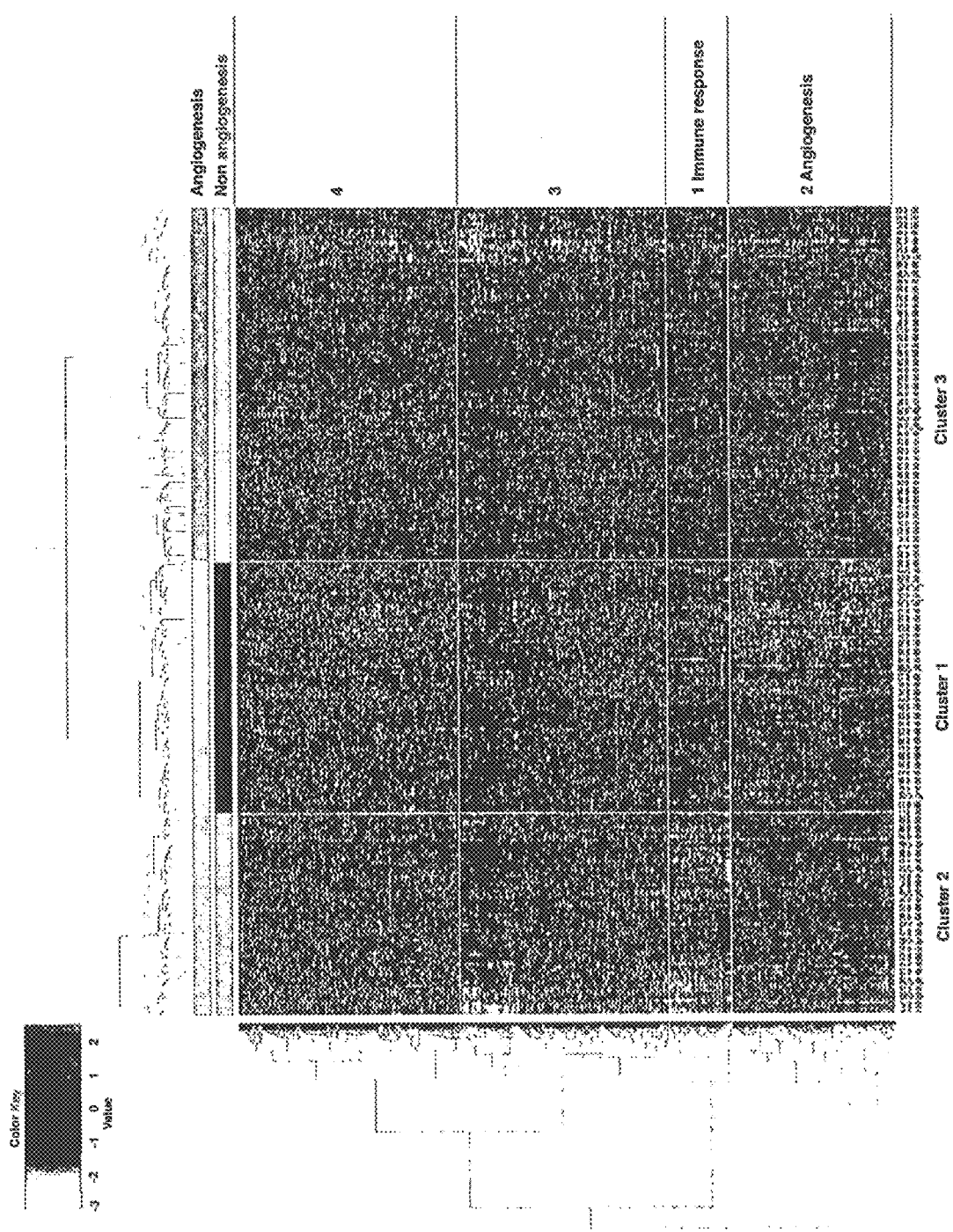
FIG. 6 provides a heatmap representing the hierarchical agglomerative clustering analysis of the most variable genes across 265 serous samples of an epithelial ovarian cancer sample set reclassified according to updated pathological classification criteria. The functional analysis of the probe set clusters is summarized on the right hand side of the image. The legend across the top of the image indicates the classifier group each sample was assigned to for classifier generation (i.e. Class labels) of both "angiogenesis" and "non-angiogenesis" subtypes.
Figure 7A:
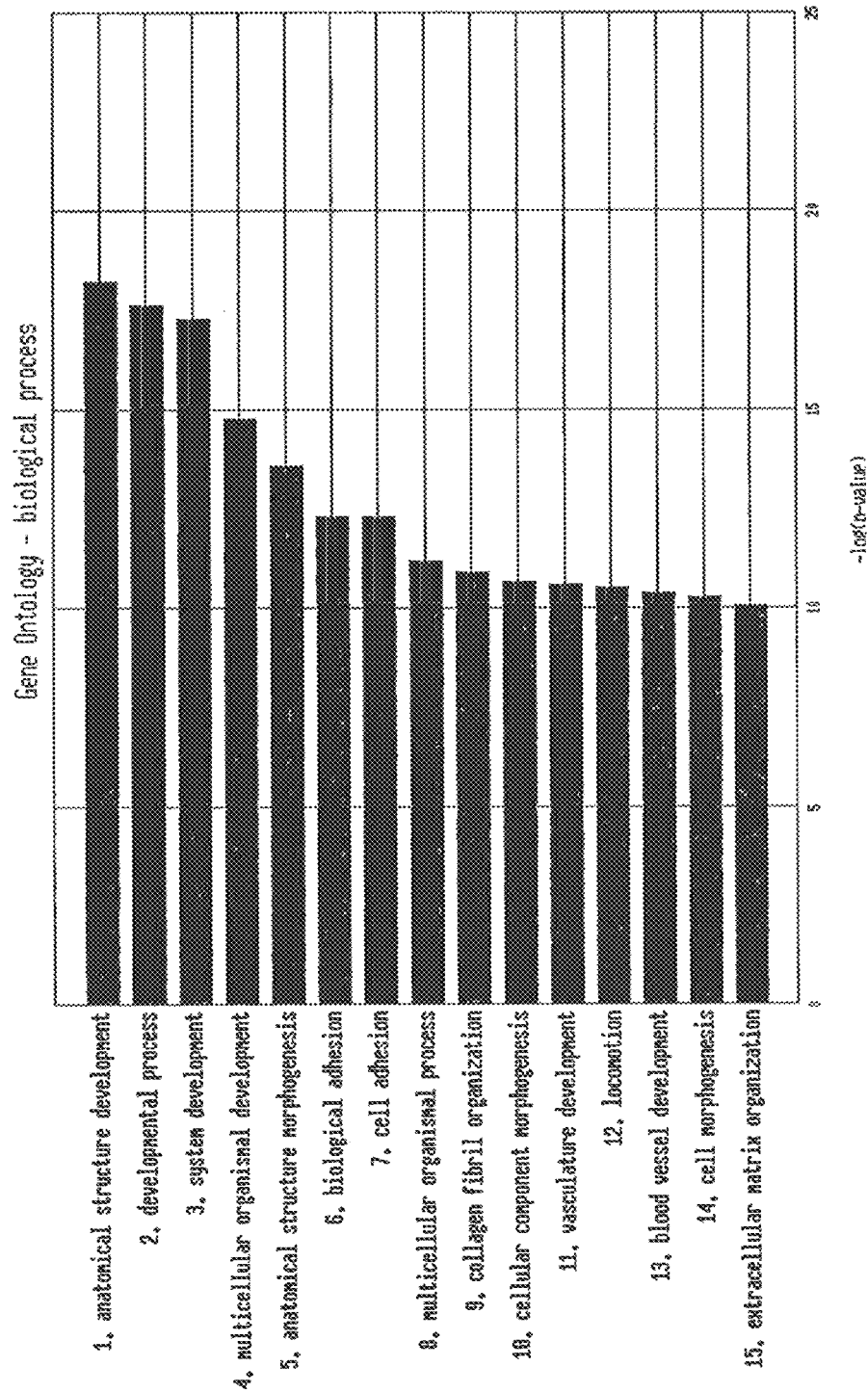
FIGS. 7A and 7B represents the functional analysis results of the angiogenesis probe set cluster of the 265 serous only samples in an epithelial ovarian cancer training set using a functional enrichment tool (FET) algorithm.
Figure 7B:
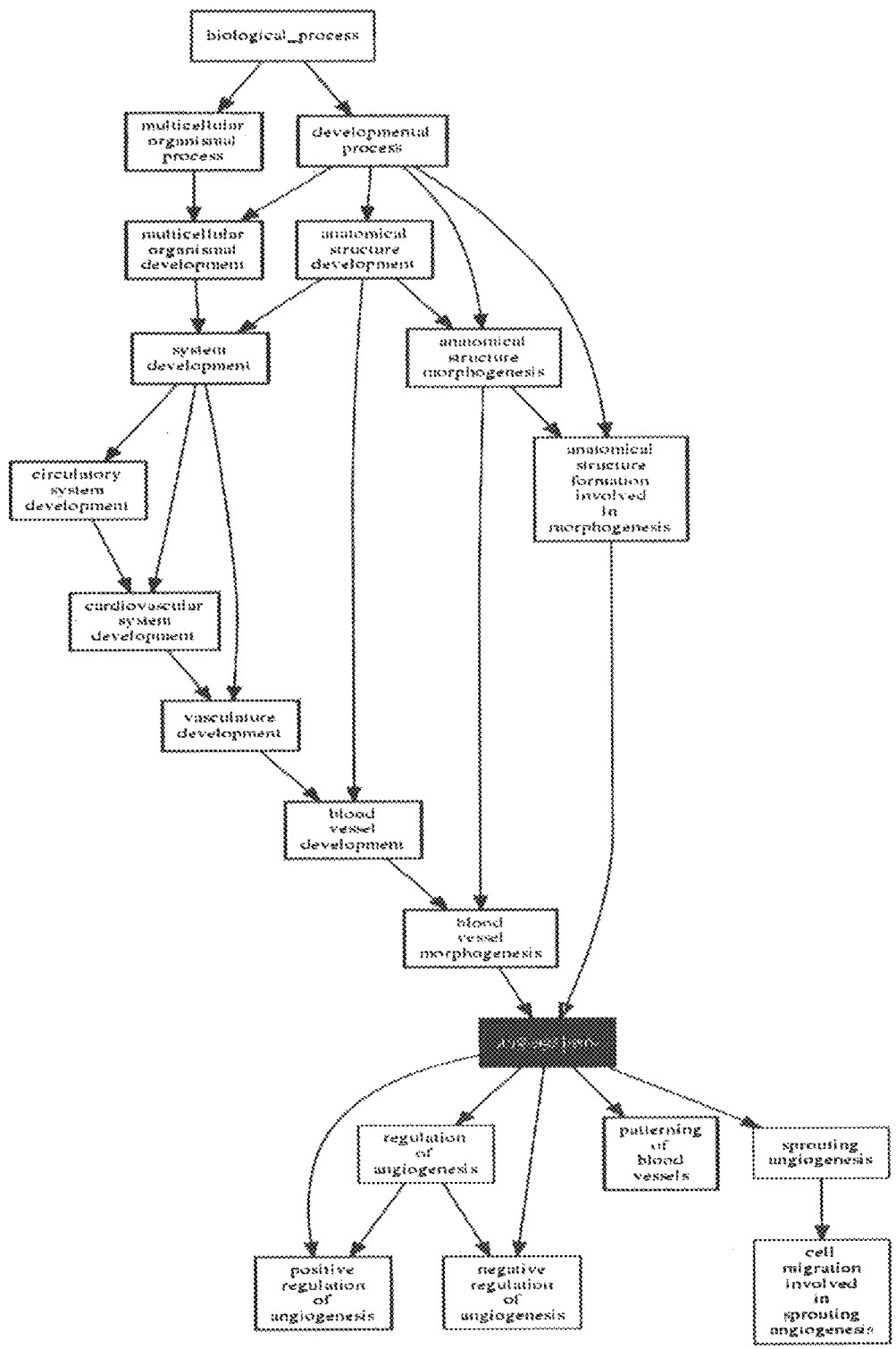
Figure 8:
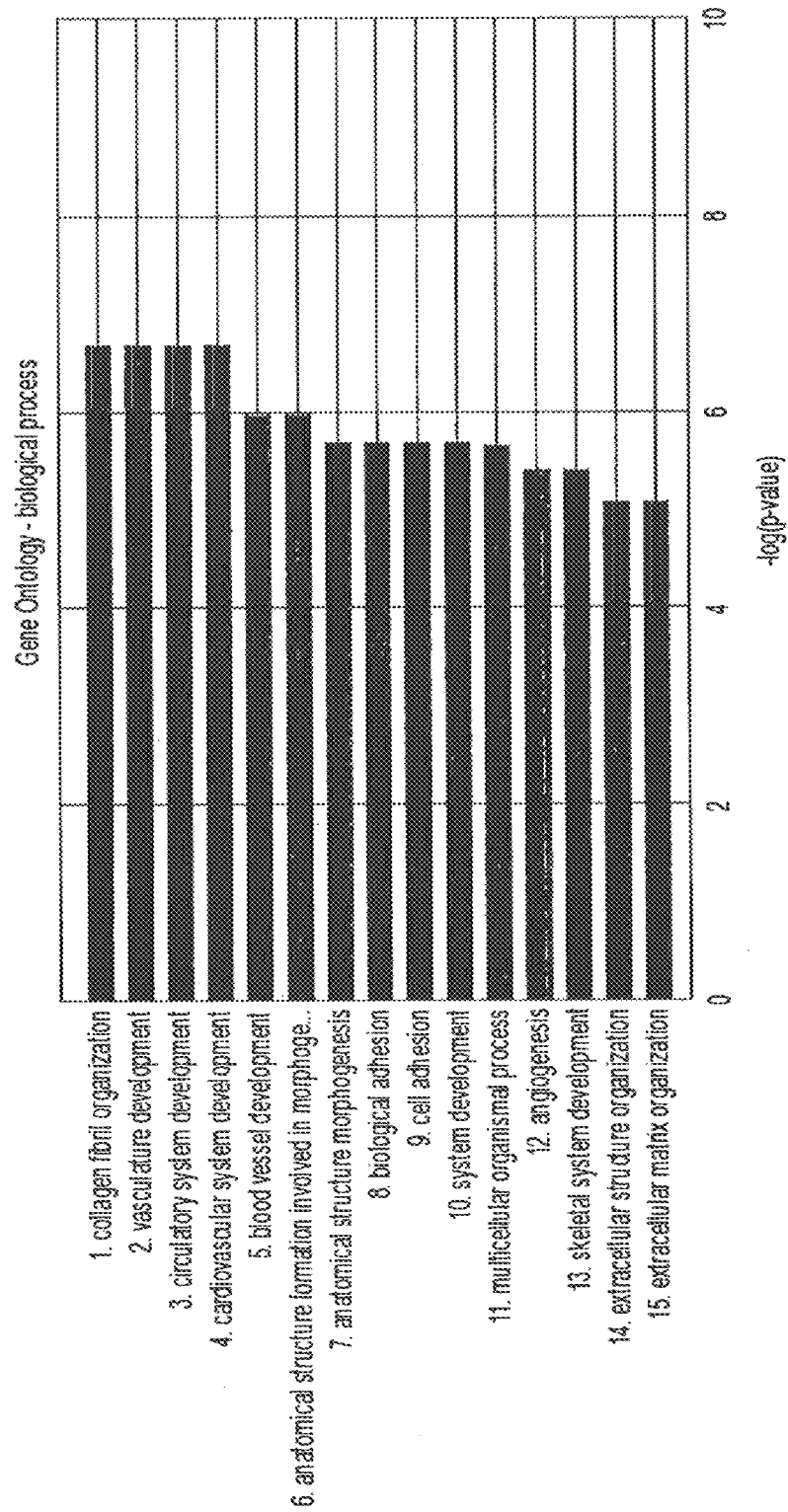
FIG. 8 represents the functional enrichment results of the genes within an exemplary 45-gene classifier model that identifies the molecular sub-type related to angiogenesis. Red bars indicate significance of a process at a p-value of 0.05 after False Discovery Rate correction.
Figure 9:
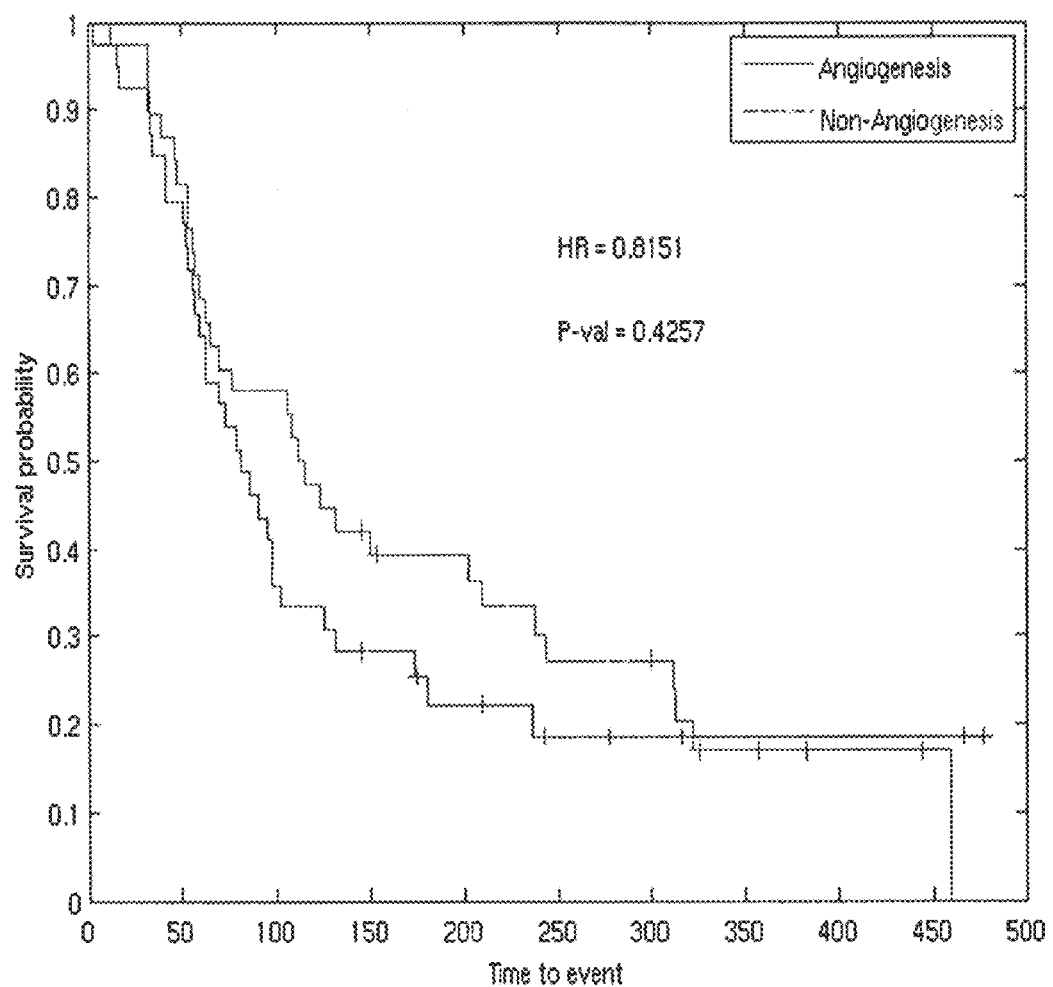
FIG. 9 provides a diagram of a ROC curve of the classification performance of the 45-gene classifier model within 16 prostate cell-lines following treatment with Dasatanib. The AUC is ~0.95 following application of the classifier model. The 95% confidence limits were determined using 1000 bootstrap iterations.

Genes in Clusters of FIG. 6

| SEQ NO: | Orientation | Gene Symbol |
|---|---|---|
| 2 | Sense (Fully Exonic) | PDGFC |
| 3 | Sense (Fully Exonic) | TGFB3 |

TABLE 1B-continued
Genes in Clusters of FIG. 6

| SEQ NO: | Orientation | Gene Symbol |
|---|---|---|
| 4 | Sense (Fully Exonic) | RAC2 |
| 5 | Sense (Fully Exonic) | MARCKS |
| 6 | Sense (Fully Exonic) | ALOX5 |
| 7 | Sense (Fully Exonic) | COL8A1 |
| 11 | Sense (Fully Exonic) | KCNAB2 |
| 12 | Sense (Fully Exonic) | THBS1 |
| 14 | Sense (Fully Exonic) | CTGF |
| 15 | Sense (Fully Exonic) | CTGF |
| 16 | Sense (Fully Exonic) | VCAN |
| 18 | Sense (Fully Exonic) | IGKC |
| 19 | Sense (Fully Exonic) | IGKC |
| 21 | Sense (includes Intronic) | NFATC1 |
| 22 | Sense (Fully Exonic) | HMHA1 |
| 23 | Sense (Fully Exonic) | FCGR1B |
| 24 | Sense (Fully Exonic) | EDA2R |
| 25 | Sense (Fully Exonic) | COL8A1 |
| 26 | Sense (Fully Exonic) | COL12A1 |
| 27 | Sense (Fully Exonic) | HLA-B |
| 28 | Sense | HLA-F |
| 37 | Sense (Fully Exonic) | EGR1 |
| 40 | Sense (Fully Exonic) | SULF2 |
| 41 | Sense (Fully Exonic) | CERCAM |
| 42 | Sense (Fully Exonic) | ATF3 |
| 43 | Sense (Fully Exonic) | MIR21 |
| 45 | Sense (Fully Exonic) | IFIT2 |
| 47 | Sense (Fully Exonic) | IGLC3 |
| 48 | Sense (Fully Exonic) | IGLC3 |
| 49 | Sense (Fully Exonic) | IGLC3 |
| 50 | Sense (Fully Exonic) | IGLC3 |
| 51 | Sense (Fully Exonic) | IGLC3 |
| 54 | Sense (Fully Exonic) | IGLC3 |
| 55 | Sense (Fully Exonic) | ANGPTL2 |
| 56 | Sense (Fully Exonic) | COL5A2 |
| 58 | Sense (Fully Exonic) | THY1 |
| 59 | Sense (Fully Exonic) | NDN |
| 60 | Sense (Fully Exonic) | RGS2 |
| 61 | Sense (Fully Exonic) | MEIS3P2 |
| 62 | Sense (Fully Exonic) | GBP2 |
| 65 | Sense (Fully Exonic) | FAT1 |
| 66 | Sense (Fully Exonic) | COL1A1 |
| 68 | Sense (Fully Exonic) | MMP11 |
| 69 | Sense (Fully Exonic) | GADD45B |
| 71 | Sense (Fully Exonic) | MMP14 |
| 72 | Sense (Fully Exonic) | IGHG4 |
| 80 | Sense (Fully Exonic) | HCLS1 |
| 83 | No Transcript match | |
| 84 | Sense (Fully Exonic) | JAM3 |
| 86 | Sense (Fully Exonic) | TMEM49 |
| 87 | Sense (Fully Exonic) | LTBP2 |
| 88 | Sense (Fully Exonic) | IRS1 |
| 90 | Sense (Fully Exonic) | C17orf91 |
| 91 | Sense (Fully Exonic) | GPNMB |
| 92 | Sense (Fully Exonic) | FAM198B |
| 95 | Sense (Fully Exonic) | CHST15 |
| 97 | Sense (Fully Exonic) | DCN |
| 98 | Sense (Fully Exonic) | VCAM1 |
| 105 | Sense (Fully Exonic) | CIITA |
| 106 | Sense (Fully Exonic) | GAS7 |
| 107 | Sense (Fully Exonic) | COL3A1 |
| 110 | Sense (Fully Exonic) | ITGB2 |
| 111 | Sense (Fully Exonic) | ELN |
| 112 | Sense (Fully Exonic) | CMTM3 |
| 113 | Sense (Fully Exonic) | ANTXR1 |
| 118 | Sense (Fully Exonic) | IL4I1 |
| 119 | Sense (Fully Exonic) | ANTXR2 |
| 120 | Sense (Fully Exonic) | IGLC2 /// IGLC3 |
| 123 | Sense (Fully Exonic) | IGLC3 |
| 124 | Sense (Fully Exonic) | BST2 |
| 126 | Sense (Fully Exonic) | COL10A1 |
| 127 | Sense (Fully Exonic) | IGLC3 |
| 128 | Sense (Fully Exonic) | FBP1 |
| 129 | Sense (Fully Exonic) | RHOBTB3 |
| 131 | Sense (Fully Exonic) | CD74 |
| 132 | Sense (Fully Exonic) | ISM1 |
| 135 | Sense (Fully Exonic) | CSRNP1 |
| 138 | Sense (Fully Exonic) | DCN |
| 139 | Sense (Fully Exonic) | IGFBP4 |
| 143 | Sense (Fully Exonic) | CCDC80 |
| 148 | Sense (Fully Exonic) | COL3A1 |
| 150 | Sense (Fully Exonic) | ZFP36 |
| 151 | Sense (Fully Exonic) | MMP11 |
| 152 | Sense (Fully Exonic) | COL1A2 |
| 153 | Sense (Fully Exonic) | HLA-DPA1 |
| 154 | Sense (Fully Exonic) | TWIST1 |
| 155 | Sense (Fully Exonic) | ZNF154 |
| 157 | Sense (Fully Exonic) | IGLC3 |
| 159 | Sense (Fully Exonic) | IGKC |
| 160 | Sense (Fully Exonic) | IGHG1 |
| 162 | Sense (Fully Exonic) | COL1A2 |
| 163 | Sense (Fully Exonic) | APOC1 |
| 167 | AntiSense | EGR1 |
| 171 | Sense (Fully Exonic) | KIAA0146 |
| 174 | Sense (Fully Exonic) | TPM1 |
| 176 | Sense (includes Intronic) | DMD |
| 180 | No Transcript match | |
| 181 | Sense (Fully Exonic) | DUSP1 |
| 182 | Sense (Fully Exonic) | GBP1 |
| 185 | Sense (includes Intronic) | PDGFC |
| 186 | Sense (includes Intronic) | MSN |
| 188 | Sense (includes Intronic) | TPM1 |
| 189 | Sense (Fully Exonic) | EMB |
| 191 | Sense (Fully Exonic) | FOS |
| 195 | Sense (includes Intronic) | DPYSL3 |
| 197 | AntiSense | EGR1 |
| 198 | AntiSense | NRP2 |
| 201 | Sense (Fully Exonic) | MMP2 |
| 204 | Sense (Fully Exonic) | CTGF |
| 211 | Sense (Fully Exonic) | ACTA2 |
| 213 | Sense (Fully Exonic) | LOXL1 |
| 216 | Sense (Fully Exonic) | CDH11 |
| 218 | Sense (Fully Exonic) | LUM |
| 219 | Sense (Fully Exonic) | NNMT |
| 222 | Sense (Fully Exonic) | GJA1 |
| 225 | AntiSense | CTHRC1 |
| 229 | Sense (Fully Exonic) | CTSB |
| 232 | Sense (Fully Exonic) | PLAU |
| 233 | Sense (Fully Exonic) | PDGFRA |
| 242 | Sense (Fully Exonic) | VCAN |
| 243 | AntiSense | — |
| 244 | Sense (Fully Exonic) | IGHG4 /// IGHG2 /// IGHG1 ///IGHGP |
| 245 | Sense (Fully Exonic) | IGHG2 |
| 246 | Sense (includes Intronic) | C3orf26 |
| 247 | AntiSense | ATF3 |
| 248 | AntiSense | ATF3 |
| 250 | Sense (Fully Exonic) | FN1 |
| 251 | AntiSense | CALD1 |
| 252 | AntiSense | CALD1 |
| 256 | AntiSense | EGR1 |
| 261 | AntiSense | TWIST1 |
| 262 | AntiSense | TWIST1 |
| 263 | AntiSense | BATF2 |
| 264 | AntiSense | NFKBIZ |
| 265 | Sense (includes Intronic) | C3orf26 |
| 266 | AntiSense | LOXL1 |
| 267 | Sense (includes Intronic) | — |
| 269 | AntiSense | FN1 |
| 270 | AntiSense | COL1A1 |
| 272 | Sense (Fully Exonic) | TREH |
| 274 | AntiSense | APOL1 |
| 281 | Sense (Fully Exonic) | COL10A1 |
| 282 | Sense (Fully Exonic) | GAL3ST4 |
| 284 | Sense (Fully Exonic) | TAGLN |
| 285 | Sense (Fully Exonic) | TWIST1 |
| 286 | Sense (Fully Exonic) | HCLS1 |
| 288 | Sense (Fully Exonic) | ITGB2 |
| 290 | Sense (Fully Exonic) | HLA-B |
| 291 | Sense (Fully Exonic) | C17orf91 |
| 296 | Sense (Fully Exonic) | FBLIM1 |
| 297 | Sense (Fully Exonic) | COL15A1 |

TABLE 1B-continued

Genes in Clusters of FIG. 6

| SEQ NO: | Orientation | Gene Symbol |
|---|---|---|
| 298 | Sense (Fully Exonic) | AQP7P3 |
| 299 | AntiSense | IGFBP5 |
| 300 | Sense (Fully Exonic) | FANK1 |
| 301 | AntiSense | INS |
| 302 | Sense (Fully Exonic) | COL27A1 |
| 303 | Sense (Fully Exonic) | COL5A1 |
| 304 | Sense (Fully Exonic) | PRICKLE2 |
| 305 | Sense (Fully Exonic) | N/A |
| 306 | Sense (Fully Exonic) | GXYLT2 |
| 307 | Sense (includes Intronic) | KLF12 |
| 308 | No Transcript match | |
| 309 | Sense (Fully Exonic) | FBXO32 |
| 310 | No Transcript match | |
| 311 | Sense (Fully Exonic) | ASAH2B |
| 312 | AntiSense | PPFIBP1 |
| 313 | AntiSense | XIST |
| 314 | Sense (Fully Exonic) | IGFBP6 |
| 315 | Sense (Fully Exonic) | ROBO1 |
| 316 | Sense (Fully Exonic) | TPM1 |
| 317 | AntiSense | N/A |
| 318 | AntiSense | PLEKHG1 |
| 319 | Sense (Fully Exonic) | NR2F1 |
| 320 | Sense (Fully Exonic) | NPDC1 |
| 321 | AntiSense | INS |
| 322 | Sense (Fully Exonic) | TRAF5 |
| 323 | Sense (Fully Exonic) | CALD1 |
| 324 | Sense (includes Intronic) | CHRM3 |
| 325 | Sense (Fully Exonic) | AMOTL1 |
| 326 | Sense (includes Intronic) | COL12A1 |
| 327 | Sense (Fully Exonic) | PLXNA4 |
| 328 | Sense (includes Intronic) | TMEM43 |
| 329 | Sense (includes Intronic) | RORA |
| 330 | AntiSense | INS |
| 331 | Sense (Fully Exonic) | TSPAN18 |
| 332 | No Transcript match | |
| 333 | Sense (Fully Exonic) | TNC |
| 334 | Sense (Fully Exonic) | TYRO3 |
| 335 | AntiSense | EFNA5 |
| 336 | Sense (Fully Exonic) | MYL9 |
| 337 | Sense (Fully Exonic) | MIR198 |
| 338 | Sense (includes Intronic) | N/A |
| 339 | Sense (includes Intronic) | PLA2R1 |
| 340 | Sense (Fully Exonic) | COL14A1 |
| 341 | Sense (Fully Exonic) | NRP1 |
| 342 | Sense (Fully Exonic) | FSCN1 |
| 343 | Sense (includes Intronic) | PDGFD |
| 344 | No Transcript match | |
| 345 | Sense (includes Intronic) | DOCK4 |
| 346 | Sense (Fully Exonic) | TRIM13 |
| 347 | Sense (Fully Exonic) | IGFBP5 |
| 348 | Sense (Fully Exonic) | C19orf63 |
| 349 | AntiSense | KLF6 |
| 350 | AntiSense | TRIO |
| 351 | Sense (Fully Exonic) | COL4A1 |
| 352 | Sense (Fully Exonic) | EPDR1 |
| 353 | Sense (Fully Exonic) | FNDC1 |
| 354 | Sense (Fully Exonic) | IL1R1 |
| 355 | Sense (Fully Exonic) | CES4 |
| 356 | Sense (Fully Exonic) | GPR176 |
| 357 | Sense (includes Intronic) | GXYLT2 |
| 358 | AntiSense | WHSC1L1 |
| 359 | Sense (Fully Exonic) | N/A |
| 360 | Sense (Fully Exonic) | RGN |
| 361 | Sense (includes Intronic) | CA3 |
| 362 | Sense (Fully Exonic) | TIMP3 |
| 363 | Sense (Fully Exonic) | EFNA5 |
| 364 | Sense (Fully Exonic) | RASGRF2 |
| 365 | Sense (includes Intronic) | RELL1 |
| 366 | AntiSense | ACSS3 |
| 367 | Sense (Fully Exonic) | STMN3 |
| 368 | Sense (Fully Exonic) | N/A |
| 369 | AntiSense | C7orf29 |
| 370 | Sense (Fully Exonic) | HOXC6 |
| 371 | Sense (Fully Exonic) | KLF8 |
| 372 | Sense (includes Intronic) | SERINC5 |
| 373 | Sense (Fully Exonic) | AKT3 |
| 374 | Sense (Fully Exonic) | TGFB2 |
| 375 | AntiSense | WNT5A |
| 376 | No Transcript match | |
| 377 | No Transcript match | |
| 378 | AntiSense | IGFBP7 |
| 379 | No Transcript match | |
| 380 | Sense (includes Intronic) | SULT1C4 |
| 381 | Sense (Fully Exonic) | AASS |
| 382 | Sense (Fully Exonic) | HEPH |
| 383 | Sense (Fully Exonic) | ADH5 |
| 384 | Sense (Fully Exonic) | TIMP2 |
| 385 | Sense (Fully Exonic) | EMP1 |
| 386 | Sense (Fully Exonic) | CXCL14 |
| 387 | Sense (Fully Exonic) | ZNF548 |
| 388 | Sense (Fully Exonic) | SGCB |
| 389 | Sense (includes Intronic) | ASH2L |
| 390 | Sense (includes Intronic) | SERINC5 |
| 391 | No Genome match | |
| 392 | Sense (Fully Exonic) | TMEM159 |
| 393 | Sense (includes Intronic) | RBMS3 |
| 394 | Sense (Fully Exonic) | TMEM49 |
| 395 | Sense (includes Intronic) | RORA |
| 396 | No Transcript match | |
| 397 | AntiSense | ZNF608 |
| 398 | No Genome match | |
| 399 | Sense (Fully Exonic) | ADAMTS2 |
| 400 | Sense (Fully Exonic) | APCDD1 |
| 401 | AntiSense | GXYLT2 |
| 402 | Sense (Fully Exonic) | XIST |
| 403 | Sense (Fully Exonic) | MBNL2 |
| 404 | Sense (Fully Exonic) | SHF |
| 405 | Sense (includes Intronic) | APBB2 |
| 406 | No Transcript match | |
| 407 | Sense (Fully Exonic) | COL14A1 |
| 408 | Sense (Fully Exonic) | IGFBP5 |
| 409 | Sense (Fully Exonic) | CREB5 |
| 410 | AntiSense | INS |
| 411 | Sense (Fully Exonic) | BAHCC1 |
| 412 | Sense (Fully Exonic) | RFXAP |
| 413 | Sense (Fully Exonic) | INS |
| 414 | Sense (Fully Exonic) | DDR2 |
| 415 | Sense (Fully Exonic) | CA12 |
| 416 | Sense (Fully Exonic) | RHOB |
| 417 | Sense (Fully Exonic) | N/A |
| 418 | Sense (Fully Exonic) | SNORD116-4 |
| 419 | Sense (Fully Exonic) | MEG3 |
| 420 | Sense (Fully Exonic) | WNT4 |
| 421 | Sense (Fully Exonic) | FBLN2 |
| 422 | AntiSense | DAAM1 |
| 423 | No Transcript match | |
| 424 | Sense (Fully Exonic) | CHN1 |
| 425 | Sense (includes Intronic) | APBB2 |
| 426 | Sense (Fully Exonic) | PTRF |
| 427 | AntiSense | IGF1 |
| 428 | Sense (Fully Exonic) | UST |
| 429 | Sense (Fully Exonic) | SMARCA1 |
| 430 | Sense (includes Intronic) | N/A |
| 431 | Sense (Fully Exonic) | IGLC3 |
| 432 | AntiSense | INS |
| 433 | Sense (Fully Exonic) | KANK4 |
| 434 | AntiSense | IGF1 |
| 435 | Sense (Fully Exonic) | CYP27A1 |
| 436 | AntiSense | EIF2B5 |
| 437 | No Transcript match | |
| 438 | Sense (Fully Exonic) | SNRNP25 |
| 439 | Sense (Fully Exonic) | SETD7 |
| 440 | Sense (Fully Exonic) | MSX1 |
| 441 | Sense (Fully Exonic) | HOPX |
| 442 | Sense (Fully Exonic) | NID2 |
| 443 | Sense (Fully Exonic) | IGF1 |
| 444 | Sense (Fully Exonic) | PSD3 |
| 445 | Sense (Fully Exonic) | FGFR1 |
| 446 | Sense (Fully Exonic) | ETV1 |
| 447 | Sense (Fully Exonic) | ZNF655 |
| 448 | No Genome match | |
| 449 | AntiSense | INS |

TABLE 1B-continued

Genes in Clusters of FIG. 6

| SEQ NO: | Orientation | Gene Symbol |
|---|---|---|
| 450 | Sense (Fully Exonic) | SFRP2 |
| 451 | Sense (Fully Exonic) | SPAG16 |
| 452 | AntiSense | NR2F2 |
| 453 | Sense (includes Intronic) | SYNPO2 |
| 454 | Sense (Fully Exonic) | FAM101B |
| 455 | AntiSense | IGF2 |
| 456 | Sense (Fully Exonic) | CA3 |
| 457 | Sense (Fully Exonic) | XIST |
| 458 | No Transcript match | |
| 459 | Sense (Fully Exonic) | WNT7A |
| 460 | Sense (includes Intronic) | N/A |
| 461 | Sense (Fully Exonic) | FGFR1 |
| 462 | AntiSense | FXYD6 |
| 463 | Sense (Fully Exonic) | FGFR1 |
| 464 | Sense (includes Intronic) | IGFBP7 |
| 465 | Sense (Fully Exonic) | TIMP2 |
| 466 | Sense (Fully Exonic) | DUSP1 |
| 467 | Sense (includes Intronic) | SERINC5 |
| 468 | No Transcript match | |
| 469 | Sense (Fully Exonic) | ABLIM1 |
| 470 | Sense (Fully Exonic) | ARL4A |
| 471 | AntiSense | SH3TC2 |
| 472 | AntiSense | NR2F2 |
| 473 | Sense (Fully Exonic) | ENG |
| 474 | Sense (Fully Exonic) | MGP |
| 475 | Sense (Fully Exonic) | MEG3 |
| 476 | AntiSense | FAM115A |
| 477 | Sense (Fully Exonic) | EGR1 |
| 478 | Sense (Fully Exonic) | SNORD116-3 |
| 479 | Sense (Fully Exonic) | AEBP1 |
| 480 | Sense (includes Intronic) | SDK1 |
| 481 | Sense (Fully Exonic) | ENC1 |
| 482 | Sense (Fully Exonic) | SNORD116-7 |
| 483 | Sense (Fully Exonic) | N/A |
| 484 | Sense (Fully Exonic) | APOD |
| 485 | AntiSense | N/A |
| 486 | AntiSense | GAS1 |
| 487 | Sense (Fully Exonic) | VPS36 |
| 488 | No Transcript match | |
| 489 | Sense (Fully Exonic) | SPHK2 |
| 490 | Sense (Fully Exonic) | SNORD116-8 |
| 491 | Sense (Fully Exonic) | MYO10 |
| 492 | Sense (Fully Exonic) | HOXC6 |
| 493 | Sense (Fully Exonic) | RNF149 |
| 494 | Sense (Fully Exonic) | BTG2 |
| 495 | Sense (includes Intronic) | MAP3K1 |
| 496 | Sense (Fully Exonic) | SNORD116-23 |
| 497 | Sense (includes Intronic) | ACSL4 |
| 498 | Sense (Fully Exonic) | CYP27C1 |
| 499 | Sense (includes Intronic) | COL12A1 |
| 500 | Sense (Fully Exonic) | IGFBP5 |
| 501 | Sense (Fully Exonic) | DUSP4 |
| 502 | Sense (Fully Exonic) | PFKFB3 |
| 503 | Sense (Fully Exonic) | SDC2 |
| 504 | AntiSense | FXYD6 |
| 505 | Sense (Fully Exonic) | COL5A1 |
| 506 | Sense (Fully Exonic) | MARCKS |
| 507 | Sense (Fully Exonic) | IRS2 |
| 508 | Sense (Fully Exonic) | N/A |
| 509 | AntiSense | FSCN1 |
| 510 | Sense (Fully Exonic) | FYN |
| 511 | Sense (Fully Exonic) | IGFBP5 |
| 512 | Sense (Fully Exonic) | NUDT4P1 |
| 513 | Sense (Fully Exonic) | NFKBIZ |
| 514 | Sense (Fully Exonic) | N/A |
| 515 | Sense (Fully Exonic) | C7orf41 |
| 516 | Sense (Fully Exonic) | MEG3 |
| 517 | Sense (Fully Exonic) | N/A |
| 518 | Sense (Fully Exonic) | PLEKHG1 |
| 519 | Sense (Fully Exonic) | ZNF827 |
| 520 | Sense (Fully Exonic) | ZNF175 |
| 521 | Sense (Fully Exonic) | XIST |
| 522 | Sense (includes Intronic) | GSN |
| 523 | Sense (includes Intronic) | RORA |
| 524 | Sense (Fully Exonic) | CA13 |
| 525 | AntiSense | TMX4 |
| 526 | Sense (Fully Exonic) | KIT |
| 527 | Sense (includes Intronic) | WDR78 |
| 528 | Sense (Fully Exonic) | ECEL1 |
| 529 | Sense (Fully Exonic) | XIST |
| 530 | Sense (Fully Exonic) | PROCR |
| 531 | Sense (Fully Exonic) | C9orf167 |
| 532 | Sense (Fully Exonic) | MUC6 |
| 533 | Sense (includes Intronic) | P4HA2 |
| 534 | Sense (Fully Exonic) | FAM69C |
| 535 | Sense (Fully Exonic) | NOX4 |
| 536 | Sense (includes Intronic) | N/A |
| 537 | No Transcript match | |
| 538 | Sense (Fully Exonic) | SMOX |
| 539 | Sense (Fully Exonic) | KIAA0922 |
| 540 | No Transcript match | |
| 541 | Sense (Fully Exonic) | XIST |
| 542 | Sense (Fully Exonic) | NPAS2 |
| 543 | Sense (Fully Exonic) | NAV1 |
| 544 | Sense (includes Intronic) | N/A |
| 545 | Sense (Fully Exonic) | HLA-A |
| 546 | Sense (Fully Exonic) | FAM46C |
| 547 | Sense (Fully Exonic) | N/A |
| 548 | Sense (Fully Exonic) | SLAMF7 |
| 549 | Sense (Fully Exonic) | FCER1G |
| 550 | Sense (Fully Exonic) | C1S |
| 551 | Sense (Fully Exonic) | NUPR1 |
| 552 | AntiSense | C1QC |
| 553 | AntiSense | SAT1 |
| 554 | Sense (Fully Exonic) | SOD2 |
| 555 | Sense (Fully Exonic) | IRF1 |
| 556 | Sense (Fully Exonic) | SFN |
| 557 | AntiSense | LTB |
| 558 | Sense (Fully Exonic) | ARID5A |
| 559 | Sense (Fully Exonic) | BST2 |
| 560 | Sense (Fully Exonic) | HLA-F |
| 561 | Sense (Fully Exonic) | XAF1 |
| 562 | Sense (Fully Exonic) | TCOF1 |
| 563 | Sense (Fully Exonic) | RPL23AP1 |
| 564 | Sense (Fully Exonic) | IL1RN |
| 565 | Sense (Fully Exonic) | IFIT5 |
| 566 | Sense (Fully Exonic) | B2M |
| 567 | AntiSense | GBP1 |
| 568 | Sense (Fully Exonic) | HLA-F |
| 569 | Sense (Fully Exonic) | DGKA |
| 570 | Sense (Fully Exonic) | XBP1 |
| 571 | Sense (Fully Exonic) | PLCG2 |
| 572 | Sense (Fully Exonic) | FAM46C |
| 573 | No Genome match | |
| 574 | Sense (Fully Exonic) | TREM2 |
| 575 | Sense (Fully Exonic) | LGALS9 |
| 576 | Sense (Fully Exonic) | HLA-DPB1 |
| 577 | AntiSense | ODF3B |
| 578 | Sense (Fully Exonic) | MX1 |
| 579 | Sense (Fully Exonic) | STAT1 |
| 580 | Sense (Fully Exonic) | CTSB |
| 581 | Sense (Fully Exonic) | FAM26F |
| 582 | Sense (includes Intronic) | PARP14 |
| 583 | AntiSense | SAT1 |
| 584 | Sense (Fully Exonic) | CTSS |
| 585 | No Transcript match | |
| 586 | Sense (Fully Exonic) | CTSB |
| 587 | Sense (Fully Exonic) | ADAM8 |
| 588 | Sense (includes Intronic) | B2M |
| 589 | Sense (Fully Exonic) | FLVCR2 |
| 590 | Sense (Fully Exonic) | TYROBP |
| 591 | AntiSense | SAMD9L |
| 592 | Sense (Fully Exonic) | SAMD9L |
| 593 | Sense (Fully Exonic) | SIGLEC1 |
| 594 | Sense (Fully Exonic) | MMP7 |
| 595 | Sense (Fully Exonic) | APOL1 |
| 596 | Sense (Fully Exonic) | CYLD |
| 597 | Sense (Fully Exonic) | HLA-B |
| 598 | Sense (Fully Exonic) | SAT1 |
| 599 | Sense (Fully Exonic) | C1QB |
| 600 | Sense (Fully Exonic) | HLA-DMB |
| 601 | Sense (Fully Exonic) | NLRC5 |

TABLE 1B-continued

Genes in Clusters of FIG. 6

| SEQ NO: | Orientation | Gene Symbol |
|---|---|---|
| 602 | Sense (Fully Exonic) | FAM20A |
| 603 | AntiSense | N/A |
| 604 | Sense (Fully Exonic) | STAT1 |
| 605 | Sense (includes Intronic) | STAT1 |
| 606 | Sense (Fully Exonic) | STAT1 |
| 607 | AntiSense | N/A |
| 608 | Sense (Fully Exonic) | DERL3 |
| 609 | Sense (Fully Exonic) | HLA-F |
| 610 | Sense (Fully Exonic) | MAFB |
| 611 | Sense (Fully Exonic) | CD4 |
| 612 | Sense (Fully Exonic) | HLA-A |
| 613 | Sense (Fully Exonic) | UBE2L6 |
| 614 | Sense (Fully Exonic) | C1QC |
| 615 | Sense (Fully Exonic) | CD163 |
| 616 | Sense (Fully Exonic) | LRMP |
| 617 | Sense (Fully Exonic) | C11orf17 |
| 618 | Sense (Fully Exonic) | XAF1 |
| 619 | Sense (Fully Exonic) | GLRX |
| 620 | Sense (Fully Exonic) | IFIH1 |
| 621 | Sense (Fully Exonic) | CD44 |
| 622 | Sense (Fully Exonic) | LITAF |
| 623 | Sense (Fully Exonic) | CCDC69 |
| 624 | Sense (Fully Exonic) | GBP5 |
| 625 | Sense (Fully Exonic) | PML |
| 626 | Sense (Fully Exonic) | SAMD9 |
| 627 | Sense (Fully Exonic) | CBR3 |
| 628 | Sense (Fully Exonic) | RASGRP2 |
| 629 | Sense (Fully Exonic) | FCGR2A |
| 630 | Sense (Fully Exonic) | BST2 |
| 631 | Sense (Fully Exonic) | HLA-A |

TABLE 1C

Figure 11A:
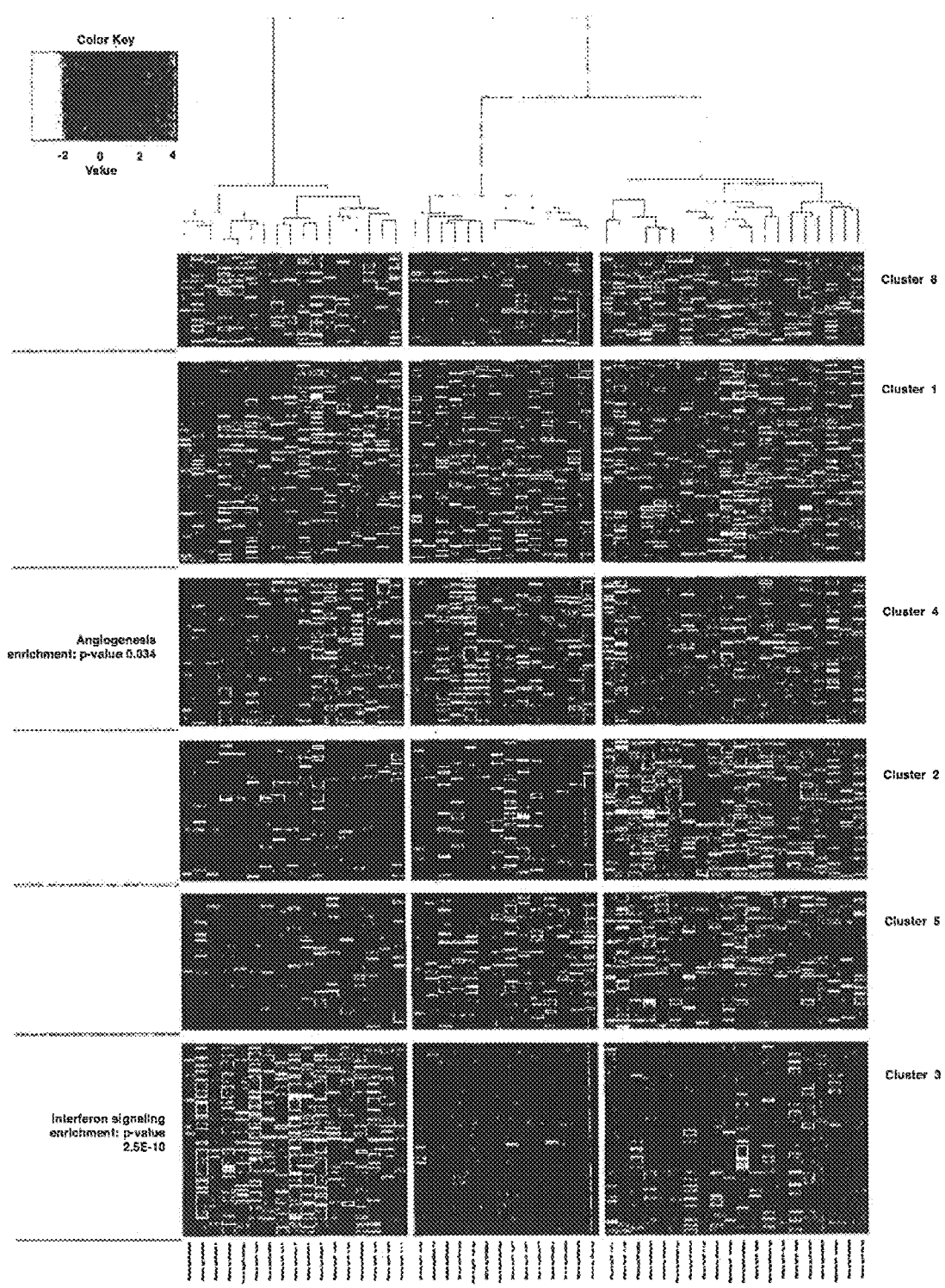
FIGS. 11A and 11B provide heatmaps representing the hierarchical agglomerative clustering analysis of the most variable genes across 51 ER negative samples (FIG. 11A) of a breast cancer sample set and the most variable genes across 56 ER positive samples of a breast cancer sample set (FIG. 11B). The functional analysis of the probe set clusters is summarized on the right hand side of the image for those clusters showing vasculature development/angiogenesis or immune response/IFN signalling.
Figure 11B:
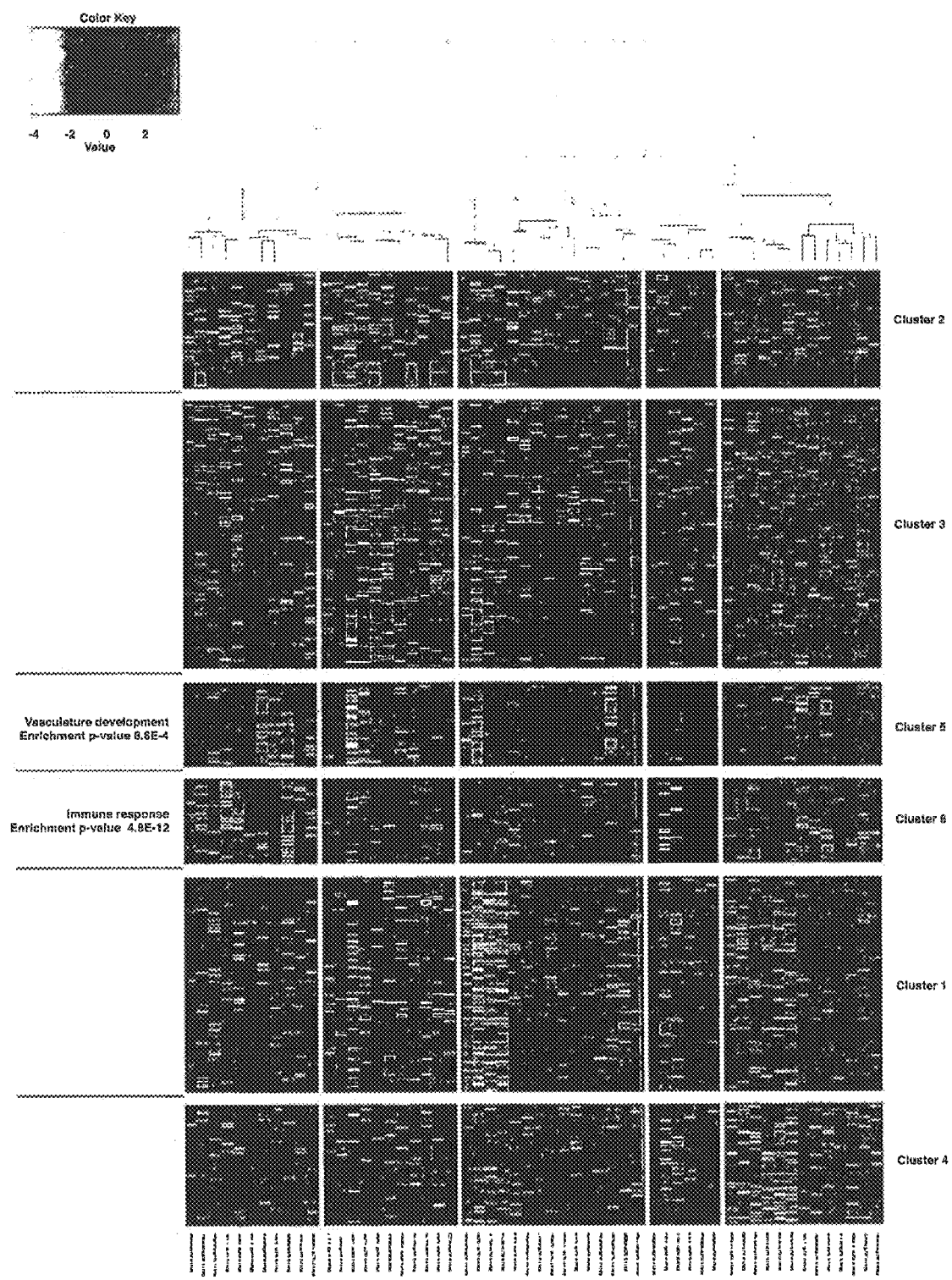

Angiogenesis and immune response cluster genes of FIGS. 11A and 11B

| SEQ No. | ER group | Gene Symbol | Orientation |
|---|---|---|---|
| 632 | ER pos | STAT1 | Sense (Fully Exonic) |
| 709 | ER pos | STAT1 | Sense (Fully Exonic) |
| 803 | ER neg | HOXD3 | Sense (includes Intronic) |
| 804 | ER neg | LCP1 | Sense (Fully Exonic) |
| 875 | ER neg | SPON1 | Sense (Fully Exonic) |
| 633 | ER pos | IGF1 | Sense (Fully Exonic) |
| 805 | ER neg | FHL1 | Sense (Fully Exonic) |
| 806 | ER neg | MS4A1 | Sense (Fully Exonic) |
| 876 | ER neg | FN1 | Sense (Fully Exonic) |
| 710 | ER pos | FN1 | Sense (Fully Exonic) |
| 634 | ER pos | HLA-DPA1 | Sense (Fully Exonic) |
| 877 | ER neg | ADAM12 | Sense (Fully Exonic) |
| 711 | ER pos | ITGBL1 | Sense (Fully Exonic) |
| 712 | ER pos | POSTN | Sense (Fully Exonic) |
| 635 | ER pos | IGKV3-20 /// IGKV3D-20 | AntiSense |
| 748 | ER neg, ER pos | DDX58 | Sense (Fully Exonic) |
| 636 | ER pos | SLAMF7 | Sense (Fully Exonic) |
| 878 | ER neg | AGPAT4 | Sense (Fully Exonic) |
| 959 | ER neg, ER pos | FAM46C | Sense (Fully Exonic) |
| 713 | ER pos | GXYLT2 | Sense (includes Intronic) |
| 714 | ER pos | SNX5 | Sense (Fully Exonic) |
| 637 | ER pos | | No Genome match |
| 879 | ER neg | PRICKLE1 | Sense (Fully Exonic) |
| 922 | ER neg, ER pos | IL7R | Sense (Fully Exonic) |
| 750 | ER neg, ER pos | CMPK2 | Sense (Fully Exonic) |
| 638 | ER pos | KLHL36 | Sense (Fully Exonic) |
| 807 | ER neg | CD274 | Sense (Fully Exonic) |
| 880 | ER neg | NRP2 | AntiSense |
| 924 | ER neg, ER pos | POSTN | Sense (includes Intronic) |
| 639 | ER pos | CAMK2N1 | AntiSense |
| 881 | ER neg | COL1A2 | Sense (Fully Exonic) |
| 715 | ER pos | N/A | AntiSense |
| 716 | ER pos | | No Transcript match |
| 717 | ER pos | COL12A1 | Sense (Fully Exonic) |
| 640 | ER pos | MIR143 | Sense (Fully Exonic) |
| 808 | ER neg | | No Genome match |
| 960 | ER neg, ER pos | DNM3 | AntiSense |
| 718 | ER pos | BNC2 | Sense (includes Intronic) |
| 641 | ER pos | BCL11B | Sense (includes Intronic) |
| 809 | ER neg | CYBB | Sense (Fully Exonic) |
| 882 | ER neg | COL12A1 | Sense (Fully Exonic) |
| 642 | ER pos | OR2I1P | AntiSense |
| 752 | ER neg, ER pos | EPSTI1 | Sense (Fully Exonic) |
| 926 | ER neg, ER pos | GXYLT2 | Sense (Fully Exonic) |
| 643 | ER pos | SAMD9L | Sense (Fully Exonic) |
| 810 | ER neg | SLC2A3 | Sense (Fully Exonic) |
| 927 | ER neg, ER pos | IGKJ3 /// IGKJ4 | Sense (Fully Exonic) |
| 644 | ER pos | THBS1 | Sense (Fully Exonic) |
| 811 | ER neg | GLUL | Sense (Fully Exonic) |
| 812 | ER neg | | No Transcript match |
| 813 | ER neg | THSD7A | Sense (includes Intronic) |
| 928 | ER neg, ER pos | COL11A1 | Sense (Fully Exonic) |
| 645 | ER pos | | No Transcript match |
| 814 | ER neg | SPP1 | AntiSense |
| 815 | ER neg | TIMP3 | Sense (Fully Exonic) |
| 883 | ER neg | FBN1 | Sense (Fully Exonic) |
| 646 | ER pos | IGFBP5 | Sense (Fully Exonic) |
| 816 | ER neg | IKZF1 | Sense (Fully Exonic) |
| 817 | ER neg | CTGF | AntiSense |
| 884 | ER neg | COL5A2 | AntiSense |
| 647 | ER pos | PALMD | Sense (Fully Exonic) |
| 818 | ER neg | IGKV4-1 | Sense (Fully Exonic) |
| 756 | ER neg, ER pos | N/A | Sense (Fully Exonic) |
| 648 | ER pos | NLRC3 | Sense (Fully Exonic) |
| 819 | ER neg | TNFRSF13B | Sense (Fully Exonic) |
| 885 | ER neg | APOC1 | Sense (Fully Exonic) |
| 649 | ER pos | ELN | Sense (Fully Exonic) |
| 757 | ER neg, ER pos | | No Genome match |
| 650 | ER pos | ELN | Sense (Fully Exonic) |
| 758 | ER neg, ER pos | IGKC | Sense (Fully Exonic) |
| 651 | ER pos | CIITA | Sense (Fully Exonic) |
| 788 | ER neg, ER pos | CCR7 | Sense (Fully Exonic) |
| 719 | ER pos | STAT1 | Sense (Fully Exonic) |
| 720 | ER pos | SDC1 | Sense (Fully Exonic) |
| 721 | ER pos | ISG15 | Sense (Fully Exonic) |
| 722 | ER pos | APOC1 | Sense (Fully Exonic) |
| 652 | ER pos | INS /// IGF2 | Sense (Fully Exonic) |
| 820 | ER neg | LPL | Sense (Fully Exonic) |
| 962 | ER neg, ER pos | IFI27 | Sense (Fully Exonic) |
| 723 | ER pos | CTSK | Sense (Fully Exonic) |
| 724 | ER pos | PLEK | Sense (Fully Exonic) |
| 725 | ER pos | MIR198 | Sense (Fully Exonic) |
| 759 | ER neg, ER pos | IGJ | AntiSense |
| 653 | ER pos | PXDN | Sense (Fully Exonic) |
| 790 | ER neg, ER pos | ENO2 | Sense (Fully Exonic) |
| 726 | ER pos | CILP | Sense (Fully Exonic) |
| 726 | ER neg, ER pos | GBP4 | Sense (Fully Exonic) |
| 654 | ER pos | GBP1 | Sense (Fully Exonic) |
| 886 | ER neg | SULF1 | Sense (Fully Exonic) |
| 655 | ER pos | EFEMP1 | Sense (Fully Exonic) |

TABLE 1C-continued

Angiogenesis and immune response cluster genes of FIGS. 11A and 11B

| SEQ No. | ER group | Gene Symbol | Orientation |
|---|---|---|---|
| 761 | ER neg, ER pos | MX1 | Sense (Fully Exonic) |
| 656 | ER pos | CD109 | Sense (Fully Exonic) |
| 887 | ER neg | | No Transcript match |
| 762 | ER neg, ER pos | CXCL10 | Sense (Fully Exonic) |
| 657 | ER pos | FYB | Sense (Fully Exonic) |
| 791 | ER neg, ER pos | IFI44 | Sense (Fully Exonic) |
| 727 | ER pos | COL5A1 | Sense (Fully Exonic) |
| 658 | ER pos | TIMP3 | Sense (Fully Exonic) |
| 888 | ER neg | CADM1 | AntiSense |
| 659 | ER pos | STAT1 | AntiSense |
| 889 | ER neg | MXRA5 | AntiSense |
| 660 | ER pos | CCDC152 | Sense (Fully Exonic) |
| 821 | ER neg | MX1 | AntiSense |
| 890 | ER neg | C1QC | AntiSense |
| 792 | ER neg, ER pos | N/A | Sense (includes Intronic) |
| 728 | ER pos | FNDC1 | AntiSense |
| 661 | ER pos | HOXC5 /// HOXC10 | AntiSense |
| 822 | ER neg | GABBR1 /// UBD | AntiSense |
| 823 | ER neg | CYP1B1 | AntiSense |
| 824 | ER neg | SPP1 | Sense (Fully Exonic) |
| 824 | ER neg, ER pos | FYB | Sense (Fully Exonic) |
| 662 | ER pos | | No Transcript match |
| 825 | ER neg | GBP5 | Sense (Fully Exonic) |
| 937 | ER neg, ER pos | IGHA1 | Sense (Fully Exonic) |
| 663 | ER pos | CAMK2N1 | Sense (Fully Exonic) |
| 826 | ER neg | SASH3 | Sense (Fully Exonic) |
| 827 | ER neg | COL14A1 | Sense (Fully Exonic) |
| 793, | ER neg, ER pos | CD79A /// ARHGEF1 | Sense (Fully Exonic) |
| 729 | ER pos | LAIR1 | Sense (Fully Exonic) |
| 664 | ER pos | APOBEC3G | Sense (Fully Exonic) |
| 828 | ER neg | GPX8 | Sense (Fully Exonic) |
| 829 | ER neg | RTP4 | Sense (Fully Exonic) |
| 830 | ER neg | IFIH1 | Sense (Fully Exonic) |
| 891 | ER neg | IFI6 | Sense (Fully Exonic) |
| 730 | ER pos | IFI6 | Sense (Fully Exonic) |
| 665 | ER pos | C1orf113 | Sense (Fully Exonic) |
| 831 | ER neg | FAM26F | Sense (Fully Exonic) |
| 832 | ER neg | PARP9 | Sense (Fully Exonic) |
| 833 | ER neg | ARHGAP9 | Sense (Fully Exonic) |
| 765 | ER neg, ER pos | FNDC1 | Sense (Fully Exonic) |
| 666 | ER pos | C13orf33 | Sense (Fully Exonic) |
| 766 | ER neg, ER pos | GBP5 | Sense (Fully Exonic) |
| 667 | ER pos | VNN2 | Sense (Fully Exonic) |
| 892 | ER neg | RSAD2 | Sense (Fully Exonic) |
| 668 | ER pos | PTPRC | Sense (Fully Exonic) |
| 893 | ER neg | LRRC15 | Sense (Fully Exonic) |
| 731 | ER pos | CTHRC1 | Sense (Fully Exonic) |
| 669 | ER pos | SMARCA1 | Sense (Fully Exonic) |
| 894 | ER neg | STAT1 | Sense (Fully Exonic) |
| 767 | ER neg, ER pos | IGJ | Sense (Fully Exonic) |
| 670 | ER pos | DACT3 | Sense (Fully Exonic) |
| 834 | ER neg | PHLDB2 | Sense (Fully Exonic) |
| 967 | ER neg, ER pos | IL2RG | Sense (Fully Exonic) |
| 732 | ER pos | C1orf162 | Sense (Fully Exonic) |
| 768 | ER neg, ER pos | CECR1 | Sense (Fully Exonic) |
| 671 | ER pos | BTN3A2 /// BTN3A3 | Sense (Fully Exonic) |
| 835 | ER neg | CES1 /// CES4 | Sense (Fully Exonic) |
| 836 | ER neg | TBC1D10C | Sense (Fully Exonic) |
| 837 | ER neg | CCDC80 | Sense (Fully Exonic) |
| 895 | ER neg | GAS7 | Sense (Fully Exonic) |
| 672 | ER pos | LPL | Sense (Fully Exonic) |
| 896 | ER neg | CD163 | Sense (Fully Exonic) |
| 795 | ER neg, ER pos | LYZ | Sense (Fully Exonic) |
| 733 | ER pos | NAPSB | Sense (Fully Exonic) |
| 673 | ER pos | OAS2 | Sense (Fully Exonic) |
| 769 | ER neg, ER pos | ZNF469 | Sense (Fully Exonic) |
| 674 | ER pos | KIF26A | Sense (Fully Exonic) |
| 770 | ER neg, ER pos | IGHG1 /// IGHG2 /// IGHG3 | Sense (Fully Exonic) |
| 675 | ER pos | N/A | Sense (Fully Exonic) |
| 838 | ER neg | DDX60L | Sense (Fully Exonic) |
| 839 | ER neg | SCD5 | Sense (Fully Exonic) |
| 840 | ER neg | ANPEP | Sense (Fully Exonic) |
| 841 | ER neg | FABP4 | Sense (Fully Exonic) |
| 771 | ER neg, ER pos | IL10RA | Sense (Fully Exonic) |
| 676 | ER pos | CXCL10 | Sense (Fully Exonic) |
| 897 | ER neg | APOC1 | Sense (Fully Exonic) |
| 677 | ER pos | APOD | Sense (Fully Exonic) |
| 842 | ER neg | APOD | Sense (Fully Exonic) |
| 843 | ER neg | DST | Sense (Fully Exonic) |
| 772 | ER neg, ER pos | CD2 | Sense (Fully Exonic) |
| 678 | ER pos | CD22 | Sense (Fully Exonic) |
| 844 | ER neg | CD52 | Sense (Fully Exonic) |
| 898 | ER neg | CTSK | Sense (Fully Exonic) |
| 773, | ER neg, ER pos | CCR7 | Sense (Fully Exonic) |
| 679 | ER pos | CTGF | Sense (Fully Exonic) |
| 899 | ER neg | EDN2 | Sense (Fully Exonic) |
| 680 | ER pos | EGR1 | Sense (Fully Exonic) |
| 845 | ER neg | ENO2 | Sense (Fully Exonic) |
| 900 | ER neg | IFI6 | Sense (Fully Exonic) |
| 681 | ER pos | HLA-DOA | Sense (Fully Exonic) |
| 846 | ER neg | TNC | Sense (Fully Exonic) |
| 847 | ER neg | IDO1 | Sense (Fully Exonic) |
| 848 | ER neg | ID1 | Sense (Fully Exonic) |
| 901 | ER neg | IRF1 | Sense (Fully Exonic) |
| 774, | ER neg, ER pos | ITGAL | Sense (Fully Exonic) |
| 682 | ER pos | KRT81 | Sense (Fully Exonic) |
| 902 | ER neg | LUM | Sense (Fully Exonic) |
| 734 | ER pos | MFAP2 | Sense (Fully Exonic) |
| 683 | ER pos | CXCL9 | Sense (Fully Exonic) |
| 775, | ER neg, ER pos | MMP13 | Sense (Fully Exonic) |
| 684 | ER pos | MSX1 | Sense (Fully Exonic) |
| 903 | ER neg | MX1 | Sense (Fully Exonic) |
| 685 | ER pos | TWIST1 | Sense (Fully Exonic) |
| 904 | ER neg | OAS2 | Sense (Fully Exonic) |
| 686 | ER pos | PIK3CG | Sense (Fully Exonic) |
| 905 | ER neg | PLAU | Sense (Fully Exonic) |
| 735 | ER pos | COL10A1 | Sense (Fully Exonic) |
| 687 | ER pos | PSMB9 | Sense (Fully Exonic) |
| 849 | ER neg | FBP1 | Sense (Fully Exonic) |
| 850 | ER neg | PTN | Sense (Fully Exonic) |
| 776 | ER neg, ER pos | RAC2 | Sense (Fully Exonic) |
| 688 | ER pos | CCL5 | Sense (Fully Exonic) |
| 851 | ER neg | CCL5 | Sense (Fully Exonic) |
| 852 | ER neg | CCL21 | Sense (Fully Exonic) |
| 906 | ER neg | THBS2 | Sense (Fully Exonic) |
| 689 | ER pos | TAP1 | Sense (Fully Exonic) |
| 853 | ER neg | IGFBP5 | Sense (Fully Exonic) |
| 854 | ER neg | IGF2 | Sense (Fully Exonic) |
| 855 | ER neg | SELL | Sense (Fully Exonic) |
| 777, | ER neg, ER pos | GJB2 | Sense (Fully Exonic) |
| 690 | ER pos | F2RL2 | Sense (Fully Exonic) |
| 907 | ER neg | VCAN | Sense (Fully Exonic) |
| 691 | ER pos | ALDH1A3 | Sense (Fully Exonic) |
| 856 | ER neg | EGR3 | Sense (Fully Exonic) |
| 796 | ER neg, ER pos | MMP2 | Sense (Fully Exonic) |
| 736 | ER pos | MMP2 | Sense (Fully Exonic) |

TABLE 1C-continued

Angiogenesis and immune response cluster genes of FIGS. 11A and 11B

| SEQ No. | ER group | Gene Symbol | Orientation |
|---|---|---|---|
| 778 | ER neg, ER pos | SPOCK1 | Sense (Fully Exonic) |
| 797 | ER neg, ER pos | SPOCK1 | Sense (Fully Exonic) |
| 737 | ER pos | COL1A1 | Sense (Fully Exonic) |
| 692 | ER pos | SPARCL1 | Sense (Fully Exonic) |
| 857 | ER neg | CD3D | Sense (Fully Exonic) |
| 798 | ER neg, ER pos | CD3E | Sense (Fully Exonic) |
| 738 | ER pos | COL3A1 | Sense (Fully Exonic) |
| 693 | ER pos | CXCL14 | Sense (Fully Exonic) |
| 908 | ER neg | ADAMTS4 | Sense (Fully Exonic) |
| 779 | ER neg, ER pos | NCKAP1L | Sense (Fully Exonic) |
| 694 | ER pos | CALCOCO2 | Sense (Fully Exonic) |
| 909 | ER neg | MMP11 | Sense (Fully Exonic) |
| 695 | ER pos | TRM22 | Sense (Fully Exonic) |
| 910 | ER neg | OAS3 | Sense (Fully Exonic) |
| 739 | ER pos | OAS3 | Sense (Fully Exonic) |
| 696 | ER pos | POU2AF1 | Sense (Fully Exonic) |
| 780 | ER neg, ER pos | GABBR1 /// UBD | Sense (Fully Exonic) |
| 697 | ER pos | FOSB | Sense (Fully Exonic) |
| 781 | ER neg, ER pos | IFI44L | Sense (Fully Exonic) |
| 698 | ER pos | PIM2 | Sense (Fully Exonic) |
| 858 | ER neg | KLRK1 | Sense (Fully Exonic) |
| 859 | ER neg | TAGLN | Sense (Fully Exonic) |
| 860 | ER neg | CD36 | Sense (Fully Exonic) |
| 861 | ER neg | CYP27C1 | Sense (Fully Exonic) |
| 862 | ER neg | PDLIM3 | Sense (Fully Exonic) |
| 911 | ER neg | RNF144A | Sense (Fully Exonic) |
| 782 | ER neg, ER pos | SPOCK2 | Sense (Fully Exonic) |
| 699 | ER pos | FAM19A5 | Sense (Fully Exonic) |
| 863 | ER neg | ABI3BP | Sense (Fully Exonic) |
| 912 | ER neg | TMEM158 | Sense (Fully Exonic) |
| 700 | ER pos | CCDC69 | Sense (Fully Exonic) |
| 913 | ER neg | C1QA | Sense (Fully Exonic) |
| 701 | ER pos | ETV7 | Sense (Fully Exonic) |
| 914 | ER neg | N/A | Sense (Fully Exonic) |
| 702 | ER pos | USP18 | Sense (Fully Exonic) |
| 915 | ER neg | XAF1 | Sense (Fully Exonic) |
| 703 | ER pos | PARP14 | Sense (Fully Exonic) |
| 916 | ER neg | SAMD9 | Sense (Fully Exonic) |
| 740 | ER pos | ASPN | Sense (Fully Exonic) |
| 704 | ER pos | FAM46C | Sense (Fully Exonic) |
| 864 | ER neg | PINX1 | Sense (Fully Exonic) |
| 865 | ER neg | GIMAP4 | Sense (Fully Exonic) |
| 866 | ER neg | N/A | Sense (includes Intronic) |
| 917 | ER neg | COL3A1 | Sense (Fully Exonic) |
| 741 | ER pos | COL1A2 | Sense (Fully Exonic) |
| 799 | ER neg, ER pos | IGHG1 | AntiSense |
| 742 | ER pos | FN1 | AntiSense |
| 800 | ER neg, ER pos | RAC2 | Sense (Fully Exonic) |
| 743 | ER pos | GLRX | Sense (Fully Exonic) |
| 744 | ER pos | BIRC3 | AntiSense |
| 783 | ER neg, ER pos | TAP1 | Sense (Fully Exonic) |
| 957 | ER neg, ER pos | POSTN | Sense (Fully Exonic) |
| 705 | ER pos | THBS1 | AntiSense |
| 867 | ER neg | TNFAIP8 | AntiSense |
| 958 | ER neg, ER pos | N/A | Sense (Fully Exonic) |
| 974 | ER neg, ER pos | IGJ | Sense (Fully Exonic) |
| 745 | ER pos | ADAM12 | Sense (Fully Exonic) |
| 706 | ER pos | COL14A1 | Sense (Fully Exonic) |
| 868 | ER neg | | No Transcript match |
| 869 | ER neg | CD53 | Sense (Fully Exonic) |
| 918 | ER neg | MIR1245 | Sense (Fully Exonic) |
| 707 | ER pos | | No Genome match |
| 919 | ER neg | | No Transcript match |
| 708 | ER pos | TNFSF10 | Sense (Fully Exonic) |
| 870 | ER neg | NLRC5 | Sense (Fully Exonic) |
| 871 | ER neg | WWC2 | Sense (includes Intronic) |
| 872 | ER neg | RORA | AntiSense |
| 873 | ER neg | IGKV4-1 | AntiSense |
| 874 | ER neg | | No Genome match |
| 975 | ER neg, ER pos | MIAT | Sense (Fully Exonic) |
| 746 | ER pos | COL8A1 | Sense (Fully Exonic) |
| 747 | ER neg, ER pos | IFI44 | Sense (Fully Exonic) |

In certain exemplary embodiments, all or a portion of the biomarkers recited in Table 1A, Table 1B and Table 1C, may be used in an expression signature. For example, expression signatures comprising the biomarkers in Table 1A, Table 1B, and Table 1C can be generated using the methods provided herein and can comprise between one, and all of the markers set forth in Tables 1A, 1B, 1C and each and every combination in between (e.g., four selected markers, 16 selected markers, 74 selected markers, etc.). In some embodiments, the expression signature comprises at least 5, 10, 20, 40, 60, 100, 150, 200, or 300 or more markers. In other embodiments, the predictive biomarker panel comprises no more than 5, 10, 20, 40, 60, 100, 150, 200, 300, 400, 500, 600 or 700 markers. In one exemplary embodiment, the expression signature includes a plurality of markers listed in Table 1A. In another exemplary embodiment, the expression signature includes a plurality of biomarkers listing in Table 1B. In another exemplary embodiment, the expression signature includes a plurality of biomarkers listed in Table 1C. In yet another exemplary embodiment, the expression signature includes a plurality of biomarkers listed in Table 1A, Table 1B, and Table 1C. In some embodiments the expression signature includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1A, Table 1B, Table 1C, or a combination thereof. Selected expression signatures can be assembled from the biomarkers provided using methods described herein and analogous methods known in the art. In one embodiment, the expression signature contains all 250 genes or gene products in Table 1A. In another exemplary embodiment, the expression signature contains all 486 genes or gene products in Table 1B. In another exemplary embodiment, the expression signature contains all 343 genes or gene products in Table 1C.

4. Mathematical Models

The following methods may be used to derive expression signatures for distinguishing between subjects that are responsive or non-responsive to anti-angiogenic therapeutics, or as prognostic indicators of certain cancer types, including expression signatures derived from the biomarkers disclosed above. In certain other exemplary embodiments, the expression signature is derived using a decision tree (Hastie et al. The Elements of Statistical Learning, Springer, New York 2001), a random forest (Breiman, 2001 Random Forests, Machine Learning 45:5), a neural network (Bishop, Neural Networks for Pattern Recognition, Clarendon Press, Oxford 1995), discriminant analysis (Duda et al. Pattern Classification, 2nd ed., John Wiley, New York 2001), including, but not limited to linear, diagonal linear, quadratic and logistic discriminant analysis, a Prediction Analysis for Microarrays (PAM, (Tibshirani et al., 2002, Proc. Natl. Acad. Sci. USA 99:6567-6572)) or a Soft Independent Modeling of Class Analogy analysis. (SIMCA, (Wold, 1976, Pattern Recogn. 8:127-139)).

Biomarker expression values may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which expression profiles from samples may be resolved into discrete classes of responder or non-responder, resistant or non-resistant, to a specified drug, drug class, or treatment regimen. Such predictive models, including biomarker membership, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance.

In one embodiment, the biomarkers are used to form a weighted sum of their signals, where individual weights can be positive or negative. The resulting sum ("expression score") is compared with a pre-determined reference point or value. The comparison with the reference point or value may be used to diagnose, or predict a clinical condition or outcome.

As described above, one of ordinary skill in the art will appreciate that the biomarkers included in the classifier provided in Tables 1A, 1B, and Table 1C will carry unequal weights in a classifier for responsiveness or resistance to a therapeutic agent. Therefore, while as few as one sequence may be used to diagnose or predict an outcome such as responsiveness to therapeutic agent, the specificity and sensitivity or diagnosis or prediction accuracy may increase using more sequences.

As used herein, the term "weight" refers to the relative importance of an item in a statistical calculation. The weight of each biomarker in a gene expression classifier may be determined on a data set of patient samples using analytical methods known in the art. As used herein the term "bias" or "offset" refers to a constant term derived using the mean expression of the signatures genes in a training set and is used to mean-center the each gene analyzed in the test dataset.

In certain exemplary embodiments, the expression signature is defined by a decision function. A decision function is a set of weighted expression values derived using a linear classifier. All linear classifiers define the decision function using the following equation:

$$f(x) = w'x + b = \Sigma w_i x_i + b \quad (1)$$

All measurement values, such as the microarray gene expression intensities $x_i$, for a certain sample are collected in a vector x. Each intensity is then multiplied with a corresponding weight $w_i$ to obtain the value of the decision function $f(x)$ after adding an offset term b. In deriving the decision function, the linear classifier will further define a threshold value that splits the gene expression data space into two disjoint halves. Exemplary linear classifiers include but are not limited to partial least squares (PLS), (Nguyen et al., Bioinformatics 18 (2002) 39-50), support vector machines (SVM) (Schölkopf et al., Learning with Kernels, MIT Press, Cambridge 2002), and shrinkage discriminant analysis (SDA) (Ahdesmäki et al., Annals of applied statistics 4, 503-519 (2010)). In one exemplary embodiment, the linear classifier is a PLS linear classifier.

The decision function is empirically derived on a large set of training samples, for example from patients showing responsiveness or resistance to a therapeutic agent. The threshold separates a patient group based on different characteristics such as, but not limited to, responsiveness/non-responsiveness to treatment. The interpretation of this quantity, i.e. the cut-off threshold responsiveness or resistance to a therapeutic agent, is derived in the development phase ("training") from a set of patients with known outcome. The corresponding weights and the responsiveness/resistance cut-off threshold for the decision score are fixed a priori from training data by methods known to those skilled in the art. In one exemplary embodiment, Partial Least Squares Discriminant Analysis (PLS-DA) is used for determining the weights. (L. Stable, S. Wold, J. Chemom. 1 (1987) 185-196; D. V. Nguyen, D. M. Rocke, Bioinformatics 18 (2002) 39-50).

Effectively, this means that the data space, i.e. the set of all possible combinations of biomarker expression values, is split into two mutually exclusive groups corresponding to different clinical classifications or predictions, for example, one corresponding to responsiveness to a therapeutic agent and the other to non-responsiveness. In the context of the overall classifier, relative over-expression of a certain biomarker can either increase the decision score (positive weight) or reduce it (negative weight) and thus contribute to an overall decision of, for example, responsiveness or resistance to a therapeutic agent.

In certain exemplary embodiments of the invention, the data is transformed non-linearly before applying a weighted sum as described above. This non-linear transformation might include increasing the dimensionality of the data. The non-linear transformation and weighted summation might also be performed implicitly, for example, through the use of a kernel function. (Schölkopf et al. Learning with Kernels, MIT Press, Cambridge 2002).

In certain exemplary embodiments, the patient training set data is derived by isolated RNA from a corresponding cancer tissue sample set and determining expression values by hybridizing the isolated RNA to a microarray. In certain exemplary embodiments, the microarray used in deriving the expression signature is a transcriptome array. As used herein a "transcriptome array" refers to a microarray containing probe sets that are designed to hybridize to sequences that have been verified as expressed in the diseased tissue of interest. Given alternative splicing and variable poly-A tail processing between tissues and biological contexts, it is possible that probes designed against the same gene sequence derived from another tissue source or biological context will not effectively bind to transcripts expressed in the diseased tissue of interest, leading to a loss of potentially relevant biological information. Accordingly, it is beneficial to verify what sequences are expressed in the disease tissue of interest before deriving a microarray probe set. Verification of expressed sequences in a particular disease context may be done, for example, by isolating and sequencing total RNA from a diseased tissue sample set and cross-referencing the isolated sequences with known nucleic acid sequence databases to verify that the probe set on the transcriptome array is designed against the sequences actually expressed in the diseased tissue of interest. Methods for making transcriptome arrays are described in United States Patent Application Publication No. 2006/0134663, which is incorporated herein by reference. In certain exemplary embodiments, the probe set of the transcriptome array is designed to bind within 300 nucleotides of the 3' end of a transcript. Methods for designing transcriptome arrays with probe sets that bind within 300 nucleotides of the 3' end of target transcripts are disclosed in United States Patent Application Publication No. 2009/0082218, which is incorporated by reference herein. In certain exemplary embodiments, the microarray used in deriving the gene expression profiles of the present invention is the Almac Ovarian Cancer DSA™ microarray (Almac Group, Craigavon, United Kingdom).

An optimal linear classifier can be selected by evaluating a linear classifier's performance using such diagnostics as "area under the curve" (AUC). AUC refers to the area under the curve of a receiver operating characteristic (ROC) curve, both of which are well known in the art. AUC measures are useful for comparing the accuracy of a classifier across the complete data range. Linear classifiers with a higher AUC have a greater capacity to classify unknowns correctly between two groups of interest (e.g., ovarian cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

In one exemplary embodiment an angiogenesis expression signature is directed to the 25 biomarkers detailed in Table 2A with corresponding ranks, weights and associated bias detailed in the table or alternative rankings, weightings and bias, depending, for example, on the disease setting. In another exemplary embodiment, an angiogenesis expression signature is directed to the 45 biomarkers detailed in Table 2B with corresponding ranks, weights and associated bias detailed in the table or alternative rankings, weightings and bias, depending, for example, on the disease setting. In another exemplary embodiment, a non-angiogeneis expression signature is directed to the 63 biomarkers detailed in Table 2C with corresponding ranks, and weights and associated bias detailed in the table or alternative rankings, and weightings and bias, depending, for example, on the disease setting. Tables 2A, 2B and 2C rank the biomarkers in order of absolute decreasing weight, in an example classifier, in the compound decision score function.

TABLE 2A

25 Biomarker Signature

| Rank | Gene Symbol | Weight | Bias |
|---|---|---|---|
| 1 | CCDC80 | 0.0584 | 5.9594 |
| 2 | INHBA | 0.0508 | 3.8146 |
| 3 | THBS2 | 0.0504 | 3.4342 |
| 4 | SFRP2 | 0.0437 | 4.3293 |
| 5 | MMP2 | 0.0367 | 5.3319 |
| 6 | PLAU | −0.0323 | 8.3844 |
| 7 | FAP | 0.0300 | 3.4689 |
| 8 | FN1 | 0.0277 | 10.0610 |
| 9 | COL8A1 | −0.0248 | 5.1984 |
| 10 | RAB31 | 0.0244 | 5.6121 |
| 11 | FAM38B | 0.0242 | 5.0883 |
| 12 | VCAN | 0.0230 | 4.4460 |
| 13 | GJB2 | 0.0223 | 5.8677 |
| 14 | ITGA5 | 0.0216 | 5.4455 |
| 15 | CRISPLD2 | 0.0192 | 6.5088 |
| 16 | C17orf91 | 0.0167 | 6.4830 |
| 17 | BGN | −0.0142 | 5.5396 |
| 18 | TIMP3 | 0.0130 | 4.6739 |
| 19 | ALPK2 | 0.0123 | 7.3709 |
| 20 | LUM | 0.0104 | 8.3279 |
| 21 | NKD2 | −0.0098 | 5.4448 |
| 22 | LOX | −0.0082 | 8.2117 |
| 23 | MIR1245 | 0.0059 | 4.9959 |
| 24 | LOXL1 | 0.0052 | 2.9463 |
| 25 | CXCL12 | 0.0048 | 9.7132 |

TABLE 2B

45 Biomarker Signature

| Rank | Gene Symbol | Weight | Bias |
|---|---|---|---|
| 1 | TMEM200A | 0.0595 | 3.6813 |
| 2 | GJB2 | 0.0560 | 4.4798 |
| 3 | MMP13 | 0.0383 | 3.7241 |
| 4 | GFPT2 | 0.0380 | 4.8602 |
| 5 | POSTN | −0.0355 | 4.3599 |
| 6 | BICC1 | 0.0304 | 3.6982 |
| 7 | CDH11 | 0.0283 | 4.9968 |
| 8 | MRVI1 | 0.0256 | 5.0761 |
| 9 | PMP22 | 0.0240 | 5.5645 |
| 10 | COL11A1 | −0.0237 | 3.5002 |
| 11 | IGFL2 | 0.0222 | 3.3104 |
| 12 | LUM | −0.0220 | 8.3363 |
| 13 | NTM | −0.0218 | 4.2302 |
| 14 | BGN | 0.0211 | 10.1524 |
| 15 | COL3A1 | −0.0210 | 8.3236 |
| 16 | COL10A1 | 0.0197 | 6.3538 |
| 17 | RAB31 | 0.0180 | 5.3171 |
| 18 | ANGPTL2 | 0.0166 | 5.6396 |
| 19 | PLAU | 0.0166 | 5.8488 |
| 20 | COL8A1 | 0.0164 | 6.4193 |
| 21 | MIR1245 | 0.0153 | 5.4552 |
| 22 | POLD2 | 0.0146 | 9.3878 |
| 23 | NKD2 | 0.0145 | 7.3717 |
| 24 | FZD1 | 0.0143 | 4.1519 |
| 25 | COPZ2 | 0.0139 | 5.1039 |
| 26 | ITGA5 | 0.0136 | 8.3663 |
| 27 | VGLL3 | 0.0125 | 4.5019 |
| 28 | INHBA | −0.0118 | 4.6843 |
| 29 | MMP14 | 0.0110 | 10.0841 |
| 30 | VCAN | 0.0100 | 5.5518 |
| 31 | THBS2 | −0.0087 | 8.1309 |
| 32 | RUNX2 | 0.0083 | 4.7345 |
| 33 | TIMP3 | 0.0081 | 6.4983 |
| 34 | SFRP2 | −0.0079 | 5.6017 |
| 35 | COL1A2 | 0.0078 | 6.0100 |
| 36 | COL5A2 | −0.0072 | 3.5671 |
| 37 | SERPINF1 | 0.0068 | 10.8334 |

TABLE 2B-continued

45 Biomarker Signature

| Rank | Gene Symbol | Weight | Bias |
|---|---|---|---|
| 38 | KIF26B | −0.0052 | 4.9782 |
| 39 | TNFAIP6 | 0.0050 | 5.3618 |
| 40 | MMP2 | 0.0040 | 5.3622 |
| 41 | FN1 | 0.0031 | 4.9840 |
| 42 | ALPK2 | 0.0024 | 3.5136 |
| 43 | CTSK | 0.0015 | 5.7322 |
| 44 | LOXL1 | −0.0014 | 9.5939 |
| 45 | FAP | 0.0000 | 5.2254 |

TABLE 2C

63 Biomarker Signature

| Rank | Gene Symbol | Weight | Bias |
|---|---|---|---|
| 1 | IGF2 | −0.01737 | 9.8884 |
| 2 | SOX11 | −0.01457 | 4.5276 |
| 3 | INS | −0.01409 | 7.0637 |
| 4 | CXCL17 | 0.012568 | 4.8478 |
| 5 | SLC5A1 | 0.012426 | 4.8920 |
| 6 | TMEM45A | −0.0124 | 6.1307 |
| 7 | CXCR2P1 | 0.011427 | 3.1478 |
| 8 | MFAP2 | −0.01039 | 9.0516 |
| 9 | MATN3 | −0.01028 | 3.7313 |
| 10 | RTP4 | 0.010052 | 4.9852 |
| 11 | COL3A1 | −0.01002 | 8.4130 |
| 12 | CDR1 | −0.00916 | 8.1778 |
| 13 | RARRES3 | 0.009056 | 6.8964 |
| 14 | TNFSF10 | 0.008876 | 6.2325 |
| 15 | NUAK1 | −0.0087 | 6.6771 |
| 16 | SNORD114-14 | −0.00864 | 5.6385 |
| 17 | SRPX | −0.00862 | 5.0850 |
| 18 | SPARC | −0.00848 | 6.0135 |
| 19 | GJB1 | 0.008445 | 5.8142 |
| 20 | TIMP3 | −0.00823 | 6.5937 |
| 21 | ISLR | −0.0079 | 8.9876 |
| 22 | TUBA1A | −0.00754 | 9.6540 |
| 23 | DEXI | 0.007271 | 5.5913 |
| 24 | BASP1 | −0.00724 | 8.4396 |
| 25 | PXDN | −0.00724 | 7.7570 |
| 26 | GBP4 | 0.007226 | 3.1119 |
| 27 | SLC28A3 | 0.007201 | 4.2125 |
| 28 | HLA-DRA | 0.007197 | 8.3089 |
| 29 | TAP2 | 0.007189 | 4.8464 |
| 30 | ACSL5 | 0.007155 | 6.8703 |
| 31 | CDH11 | −0.00708 | 4.9925 |
| 32 | PSMB9 | 0.006962 | 4.1122 |
| 33 | MMP14 | −0.00683 | 10.1689 |
| 34 | CD74 | 0.006825 | 9.2707 |
| 35 | LOXL1 | −0.00676 | 9.6429 |
| 36 | CIITA | 0.006623 | 5.5396 |
| 37 | ZNF697 | −0.00658 | 7.0319 |
| 38 | SH3RF2 | 0.006549 | 5.0029 |
| 39 | MIR198 | −0.00654 | 5.1935 |
| 40 | COL1A2 | −0.00645 | 6.0427 |
| 41 | TNFRSF14 | 0.006421 | 9.0366 |
| 42 | COL8A1 | −0.00642 | 6.4565 |
| 43 | C21orf63 | 0.006261 | 5.9811 |
| 44 | TAP1 | 0.006215 | 8.6458 |
| 45 | PDPN | −0.00612 | 5.3198 |
| 46 | RHOBTB3 | −0.00597 | 3.5609 |
| 47 | BCL11A | 0.005943 | 4.3818 |
| 48 | HLA-DOB | 0.005851 | 4.6075 |
| 49 | XAF1 | 0.005742 | 7.9229 |
| 50 | ARHGAP26 | 0.005632 | 4.3991 |
| 51 | POLD2 | −0.00558 | 9.4183 |
| 52 | DPYSL2 | −0.00533 | 8.3469 |
| 53 | COL4A1 | −0.0052 | 7.0317 |
| 54 | ID3 | −0.00516 | 7.5673 |
| 55 | CFB | 0.005077 | 5.7951 |
| 56 | NID1 | −0.00494 | 4.7186 |
| 57 | FKBP7 | −0.00489 | 2.9437 |
| 58 | TIMP2 | −0.00468 | 7.5253 |
| 59 | RCBTB1 | −0.00458 | 7.4491 |
| 60 | ANGPTL2 | −0.00448 | 5.6807 |
| 61 | ENTPD7 | −0.00442 | 7.3772 |
| 62 | SHISA4 | −0.00403 | 6.0601 |
| 63 | HINT1 | 0.003651 | 6.0724 |

In one exemplary embodiment, an expression signature comprises all or a portion of the following biomarkers: CCDC80, INHBA, THBS2, SFRP2, MMP2, PLAU, FAP, FN1, COL8A1, RAB31, FAM38B, VCAN, GJB2, ITGA5, CRISPLD2, C17, f91, BGN, TIMP3, ALPK2, LUM, NKD2, LOX, MIR1245, LOXL1, and CXCL12.

In another exemplary embodiment, an expression signature comprises CCDC80, INHBA, THBS2 and SFRP2 and at least N additional biomarkers selected from the list of biomarkers in Table 2A, wherein N equals 2, 3, 4, 5, 6, 7, 8, 9, 10, 11, 12, 13, 14, 15, 16, 17, 18, 19, 20, or 21.

In another exemplary embodiment, the expression signature comprises CCDC80 and at least N additional biomarkers selected from the list of biomarkers in Table 2A, wherein N equals 2, 3, 4, 5, 6, 7, 8, 9, 10, 11, 12, 13, 14, 15, 16, 17, 18, 19, 20, 21, 22, 23, or 24.

In another exemplary embodiment, the expression signature comprises INHBA and at least N additional biomarkers selected from the list of biomarkers in Table 2A, wherein N equals 2, 3, 4, 5, 6, 7, 8, 9, 10, 11, 12, 13, 14, 15, 16, 17, 18, 19, 20, 21, 22, 23, or 24.

In another exemplary embodiment, the expression signature comprises THBS2 and at least N additional biomarkers selected from the list of biomarkers in Table 2A, wherein N equals 2, 3, 4, 5, 6, 7, 8, 9, 10, 11, 12, 13, 14, 15, 16, 17, 18, 19, 20, 21, 22, 23, or 24.

In another exemplary embodiment, the expression signature comprises SFRP2 and at least N additional biomarkers selected from the list of biomarkers in Table 2A, wherein N equals 2, 3, 4, 5, 6, 7, 8, 9, 10, 11, 12, 13, 14, 15, 16, 17, 18, 19, 20, 21, 22, 23, or 24.

In another example embodiment, an example expression signatures comprises the biomarkers and the corresponding biomarker weighted values listed in Table 2A. In another exemplary embodiment, an example expression signature consists of the biomarkers and the corresponding biomarker weighted values listed in Table 2A In a further aspect, the methods of the present invention comprise conducting an assay on a biological sample from an individual to determine the expression levels of one or more biomarkers in a biomarker panel, the biomarker panel comprising CCDC80, INHBA, THBS2 and SFRP2 and at least N additional biomarkers selected from the list of biomarkers in Table 2A, wherein N equals 1, 2, 3, 4, 5, 6, 7, 8, 9, 10, 11, 12, 13, 14, 15, 16, 17, 18, 19, 20 or 21.

In a further aspect, the methods of the present invention comprise conducting an assay on a biological sample from an individual to determine the expression levels of one or more biomarkers in a biomarker panel, the biomarker panel comprising CCDC80 and at least N additional biomarkers selected from the list of biomarkers in Table 2A, wherein N equals 1, 2, 3, 4, 5, 6, 7, 8, 9, 10, 11, 12, 13, 14, 15, 16, 17, 18, 29, 20, 21, 22, 23 or 24.

In a further aspect, the methods of the present invention comprise conducting an assay on a biological sample from an individual to determine the expression levels of one or more biomarkers in a biomarker panel, the biomarker panel comprising INHBA and at least N additional biomarkers selected from the list of biomarkers in Table 2A, wherein N equals 1, 2, 3, 4, 5, 6, 7, 8, 9, 10, 11, 12, 13, 14, 15, 16, 17, 18, 29, 20, 21, 22, 23 or 24.

In a further aspect, the methods of the present invention comprise conducting an assay on a biological sample from an individual to determine the expression levels of one or more biomarkers in a biomarker panel, the biomarker panel comprising THBS2 and at least N additional biomarkers selected from the list of biomarkers in Table 2A, wherein N equals 1, 2, 3, 4, 5, 6, 7, 8, 9, 10, 11, 12, 13, 14, 15, 16, 17, 18, 29, 20, 21, 22, 23 or 24.

In a further aspect, the methods of the present invention comprise conducting an assay on a biological sample from an individual to determine the expression levels of one or more biomarkers in a biomarker panel, the biomarker panel comprising SFRP2 and at least N additional biomarkers selected from the list of biomarkers in Table 2A, wherein N equals 1, 2, 3, 4, 5, 6, 7, 8, 9, 10, 11, 12, 13, 14, 15, 16, 17, 18, 29, 20, 21, 22, 23 or 24.

In another exemplary embodiment, an expression signature comprises all or a portion of the following biomarkers; TMEM200A, GJB2, MMP13, GFPT2, POSTN, BICC1, CDH11, MRVI1, PMP22, COL11A1, IGFL2, LUM, NTM, BGN, COL3A1, COL10A1, RAB31, ANGPTL2, PLAU, COL8A1, MIR1245, POLD2, NKD2, FZD1, COPZ2, ITGA5, VGLL3, INHBA, MMP14, VCAN, THBS2, RUNX2, TIMP3, SFRP2, COL1A2, COL5A2, SERPINF1, KIF26B, TNFAIP6, MMP2, FN1, ALPK2, CTSK, LOXL1 and FAP.

In another exemplary embodiment, an expression signature comprises TMEM200A, GJB2, MMP13 and GFPT2 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41.

In another exemplary embodiment, an expression signature comprises TMEM200A and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44.

In another exemplary embodiment, an expression signature comprises GJB2 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44.

In another exemplary embodiment, an expression signature comprises MMP13 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44.

In another exemplary embodiment, an expression signature comprises GFPT2 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 or 44.

In another exemplary embodiment, an example expression signature comprises the biomarkers and the corresponding biomarker weighted values listed in Table 2B. In another exemplary embodiment, the expression signature consists of the biomarkers and corresponding biomarker weighted values listed in Table 2B.

In a further aspect, the methods of the present invention comprise conducting an assay on a biological sample from an individual to determine the expression levels of one or more biomarkers in a biomarker panel, the biomarker panel comprising TMEM200A, GJB2, MMP13 and GFPT2 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

In a further aspect, the methods of the present invention comprise conducting an assay on a biological sample from an individual to determine the expression levels of one or more biomarkers in a biomarker panel, the biomarker panel comprising TMEM200A and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44.

In a further aspect, the methods of the present invention comprise conducting an assay on a biological sample from an individual to determine the expression levels of one or more biomarkers in a biomarker panel, the biomarker panel comprising GJB2 and at least N additional biomarkers selected from the list of biomarkers in Table 2a, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44.

In a further aspect, the methods of the present invention comprise conducting an assay on a biological sample from an individual to determine the expression levels of one or more biomarkers in a biomarker panel, the biomarker panel comprising MMP13 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44.

In a further aspect, the methods of the present invention comprise conducting an assay on a biological sample from an individual to determine the expression levels of one or more biomarkers in a biomarker panel, the biomarker panel comprising GFPT2 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44.

In another exemplary embodiment, an expression signature comprises all or a portion of the following biomarkers; IGF2, SOX11, INS, CXCL17, SLC5A1, TMEM45A, CXCR2P1, MFAP2, MATN3, RTP4, COL3A1, CDR1, RARRES3, TNFSF10, NUAK1, SNORD114-14, SRPX, SPARC, GJB1, TIMP3, ISLR, TUBA1A, DEXI, BASP1, PXDN, GBP4, SLC28A3, HLA-DRA, TAP2, ACSL5, CDH11, PSMB9, MMP14, CD74, LOXL1, CIITA, ZNF697, SH3RF2, MIR198, COL1A2, TNFRSF14, COL8A1, C21orf63, TAP1, PDPN, RHOBTB3, BCL11A, HLA-DOB, XAF1, ARHGAP26, POLD2, DPYSL2, COL4A1, IDS, CFB, NID1, FKBP7, TIMP2, RCBTB1, ANGPTL2, ENTPD7, SHISA4, and HINT1, In another exemplary embodiment, an expression signature comprises IGF2, SOX11, INS, and CXCL17 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In another exemplary embodiment, an expression signature comprises IGF2 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another exemplary embodiment, an expression signature comprises SOX11 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another exemplary embodiment, an expression signature comprises INS and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another exemplary embodiment, an expression signature comprises CXCL17 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In another exemplary embodiment, an example expression signature comprises the biomarkers and corresponding biomarker weighted values listed in Table 2C. In another exemplary embodiment, and example expression signature consists of the biomarkers and corresponding biomarker weighted values listed in Table 2C.

In a further aspect, the methods of the present invention comprise conducting an assay on a biological sample from an individual to determine the expression levels of one or more biomarkers in a biomarker panel, the biomarker panel comprising all or a portion of the biomarkers listed in Table 2C.

In a further aspect, the methods of the present invention comprise conducting an assay on a biological sample from an individual to determine the expression levels of one or more biomarkers in a biomarker panel, the biomarker panel comprising IGF2, SOX11, INS, and CXCL17 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59.

In a further aspect, the methods of the present invention comprise conducting an assay on a biological sample from an individual to determine the expression levels of one or more biomarkers in a biomarker panel, the biomarker panel comprising IGF2 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising SOX11 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising INS and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In a further aspect, the methods of the present invention comprise conducting an assay on a biological sample from an individual to determine the expression levels of one or more biomarkers in a biomarker panel, the biomarker panel comprising CXCL17 and at least N additional biomarkers selected from the list of biomarkers in Table 2C, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62.

In one exemplary embodiment, the expression signature comprises all or a portion of the following biomarkers; ALPK2, BGN, COL8A1, FAP, FN1, GJB2, INHBA, ITGA5, LOXL1, LUM, MIR1245, MMP2, NKD2, PLAU, RAB31, SFRP2, THBS2, TIMP3 and VCAN.

In another exemplary embodiment, the expression signature comprises ALPK2, BGN, COL8A1, FAP and at least N additional biomarkers selected from FN1, GJB2, INHBA, ITGA5, LOXL1, LUM, MIR1245, MMP2, NKD2, PLAU, RAB31, SFRP2, THBS2, TIMP3 and VCAN, wherein N equals 1, 2, 3, 4, 5, 6, 7, 8, 9, 10, 11, 12, 13, 14 or 15.

In a further aspect, the methods of the present invention comprise conducting an assay on a biological sample from an individual to determine the expression levels of one or more biomarkers in a biomarker panel, the biomarker panel comprising ALPK2, BGN, COL8A1 and FAP at least N additional biomarkers selected from FN1, GJB2, INHBA, ITGA5, LOXL1, LUM, MIR1245, MMP2, NKD2, PLAU, RAB31, SFRP2, THBS2, TIMP3 and VCAN, wherein N equals 1, 2, 3, 4, 5, 6, 7, 8, 9, 10, 11, 12, 13, 14 or 15.

In a further aspect, the methods of the present invention comprise conducting an assay on a biological sample from an individual to determine the expression levels of one or more biomarkers in a biomarker panel, the biomarker panel comprising ALPK2 and at least N additional biomarkers selected from the list of biomarkers BGN, COL8A1, FAP, FN1, GJB2, INHBA, ITGA5, LOXL1, LUM, MIR1245, MMP2, NKD2, PLAU, RAB31, SFRP2, THBS2, TIMP3 and VCAN wherein N equals 1, 2, 3, 4, 5, 6, 7, 8, 9, 10, 11, 12, 13, 14 or 15.

In a further aspect, the methods of the present invention comprise conducting an assay on a biological sample from an individual to determine the expression levels of one or more biomarkers in a biomarker panel, the biomarker panel comprising BGN and at least N additional biomarkers selected from the list of biomarkers ALPK2, COL8A1, FAP, FN1, GJB2, INHBA, ITGA5, LOXL1, LUM, MIR1245, MMP2, NKD2, PLAU, RAB31, SFRP2, THBS2, TIMP3 and VCAN, wherein N equals 1, 2, 3, 4, 5, 6, 7, 8, 9, 10, 11, 12, 13, 14 or 15.

In a further aspect, the methods of the present invention comprise conducting an assay on a biological sample from an individual to determine the expression levels of one or more biomarkers in a biomarker panel, the biomarker panel comprising COL8A1 and at least N additional biomarkers selected from the list of biomarkers ALPK2, BGN, FAP, FN1, GJB2, INHBA, ITGA5, LOXL1, LUM, MIR1245, MMP2, NKD2, PLAU, RAB31, SFRP2, THBS2, TIMP3 and VCAN, wherein N equals 1, 2, 3, 4, 5, 6, 7, 8, 9, 10, 11, 12, 13, 14 or 15.

In a further aspect, the methods of the present invention comprise conducting an assay on a biological sample from an individual to determine the expression levels of one or more biomarkers in a biomarker panel, the biomarker panel comprising FAP and at least N additional biomarkers selected from the list of biomarkers ALPK2, BGN, COL8A1, FN1, GJB2, INHBA, ITGA5, LOXL1, LUM, MIR1245, MMP2, NKD2, PLAU, RAB31, SFRP2, THBS2, TIMP3 and VCAN, wherein N equals 1, 2, 3, 4, 5, 6, 7, 8, 9, 10, 11, 12, 13, 14 or 15.

In another exemplary embodiment, an expression signature comprises all or a portion of the following biomarkers; GJB2, INHBA, THBS2, SFRP2, PLAU and at least N additional biomarkers from Table 1A-1C, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, or 70.

In another exemplary embodiment, an expression signature comprises all GJB2 and at least N additional biomarkers from Table 1A-1C, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74.

In another exemplary embodiment, an expression signature comprises all INHBA and at least N additional biomarkers from Table 1A-1C, wherein N is. 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74.

In another exemplary embodiment, an expression signature comprises all THBS2 and at least N additional biomarkers from Table 1A-1C, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74.

In another exemplary embodiment, an expression signature comprises all SFRP2 wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74.

In another exemplary embodiment, an expression signature comprises all PLAU and at least N additional biomarkers from Table 1A-1C, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, or 70.

In another exemplary embodiment, an expression signature comprises all GJB2, INHBA, THBS2, SFRP2, PLAU and at least about 1%, about 5%, about 10%, about 20%, about 30%, about 40%, about 50%, about 60%, about 70%, about 80%, about 90%, about 95%, or about 99% of the biomarkers listed in Table 1A and Table 1B or a combination thereof.

Classifying New Test Samples Using an Expression Signature

To classify new test samples using an expression signature, such as those described above, the relative expression levels of biomarkers in a cancer tissue are measured to form a test sample expression profile. In certain exemplary embodiments, the test sample expression profile is summarized in the form of a compound decision score ("expression score") and compared to a threshold score that is mathematically derived from a training set of patient data. The score threshold separates a patient group based on different characteristics such as, but not limited to, responsiveness/non-responsiveness to treatment. The patient training set data is preferably derived from cancer tissue samples having been characterized by prognosis, likelihood of recurrence, long term survival, clinical outcome, treatment response, diagnosis, cancer classification, or personalized genomics profile. Expression profiles, and corresponding decision scores from patient samples may be correlated with the characteristics of patient samples in the training set that are on the same side of the mathematically derived score decision threshold. The threshold of the linear classifier scalar output is optimized to maximize the sum of sensitivity and specificity under cross-validation as observed within the training dataset.

The overall expression data for a given sample is normalized using methods known to those skilled in the art in order to correct for differing amounts of starting material, varying efficiencies of the extraction and amplification reactions, etc.

In one embodiment, the biomarker expression profile of a patient tissue sample is evaluated by a linear classifier. As used herein, a linear classifier refers to a weighted sum of the individual biomarker intensities into a compound decision score ("decision function"). The decision score is then compared to a pre-defined cut-off score threshold, corresponding to a certain set-point in terms of sensitivity and specificity which indicates if a sample is above the score threshold (decision function positive) or below (decision function negative).

Using a linear classifier on the normalized data to make a diagnostic or prognostic call (e.g. responsiveness or resistance to therapeutic agent) effectively means to split the data space, i.e. all possible combinations of expression values for all genes in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, i.e. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

There are a number of suitable methods for measuring expression profiles of test samples depending on the type of biomarker to be assayed. Measuring mRNA in a biological sample may be used as a surrogate for detection of the level of the corresponding protein in the biological sample. Thus, any of the biomarkers or biomarker panels described herein can also be detected by detecting the appropriate RNA. Methods of gene expression profiling include, but are not limited to, microarray, RT-PCT, qPCR, NGS, northern blots, SAGE, mass spectrometry.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve widespread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Gene expression may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for predicting responsiveness of a cancer therapeutic agent, where the methods comprise detecting, in a biological sample from an individual, at least N biomarker values that each correspond to a biomarker selected from the group consisting of the biomarkers provided in Tables 1A, 1B, 2A, 2B or Groups I and II, wherein a classification, as described in detail below, using the biomarker values indicates whether the individual will be responsive to a therapeutic agent. While certain of the described predictive biomarkers are useful alone for predicting responsiveness to a therapeutic agent, methods are also described herein for the grouping of multiple subsets of the biomarkers that are each useful as a panel of two or more biomarkers. Thus, various embodiments of the instant application provide combinations comprising N biomarkers, wherein N is at least three biomarkers. It will be appreciated that N can be selected to be any number from any of the above-described ranges, as well as similar, but higher order, ranges. In accordance with any of the methods described herein, biomarker values can be detected and classified individually or they can be detected and classified collectively, as for example in a multiplex assay format.

b) Microarray Methods

In one embodiment, the present invention makes use of "oligonucleotide arrays" (also called herein "microarrays").

Microarrays can be employed for analyzing the expression of biomarkers in a cell, and especially for measuring the expression of biomarkers of cancer tissues.

In one embodiment, biomarker arrays are produced by hybridizing detectably labeled polynucleotides representing the mRNA transcripts present in a cell (e.g., fluorescently-labeled cDNA synthesized from total cell mRNA or labeled cRNA) to a microarray. A microarray is a surface with an ordered array of binding (e.g., hybridization) sites for products of many of the genes in the genome of a cell or organism, preferably most or almost all of the genes. Microarrays can be made in a number of ways known in the art. However produced, microarrays share certain characteristics. The arrays are reproducible, allowing multiple copies of a given array to be produced and easily compared with each other. Preferably the microarrays are small, usually smaller than 5 cm$^2$, and they are made from materials that are stable under binding (e.g., nucleic acid hybridization) conditions. A given binding site or unique set of binding sites in the microarray will specifically bind the product of a single gene in the cell. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene/biomarker. For example, when detectably labeled (e.g., with a fluorophore) cDNA or cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal. Nucleic acid hybridization and wash conditions are chosen so that the probe "specifically binds" or "specifically hybridizes' to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can be demonstrated that specific hybridization conditions result in specific hybridization by carrying out a hybridization assay including negative controls using routine experimentation.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

c) Immunoassay Methods

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoas say, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Kits

Reagents, tools, and/or instructions for performing the methods described herein can be provided in a kit. For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for performing a gene or gene product expression analysis, such as reagents for performing nucleic acid amplification (e.g. RT-PCR, qPCR), sequencing (e.g. next generation sequencing), northern blot, proteomic analysis, or immunohistochemistry to determine expression levels of gene or gene product markers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below. The kits may include suitable primers and/or probes to detect the expression levels of at least one (up to all) of the biomarkers of in Table 2A and/or 2B and/or 2C. Where expression is determined at the protein level the kit may contain binding reagents specific for the proteins of interest. The binding reagents may comprise antibodies to include all fragments and derivatives thereof. In the context of the various embodiments of the present invention the term "antibody" includes all immunoglobulins or immunoglobulin-like molecules with specific binding affinity for the relevant protein (including by way of example and without limitation, IgA, IgD, IgE, IgG and IgM, combinations thereof, and similar molecules produced during an immune response in any vertebrate, for example, in mammals such as humans, goats, rabbits and mice). Specific immunoglobulins useful in the various embodiments of the invention include IgG isotypes. The antibodies useful in the various embodiments of the invention may be monoclonal or polyclonal in origin, but are typically monoclonal antibodies. Antibodies may be human antibodies, non-human antibodies, or humanized versions of non-human antibodies, or chimeric antibodies. Various techniques for antibody humanization are well established and any suitable technique may be employed. The term "antibody" also refers to a polypeptide ligand comprising at least a light chain or heavy chain immunoglobulin variable region which specifically recognizes and binds an epitope of an antigen, and it extends to all antibody derivatives and fragments that retain the ability to specifically bind to the relevant protein. These derivatives and fragments may include Fab fragments, F(ab')2 fragments, Fv fragments, single chain antibodies, single domain antibodies, Fc fragments etc. The term antibody encompasses antibodies comprised of both heavy and light chains, but also heavy chain (only) antibodies (which may be derived from various species of cartilaginous fish or camelids). In specific embodiments, the antibodies may be engineered so as to be specific for more than protein, for example bi-specific to permit binding to two different target proteins as identified herein (see Tables 2A, 2B and 2C).

In some embodiments, the kits may also contain the specific anti-angiogenic therapeutic agent to be administered in the event that the test predicts responsiveness. This agent may be provided in a form, such as a dosage form, that is tailored to the specific treatment. The kit may be provided with suitable instructions for administration according to an appropriate treatment regimen.

The kits featured herein can also include an instruction sheet describing how to perform the assays for measuring gene or gene product expression. The instruction sheet can also include instructions for how to determine a reference cohort, including how to determine expression levels of gene or gene product markers in the reference cohort and how to assemble the expression data to establish a reference for comparison to a test patient. The instruction sheet can also include instructions for assaying gene or gene product expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human's likelihood of having a positive response to a specific therapeutic agent.

The kits featured herein can also contain software necessary to infer a patient's likelihood of having a positive response to a specific therapeutic agent from the gene product marker expression.

Therapeutic Agents

As described above, the methods described herein permit the classification of a patient as responsive or non-responsive to a therapeutic agent that targets angiogenic processes and signaling within tumors. Some current such therapeutics used to treat cancer include, but are not limited to, the following agents; VEGF pathway-targeted therapeutic agent, including multi-targeted pathway inhibitors (VEGF/PDGF/FGF/EGFT/FLT-3/c-KIT), Angiopoietin-TIE2 pathway inhibitors, endogenous angiogenic inhibitors, immunomodulatory Agents. VEGF specific inhibitors include, but are not limited to, Bevacizumab (Avastin), Afibercept (VEGF Trap), IMC-1121B (Ramucirumab). Multi-targeted pathway inhibitors include, but are not limited to, Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258. Angiopoietin-TIE2 pathway inhibitors include, but are not limited to, AMG-386, PF-4856884 CVX-060, CEP-11981, CE-245677, MEDI-3617, CVX-241, Trastuzumab (Herceptin). Endogenous angiogenic inhibitors include, but are not limited to, Thombospondin, Endostatin, Tumstatin, Canstatin, Arrestin, Angiostatin, Vasostatin, Interferon alpha. Immunomodulatory Agents include, but are not limited to, Thalidomide and Lenalidomide.

The invention is further defined with reference to the following numbered clauses:

1. A method of predicting a subject's responsiveness to an anti-angiogenic therapeutic agent comprising:
   measuring expression levels of one or more biomarkers in a test sample of diseased tissue obtained from the subject to determine a sample expression score, wherein the biomarkers are defined by an expression signature;
   comparing the sample expression score to a threshold expression score; and
   classifying the subject as responsive or non-responsive, based on whether the sample expression score is above or below the threshold expression score.
2. The method of clause 1, wherein the diseased tissue is cancer tissue.
3. The method of clause 2, wherein the cancer is ovarian cancer, glioblastoma, lung cancer, colon cancer, prostate cancer, or breast cancer.
4. The method of any one of clauses 1 to 3, wherein the sample expression value is determined by measuring an expression level for each biomarker and multiplying it by a corresponding weight, wherein the weight for each biomarker is determined by the expression signature.
5. The method of clause 4, wherein the expression signature is derived by a method comprising:
   isolating total RNA from a sample set of diseased tissue;
   hybridizing the isolated total RNA to a microarray to obtain a sample expression data set;
   selecting those probes on the microarray with a variability above a defined significance threshold to form a preliminary biomarker set;
   generating clusters of biomarkers within the preliminary biomarker set having a similar expression profile using a clustering algorithm;
   identifying the biological processes or biological pathways for each cluster of biomarkers;
   selecting the cluster corresponding to the biological process or biological pathway of interest; and
   defining an expression signature by analysing the expression levels of the biomarkers in the selected cluster in a the sample set of diseased tissue using a supervised or unsupervised training algorithm.
6. The method of clause 5, wherein the microarray is a transcriptome array comprising probe sets that binds to RNA transcripts verified as expressed in a test sample set by isolating and sequencing RNA transcripts from the test sample set and cross-validating the isolated RNA transcript sequences to known RNA transcript sequences, wherein the test sample set comprises the same tissue as the patient test sample
7. The method of clause 6, wherein the probe set comprises probes that bind within 300 nucleotides of the 3' end of each RNA transcript.
8. The method of any one of clauses 5 to 7, wherein RNA transcripts comprising coding and non-coding transcripts that include messenger RNAs (mRNA), alternatively spliced mRNAs, ribosomal RNAs (rRNA), transfer RNAs (tRNA), small nuclear RNAs (snRNA), microRNAs (miRNAs) and antisense RNAs.
9. The method of any one of clauses 5 to 8, wherein the expression signature is defined using a PLS classifier, a SVM classifier, a SDA classifier, or a DSDA classifier.
10. The method of clause 9, wherein the expression signature is defined using a PLS classifier.
11. The method of any one of clauses 1 to 10, wherein the expression signature comprises two or more genes from Table 1A, Table 1B, or Table 2C.
12. The method of any one of clauses 1 to 10, wherein the expression signature comprises two or more genes from Table 2A, 2B, or 2C.
13. The method of any one of clauses 1 to 10, wherein the expression signature comprises ALPK2, BGN, COL8A1, FAP, FN1, GJB2, INHBA, ITGA5, LOXL1, LUM, MIR1245, MMP2, NKD2, PLAU, RAB31, SFRP2, THBS2, TIMP3, VCAN.
14. The method of any one of clauses 1 to 10, wherein the expression signature comprises CCDC80, INHBA, THBS2, SFRP2, and MMP2.
15. The method of any one of clauses 1 to 10, wherein the expression signature comprises TMEM200A, GJB2, MMP13, GFPT2, and POSTN.
16. The method of any one of clauses 1 to 10, wherein the expression signature comprises IGF2, SOX11, INS, CSCL17, and SLC5A1.
17. The method of any one of clauses 1 to 10, wherein the expression signatures comprises the genes listed in Table 2A.
18. The method of any one of clauses 1 to 10, wherein the expression signature comprises the genes listed in Table 2B.
19. The method of any one of clauses 1 to 10, wherein the expression signature comprises the genes listed in Table 2C.
20. The method of any one of clauses 1 to 10, wherein the expression signature comprises GJB2, INHBA, THBS2, SFRP2, and PLAU.
21. The method of any one of clauses 1 to 20, wherein the anti-angiogenic therapeutic agent is a VEGF-pathway-targeted therapeutic agent, an angiopoietin-TIE2 pathway inhibitor, endogenous angiogenic inhibitors, and immunomodulatory agents.
22. The method of clause 21, wherein the VEGF pathway-targeted therapeutic agents include Bevacizumab (Avastin), Afibercept (VEGF Trap), IMC-1121B (Ramucirumab), Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258 or a combination thereof.
23. The method of clause 21, wherein the angiopoietin-TIE2 pathway inhibitor includes AMG-386, PF-4856884 CVX-060, CEP-11981, CE-245677, MEDI-3617, CVX-241, Trastuzumab (Herceptin) or a combination thereof.
24. The method of clause 21, wherein the endogenous angiogenic inhibitors include Thombospondin, Endostatin, Tumstatin, Canstatin, Arrestin, Angiostatin, Vasostatin, Interferon alpha or a combination thereof.
25. The method of clause 21, wherein the immunomodulatory agents include thalidomide and lenalidomide or a combination thereof.
26. A method of diagnosing a subject as having a cancer or being susceptible to developing the cancer response to anti-angiogenic therapeutics comprising:
   measuring expression levels of biomarkers in a test sample of a diseased tissue obtained from the subject to determine obtain a sample expression score, wherein the biomarkers are defined by an expression signature;
   comparing the sample expression value to a threshold score; and classifying the subject as responsive or non-responsive based on whether the expression score is above or below the threshold score.

27. The method of clause 26, wherein the cancer is ovarian cancer, breast cancer, prostate cancer, lung cancer, colon cancer or a glioblastoma.

28. The method of any one of clauses 26 to 27, wherein the reference expression value is determined by calculating an expression value for each biomarker and multiplying it by a corresponding weight, wherein the weight for each biomarker is determined by the expression signature.

29. The method of clause 26, wherein the expression signature is derived by a method comprising:
isolating total RNA from a sample set of the diseased tissue;
hybridizing the isolated total RNA to a microarray to obtain a set of expression values; selecting those probes on the microarray with the variability above a defined significance threshold to form a preliminary biomarker set;
generating clusters of biomarkers within the preliminary biomarker set having a similar gene expression profile using a clustering algorithm;
identifying the biological process or biological pathway for each cluster of biomarkers; selecting the cluster corresponding to the biological processes or biological pathways of interest; and
deriving the expression signature by analysing the expression levels of the biomarkers in the selected cluster in a the sample set of cancer tissue using a supervised or unsupervised training algorithm, wherein the expression value defines a set of biomarkers, corresponding weights for each biomarker and the reference expression value.

30. The method of clause 29, wherein the microarray is a transcriptome array comprising a probe set that binds to RNA transcripts verified as expressed in a sample set of cancer tissue by isolating and sequencing RNA transcripts from the cancer tissue and cross-validating the isolated RNA transcript sequences to known RNA transcript sequences.

31. The method of clause 30, wherein the probe set comprises probes that bind within 300 nucleotides of the 3' end of each RNA transcript.

32. The method of any one of clauses 29 to 31, wherein RNA transcripts comprising coding and non-coding transcripts that include messenger RNAs (mRNA), alternatively spliced mRNAs, ribosomal RNAs (rRNA), transfer RNAs (tRNA), small nuclear RNAs (snRNA), microRNAs (miRNAs) and antisense RNA.

33. The method of any one of clauses 27 to 32, wherein the expression signature is defined using a PLS classifier, a SVM classifier, a SDA classifier, or a DSDA classifier.

34. The method of clause 33, wherein the expression signature is defined using a PLS classifier.

35. The method of any one of clauses 26 to 34, wherein the expression signature comprises two or more genes from Table 1A, Table 1B, or Table 1C.

36. The method of any one of clauses 26 to 34, wherein the expression signature comprises two or more genes from Table 2A, Table 2B, or Table 2C.

37. The method of any one of clauses 26 to 34, wherein the expression signature comprises ALPK2, BGN, COL8A1, FAP, FN1, GJB2, INHBA, ITGA5, LOXL1, LUM, MIR1245, MMP2, NKD2, PLAU, RAB31, SFRP2, THBS2, TIMP3, VCAN.

38. The method of any one of clauses 26 to 34, wherein the expression signature comprises CCDC80, INHBA, THBS2, SFRP2, MMP2.

39. The method of any one of clauses 26 to 34, wherein the expression signature comprises TMEM200A, GJB2, MMP13, GFPT2, and POSTN.

40. The method of any one of clauses 26 to 34, wherein the expression signature comprises IGF2, SOX11, INS, CSCL17, and SLC5A1.

41. The method of any one of clauses 26 to 34, wherein the expression signature comprises the genes listed in Table 2A.

42. The method of any one of clauses 26 to 34, wherein the expression signature comprises the genes listed in Table 2B.

43. The method of any one of clauses 26 to 34, wherein the expression signature comprises the genes liste in Table 2C.

44. The method of any one of clauses 26 to 34, wherein the expression signature comprises GJB2, INHBA, THBS2, SFRP2, and PLAU 45. The method of any one of clauses 26 to 44, wherein the anti-angiogenic agent is a VEGF-pathway-targeted therapeutic agent, an angiopoietin-TIE2 pathway inhibitor, endogenous angiogenic inhibitors, and immunomodulatory agents.

46. The method of clause 45, wherein the VEGF pathway-targeted therapeutic agents include Bevacizumab (Avastin), Afibercept (VEGF Trap), IMC-1121B (Ramucirumab), Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, and TKI-258.

47. The method of clause 45, wherein the angiopoietin-TIE2 pathway inhibitor includes AMG-386, PF-4856884 CVX-060, CEP-11981, CE-245677, MEDI-3617, CVX-241, Trastuzumab (Herceptin).

48. The method of clause 45, wherein the endogenous angiogenic inhibitors include Thombospondin, Endostatin, Tumstatin, Canstatin, Arrestin, Angiostatin, Vasostatin, Interferon alpha.

49. The method of clause 45, wherein the immunomodulatory agents include thalidomide and lenalidomide.

50. A method of determining a prognosis of a subject with cancer comprising:
measuring expression levels of one or more biomarkers in a test sample of diseased tissue obtained from the subject to determine a sample expression score, wherein the biomarkers are defined by an expression signature;
comparing the sample expression score to a threshold expression score; and
classifying the subject as responsive or non-responsive, based on whether the sample expression score is above or below the threshold expression score.

47. The method of clause 46, wherein the diseased tissue is cancer tissue.

48. The method of clause 47, wherein the cancer is ovarian cancer, lung cancer, colon cancer, prostate cancer, glioblastoma, or breast cancer.

49. The method of any one clauses 46 to 48, wherein the sample expression value is determined by measuring an expression level for each biomarker and multiplying it by a corresponding weight, wherein each weight for each biomarker is determined by the expression signature.

50. The method of clause 49, wherein the expression signature is derived by a method comprising:
isolating total RNA from a sample set of diseased tissue;
hybridizing the isolated total RNA to a microarray to obtain a sample expression data set;
selecting those probes on the microarray with a variability above a defined significance threshold to form a preliminary biomarker set;

generating clusters of biomarkers within the preliminary biomarker set having a similar expression profile using a clustering algorithm;

identifying the biological processes or biological pathways for each cluster of biomarkers;

selecting the cluster corresponding to the biological process or biological pathway of interest; and defining an expression signature by analysing the expression levels of the biomarkers in the selected cluster in a the sample set of diseased tissue using a supervised or unsupervised training algorithm.

51. The method of clause 50, wherein the microarray is a transcriptome array comprising probe sets that binds to RNA transcripts verified as expressed in a test sample set by isolating and sequencing RNA transcripts from the test sample set and cross-validating the isolated RNA transcript sequences to known RNA transcript sequences, wherein the test sample set comprises the same tissue as the patient test sample 52. The method of clause 51, wherein the probe set comprises probes that bind within 300 nucleotides of the 3' end of each RNA transcript.

53. The method of any one of clauses 50 to 57, wherein RNA transcripts comprising coding and non-coding transcripts that include messenger RNAs (mRNA), alternatively spliced mRNAs, ribosomal RNAs (rRNA), transfer RNAs (tRNA), small nuclear RNAs (snRNA), microRNAs (miRNAs) and antisense RNAs.

54. The method of any one of clauses 50 to 53, wherein the expression signature is defined using a PLS classifier, a SVM classifier, a SDA classifier, or a DSDA classifier.

55. The method of clause 46 to 54, wherein the expression signature is defined using a PLS classifier.

56. The method of any one of clauses 46 to 55, wherein the expression signature comprises two or more genes from Table 1A, Table 1B, or Table 1C.

57. The method of any one of clauses 46 to 55, wherein the expression signature comprises two or more genes from Table 2A, 2B, or 2C.

58. The method of any one of clauses 46 to 55, wherein the expression signature comprises ALPK2, BGN, COL8A1, FAP, FN1, GJB2, INHBA, ITGA5, LOXL1, LUM, M1R1245, MMP2, NKD2, PLAU, RAB31, SFRP2, THBS2, TIMP3, VCAN.

59. The method of any one of clauses 46 to 55, wherein the expression signature comprises CCDC80, INHBA, THBS2, SFRP2, and MMP2.

60. The method of any one of clauses 46 to 55, wherein the expression signature comprises TMEM200A, GJB2, MMP13, GFPT2, and POSTN.

61. The method of any one of clauses 46 to 55, wherein the expression signature comprises IGF2, SOX11, INS, CSCL17, and SLC5A1.

62. The method of any one of clauses 46 to 55, wherein the expression signatures comprises the genes listed in Table 2A.

63. The method of any one of clauses 46 to 55, wherein the expression signature comprises the genes listed in Table 2B.

64. The method of any one of clauses 46 to 55, wherein the expression signature comprises the genes listed in Table 2C.

65. The method of any one of clauses 46 to 55, wherein the expression signature comprises GJB2, INHBA, THBS2, SFRP2, and PLAU.

66. A method for determining a course of treatment for a subject with cancer comprising:

measuring expression levels of one or more biomarkers in a test sample of diseased tissue obtained from the subject to determine a sample expression score using a non-angiogenesis expression signature, wherein the biomarkers are defined by the expression signature determining a prognosis for the subject by comparing the sample expression score from the non-angiogenesis signature to a threshold score, wherein a sample expression score greater than the threshold score indicates a good prognosis and a sample expression score below the threshold scored indicates a poor prognosis;

measuring expression levels of one or more biomarkers in a test sample of diseased tissue obtained from the subject to determine a sample expression score using an angiogenesis expression signature, wherein the biomarkers are defined by the angiogenesis expression signature;

determining the subject's responsiveness to a therapeutic agent by comparing the sample expression score to a threshold score, wherein a sample expression score greater than the threshold value indicates responsiveness to the therapeutic agent and a sample expression score less than the threshold value indicates non-responsiveness to the therapeutic agent.

67. The method of clause 66, wherein the non-angiogenesis signature comprises two or more biomarkers listed in Table 2C 68. The method of clause 66, wherein the non-angiogenesis signature consists of the biomarkers listed in Table 2C.

69. The method of clause 66, wherein the angiogenesis signature comprises two or more biomarkers listed in Table 2A, Table 2B, or a combination thereof. 70.

71. The method of clause 66, wherein the angiogenesis signature consists of the biomarkers listed in Table 1A.

72. The method of clause 66, wherein the angiogenesis signature consists of the biomarkers listed in Table 1B.

73. The method of clause 66, wherein the cancer is ovarian cancer, breast cancer, colon cancer, prostate cancer, lung cancer, or glioblastoma.

74. The method of clause 66, wherein the therapeutic agent is an anti-angiogenic therapeutic agent.

75. The method of clause 74, wherein the anti-angiogenic therapeutic agent is a VEGF-pathway-targeted therapeutic agent, an angiopoietin-TIE2 pathway inhibitor, endogenous angiogenic inhibitors, and immunomodulatory agents.

76. The method of clause 75, wherein the VEGF pathway-targeted therapeutic agents include Bevacizumab (Avastin), Afibercept (VEGF Trap), IMC-1121B (Ramucirumab), Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258 or a combination thereof.

77. The method of clause 75, wherein the angiopoietin-TIE2 pathway inhibitor includes AMG-386, PF-4856884 CVX-060, CEP-11981, CE-245677, MEDI-3617, CVX-241, Trastuzumab (Herceptin) or a combination thereof.

78. The method of clause 75, wherein the endogenous angiogenic inhibitors include Thombospondin, Endostatin, Tumstatin, Canstatin, Arrestin, Angiostatin, Vasostatin, Interferon alpha or a combination thereof.

79. The method of clause 75, wherein the immunomodulatory agents include thalidomide and lenalidomide or a combination thereof.

For the avoidance of doubt, the scope of the invention is defined by the appended claims.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or scope of the appended claims.

EXAMPLES

Example 1

Tissue Processing, Hierarchical Clustering, Subtype Identification and Classifier Development Tumor Material Exemplary expression signatures were identified from gene expression analysis of a cohort of macrodissected epithelial serous ovarian tumor FFPE tissue samples sourced from the NHS Lothian and University of Edinburgh.

The protocol for histological classification of epithelial ovarian cancer to define serous, endometrioid, clear cell and mucinous histologies has recently been updated. One of the consequences of this is that many tumors that would previously been classified as endometrioid are now being classified as serous. (McCluggage, W. G. "Morphological subtypes of ovarian carcinoma: a review with emphasis on new developments and pathogenesis," PATHOLOGY 2011 August; 43(5):420-32). Serous samples that were used in this study were among a larger set of epithelial ovarian cancer samples of all histologies that were harvested between 1984 and 2006. Pathology to assign histology status was performed by the pathologists at each of the centers at the time of harvesting. During March and April 2012, 357 of these epithelial ovarian samples were reviewed for histology classification by two independent consultant ovarian cancer pathologists according to the revised protocol. This resulted in a reclassification of several of these samples as indicated Table 3.

TABLE 3 results of pathology review of 357 epithelial ovarian cancer samples. (Original histological status is presented in rows, and updated histological status is presented in columns)

| | Updated | | | | |
|---|---|---|---|---|---|
| Original | CLEAR CELL | ENDO-METRIOID | MUCIN-OUS | SE-ROUS | TO-TAL |
| CLEAR CELL | 19 | 1 | 0 | 5 | 25 |
| ENDOMETRIOID | 2 | 33 | 0 | 38 | 73 |
| MUCINOUS | 0 | 1 | 8 | 1 | 10 |
| OTHER MIXED | 3 | 5 | 0 | 8 | 16 |
| SEROUS | 1 | 3 | 1 | 193 | 198 |
| SEROUS/ENDO | 0 | 2 | 0 | 25 | 27 |
| UNCLASSIFIED | 0 | 0 | 0 | 4 | 4 |
| UNDIFFER-ENTIATED | 1 | 0 | 0 | 3 | 4 |
| TOTAL | 26 | 45 | 9 | 277 | 357 |

The original three serous subtypes identified below, and consequently a 25 gene signature (Table 2A) described in the example below (FIG. 1) were identified from 199 samples that were classified as serous according to the original pathologist reports. Bioinformatic analysis was similarly performed on the 277 samples classified as stage III and IV high grade serous ovarian cancer using the updated pathology classification method. This analysis identified the updated serous subgroups detailed in FIG. 6 and consequently used to define a 45 gene "angiogenesis" signature (Table 2B) and a 63 gene "non-angiogenesis" signature (Table 2C)

Gene Expression Profiling from FFPE

Total RNA was extracted from macrodissected FFPE tissue using the High Pure RNA Paraffin Kit (Roche Diagnostics GmbH, Mannheim, Germany). RNA was converted into complementary deoxyribonucleic acid (cDNA), which was subsequently amplified and converted into single-stranded form using the SPIA® technology of the WT-Ovation™ FFPE RNA Amplification System V2 (NuGEN Technologies Inc., San Carlos, Calif., USA). The amplified single-stranded cDNA was then fragmented and biotin labeled using the FL-Ovation™ cDNA Biotin Module V2 (NuGEN Technologies Inc.). The fragmented and labeled cDNA was then hybridized to the Almac Ovarian Cancer DSA™. Almac's Ovarian Cancer DSA™ research tool has been optimised for analysis of FFPE tissue samples, enabling the use of valuable archived tissue banks. The Almac Ovarian Cancer DSA™ research tool is an innovative microarray platform that represents the transcriptome in both normal and cancerous ovarian tissues. Consequently, the Ovarian Cancer DSA™ provides a comprehensive representation of the transcriptome within the ovarian disease and tissue setting, not available using generic microarray platforms. Arrays were scanned using the Affymentrix Genechip® Scanner 7G (Affymetrix Inc., Santa Clara, Calif.).

Data Preparation

Quality Control (QC) of profiled samples was carried out using MASS pre-processing algorithm. Different technical aspects were addressed: average noise and background homogeneity, percentage of present call (array quality), signal quality, RNA quality and hybridization quality. Distributions and Median Absolute Deviation of corresponding parameters were analyzed and used to identify possible outliers.

Almac's Ovarian Cancer DSA™ contains probes that primarily target the area within 300 nucleotides from the 3' end. Therefore standard Affymetrix RNA quality measures were adapted—for housekeeping genes intensities of 3' end probe sets with ratios of 3' end probe set intensity to the average background intensity were used in addition to usual 3'/5' ratios. Hybridization controls were checked to ensure that their intensities and present calls conform to the requirements specified by Affymetrix.

Pre-processing of the raw data generated from expression profiling of the epithelial serous ovarian cancer training set was performed in Expression Console v1.1 with Robust Multi-array Analysis (RMA).

Hierarchical Clustering and Functional Analysis a. Hierarchical Clustering Analysis Hierarchical clustering techniques were applied to microarray data from the epithelial serous ovarian tumors analysed using the Ovarian Cancer DSA™ (disease specific array) platform. Raw expression data was preprocessed using the standard Robust Multichip Algorithm (RMA) procedure. Non-biological systematic variance in the data set was identified and removed. Those probe sets whose expression levels varied significantly from tumor to tumor were identified. These probe sets formed the intrinsic list.

Two dimensional cluster analysis (tumor, probe set) was performed to establish tumor relationships based on the intrinsic list. Hierarchical agglomerative clustering was applied (Pearson correlation—Original analysis—or Euclidean distance—updated analysis—and Ward's linkage). Optimal partition number was selected using the GAP index (Tibshirani et al., 2002, J. R. Stat. Soc., 63:411-423). All probe sets available in the cluster subgroups were mapped to genes names.

b. Functional Analysis of Gene Clusters

To establish the functional significance of the probe set clusters, probe sets were mapped to genes (Entrez gene ID) and an enrichment analysis was performed. Enrichment significance was calculated based on the hypergeometric function (False Discovery Rate applied (Benjamini and Hochberg, 1995, J. R. Stat. Soc. 57:289:300)). Over-representation of biological processes and pathways were analysed for each gene group generated by the hierarchical clustering for the epithelial serous ovarian cancer samples using Almac Diagnostics' proprietary Functional Enrichment Tool (FET). Antisense probe sets were excluded from the analysis. Hypergeometric p-values were assessed for each enriched functional entity class. Functional entity classes with the highest p-values were selected as representative of the group and a general functional category representing these functional entities was assigned to the gene clusters based on significance of representation (i.e. p-value).

To generate an angiogenesis classifier using the original 199 epithelial serous ovarian tumors, genes in clusters enriched for angiogenesis, vasculature development and immune response general functional terms were grouped into a putative angiogenesis gene group and used for the signature generation. The sample clusters presenting high expression for the genes involved in angiogenesis, vasculature development and immune response general functional terms were selected for classification and labeled as 'angiogenesis'. Those not showing high expression for the genes involved in these functional terms were labeled as 'non-angiogenesis'.

To generate an angiogenesis classifier using the reclassified 265 epithelial serous ovarian tumors, genes in clusters enriched for angiogenesis and vasculature development general functional terms were grouped into a putative angiogenesis gene group and used for the signature generation. The sample clusters presenting high expression for the genes involved in angiogenesis and vasculature development general functional terms were selected for classification and labeled as 'angiogenesis'. Those not showing high expression for the genes involved in these functional terms were labeled as 'others' 'others' (FIG. 6 top label identifying "angiogenesis" samples (red) plus "others" (grey)).

To generate a "non-angiogenesis classifier" using the reclassified 265 epithelial serous ovarian tumors the sample clusters presenting low expression for the genes involved in angiogenesis and vasculature development general functional terms were selected for classification and labeled as "non-angiogenesis." Those not showing low expression fore the genes involved in these functional terms were labeled as 'others' (FIG. 6 bottom label identifying "non-angiogenesis" samples plus "others").

Classifier Development at a Gene Level

To facilitate validation of the classifier across multiple array platforms, the angiogenesis classifier was generated at the gene level. The following steps outline the procedures that were taken for gene level signature development (each step performed over internal cross validation using 10 repeats of 5-fold cross-validation):

Gene Level Signature Development

Pre-processing:
    RMA background correction.
    Reference set of genes are those genes (sense probe sets only) unique to the ovarian DSA platform.
    Gene level summarization was performed in two steps; first probes to probe set summarization was performed by calculating the median expression of the probes in a probe set; secondly, median expression of the (sense only) probe sets mapping to each gene in the reference distribution is calculated, yielding a "gene level" expression matrix.
    Quantile normalization was performed on the full gene expression data matrix and a reference quantile derived from the training data was used to normalize the test samples within each round of cross validation.

Feature selection: Filtering 75% of genes by variance, intensity and correlation to cDNA concentration, followed by either recursive feature elimination (RFE) or filter feature selection (FFS) based on CAT scores.

Classification algorithms: Partial Least Squares (PLS), SDA (Shrinkage Discriminate Analysis) and DSDA (Diagonal SDA).

Model Selection

The criteria used for model selection were AUC and/or hazard ratio (HR) over internal cross-validation and feature elimination. Functional enrichment of the signatures over cross validation using FET based on the gene ontologies, interim validation sets which included two sets of technical replicates for which standard deviation in signature scores for repeated samples was evaluated over cross-validation and feature elimination and an assessment of the independence to clinical and technical factors over cross validation (factors listed in Table 4).

It should be noted, since the subgroup (i.e. class label) derivation was performed using microarray expression from the same sample cohort that was used for signature development, there was an expected positive bias in any performance estimates based on AUC. This highlights the importance of widening the criteria used for model selection, by including additional metrics such as the hazard ratio, functional enrichment and assessing the independence to clinical and technical factors.

TABLE 4

List of clinical and technical factors investigated

| Clinical factors: | Technical factors: | Sample processing factors: |
| --- | --- | --- |
| Debulking | Hospital<br>Block age<br>RNA concentration<br>cDNA yield | Post Amp operator |

Calculating Classifier Scores for Validation Data Sets

All datasets were background corrected using RMA. For each validation set, the probe sets that map to the classifier genes were determined, excluding anti-sense probe sets (if applicable). Annotation for Affymetrix Plus 2.0 and U133A arrays are available from the Affymetrix website. The median intensity over all probes mapping to each gene in the classifier was calculated and the quantile normalization model from the training set was applied to normalize the testing samples one at a time, resulting in a gene intensity matrix. The classifier was then applied to this data matrix to produce a classifier score/prediction for each sample.

Univariate and Multivariate Analysis

Univariate and multivariate analysis may be carried out in relation to the glioblastoma dataset to assess respectively the association between the angiogenesis subtype classifier and survival, and to determine if the association, if any, was independent to known clinical predictors. The p-values for univariate analysis were calculated using logistic regression in MATLAB. For the multivariate analysis we used a likelihood ratio test from logistic regression was used, where the p-values represent the drop in the log-likelihood when comparing the model with the clinical covariates and the predictions to a reduced model with clinical covariates only. The likelihood ratio test measures the importance of the gene predictor in modeling survival, and highlights its independence as a predictor relative to the clinical predictors. In both univariate and multivariate analysis, a p-value<0.05 was used as the criterion for significance. Furthermore, samples with unknown clinical factors were excluded in this assessment.

Results

Identification of Subgroups and Generation of Signature from Original and Updated Histology Classification Hierarchical Clustering Analysis Feature selection resulted in the selection of 1200 probe sets from the original epithelial serous ovarian cancer data set (199 samples) and 1400 PS from the reclassified epithelial serous ovarian cancer data set (265 samples). The GAP analysis revealed three sample clusters and three probe set cluster groups within both sample sets (FIG. 1, FIG. 6).

Classification of Tumors into 'Angiogenesis' or 'Non-Angiogenesis' Sample Groups The classification of samples as 'anigogenesis' or 'non-angiogenesis' was based upon the results of the functional analysis of the epithelial serous ovarian cancer dataset (FIG. 1 FIG. 6). The objective of this study was to characterize at a transcriptomic level a set of genes that would be capable of determining responsiveness or resistance of a pathogenic cell to anti-angiogenic agents and potentially identify patients who could benefit from anti-angiogenic therapy. With this in mind, those samples within the epithelial serous ovarian cancer datasets that best represented this biology were to be selected and compared to the remaining samples for classifier generation (see next section). It was decided that the samples from the sample angiogenesis cluster within the original epithelial serous ovarian cancer sample set (199 samples) (FIG. 1) were the most relevant samples for this selection as these samples demonstrated an up-regulation of genes involved in signaling related to angiogenic and immune response processes and pathways as defined by functional analysis (FIGS. 2A and 2B) It was decided that the samples from sample cluster three within the reclassified epithelial serous ovarian cancer sample set (265 samples) (FIG. 6) were the most relevant samples for this selection as these samples demonstrated an up-regulation of genes involved in signaling related to angiogenic processes and pathways as defined by functional analysis (FIGS. 2A and 2B).

Figure 2A:
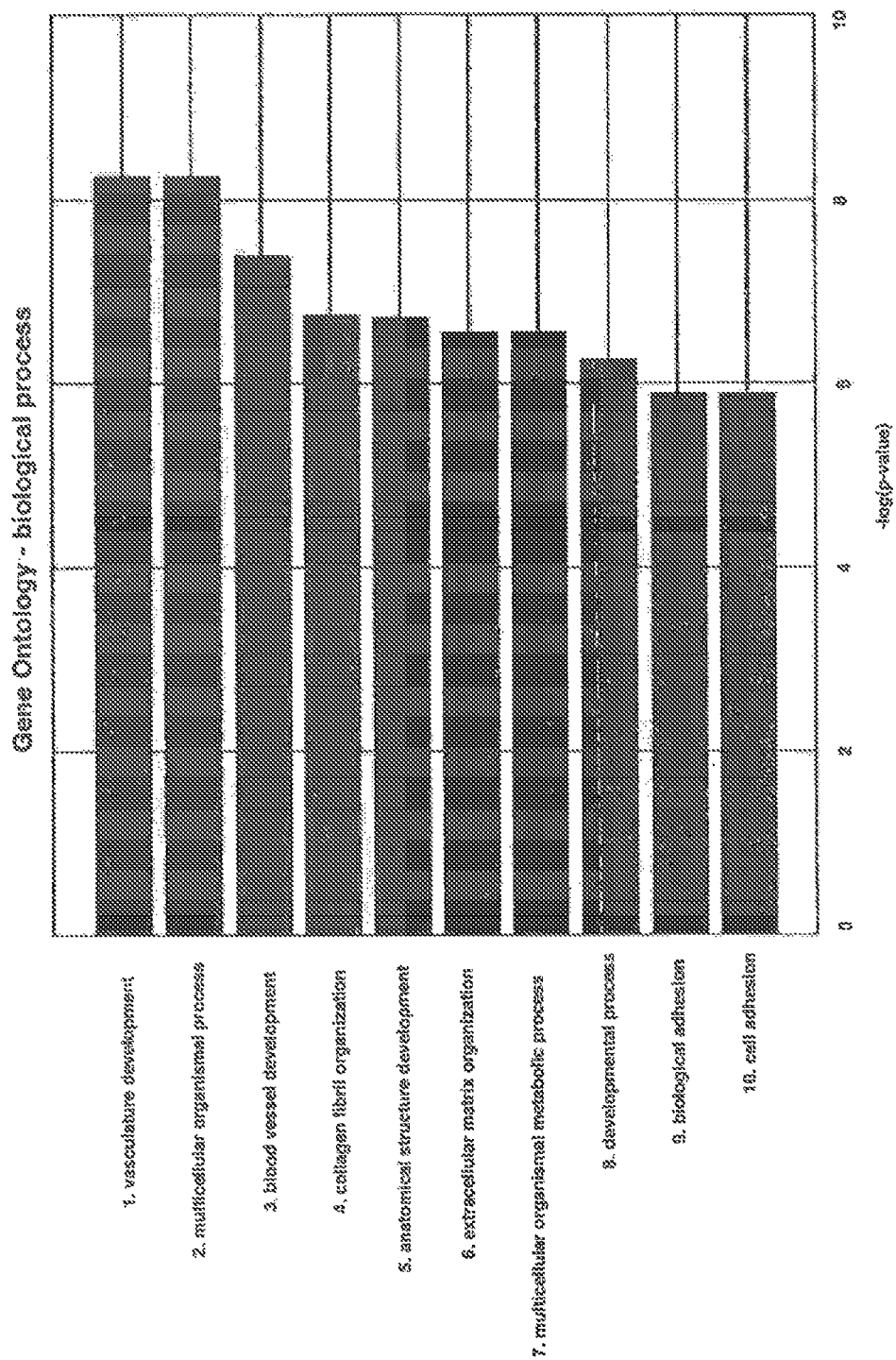
FIGS. 2A and 2B represents the functional analysis results of the angiogenesis probe set cluster in the 199 serous only samples in an epithelial ovarian cancer training set using a functional enrichment analysis.
Figure 2B:
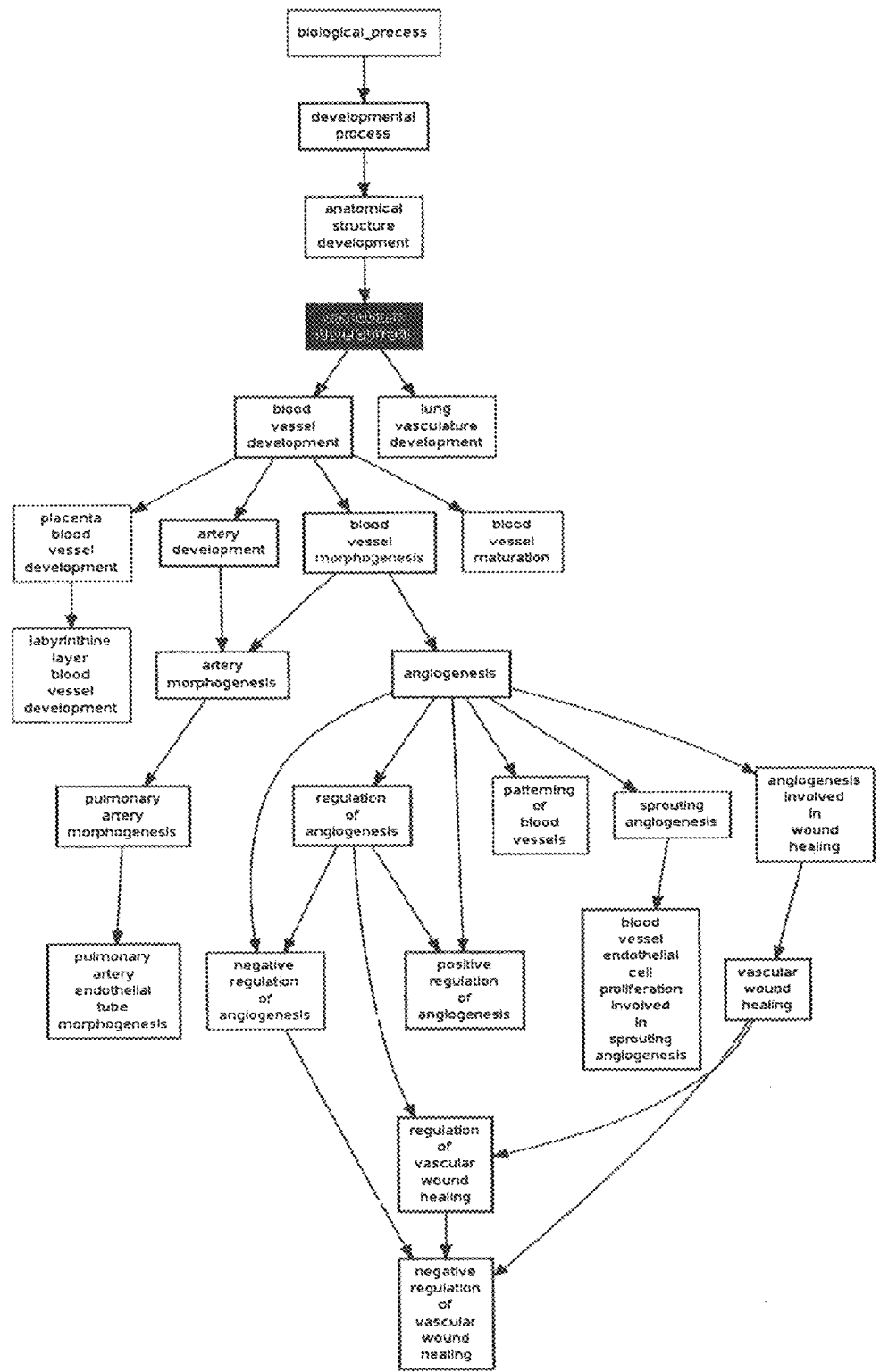
Figure 3:
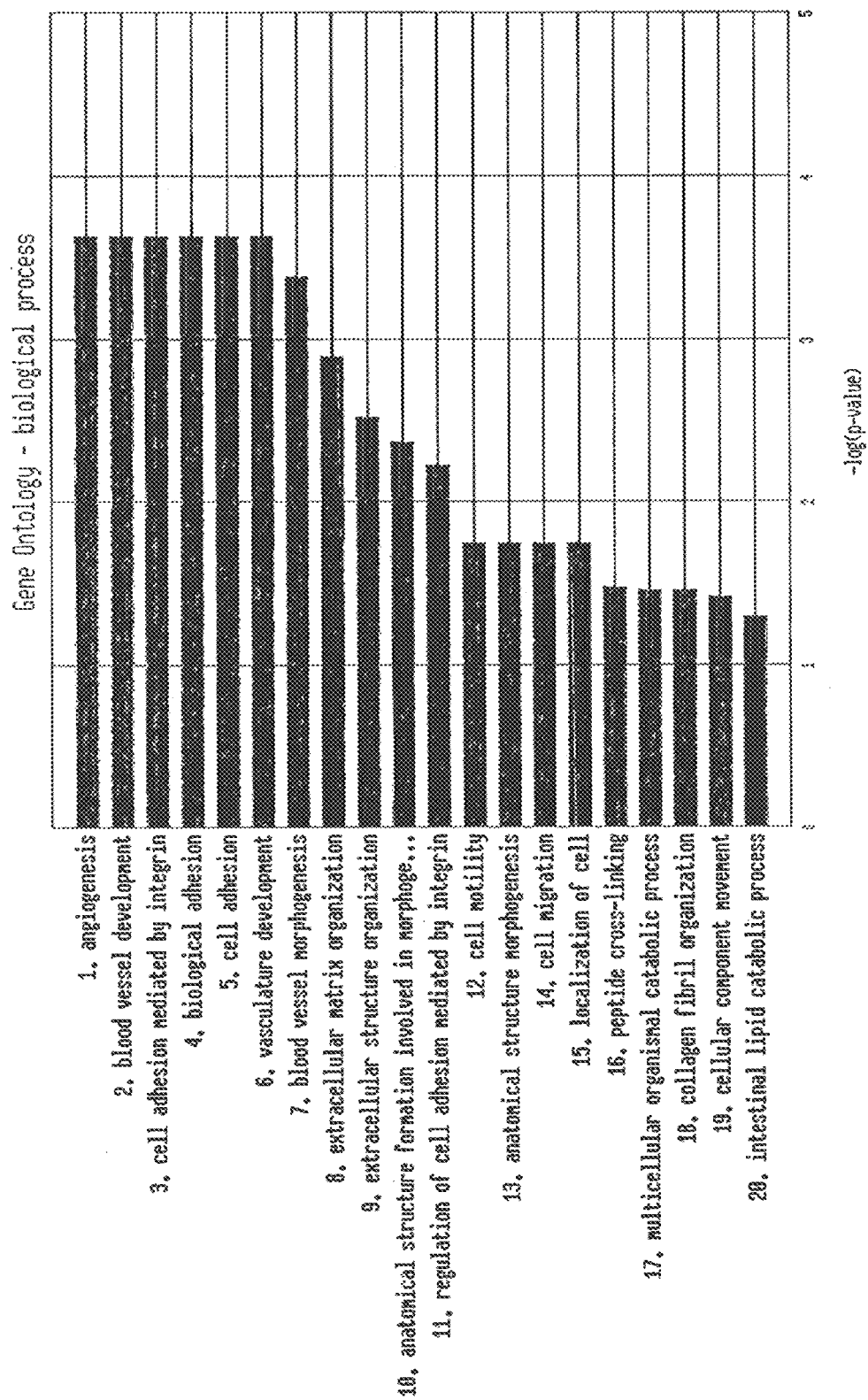
FIG. 3 represents the functional enrichment results of the genes within an exemplary 25-gene expression signature that identifies the molecular subtype related to angiogenesis. Red bars indicate significance of a process at a p-value of 0.05 after False Discovery Rate correction.
Figure 4:
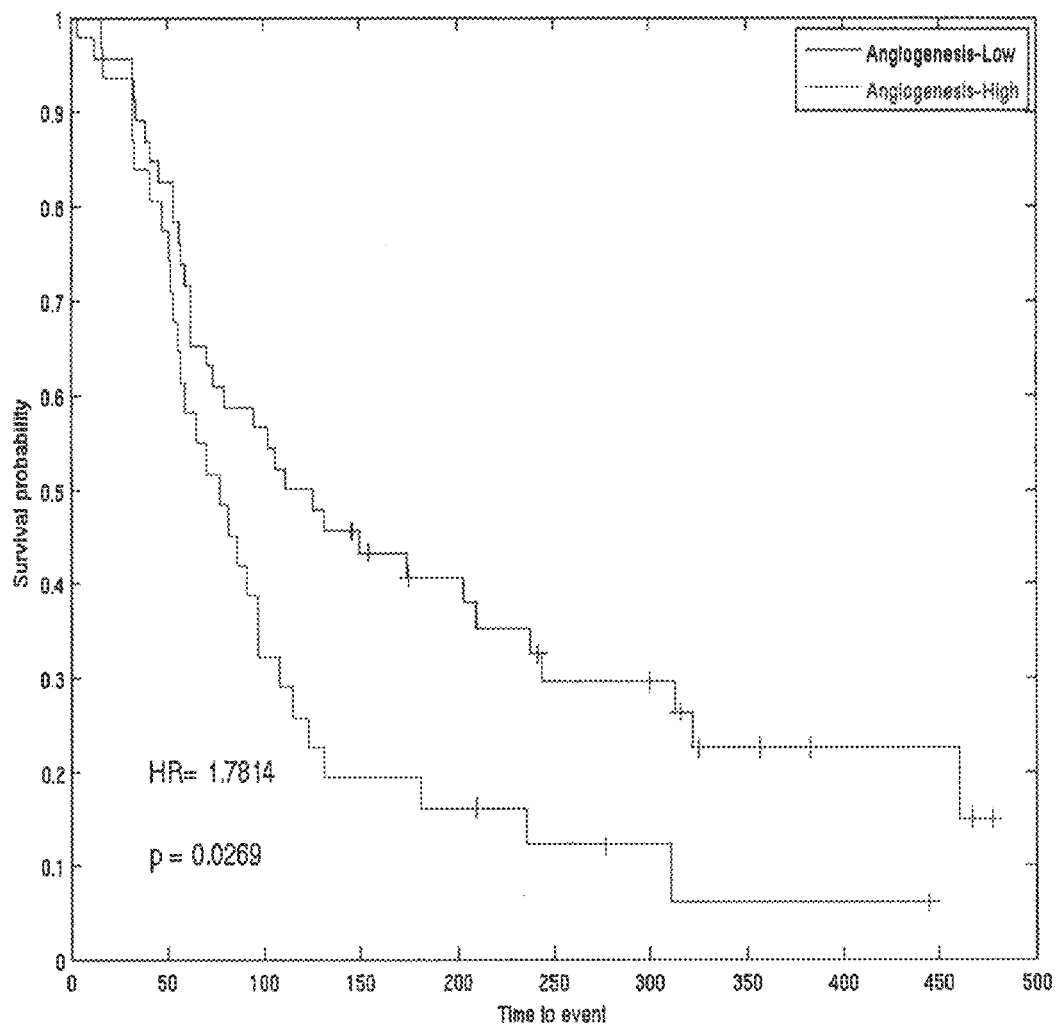
FIG. 4 provides Kaplan-Meier curves for recurrence-free survival (time-to-event in weeks) following initial surgical resection from patients with high-grade glioblastoma without prior treatment (Phillips H S, Kharbanda S, Chen R, Forrest W F et al. "Molecular subclasses of high-grade glioma predict prognosis, delineate a pattern of disease progression, and resemble stages in neurogenesis," CANCER CELL 2006 March; 9(3):157-73. PMID: 16530701; Costa B M, Smith J S, Chen Y, Chen J et al. "Reversing HOXA9 oncogene activation by PI3K inhibition: epigenetic mechanism and prognostic significance in human glioblastoma," CANCER RES 2010 Jan. 15; 70(2):453-62. PMID: 20068170).
Figure 5:
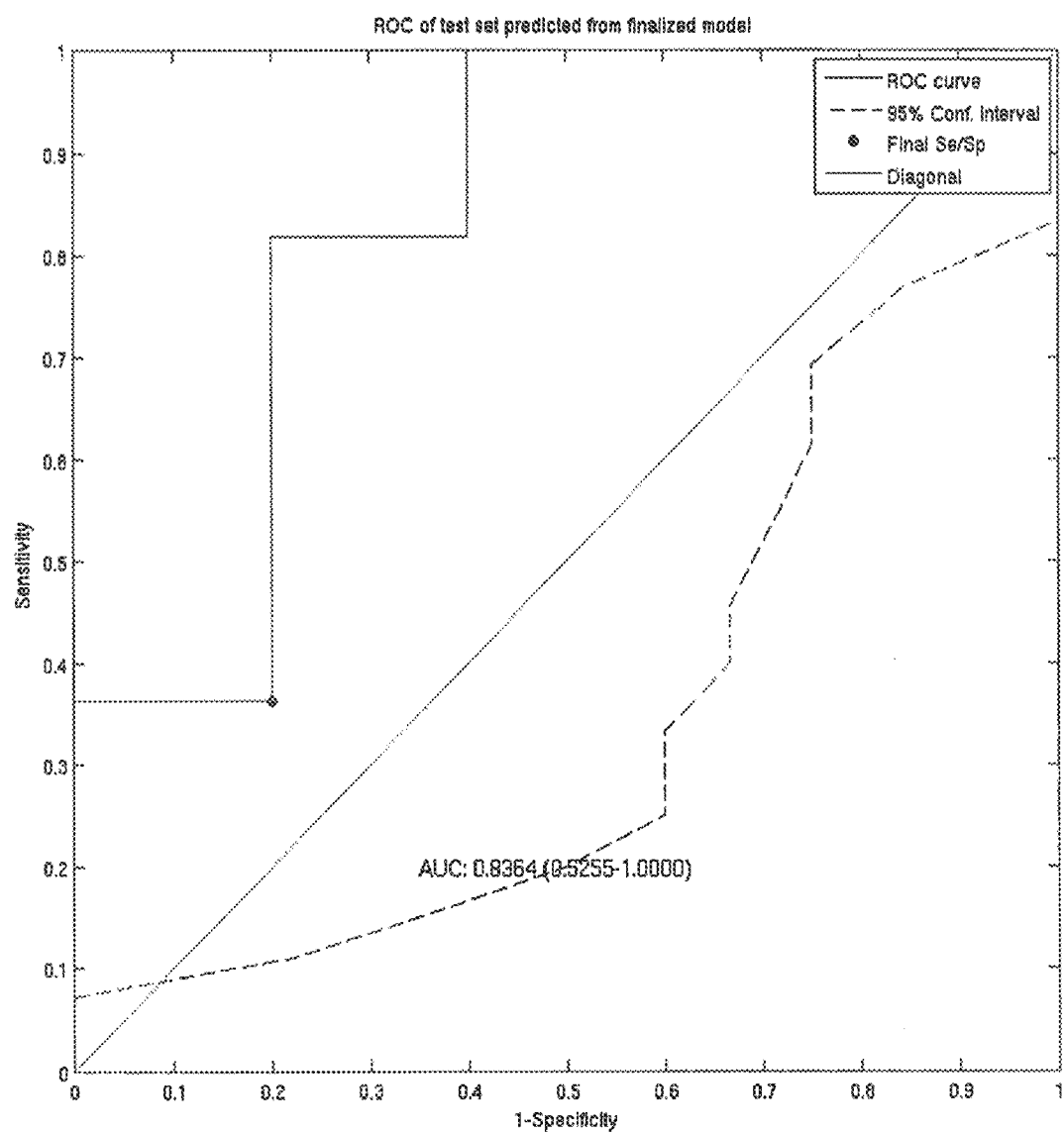
FIG. 5 provides a diagram of a ROC curve of the classification performance of an exemplary 25-gene classifier model within 16 prostate cell-lines following treatment with Dasatanib. The AUC is approximately 0.84 following application of the classifier model. The 95% confidence limits were determined using 1000 bootstrap iterations (Wang X D, Reeves K, Luo F R, Xu L A et al. "Identification of candidate predictive and surrogate molecular markers for dasatinib in prostate cancer: rationale for patient selection and efficacy monitoring," GENOME BIOL 2007; 8(11):R255. PMID: 18047674).

It was decided that the samples from sample cluster 1 within the reclassified epithelial serous ovarian cancer sample set (265 samples) (FIG. 6) were the most relevant samples for selection to represent the "non-angiogenic" subgroup as these samples demonstrated a down-regulation of genes involved in signaling related to angiogenic processes and pathways as defined by functional analysis (FIGS. 2A and 2B).

An identical hierarchical clustering approach was applied to 105 breast cancer samples. The dominant biology in Breast cancer is ER status and therefore in order to identify the structure in the biology of the samples this cohort was divided into 2 populations for cluster analysis. We identified angiogenesis and vasculature development subtypes (FIGS. 11A and 11B) demonstrating the expositing of an angiogenesis subtype from breast cancer samples.

Development and Validation of the Angiogenesis Subtype Classifier Models

For ease of reference, the following steps are detailed in reference to expression signatures derived from Table 1A or Table 1B. Following the identification of a class of tumors, that form the putative 'angiogenesis' subgroup, computational classification of these tumors versus all others in the tumor cohort with reference to the functional 'angiogenesis' (angiogenesis, vasculature development, immune response) gene list (Table 1A or Table 1B) was performed to identify a refined gene classification model, which classifies the 'angiogenesis' subtype.

The classification pipeline was used to derive a model using the set of epithelial serous ovarian cancer samples. The classification pipeline has been developed in accordance with commonly accepted good practice (MAQC Consortium, Nat Biotechnol 2010). The process will, in parallel: 1) derive gene classification models from empirical data; and 2) assess the classification performance of the models, both under cross-validation. The performance and success of the classifier generation depends on a number of parameters that can be varied, for instance the choice of classification method or probe set filtering. Taking this into account, two feature sets were evaluated (i) the full feature list with 75% variance/intensity filtering (with forced inclusion of the angiogenesis gene list, Table 1A) and (ii) the angiogenesis gene list only; and three classification algorithms were evaluated, namely PLS; SDA and DSDA. Two feature elimination methods were adopted: (i) Recursive Feature Elimination (RFE) which is an iterative procedure removing a fraction of the lowest-ranked features at each iteration; stopping when only a minimum number of features remain; (ii) Filter Feature Selection (FFS) which pre-ranks the features based on correlation adjusted t-scores (CAT-scores) (ref) and removes the lowest ranking features at each round of feature elimination. The Area Under the Receiver Operator Characteristic Curve (AUC) was used to assess the classification performance, as this measure is independent of cut-off between groups and prevalence rates in the data. It is also one of the recognized measurements of choice for classification performance. As such, the best number of features for each model was chosen based on the average AUC under cross-validation.

From the analysis described above, the PLS FFS model was deemed to be the most suitable classifier model. Weights were calculated for each gene using PLS regression, resulting in the final gene classifier models (25-gene classifier model for the original approach, and a 45-gene classifier for samples reclassified reflecting recent changes to standard histology protocols) that may be used for validation on external data sets from different array platforms. The gene signature development process was focused upon identification of the ontological processes and pathways relevant to angiogenesis to ensure biological relevance of any signature developed. As such, functional analysis was performed upon both signatures to qualify their relevance to angiogenesis Example 2

In Silico Validation of the Angiogenesis Subtype and Angiogenesis Classifier Models The performance of both the 25-gene (original approach) and 45-gene (reclassification approach) angiogenesis classifier models were validated by the Area Under the ROC (Receiver Operator Characteristic) Curve (AUC) within the original Almac epithelial serous ovarian cancer dataset and two independent datasets. The AUC is a statistic calculated on the observed disease scale and is a measure of the efficacy of prediction of a phenotype using a classifier model (Wray et al., PLoS Genetics Vol 6, 1-9). An AUC of 0.5 is typical of a random classifier, and an AUC of 1.0 would represent perfect separation of classes. Therefore, in order to determine if the angiogenesis subtype classifier model is capable of predicting response to, and selecting patients for anti-angiogenic ovarian cancer therapeutic drug classes either as single agent or in combination with standard of care therapies, the hypothesis is that the AUCs following application within these datasets should be above 0.5 with the lowest confidence interval also above 0.5.

Application of the Classifier Models to an Independent Prostate Cancer Cell-Line Dataset To assess the predictive power of the 25-gene and 45-gene classifier models, they were applied to a dataset of 16 prostate cell-lines following treatment with Dasatanib. The cell-lines were defined as being either a 'responder' or 'non-responder' based upon cell-proliferation assays. This analysis revealed that the 25-gene classifier model is associated with response to Dasatanib, with an AUC of 0.8364 (CI=0.5255-1.0000), indicating that the 25-gene classifier is predictive of response to Dasatanib. The analysis revealed that the 45-gene classifier model is associated with response to the same compound, with an AUC of 0.9455 (CI=0.7949-1.0000) indicating that the 45-gene classifier is also predictive of response to Dasatanib.

Example 3

Figure 10:
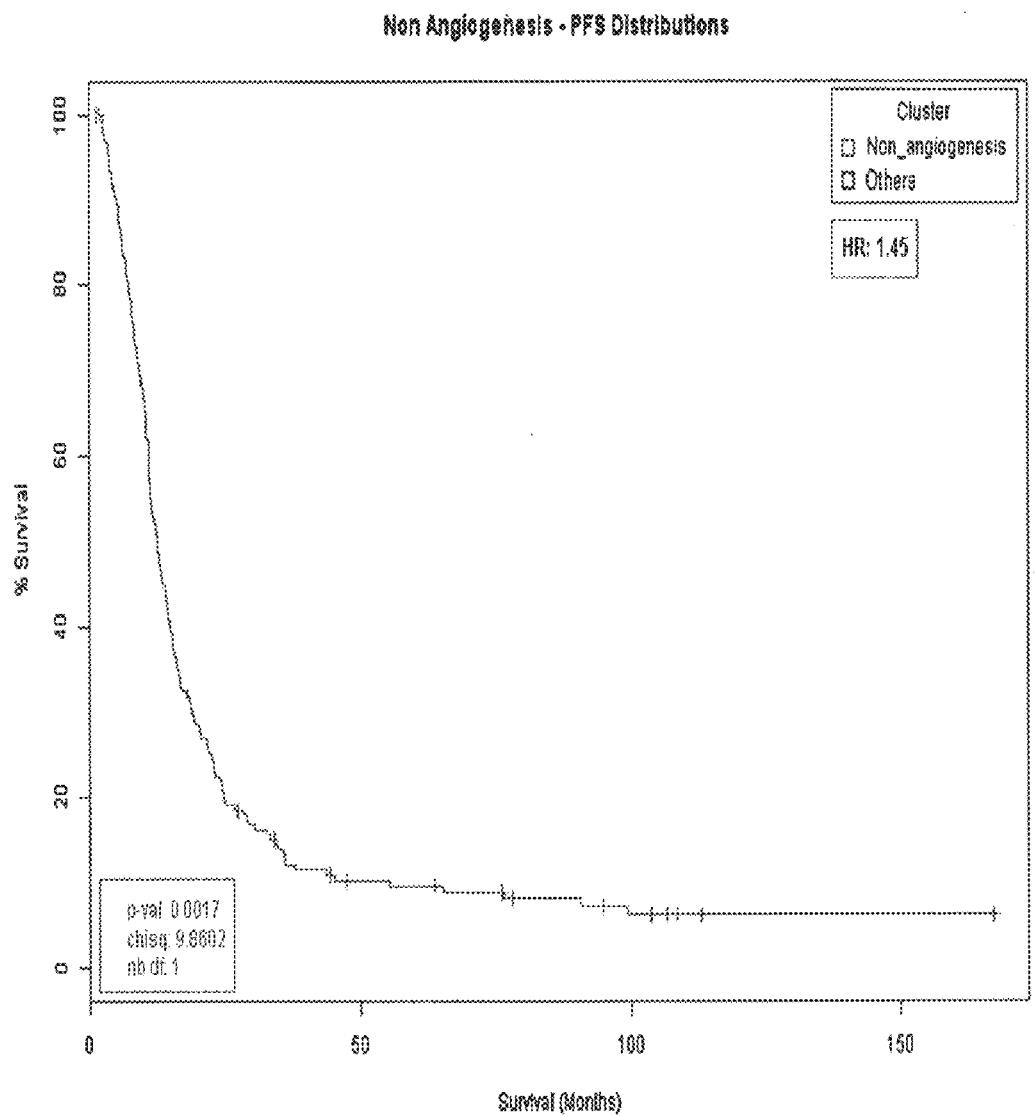
FIG. 10 provides Kaplan-Meier curves for progression-free survival (in weeks) for the non-angiogenesis sample group versus the "other" samples not labelled as "non-angiogenesis" sample group in the reclassified ovarian sample set.

Identification of and in Silico Validation of a "Non-Angiogenic Subgroup of Ovarian Cancer Classification of Tumors into 'Non-Angiogenesis' Sample Groups The expression of angiogenesis genes in probe set cluster 2 is down regulated in all samples in sample Cluster 1 of hierarchical clustering of 265 samples newly classified as serous (FIG. 6 bottom labelled Blue bar)). These samples in sample cluster 2 have a better prognosis than the rest of the serous samples in samples from cluster 1 and 3 combined together as demonstrated in FIG. 10. This indicated that this group is defined by down regulation of expression of the angiogenesis genes identified in Table 1B. Patients with downregulation of genes involved in angiogeniesis and therefore this subgroup is termed a "non-angiogenesis" group. This phenotype has also been identified in ER+ and ER-breast cancer as can be see the middle sample group in FIG. 11A and the second sample group in FIG. 11B.

Development and Validation of the Non-Angiogenesis Subtype Classifier Models

Following the identification of a class of tumors, within the 265 samples newly classified as serous, that form the putative 'non-angiogenesis' subgroup, computational classification of these tumors versus all others in the tumor cohort with reference to the functional 'angiogenesis' (angiogenesis, vasculature development, immune response) gene list (Table 1A or Table 1B) was performed to identify a refined gene classification model, which classifies the 'non-angiogenesis' subtype.

The classification pipeline was used to derive a model using the set of epithelial serous ovarian cancer samples. The methods are analogous to those described above in Example 1.

Applying the analysis described in Example 1, the PLS FFS model was deemed to be the most suitable classifier model. Weights were calculated for each gene using PLS regression, resulting in the final gene classifier model (63-gene classifier model) that may be used for validation on external data sets from different array platforms.

Application of Non-Angiogenesis Classifier Model to the Discovery Data and an Independent Microarray Dataset The performance of the 63-gene non-angiogenesis classifier model was validated using hazard ratio (HR) within the original Almac epithelial serous ovarian cancer dataset and one independent dataset. The hazard ratio is the ratio of the hazard rates corresponding to the conditions described by two sets of explanatory variables. For example, a treated population may die at twice the rate per unit time as the control population. The hazard ratio would be 2, indicating higher hazard of death from the treatment. Therefore, in order to determine if the non-angiogenesis subtype classifier model is capable of predicting non-response to, and selecting patients that should not be treated with anti-angiogenic cancer therapeutic drug classes, either as single agent or in combination with standard of care therapies, it is expected that the HRs should be below 1.0 with a p-value less than 0.05.

To assess the prognostic power of the 63-gene classifier models, it was applied first to the discovery data of 265 epithelial serous ovarian samples and then to a dataset of 275 epithelial serous and endometrioid ovarian samples (14). Within both datasets the samples were taken at the time of initial surgical resection from patients without prior therapy.

Figure 12:
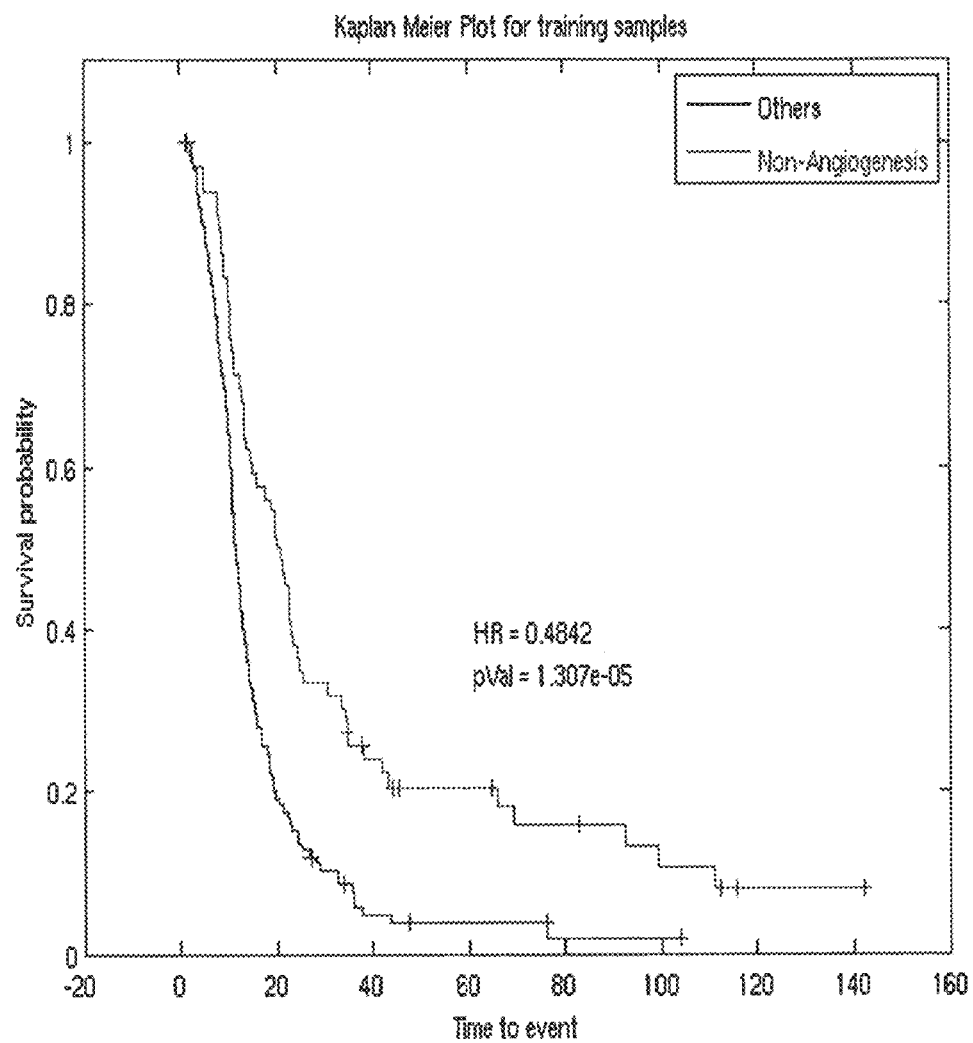
FIG. 12 provides Kaplan-Meier curves for progression-free survival (in weeks) for the samples identified as "non-angiogenesis" using the example 63 gene "non-angiogenesis" signature, versus the "other" samples not classified as "non-angiogenesis" using the example 63 gene signature, in the 265 reclassified ovarian sample set.
Figure 13:
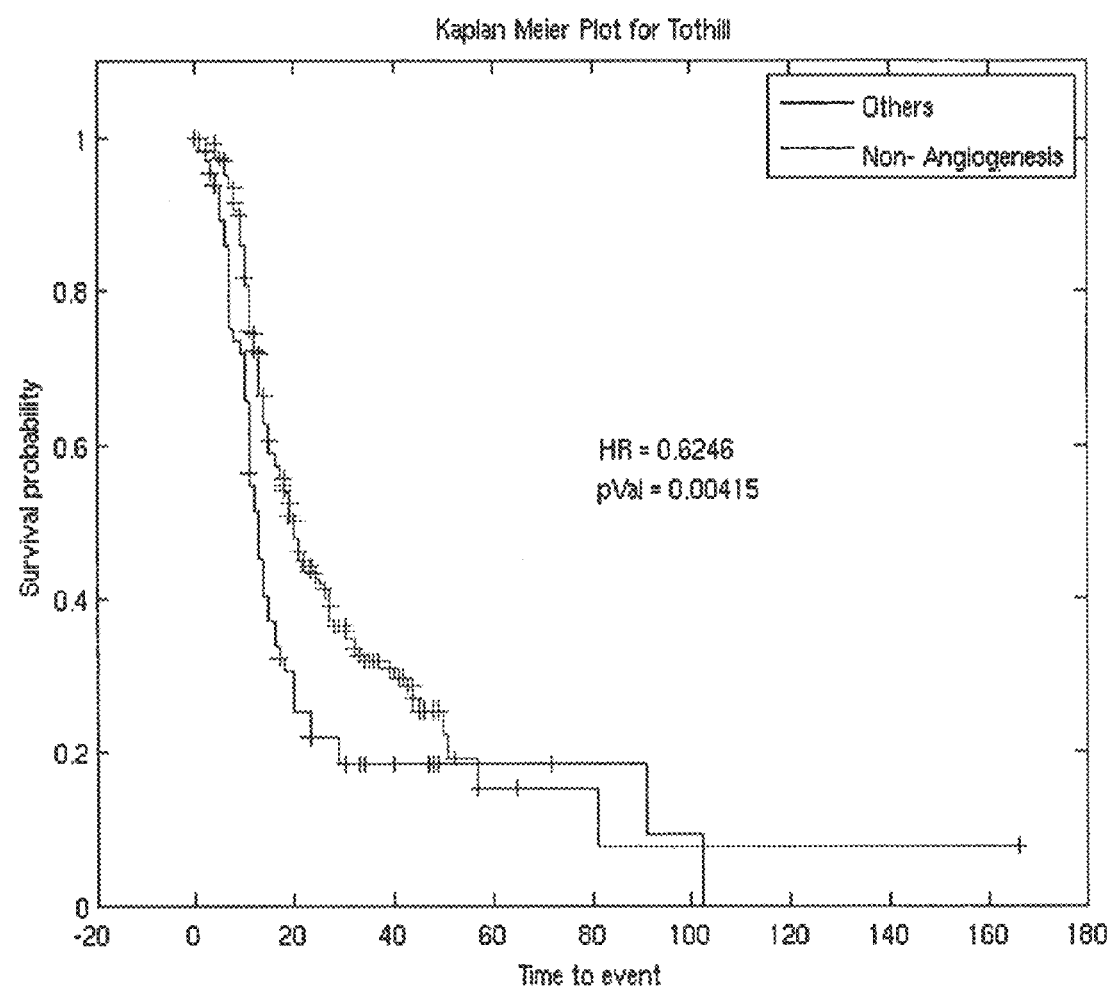
FIG. 13 provides Kaplan-Meier curves for progression-free survival (in weeks) for the samples identified as "non-angiogenesis" using the example 63 gene "non-angiogenesis" signature, versus the "other" samples not classified as "non-angiogenesis" using the example 63 gene signature, in the independent 265 epithelial and serous ovarian sample set.

This analysis revealed that the 63-gene classifier model was independently associated with prognosis in both ovarian cancer datasets. In the discovery set the non-angiogenesis group was associated with significantly better survival compared to the other samples (FIG. 12); Hazard Ratio=0.4842, p=1.307e-05). Similarly in the independent microarray dataset the non-angiogenesis group demonstrated significantly better survival compared to the other samples (FIG. 13) Hazard Ratio=0.62 [0.41-0.95], p=0.029 and OS (multivariable analysis; HR=0.32 [0.19-0.54], p=0.00001. This validates the fact that the 63-gene classifier is an independent prognostic biomarker of survival in ovarian serous and endometrioid cancer samples.

The International Collaboration on Ovarian Neoplasms 7 (ICON7) trial is a Gynecologic Cancer Intergroup phase 3 trial that assessed the effects of adding bevacizumab, concurrently and as a continuation, to standard chemotherapy with carboplatin and paclitaxel in patients with primary peritoneal carcinoma, fallopian tube carcinoma, and epithelial ovarian carcinoma (Perren T J, Swart A M, Pfisterer J, Ledermann J A, Pujade-Lauraine E, Kristensen G, et al. A phase 3 trial of bevacizumab in ovarian cancer. N Engl J Med. 365(26): 2484-96, Aghajanian C, Blank S V, Goff B A, Judson P L, Teneriello M G, Husain A, et al. OCEANS: A randomized, double-blind, placebo-controlled phase III trial of chemotherapy with or without bevacizumab in patients with platinum-sensitive recurrent epithelial ovarian, primary peritoneal, or fallopian tube cancer. Journal of Clinical Oncology. 2012; 30(17): 2039-45).

Patient characteristics, progression-free survival, toxicity, and preliminary overall survival data and a summary of quality-of-life (QoL) data have been reported from ICON7. In the standard chemotherapy group, 696 (91%) of 764 women received 18 weeks of chemotherapy by protocol. In the bevacizumab group, 719 (94%) of 764 women received 18 weeks of chemotherapy and bevacizumab and 472 (62%) continued bevacizumab to protocol completion at 54 weeks. The hazard ratio for progression-free survival with standard chemotherapy and bevacizumab was 0.81 (95% CI 0.70-0-94, p=0.004). In patients at high risk of progression, defined as International Federation of Gynecology and Obstetrics (FIGO) stage IV disease or stage III disease with greater than 1.0 cm of residual disease after debulking surgery, the hazard ratio for death in the bevacizumab group was 0.64 (95% CI 0.48-0-85; p=0.002).

Access was obtained to the ICON7 trail samples via the Medical Research Council (MRC). An honest broker holds the associated clinical data from the MRC. A randomization strategy for profiling the samples has been performed based on clinical factors. All reagents, arrays, and reference samples were previously tested and passed qualification criteria.

Total RNA was extracted from macrodissected FFPE tissue using the High Pure RNA Paraffin Kit (Roche Diagnostics GmbH, Mannheim, Germany). RNA is converted into complementary deoxyribonucleic acid (cDNA), which is subsequently amplified and converted into single-stranded form using the SPIA® technology of the WT-Ovation™ FFPE RNA Amplification System V2 (NuGEN Technologies Inc., San Carlos, Calif., USA). The amplified single-stranded cDNA is then fragemented and biotin labeled using the FL-Ovation™ cDNA Biotin Module V2 (NuGEN Technologies Inc.). The fragmented and labeled cDNA was then hybridized to the Almac Ovarian Cancer DSA, on this the signature was developed. Arrays are scanned using the Affymentrix Genechip® Scanner 7G (Affymetrix Inc., Santa Clara, Calif.).

Control UHR and a pooled clinical reference sample are processed in each post RNA extraction batch. QC is be performed at several steps of the process, from RNA Extraction QC to array QC.

Quality Control (QC) of profiled samples is carried out using the RMA pre-processing algorithm. Different technical aspects are assessed: average noise and background homogeneity, percentage of present call (array quality), signal quality, RNA quality and hybridization quality. Distributions and Median Absolute Deviation of corresponding parameters are analyzed and used to identify possible outliers.

Almac's Ovarian Cancer DSA™ contains probes that primarily target the area within 300 nucleotides from the 3' end. Therefore standard Affymetrix RNA quality measures were adapted—for housekeeping genes intensities of 3' end probe sets with ratios of 3' end probe set intensity to the average background intensity were used in addition to usual 3'/5' ratios. Hybridization controls were checked to ensure that their intensities and present calls conform to the requirements specified by Affymetrix.

Samples that pass QC metrics will be deemed suitable for inclusion in subsequent analysis, and signature scores will be calculated (per sample) using the following:
Background correction
RefRMA model to pre-process the data, one sample at a time
The signature score is calculated as a weighted sum of the expression of the genes in the signature:

$$SignatureScore = \sum_i w_i \times (ge_i - b_i) + k$$

where $w_i$ is a weight for each gene, $b_i$ is a gene-specific bias (Supplementary Table S5), $ge_i$ is the observed gene expression level after pre-processing, and k=0.2953 is a constant offset.

Sample IDs and corresponding signature scores will be sent to the honest broker to evaluate the predictive performance of the Ovarian Immune signature to predict resistance to Avastin in the treatment arm of the study.

Application of Angiogenesis Classifier Model to the Discovery Data and an Independent Microarray Dataset Class labels were assigned to samples based upon expression of the angiogenesis-related genes and a 25 and 45 gene expression signatures were developed to identify the pro-angiogenic molecular subgroup of high grade serous (HGS) carcinoma.

Angiogenesis is central to the process of cancer growth and metastasis and has a role in the progression and prognosis of ovarian cancer. VEGF is an important promoter of angiogenesis produced by normal and neoplastic cells. Bevacizumab (Avastin, Riche) is a recombinant humanised version of a murine anti-human VEGF monoclonal antibody and has been studied in the management of many tumours. The International Collaboration on Ovarian Neoplasms 7 (ICON7) trial is a Gynecologic Cancer Intergroup phase 3 trial that assessed the effects of adding bevacizumab, concurrently and as a continuation, to standard chemotherapy with carboplatin and paclitaxel in patients with primary peritoneal carcinoma, fallopian tube carcinoma, and epithelial ovarian carcinoma (Perren T J, Swart A M, Pfisterer J, Ledermann J A, Pujade-Lauraine E, Kristensen G, et al. A phase 3 trial of bevacizumab in ovarian cancer. N Engl J Med. 365(26): 2484-96, Aghajanian C, Blank S V, Goff B A, Judson P L, Teneriello M G, Husain A, et al. OCEANS: A randomized, double-blind, placebo-controlled phase III trial of chemotherapy with or without bevacizumab in patients with platinum-sensitive recurrent epithelial ovarian, primary peritoneal, or fallopian tube cancer. Journal of Clinical Oncology. 2012; 30(17): 2039-45).

Patient characteristics, progression-free survival, toxicity, and preliminary overall survival data and a summary of quality-of-life (QoL) data have been reported from ICON7. In the standard chemotherapy group, 696 (91%) of 764 women received 18 weeks of chemotherapy by protocol. In the bevacizumab group, 719 (94%) of 764 women received 18 weeks of chemotherapy and bevacizumab and 472 (62%) continued bevacizumab to protocol completion at 54 weeks. The hazard ratio for progression-free survival with standard chemotherapy and bevacizumab was 0.81 (95% CI 0.70-0-94, p=0-004). In patients at high risk of progression, defined as International Federation of Gynecology and Obstetrics (FIGO) stage IV disease or stage III disease with greater than 1.0 cm of residual disease after debulking surgery, the hazard ratio for death in the bevacizumab group was 0.64 (95% CI 0.48-0-85; p=0-002).

HGS patients with the angiogenic subgroup may benefit from anti-angiogenic targeted therapies. Access to the ICON7 trial samples was obtained via the MRC, and are being profiled on Ovarian DSAs in order to validate this hypothesis.

H & E Sections of FFPE material from ICON7 trial samples have been pathology reviewed, marked for tumour content and the tumour material macro dissected.

An honest broker obtained and holds the associated clinical data from the MRC. They have also performed the randomisation strategy, based on clinical factors, for profiling the samples. All reagents, arrays and reference samples were previously tested and passed qualification criteria.

Total RNA was extracted from macrodissected FFPE tissue using the High Pure RNA Paraffin Kit (Roche Diagnostics GmbH, Mannheim, Germany). RNA is converted into complementary deoxyribonucleic acid (cDNA), which is subsequently amplified and converted into single-stranded form using the SPIA® technology of the WT-Ovation™ FFPE RNA Amplification System V2 (NuGEN Technologies Inc., San Carlos, Calif., USA). The amplified single-stranded cDNA is then fragemented and biotin labeled using the FL-Ovation™ cDNA Biotin Module V2 (NuGEN Technologies Inc.). The fragmented and labeled cDNA was then hybridized to the Almac Ovarian Cancer DSA, on this the signature was developed. Arrays are scanned using the Affymentrix Genechip® Scanner 7G (Affymetrix Inc., Santa Clara, Calif.).

Control UHR and a pooled clinical reference sample are processed in each post RNA extraction batch. QC is be performed at several steps of the process, from RNA Extraction QC to array QC.

Quality Control (QC) of profiled samples is carried out using the RMA pre-processing algorithm. Different technical aspects are assessed: average noise and background homogeneity, percentage of present call (array quality), signal quality, RNA quality and hybridization quality. Distributions and Median Absolute Deviation of corresponding parameters are analyzed and used to identify possible outliers.

Almac's Ovarian Cancer DSA™ contains probes that primarily target the area within 300 nucleotides from the 3' end. Therefore standard Affymetrix RNA quality measures were adapted—for housekeeping genes intensities of 3' end probe sets with ratios of 3' end probe set intensity to the average background intensity were used in addition to usual 3'/5' ratios. Hybridization controls were checked to ensure that their intensities and present calls conform to the requirements specified by Affymetrix.

Samples that pass QC metrics will be deemed suitable for inclusion in subsequent analysis, and signature scores will be calculated (per sample) using the following: Background correction RefRMA model to pre-process the data, one sample at a time The signature score is calculated as a weighted sum of the expression of the genes in the signature:

$$SignatureScore = \sum_i w_i \times (ge_i - b_i) + k$$

where $w_i$ is a weight for each gene, $b_i$ is a gene-specific bias (Supplementary Table S5), $ge_i$ is the observed gene expression level after pre-processing, and k=0.2953 is a constant offset.

Sample IDs and corresponding signature scores will be sent to the honest broker to evaluate the predictive performance of the pro-angiogenic signature to predict benefit from Avastin in the treatment arm of the study.

Figure 17:
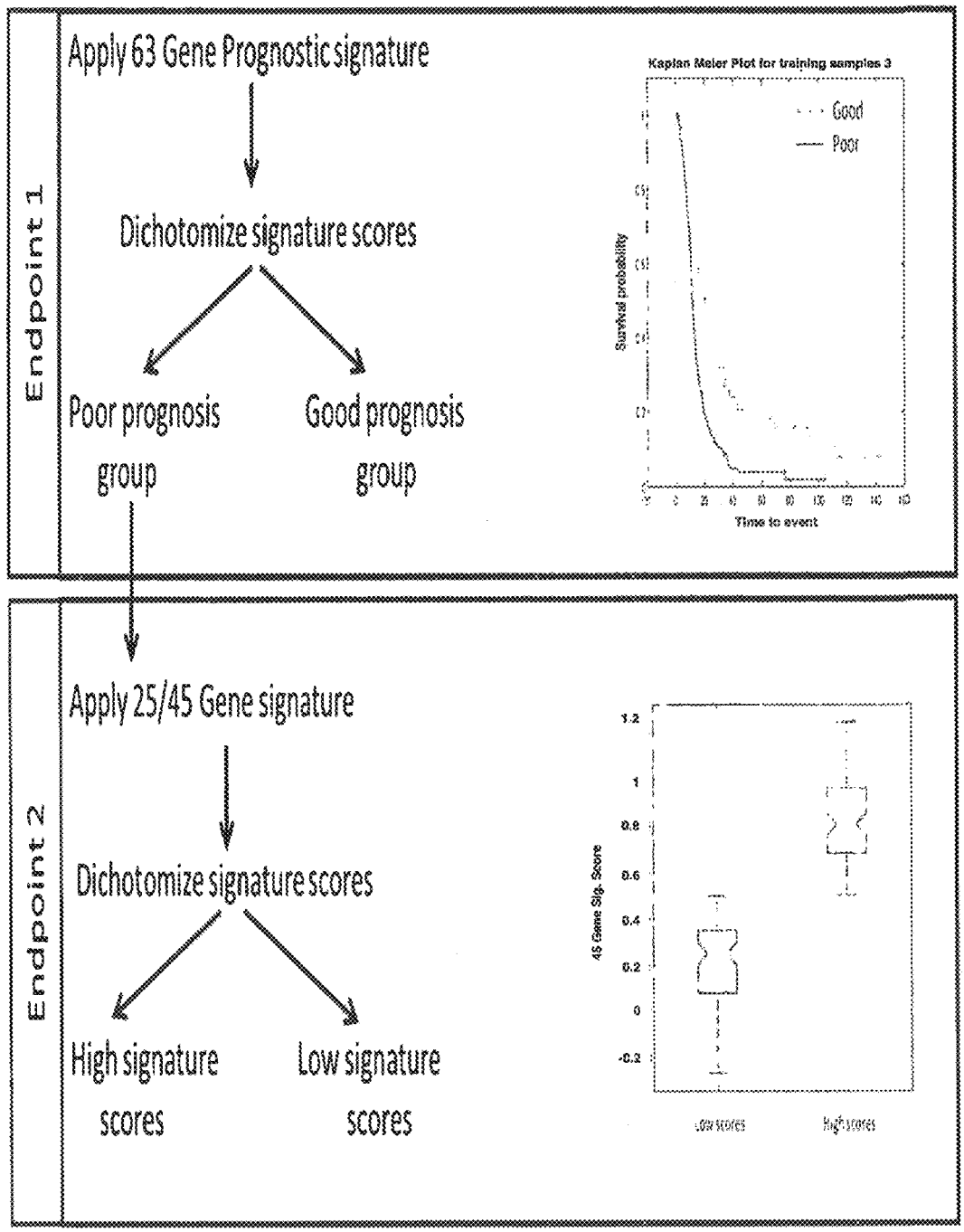
FIG. 17 provides a process flow diagram example Kaplan Meier curves for the use of a non-angiogenesis signature to classify a patient based on prognosis and then an angiogenesis signature to determine responsiveness to a given therapeutic regimen in accordance with example embodiments.

Application of Classifier Model Combination to Identify Three Molecular Subgroups As a secondary endpoint, analysis of the combined signature approach (see FIG. 17) will be evaluated. This approach utilizes the 63 gene signature to identify 2 groups, one with a better survival i.e. the group with reduced activation of angiogeneic processes, and the other with poorer survival. The 45 gene signature will be applied to the group with poorer survival outcome to identify a further 2 groups, one with elevated activation of angiogenic processes and the other with indifferent angiogenic activation. It is hypothesized that the group identified with elevated angiogenic activity should respond to Avastin in the treatment arm of the study.

Example 4

Predictive Utility of Non-Angiogenesis Signature in Colorectal Cancer

Figure 14:
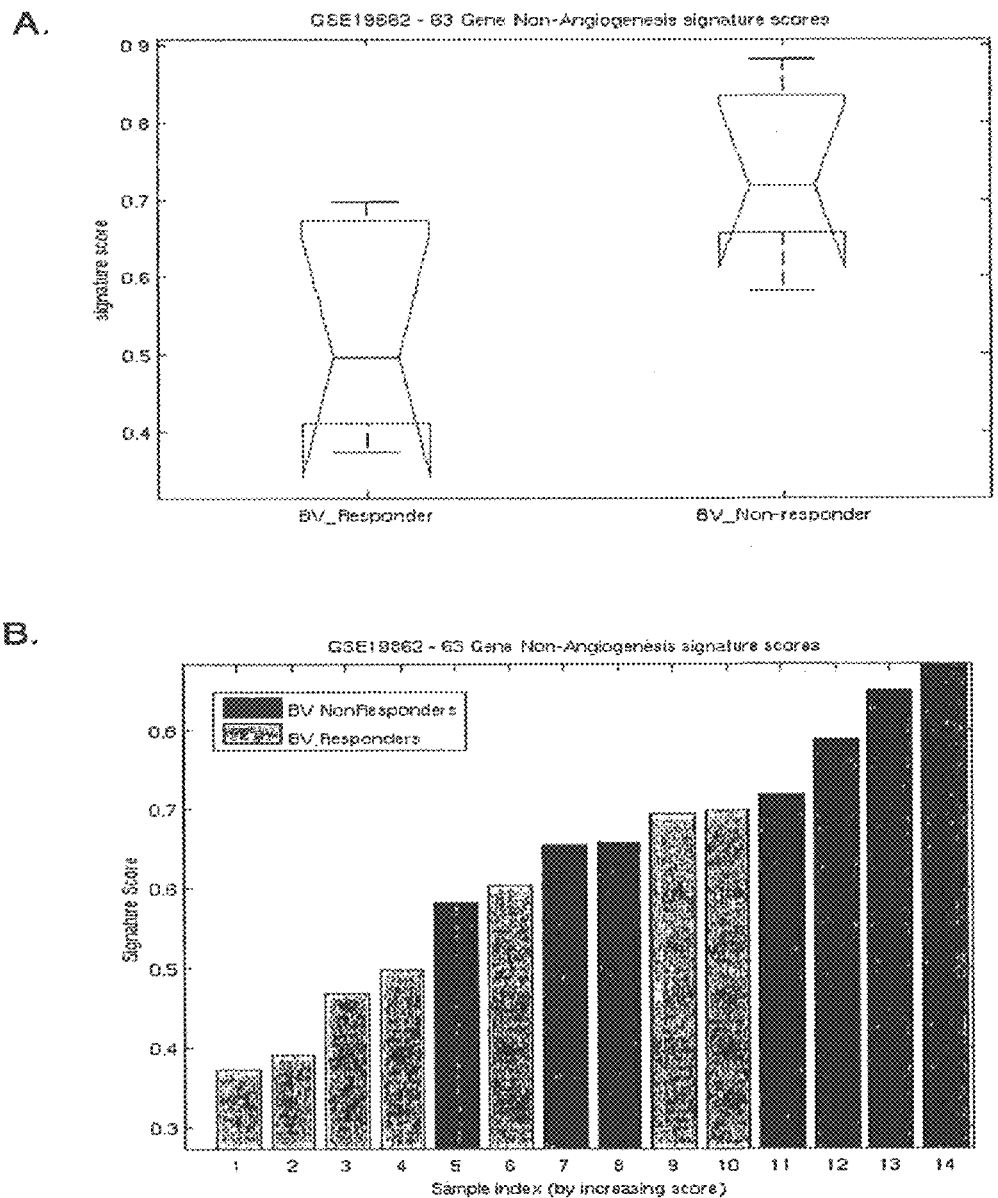
FIGS. 14A and 14B are graphs demonstrating certain classification performance benchmarks of an example non-angiogenesis signature as applied to colorectal cancer samples.
Figure 15:
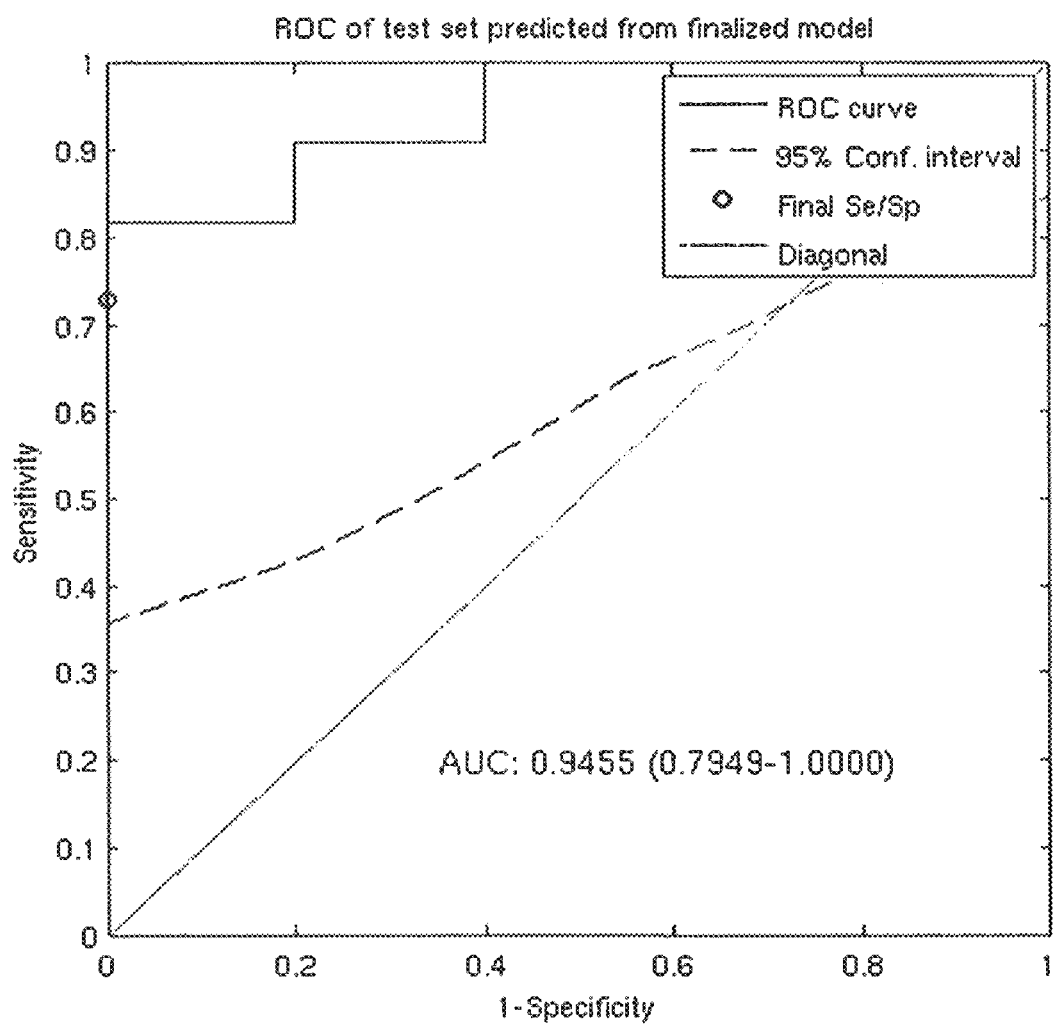
FIG. 15 provides a diagram of a ROC curve of the classification performance of the 45-gene classifier model within 16 prostate cell-lines following treatment with Dasatanib. The AUC is ~0.95 following application of the classifier model. The 95% confidence limits were determined using 1000 bootstrap iterations (Wang X D, Reeves K, Luo F R, Xu L A et al. "Identification of candidate predictive and surrogate molecular markers for dasatinib in prostate cancer: rationale for patient selection and efficacy monitoring," GENOME BIOL 2007; 8(11):R255. PMID: 18047674).
Figure 16:
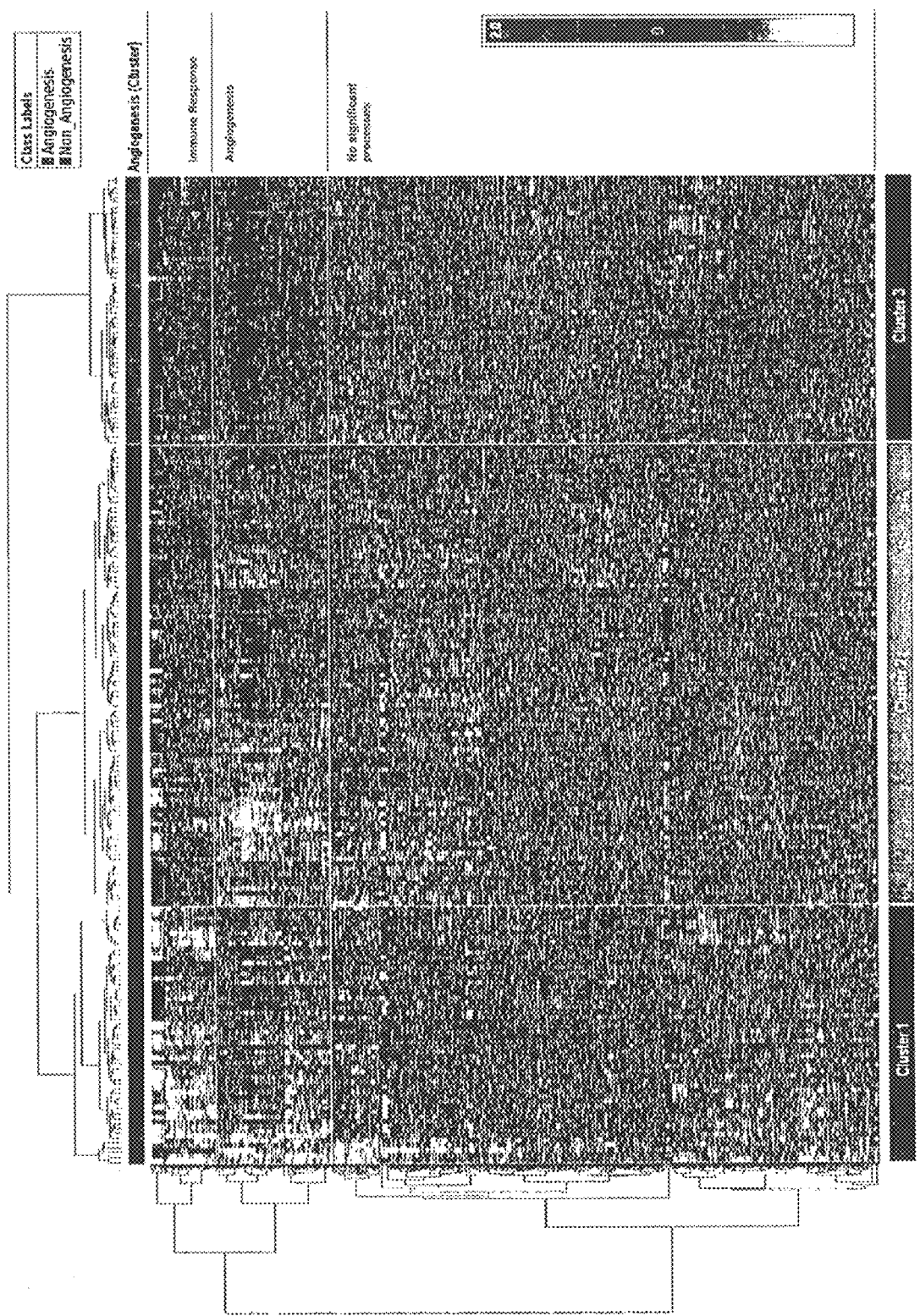
FIG. 16 provides a heatmap representing the hierarchical agglomerative clustering analysis of the most variable probe sets across 199 serous samples of the Almac Diagnostics' epithelial ovarian cancer sample set. The functional analysis of the probe set clusters is summarized on the right hand side of the image. The legend across the top of the image indicates the classifier group each sample was assigned to for classifier generation (i.e. Class labels).

A public array data set obtained from the Gene Expression Omninbus database for a cohort of recurrent or metastatic colorectal cancer responders and non-responders to Bevacizumab on plus 2 arrays (E-GEOD-19862) was obtained and analyzed using the example 63 gene signature of Table 2C. The 63 gene ovarian immune signatures predicts response to bevacizumab with an AUC: 0.86 (0.60-1.00). See FIG. 14.

Example 5

Figure 18:
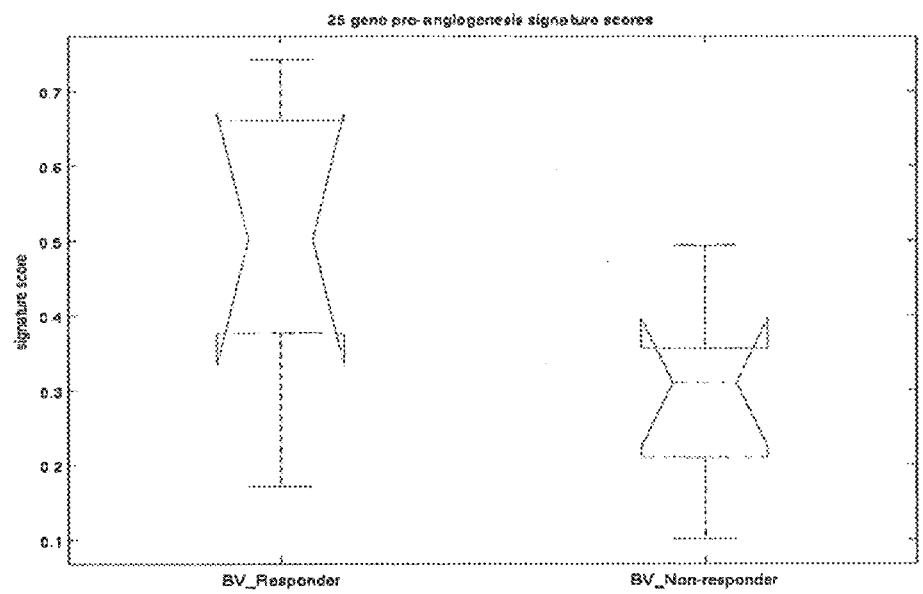
FIGS. 18A and B are graphs demonstrating certain classification performance benchmarks of an example 25 angiogenesis signature as applied to colorectal cancer samples.
Figure 18:
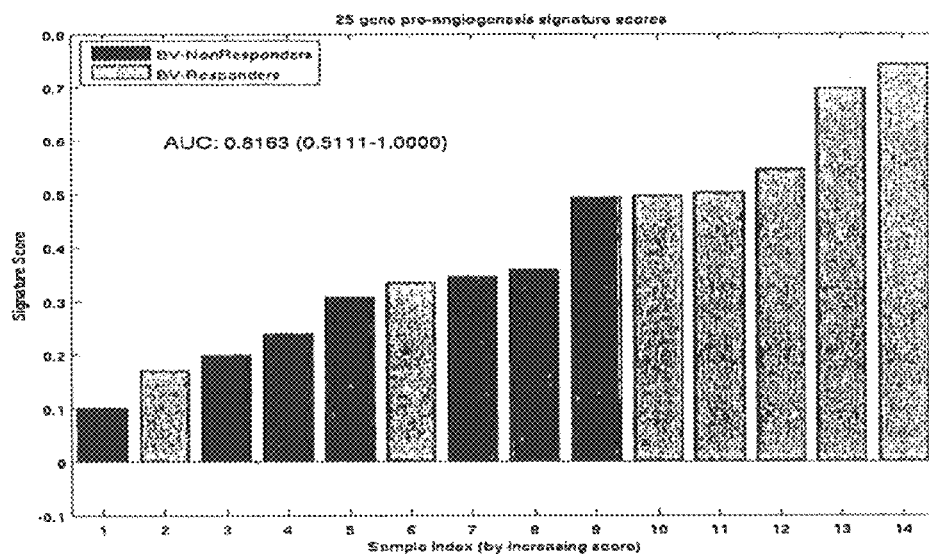
Figure 19:
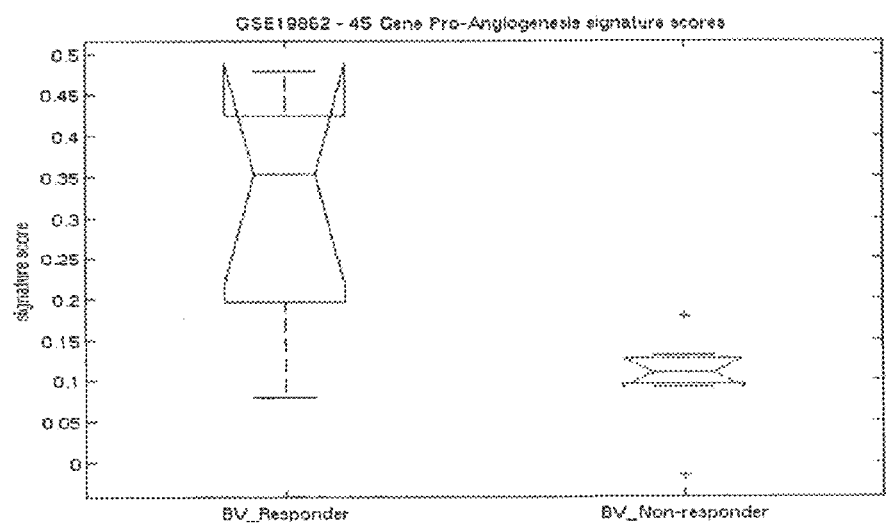
FIGS. 19A and B are graphs demonstrating certain classification performance benchmarks of a 45 gene angiogenesis signature as applied to colorectecal cancer samples.
Figure 19:
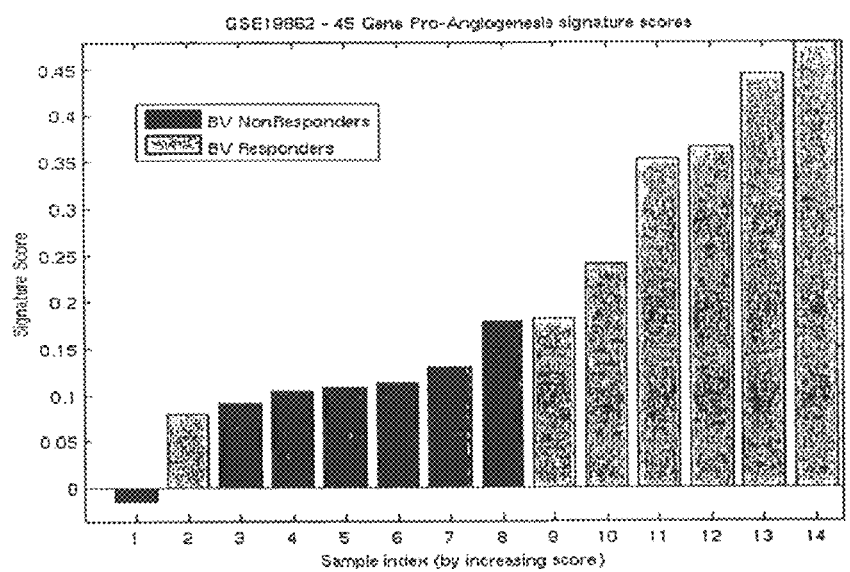

Predictive Utility of the 25 and 45 Angiogenesis Gene Signatures in Colorectal Cancer In a public array data set obtained from the Gene Expression Omnibus database from a cohort of recurrent or metastatic colorectal cancer responders and non-responders to Bevacizumab on plus 2 arrays (E-GEOD-19862), the 25 gene and 45 gene angiogenic signatures both predict response to bevacizumab—see FIGS. 18 and 19 respectively.

REFERENCES

1. Friedman H S, Prados M D, Wen P Y, et al. Bevacizumab alone and in combination with irinotecan in recurrent glioblastoma. *J Clin Oncol;* 27:4733-40 (2009).
2. Hurwitz H, Fehrenbacher L, Novotny W, et al. Bevacizumab plus irinotecan, fluorouracil, and leucovorin for metastatic colorectal cancer. *N Engl J Med;* 350:2335-42 (2004).
3. Rini B I, Halabi S, Rosenberg J E, et al. Bevacizumab plus interferon alfa compared with interferon alfa monotherapy in patients with metastatic renal cell carcinoma: CALGB 90206. *J Clin Oncol;* 26:5422-8 (2008).
4. Sandler A, Gray R, Perry M C, et al. Paclitaxel-carboplatin alone or with bevacizumab for non-small-cell lung cancer. *N Engl J Med;* 355: 2542-50 (2006).
5. Wolmark N, Yothers G, O'Connell M J, et al. A phase III trial comparing mFOLFOX6 to mFOLFOX6 plus bevacizumab in stage II or III carcinoma of the colon: results of NSABP protocol C-08. *J Clin Oncol;* 27:LBA4 (2009).

6. Yang J C, Haworth L, Sherry R M, et al., A randomized trial of bevacizumab, an anti-vascular endothelial growth factor antibody, for metastatic renal cancer, *N Engl J Med* 349 427-434 (2003).
7. Willett C G, Boucher Y, di Tomaso E, et al., Direct evidence that the VEGF-specific antibody bevacizumab has antivascular effects in human rectal cancer, *Nat. Med.* 10, 145-147 (2004).
8. Miller K, Wang M, Gralow J, et al., Paclitaxel plus bevacizumab versus paclitaxel alone for metastatic breast cancer, *N Engl J Med* 357 2666-2676 (2007).
9. Miller K D, Chap L I, Holmes F A, et al., Randomized phase III trial of capecitabine compared with bevacizumab plus capecitabine in patients with previously treated metastatic breast cancer, *J Clin Oncol* 23 792-799 (2005).
10. O'Shaughnessy J, Miles D, Gray R J, et al., A meta-analysis of overall survival data from three randomized trials of bevacizumab (B V) and first-line chemotherapy as treatment for patients with metastatic breast cancer (MBC), *J Clin Oncol* 28 (suppl) (abstr 1005) (2010).
11. Reck M, von Pawel J, Zatloukal P, et al., Phase III trial of cisplatin plus gemcitabine with either placebo or bevacizumab as first-line therapy for nonsquamous non-small-cell lung cancer: AVAil, *J Clin Oncol* 27, 1227-1234 (2009).
12. Escudier B, Bellmunt J, Negrier S et al., Phase III trial of bevacizumab plus interferon alfa-2a in patients with metastatic renal cell carcinoma (AVOREN): final analysis of overall survival, *J Clin Oncol* 28, 2144-2150 (2010)
13. Burger R A, Sill M W, Monk B J, et al. Phase II trial of bevacizumab in persistent or recurrent epithelial ovarian cancer or primary peritoneal cancer: a Gynecologic Oncology Group Study. *J Clin Oncol;* 20; 25(33):5165-71 (2007).
14. Tothill R W et al. Novel molecular subtypes of serous and endometrioid ovarian cancer linked to clinical outcome. *Clin Cancer Res.* 14(16), 5198-208 (2008).

---

We claim:

1. A method of predicting a subject's cancer responsiveness to an anti-angiogenic therapeutic agent and treating the subject with the therapeutic agent comprising:
    obtaining a test cancer sample from a cancer subject;
    measuring expression levels of a biomarker panel from the test cancer sample obtained from the cancer subject, wherein the biomarker panel comprises at least TAP1, SHISA4, ENTPD7, CDR1, SPARC, INS, NUAK1, and MATN3;
    determining a test cancer sample expression score for the biomarker panel based on the measured expression levels;
    comparing the test cancer sample expression score to a threshold score;
    classifying the subject's cancer as responsive or non-responsive to the anti-angiogenic therapeutic agent based on whether the test cancer sample expression score is above or below the threshold expression score, respectively; and
    treating the responsive subject's cancer with the anti-angiogenic therapeutic agent.

2. The method of claim 1, wherein the biomarker panel consists of TAP1, SHISA4, ENTPD7, CDR1, SPARC, INS, NUAK1, and MATN3.

3. The method of claim 1, wherein the test cancer sample expression score is determined by measuring an expression level for each biomarker and multiplying it by a corresponding weight, wherein an expression signature defines the weight for each biomarker.

4. The method of claim 1, wherein the expression level of each biomarker in the biomarker panel is measured using a microarray, quantitative PCR, or an immunoassay.

5. The method of claim 3, wherein the expression signature is derived by a method comprising:
    isolating total RNA from a sample set of diseased cancer tissue;
    hybridizing the isolated total RNA to a microarray to obtain a sample expression data set;
    selecting those probes on the microarray with a variability above a defined significance threshold to form a preliminary biomarker set;
    generating clusters of biomarkers within the preliminary biomarker set having a similar expression profile using a clustering algorithm;
    identifying the biological processes or biological pathways for each cluster of biomarkers;
    selecting the cluster corresponding to the biological process or biological pathway of interest; and
    defining an expression signature by analyzing the expression levels of the biomarkers in the selected cluster in the sample set of diseased cancer tissue using a supervised or unsupervised training algorithm.

6. The method of claim 5, wherein the expression signature is defined using a PLS classifier, a SVM classifier, a SDA classifier, or a DSDA classifier.

7. The method of claim 1, wherein the cancer is ovarian cancer, prostate, breast cancer, colon cancer, or colorectal cancer.

8. The method of claim 1, wherein the anti-angiogenic therapeutic agent is a VEGF-pathway-targeted therapeutic agent, an angiopoietin-TIE2 pathway inhibitor, an endogenous angiogenic inhibitor, or an immunomodulatory agent.

9. The method of claim 8, wherein the VEGF pathway-targeted therapeutic agent is selected from Bevacizumab (Avastin), Afibercept (VEGF Trap), IMC-1121B (Ramucirumab), Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258, and a combination thereof.

10. The method of claim 8, wherein the angiopoietin-TIE2 pathway inhibitor is selected from AMG-386, PF-4856884 CVX-060, CEP-11981, CE-245677, MEDI-3617, CVX-241, Trastuzumab (Herceptin), and a combination thereof.

11. The method of claim 8, wherein the endogenous angiogenic inhibitor is selected from Thombospondin, Endostatin, Tumstatin, Canstatin, Arrestin, Angiostatin, Vasostatin, Interferon alpha, and a combination thereof.

12. The method of claim 8, wherein the immunomodulatory agent is selected from thalidomide and lenalidomide.

13. The method of claim 1, further comprising determining the subject's cancer prognosis, wherein a classification as responsive to the anti-angiogenic therapeutic agent indicates a good prognosis, the good prognosis indicating at least an increased expected survival time as compared to a classification as non-responsive to the anti-angiogenic therapeutic agent.

14. A method for predicting a subject's cancer responsiveness to anti-angiogenic therapeutic agents, providing treatment prognosis, and treating the subject's cancer, the method comprising:
obtaining a test cancer sample from a cancer subject;
measuring expression levels of a first biomarker panel from the test cancer sample of diseased cancer tissue obtained from the cancer subject, wherein the biomarker panel comprises at least TAP1, SHISA4, ENTPD7, CDR1, SPARC, INS, NUAK1, and MATN3;
determining a first sample expression score for the first biomarker panel;
comparing the first sample expression score to a first threshold score;
classifying the cancer subject as having a good prognosis or bad prognosis based on whether the first sample expression score is above or below the first threshold score, respectively, wherein a good prognosis indicates at least an increased expected survival time as compared to a bad prognosis and wherein, in the event of a bad prognosis, measuring expression levels of a second biomarker panel from the test cancer sample of diseased cancer tissue obtained from the subject, wherein the second biomarker panel comprises one or more biomarkers selected from Table 2A or Table 2B;
determining a second sample expression score for the second biomarker panel;
comparing the second sample expression score to a second threshold score;
classifying the cancer subject as responsive or non-responsive to an anti-angiogenic therapeutic agent based on whether the second sample expression score is above or below the second threshold expression score, respectively; and
treating the responsive subject with an anti-angiogenic therapeutic agent.

15. The method of claim 14, wherein the first biomarker panel consists of the biomarkers TAP1, SHISA4, ENTPD7, CDR1, SPARC, INS, NUAK1, and MATN3, and the second biomarker panel consists of the biomarkers in Table 2A or 2B.

16. The method of claim 14, wherein the expression level of each biomarker in the biomarker panel is measured using a microarray, quantitative PCR, or an immunoassay.

17. A method of diagnosing a subject as having a cancer that is responsive to an anti-angiogenic therapeutic agent and treating the subject with the therapeutic agent, the method comprising:
obtaining a test cancer sample from a subject having a cancer;
measuring expression levels of a biomarker panel from the test cancer sample obtained from the subject, wherein the biomarker panel comprises at least TAP1, SHISA4, ENTPD7, CDR1, SPARC, INS, NUAK1, and MATN3;
determining a test cancer sample expression score for the biomarker panel from the measured expression levels;
comparing the sample expression score to a threshold score;
diagnosing the subject as having a cancer that is responsive or non-responsive to an anti-angiogenic therapeutic agent based on whether the sample expression score is above or below the threshold expression score, respectively; and
treating the subject's responsive cancer with the anti-angiogenic therapeutic agent.

18. The method of claim 17, wherein the biomarker panel consists of the biomarkers TAP1, SHISA4, ENTPD7, CDR1, SPARC, INS, NUAK1, and MATN3.

19. The method of claim 17, wherein the sample expression score is determined by measuring an expression level for each biomarker and multiplying it by a corresponding weight, wherein an expression signature defines the weight for each biomarker.

20. The method of claim 19, wherein the expression signature is defined using a PLS classifier, a SVM classifier, a SDA classifier, or a DSDA classifier.

21. The method of claim 17, wherein the cancer is ovarian cancer, glioblastoma, breast cancer, prostate cancer, colorectal cancer or colon cancer.

22. The method of claim 17, wherein the expression level of each biomarker in the biomarker panel is measured using a microarray, quantitative PCR, or an immunoassay.

* * * * *